US009598433B2

United States Patent
Sun et al.

(10) Patent No.: US 9,598,433 B2
(45) Date of Patent: Mar. 21, 2017

(54) HEPATITIS C VIRUS INHIBITORS

(71) Applicant: BRISTOL-MYERS SQUIBB COMPANY, Princeton, NJ (US)

(72) Inventors: Li-Qiang Sun, Glastonbury, CT (US); Eric P. Gillis, Cheshire, CT (US); Eric Mull, Guilford, CT (US); Michael S. Bowsher, Prospect, CT (US); Qian Zhao, Wallingford, CT (US); Paul Michael Scola, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/435,047

(22) PCT Filed: Oct. 31, 2013

(86) PCT No.: PCT/US2013/067649
§ 371 (c)(1),
(2) Date: Apr. 10, 2015

(87) PCT Pub. No.: WO2014/070964
PCT Pub. Date: May 8, 2014

(65) Prior Publication Data
US 2015/0284409 A1    Oct. 8, 2015

Related U.S. Application Data

(60) Provisional application No. 61/721,564, filed on Nov. 2, 2012.

(51) Int. Cl.
| | | |
|---|---|---|
| C07D 498/04 | (2006.01) | |
| C07K 5/083 | (2006.01) | |
| A61K 38/20 | (2006.01) | |
| A61K 38/21 | (2006.01) | |
| A61K 31/4725 | (2006.01) | |
| A61K 31/4741 | (2006.01) | |
| A61K 31/498 | (2006.01) | |
| A61K 45/06 | (2006.01) | |
| C07D 519/00 | (2006.01) | |

(52) U.S. Cl.
CPC ........ *C07D 498/04* (2013.01); *A61K 31/4725* (2013.01); *A61K 31/4741* (2013.01); *A61K 31/498* (2013.01); *A61K 38/204* (2013.01); *A61K 38/208* (2013.01); *A61K 38/2013* (2013.01); *A61K 38/212* (2013.01); *A61K 45/06* (2013.01); *C07D 519/00* (2013.01); *C07K 5/081* (2013.01)

(58) Field of Classification Search
None
See application file for complete search history.

(56) References Cited

U.S. PATENT DOCUMENTS

| | | |
|---|---|---|
| 5,223,432 A | 6/1993 | Wirz et al. |
| 7,449,479 B2 | 11/2008 | Wang et al. |
| 7,582,605 B2 | 9/2009 | Moore et al. |
| 7,601,709 B2 | 10/2009 | Miao et al. |
| 7,605,126 B2 | 10/2009 | Niu et al. |
| 7,635,683 B2 | 12/2009 | Gai et al. |
| 7,741,281 B2 * | 6/2010 | D'Andrea .......... A61K 38/2013 424/85.4 |
| 7,915,291 B2 | 3/2011 | Wang et al. |
| 8,232,246 B2 | 7/2012 | McDaniel et al. |
| 8,268,776 B2 | 9/2012 | Sun et al. |
| 8,299,094 B2 | 10/2012 | Wang et al. |
| 8,309,685 B2 | 11/2012 | Petter et al. |

(Continued)

FOREIGN PATENT DOCUMENTS

| | | |
|---|---|---|
| WO | WO 98/17679 A1 | 4/1998 |
| WO | WO 98/22106 A1 | 5/1998 |

(Continued)

OTHER PUBLICATIONS

Eley, T. et al., "Improved Bioavailability and Mitigated Food Effect for Asunaprevir (ASV) Utilizing a Lipid-Based Formulation: Similar Exposure with 100mg BID Softgel Capsule (SGC) Relative to 200mg BID of Phase 2 Tablet", Abstract No. A-1247, Interscience Conference on Antimicrobial Agents and Chemotherapy, (Sep. 12, 2012).

Lauer, G.M. et al., "Hepatitis C Virus Infection", The New England Journal of Medicine, vol. 345, No. 1, pp. 41-52 (2001).

Llinàs-Brunet, M. et al., "A Systematic Approach to the Optimization of Substrate-Based Inhibitors of the Hepatitis C Virus NS3 Protease: Discovery of Potent and Specific Tripeptide Inhibitors", Journal of Medicinal Chemistry, vol. 47, No. 26, pp. 6584-6594 (2004).

Poupart, M.-A. et al., "Solid-Phase Synthesis of Peptidomimetic Inhibitors for the Hepatitis C Virus NS3 Protease", The Journal of Organic Chemistry, vol. 66, No. 14, pp. 4743-4751 (2001).

(Continued)

*Primary Examiner* — Jeffrey S Lundgren
*Assistant Examiner* — Stephaine Springer
(74) *Attorney, Agent, or Firm* — Pamela A. Mingo

(57) ABSTRACT

Hepatitis C virus inhibitors having the general formula (I) are disclosed. Compositions comprising the compounds and methods for using the compounds to inhibit HCV are also disclosed.

6 Claims, No Drawings

(56) References Cited

U.S. PATENT DOCUMENTS

| | | |
|---|---|---|
| 8,338,606 B2 | 12/2012 | Perrone et al. |
| 8,415,374 B2 | 4/2013 | Lemm et al. |
| 8,507,722 B2 | 8/2013 | Wang |
| 8,710,229 B2 | 4/2014 | Wang et al. |
| 2005/0209135 A1 | 9/2005 | Busacca et al. |
| 2006/0199773 A1 | 9/2006 | Sausker et al. |
| 2006/0257980 A1 | 11/2006 | Li |
| 2007/0078081 A1 | 4/2007 | Casarez et al. |
| 2008/0279821 A1 | 11/2008 | Niu et al. |
| 2013/0302414 A1 | 11/2013 | Perrone |
| 2014/0235617 A1 | 8/2014 | Gao et al. |

FOREIGN PATENT DOCUMENTS

| | | | |
|---|---|---|---|
| WO | WO 99/07733 A2 | 2/1999 | |
| WO | WO 99/07734 A2 | 2/1999 | |
| WO | WO 00/09543 A2 | 2/2000 | |
| WO | WO 00/09558 A1 | 2/2000 | |
| WO | WO 00/59929 A1 | 10/2000 | |
| WO | WO 02/08244 A2 | 1/2002 | |
| WO | WO 02/060926 A2 | 8/2002 | |
| WO | WO 03/053349 A2 | 7/2003 | |
| WO | WO 03/062265 A2 | 7/2003 | |
| WO | WO 03/064416 A1 | 8/2003 | |
| WO | WO 03/064455 A2 | 8/2003 | |
| WO | WO 03/064456 A1 | 8/2003 | |
| WO | WO 03/066103 A1 | 8/2003 | |
| WO | WO 03/099274 A1 | 12/2003 | |
| WO | WO 03/099316 A1 | 12/2003 | |
| WO | WO 2004/009121 A1 | 1/2004 | |
| WO | WO 2004/032827 A2 | 4/2004 | |
| WO | WO 2004/037855 A1 | 5/2004 | |
| WO | WO 2004/043339 A2 | 5/2004 | |
| WO | WO 2004/072243 A2 | 8/2004 | |
| WO | WO 2004/093798 A2 | 11/2004 | |
| WO | WO 2004/093915 A1 | 11/2004 | |
| WO | WO 2004/094452 A2 | 11/2004 | |
| WO | WO 2004/101602 A2 | 11/2004 | |
| WO | WO 2004/101605 A1 | 11/2004 | |
| WO | WO 2004094452 A2 * | 11/2004 | ........... C07K 5/0804 |
| WO | WO 2004/103996 A1 | 12/2004 | |
| WO | WO 2004/113365 A2 | 12/2004 | |
| WO | WO 2005/010029 A1 | 2/2005 | |
| WO | WO 2005/028501 A1 | 3/2005 | |
| WO | WO 2005/037214 A2 | 4/2005 | |
| WO | WO 2005/037860 A2 | 4/2005 | |
| WO | WO 2005/046712 A1 | 5/2005 | |
| WO | WO 2005/051410 A1 | 6/2005 | |
| WO | WO 2005/051980 A1 | 6/2005 | |
| WO | WO 2005/054430 A2 | 6/2005 | |
| WO | WO 2005/070955 A1 | 8/2005 | |
| WO | WO 2005/073216 A2 | 8/2005 | |
| WO | WO 2005/095403 A1 | 10/2005 | |
| WO | WO 2005/116054 A1 | 12/2005 | |
| WO | WO 2006/000085 A1 | 1/2006 | |
| WO | WO 2006/007700 A1 | 1/2006 | |
| WO | WO 2006/007708 A1 | 1/2006 | |
| WO | WO 2006/016930 A2 | 2/2006 | |
| WO | WO 2006/020276 A2 | 2/2006 | |
| WO | WO 2006/026352 A1 | 3/2006 | |
| WO | WO 2006/033878 A1 | 3/2006 | |
| WO | WO 2006/043145 A1 | 4/2006 | |
| WO | WO 2006/086381 A2 | 8/2006 | |
| WO | WO 2006/096652 A2 | 9/2006 | |
| WO | WO 2006/119061 A2 | 11/2006 | |
| WO | WO 2006/122188 A2 | 11/2006 | |
| WO | WO 2006/130552 A2 | 12/2006 | |
| WO | WO 2006/130553 A2 | 12/2006 | |
| WO | WO 2006/130554 A2 | 12/2006 | |
| WO | WO 2006/130607 A2 | 12/2006 | |
| WO | WO 2006/130626 A2 | 12/2006 | |
| WO | WO 2006/130627 A2 | 12/2006 | |
| WO | WO 2006/130628 A2 | 12/2006 | |
| WO | WO 2006/130666 A2 | 12/2006 | |
| WO | WO 2006/130686 A2 | 12/2006 | |
| WO | WO 2006/130687 A2 | 12/2006 | |
| WO | WO 2006/130688 A2 | 12/2006 | |
| WO | WO 2007/001406 A2 | 1/2007 | |
| WO | WO 2007/008657 A2 | 1/2007 | |
| WO | WO 2007/009109 A2 | 1/2007 | |
| WO | WO 2007/009227 A1 | 1/2007 | |
| WO | WO 2007/011658 A1 | 1/2007 | |
| WO | WO 2007/014918 A1 | 2/2007 | |
| WO | WO 2007/014919 A1 | 2/2007 | |
| WO | WO 2007/014920 A1 | 2/2007 | |
| WO | WO 2007/014921 A1 | 2/2007 | |
| WO | WO 2007/014922 A1 | 2/2007 | |
| WO | WO 2007/014923 A1 | 2/2007 | |
| WO | WO 2007/014924 A1 | 2/2007 | |
| WO | WO 2007/014925 A1 | 2/2007 | |
| WO | WO 2007/014926 A1 | 2/2007 | |
| WO | WO 2007/014927 A2 | 2/2007 | |
| WO | WO 2007/015787 A1 | 2/2007 | |
| WO | WO 2007/015824 A2 | 2/2007 | |
| WO | WO 2007/015855 A1 | 2/2007 | |
| WO | WO 2007/016441 A1 | 2/2007 | |
| WO | WO 2007/016476 A2 | 2/2007 | |
| WO | WO 2007/017144 A2 | 2/2007 | |
| WO | WO 2007/025307 A2 | 3/2007 | |
| WO | WO 2007/030656 A1 | 3/2007 | |
| WO | WO 2007/044893 A2 | 4/2007 | |
| WO | WO 2007/044933 A1 | 4/2007 | |
| WO | WO 2007/056120 A1 | 5/2007 | |
| WO | WO 2007/082131 A1 | 7/2007 | |
| WO | WO 2007/106317 A2 | 9/2007 | |
| WO | WO 2007/120595 A2 | 10/2007 | |
| WO | WO 2007/131966 A1 | 11/2007 | |
| WO | WO 2007/143694 A2 | 12/2007 | |
| WO | WO 2007/148135 A2 | 12/2007 | |
| WO | WO 2008/002924 A2 | 1/2008 | |
| WO | WO 2008/005511 A2 | 1/2008 | |
| WO | WO 2008/005565 A2 | 1/2008 | |
| WO | WO 2008/008502 A1 | 1/2008 | |
| WO | WO 2008/008776 A2 | 1/2008 | |
| WO | WO 2008/019266 A2 | 2/2008 | |
| WO | WO 2008/019289 A2 | 2/2008 | |
| WO | WO 2008/019303 A2 | 2/2008 | |
| WO | WO 2008/021733 A2 | 2/2008 | |
| WO | WO 2008/021871 A2 | 2/2008 | |
| WO | WO 2008/021956 A2 | 2/2008 | |
| WO | WO 2008/021960 A2 | 2/2008 | |
| WO | WO 2008/022006 A2 | 2/2008 | |
| WO | WO 2008/051475 A2 | 5/2008 | |
| WO | WO 2008/051477 A2 | 5/2008 | |
| WO | WO 2008/051514 A2 | 5/2008 | |
| WO | WO 2008/057208 A2 | 5/2008 | |
| WO | WO 2008/057209 A1 | 5/2008 | |
| WO | WO 2008/057871 A2 | 5/2008 | |
| WO | WO 2008/057873 A2 | 5/2008 | |
| WO | WO 2008/057875 A2 | 5/2008 | |
| WO | WO 2008/057995 A2 | 5/2008 | |
| WO | WO 2008/059046 A1 | 5/2008 | |
| WO | WO 2008/060927 A2 | 5/2008 | |
| WO | WO 2008/064057 A1 | 5/2008 | |
| WO | WO 2008/064061 A1 | 5/2008 | |
| WO | WO 2008/064066 A1 | 5/2008 | |
| WO | WO 2008/070358 A2 | 6/2008 | |
| WO | WO 2008/086161 A1 | 7/2008 | |
| WO | WO 2008/092954 A2 | 8/2008 | |
| WO | WO 2008/092955 A1 | 8/2008 | |
| WO | WO 2008/095058 A1 | 8/2008 | |
| WO | WO 2008/095999 A1 | 8/2008 | |
| WO | WO 2008/096001 A1 | 8/2008 | |
| WO | WO 2008/096002 A1 | 8/2008 | |
| WO | WO 2008/098368 A1 | 8/2008 | |
| WO | WO 2008/101665 A1 | 8/2008 | |
| WO | WO 2008/106130 A2 | 9/2008 | |
| WO | WO 2008/128921 A1 | 10/2008 | |
| WO | WO 2008/134395 A1 | 11/2008 | |
| WO | WO 2008/134397 A1 | 11/2008 | |
| WO | WO 2008/134398 A1 | 11/2008 | |
| WO | WO 2008/137779 A2 | 11/2008 | |
| WO | WO 2008/141227 A1 | 11/2008 | |
| WO | WO 2009/005676 A2 | 1/2009 | |

(56) References Cited

FOREIGN PATENT DOCUMENTS

| | | |
|---|---|---|
| WO | WO 2009/005677 A2 | 1/2009 |
| WO | WO 2009/005690 A2 | 1/2009 |
| WO | WO 2009/010804 A1 | 1/2009 |
| WO | WO 2009/014730 A1 | 1/2009 |
| WO | WO 2009/047264 A1 | 4/2009 |
| WO | WO 2009/053828 A2 | 4/2009 |
| WO | WO 2009/055335 A2 | 4/2009 |
| WO | WO 2009/064955 A1 | 5/2009 |
| WO | WO 2009/064975 A1 | 5/2009 |
| WO | WO 2009/070689 A1 | 6/2009 |
| WO | WO 2009/070692 A1 | 6/2009 |
| WO | WO 2009/073713 A1 | 6/2009 |
| WO | WO 2009/073719 A1 | 6/2009 |
| WO | WO 2009/073780 A1 | 6/2009 |
| WO | WO 2009/076166 A2 | 6/2009 |
| WO | WO 2009/076173 A2 | 6/2009 |
| WO | WO 2009/079352 A1 | 6/2009 |
| WO | WO 2009/079353 A1 | 6/2009 |
| WO | WO 2009/080542 A1 | 7/2009 |
| WO | WO 2009/082697 A1 | 7/2009 |
| WO | WO 2009/082701 A1 | 7/2009 |
| WO | WO 2009/085659 A1 | 7/2009 |
| WO | WO 2009/094438 A1 | 7/2009 |
| WO | WO 2009/094443 A1 | 7/2009 |
| WO | WO 2009/108507 A1 | 9/2009 |
| WO | WO 2009/117594 A1 | 9/2009 |
| WO | WO 2009/129109 A1 | 10/2009 |
| WO | WO 2009/134624 A1 | 11/2009 |
| WO | WO 2009/134987 A1 | 11/2009 |
| WO | WO 2009/139792 A1 | 11/2009 |
| WO | WO 2009/140475 A1 | 11/2009 |
| WO | WO 2009/140500 A1 | 11/2009 |
| WO | WO 2009/142842 A2 | 11/2009 |
| WO | WO 2009/146347 A1 | 12/2009 |
| WO | WO 2009/148923 A1 | 12/2009 |
| WO | WO 2010/011566 A1 | 1/2010 |
| WO | WO 2010/015545 A1 | 2/2010 |
| WO | WO 2010/030359 A2 | 3/2010 |
| WO | WO 2010/031829 A1 | 3/2010 |
| WO | WO 2010/031832 A2 | 3/2010 |
| WO | WO 2010/033466 A1 | 3/2010 |
| WO | WO 2010/034105 A1 | 4/2010 |
| WO | WO 2010/036551 A1 | 4/2010 |
| WO | WO 2010/036871 A1 | 4/2010 |
| WO | WO 2010/036896 A1 | 4/2010 |
| WO | WO 2010/059937 A1 | 5/2010 |
| WO | WO 2010/065577 A1 | 6/2010 |
| WO | WO 2010/068760 A2 | 6/2010 |
| WO | WO 2010/068761 A2 | 6/2010 |
| WO | WO 2010/075127 A1 | 7/2010 |
| WO | WO 2010/077783 A1 | 7/2010 |
| WO | WO 2010/080389 A1 | 7/2010 |
| WO | WO 2010/088394 A1 | 8/2010 |
| WO | WO 2010/115981 A1 | 10/2010 |
| WO | WO 2010/116248 A1 | 10/2010 |
| WO | WO 2010/132163 A1 | 11/2010 |
| WO | WO 2010/145523 A1 | 12/2010 |
| WO | WO 2011/002807 A1 | 1/2011 |
| WO | WO 2011/002808 A1 | 1/2011 |
| WO | WO 2011/005646 A2 | 1/2011 |
| WO | WO 2011/014487 A1 | 2/2011 |
| WO | WO 2011/025849 A1 | 3/2011 |
| WO | WO 2011/034518 A1 | 3/2011 |
| WO | WO 2011/038283 A1 | 3/2011 |
| WO | WO 2011/038293 A1 | 3/2011 |
| WO | WO 2011/041551 A1 | 4/2011 |
| WO | WO 2011/046811 A1 | 4/2011 |
| WO | WO 2011/049908 A2 | 4/2011 |
| WO | WO 2011/063501 A1 | 6/2011 |
| WO | WO 2011/063502 A1 | 6/2011 |
| WO | WO 2011/072370 A1 | 6/2011 |
| WO | WO 2011/091757 A1 | 8/2011 |
| WO | WO 2011/112558 A2 | 9/2011 |
| WO | WO 2011/150190 A2 | 12/2011 |
| WO | WO 2011/156337 A2 | 12/2011 |
| WO | WO 2012/018829 A1 | 2/2012 |
| WO | WO 2012/019299 A1 | 2/2012 |
| WO | WO 2012/037259 A1 | 3/2012 |
| WO | WO 2012/040040 A1 | 3/2012 |
| WO | WO 2012/040167 A1 | 3/2012 |
| WO | WO 2012/040242 A1 | 3/2012 |
| WO | WO 2012/047764 A1 | 4/2012 |
| WO | WO 2012/054874 A1 | 4/2012 |
| WO | WO 2012/082672 A2 | 6/2012 |
| WO | WO 2012/092409 A2 | 7/2012 |
| WO | WO 2012/092411 A2 | 7/2012 |
| WO | WO 2012/151195 A1 | 11/2012 |
| WO | WO 2012/166459 A1 | 12/2012 |
| WO | WO 2012/173983 A1 | 12/2012 |
| WO | WO 2013/028465 A1 | 2/2013 |
| WO | WO 2013/028470 A1 | 2/2013 |
| WO | WO 2013/028471 A1 | 2/2013 |
| WO | WO 2013/040568 A1 | 3/2013 |
| WO | WO 2013/066753 A1 | 5/2013 |
| WO | WO 2013/074386 A2 | 5/2013 |
| WO | WO 2013/106689 A1 | 7/2013 |
| WO | WO 2013/120371 A1 | 8/2013 |
| WO | WO 2014/008285 A1 | 1/2014 |
| WO | WO 2014/019344 A1 | 2/2014 |
| WO | WO 2014/025736 A1 | 2/2014 |
| WO | WO 2014/062196 A1 | 4/2014 |
| WO | WO 2014/070974 A1 | 5/2014 |
| WO | WO 2014/071007 A1 | 5/2014 |
| WO | WO 2014/071032 A1 | 5/2014 |
| WO | WO 2014/137869 A1 | 9/2014 |

OTHER PUBLICATIONS

Ribeiro, C.M.R. et al., "Ultrasound in enzymatic resolution of ethyl 3-hydroxy-3-phenylpropanoate", Tetrahedron Letters, vol. 42, pp. 6477-6479 (2001).

Tsantrizos, Y.S. et al., "Olefin ring-closing metathesis as a powerful tool in drug discovery and development—potent macrocyclic inhibitors of the hepatitis C virus NS3 protease", Journal of Organometallic Chemistry, vol. 691, pp. 5163-5174 (2006).

Wirz, B. et al., "Enzymatic preparation of homochiral 2-isobutyl succinic acid derivatives", Tetrahedron: Asymmetry, vol. 8, No. 2, pp. 187-189 (1997).

Yang, S. et al., "Chemoenzymatic Synthesis of (R)-(—)-Citramalic Acid", Synthesis, pp. 365-366 (1992).

* cited by examiner

HEPATITIS C VIRUS INHIBITORS

The present disclosure is generally directed to antiviral compounds, and more specifically directed to compounds which inhibit the function of the NS3 protease (also referred to herein as "serine protease") encoded by Hepatitis C virus (HCV), compositions comprising such compounds, and methods for inhibiting the function of the NS3 protease.

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

Presently, the most effective HCV therapy employs a combination of alpha-interferon and ribavirin, leading to sustained efficacy in 40% of patients. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load. Thus, there is a clear and unmet need to develop effective therapeutics for treatment of HCV infection.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. Six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one cleaves at the NS2-NS3 junction; the second one is a serine protease contained within the N-terminal region of NS3 and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a co-factor for the NS3 protease and possibly assisting in the membrane localization of NS3 and other viral replicase components. The complex formation of the NS3 protein with NS4A is essential for efficient polyprotein processing, enhancing the proteolytic cleavage at all of the sites. The NS3 protein also exhibits nucleoside triphosphatase and RNA helicase activities. NS5B is a RNA-dependent RNA polymerase that is involved in the replication of HCV.

The present disclosure provides peptide compounds that can inhibit the functioning of the NS3 protease, e.g., in combination with the NS4A protease. Further, the present disclosure describes the administration of combination therapy to a patient whereby a compound in accordance with the present disclosure, which is effective to inhibit the HCV NS3 protease, can be administered with additional compounds having anti-HCV activity.

In its first aspect the present disclosure provides a compound of formula (I)

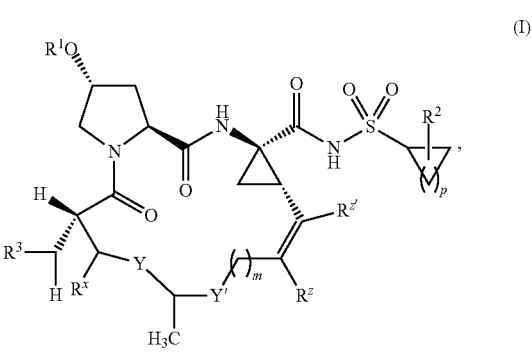

or a pharmaceutically acceptable salt thereof, wherein
p is 1 or 2;
----- is a single or double bond;
m is 0, 1, or 2;
$R^1$ is selected from

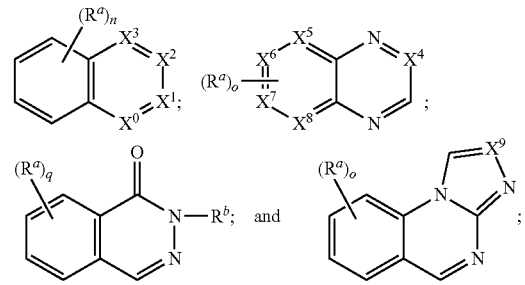

wherein $R^1$ is attached to the parent molecular moiety through any substitutable carbon atom in the group;
n is 0, 1, 2, 3, 4, 5, or 6;
o is 0, 1, 2, 3, 4, or 5;
q is 0, 1, 2, 3, or 4;
$X^0$ is selected from CH and N;
$X^1$ is selected from CH and N;
$X^2$ and $X^3$ are independently selected from CH, C($R^a$) and N; provided that at least one of $X^1$, $X^2$, and $X^3$ is other than N;
$X^4$ is selected from CH and $CR^a$;
one of $X^5$, $X^6$, $X^7$, and $X^8$ is N and the others are selected from CH and $CR^a$;
$X^9$ is selected from CR %, CH, and N;
each $R^a$ is independently selected from alkenyloxy, alkoxy, alkoxyalkoxy, alkoxycarbonyl, alkyl, benzodioxanyl, carboxamido, carboxy, carboxyalkoxy, cyano, cycloalkyl, cycloalkylalkoxy, cycloalkyloxy, deuteroalkoxy, dialkylamino, halo, haloalkyl, haloalkoxy, haloalkoxycarbonyl, hydroxy, imidazolyl, morpholinyl, oxazolyl, phenyl, piperazinyl, pyrazolyl, pyridinyl, pyrrolidinyl, thiazolyl, and —$NR^qR^{q'}$, wherein the imidazolyl, the morpholinyl, the oxazolyl, the phenyl, the piperazinyl, the pyridinyl, the pyrrolidinyl, and the thiazolyl are optionally substituted with one or two groups independently selected from alkoxy, alkyl, alkylsulfonyl, halo, haloalkoxy, haloalkyl, and morpholinyl; and wherein two adjacent $R^a$ groups, together with the carbon atoms to which they are attached, can optionally form a ring selected from dioxanyl, dioxolanyl, furanyl, morpholinyl, pyranyl, and phenyl, wherein the ring is optionally substituted with one or two groups independently selected from alkyl and halo;

$R^b$ is alkyl;

$R^x$ is selected from methyl and ethyl;

$R^z$ and $R^{z'}$ are independently selected from hydrogen and hydroxy; provided that when ----- is a double bond, $R^z$ and $R^{z'}$ are each hydrogen;

$R^2$ is selected from hydrogen, alkyl, deuteroalkyl, halo, haloalkoxy, haloalkyl, and hydroxyalkyl;

$R^3$ is selected from hydrogen, alkoxyalkoxycarbonyl, alkoxycarbonyl, alkylaminocarbonyl, alkylcarbonyl, cycloalkylalkoxycarbonyl, cycloalkylcarbonyl, cycloalkyloxycarbonyl, deuteroalkoxycarbonyl, deuterohaloalkoxycarbonyl, dialkylaminocarbonyl, dialkylaminocarbonylcarbonyl, haloalkoxycarbonyl, haloalkylaminocarbonyl, haloalkylcarbonyl, heterocyclylcarbonyl, heterocyclyloxycarbonyl, phenylcarbonyl, and phenyloxycarbonyl, wherein the cycloalkyl part of the cycloalkylalkoxycarbonyl, the cycloalkylcarbonyl, and the cycloalkyloxycarbonyl, the heterocyclyl part of the heterocyclylcarbonyl and the heterocyclyloxycarbonyl, and the phenyl part of the phenylcarbonyl and the phenyloxycarbonyl, is optionally substituted with one, two, or three groups independently selected from alkyl, alkylamino, alkylcarbonyl, cycloalkyl, dialkylamino, halo, haloalkoxy, and haloalkyl;

one of $R^q$ and $R^{q'}$ is selected from hydrogen and alkyl and the other is selected from alkylcarbonyl and phenylcarbonyl; and one of Y and Y' is oxygen and the other is $CH_2$.

In a first embodiment of the first aspect the present disclosure provides a compound of formula (I), or a pharmaceutically acceptable salt thereof, wherein p is 1. In a second embodiment of the first aspect ----- is a double bond. In a third embodiment of the first aspect m is 1. In a fourth embodiment of the first aspect $R^1$ is

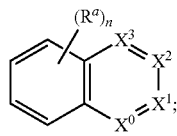

wherein
n is 1, 2, 3, or 4; and
each $R^a$ is independently selected from alkoxy, halo, and pyridinyl, wherein the pyridinyl is optionally substituted with one alkoxy group or wherein two adjacent $R^a$ groups, together with the carbon atoms to which they are attached, can optionally form a ring selected from dioxanyl and pyranyl.

In a fifth embodiment of the first aspect the present disclosure provides a compound of formula (I), or a pharmaceutically acceptable salt thereof, wherein $R^2$ is selected from alkyl and haloalkyl.

In a sixth embodiment of the first aspect the present disclosure provides a compound of formula (I), or a pharmaceutically acceptable salt thereof, wherein $R^3$ is selected from alkoxycarbonyl and haloalkoxycarbonyl.

In a seventh embodiment of the first aspect the present disclosure provides a compound of formula (I), or a pharmaceutically acceptable salt thereof, wherein
p is 1;
----- is a double bond;
m is 1.
$R^1$ is

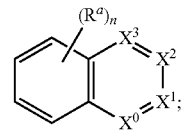

wherein
n is 1, 2, 3, or 4; and
each $R^a$ is independently selected from alkoxy, halo, and pyridinyl, wherein the pyridinyl is optionally substituted with one alkoxy group or wherein two adjacent $R^a$ groups, together with the carbon atoms to which they are attached, can optionally form a ring selected from dioxanyl and pyranyl;

$R^2$ is selected from alkyl and haloalkyl; and $R^3$ is selected from alkoxycarbonyl and haloalkoxycarbonyl.

In a second aspect the present disclosure provides a composition comprising a compound of formula (I), or a pharmaceutically acceptable salt thereof, and a pharmaceutically acceptable carrier. In a first embodiment of the second aspect the present disclosure provides a composition comprising a compound of formula (I), or a pharmaceutically acceptable salt thereof, at least one additional compound having anti-HCV activity, and a pharmaceutical carrier. In a second embodiment at least one of the additional compounds is an interferon or a ribavirin. In a third embodiment the interferon is selected from interferon alpha 2B, pegylated interferon alpha, consensus interferon, interferon alpha 2A, and lymphoblastiod interferon tau. In a fourth embodiment of the second aspect the present disclosure provides a composition comprising a compound of formula (I), or a pharmaceutically acceptable salt thereof, at least one additional compound having anti-HCV activity, and a pharmaceutical carrier, wherein at least one of the additional compounds is selected from interleukin 2, interleukin 6, interleukin 12, Imiquimod, ribavirin, an inosine 5'-monophospate dehydrogenase inhibitor, amantadine, and rimantadine. In a fifth embodiment of the second aspect the present disclosure provides a composition comprising a compound of formula (I), or a pharmaceutically acceptable salt thereof, at least one additional compound having anti-HCV activity, and a pharmaceutical carrier, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a third aspect the present disclosure provides a method of treating an HCV infection in a patient, comprising administering to the patient a therapeutically effective amount of a compound of formula (I), or a pharmaceutically acceptable salt thereof. In a first embodiment of the third aspect the method further comprises administering at least one additional compound having anti-HCV activity prior to, after, or simultaneously with the compound of formula (I), or a pharmaceutically acceptable salt thereof. In a second embodiment of the third aspect at least one of the additional compounds is an interferon or a ribavirin. In a third embodiment the interferon is selected from interferon alpha 2B, pegylated interferon alpha, consensus interferon, interferon alpha 2A, and lymphoblastiod interferon tau. In a fourth embodiment of the third aspect the present disclosure provides a method of treating an HCV infection in a patient, comprising administering to the patient a therapeutically effective amount of a compound of formula (I), or a pharmaceutically acceptable salt thereof, and at least one additional compound having anti-HCV activity prior to, after, or simultaneously with the compound of formula (I), or a pharmaceutically acceptable salt thereof, wherein at least one of the additional compounds is selected from interleukin 2, interleukin 6, interleukin 12, Imiquimod, ribavirin, an inosine 5'-monophospate dehydrogenase inhibitor, amantadine, and rimantadine. In a fifth embodiment of the third aspect the present disclosure provides a method of treating an HCV infection in a patient, comprising administering to the patient a therapeutically effective amount of a compound of formula (I), or a pharmaceutically acceptable salt thereof, and at least one additional compound having anti-HCV activity prior to, after, or simultaneously with the compound of formula (I), or a pharmaceutically acceptable salt thereof, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order to accommodate a substituent at any given location.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule. For example, when n is 2, each of the two $R^1$ groups may be the same or different.

All patents, patent applications, and literature references cited in the specification are herein incorporated by reference in their entirety. In the case of inconsistencies, the present disclosure, including definitions, will prevail.

As used herein, the singular forms "a", "an", and "the" include plural reference unless the context clearly dictates otherwise.

The term "alkenyl," as used herein, refers to a group derived from a straight or branched chain saturated hydrocarbon containing from two to ten carbon atoms and at least one double bond. In one embodiment the alkenyl groups contain from two to six carbon atoms. In another embodiment the alkenyl groups contain from two to four carbon atoms.

The term "alkenyloxy," as used herein, refers to an alkenyl group attached to the parent molecular moiety through an oxygen atom.

The term "alkoxy," as used herein, refers to an alkyl group attached to the parent molecular moiety through an oxygen atom.

The term "alkoxyalkoxy," as used herein, refers to an alkoxyalkyl group attached to the parent molecular moiety through an oxygen atom.

The term "alkoxyalkoxycarbonyl," as used herein, refers to an alkoxyalkoxy group attached to the parent molecular moiety through a carbonyl group.

The term "alkoxyalkyl," as used herein, refers to an alkyl group substituted with one, two, or three alkoxy groups.

The term "alkoxycarbonyl," as used herein, refers to an alkoxy group attached to the parent molecular moiety through a carbonyl group.

The term "alkyl," as used herein, refers to a group derived from a straight or branched chain saturated hydrocarbon containing from one to ten carbon atoms. In one embodiment the alkyl groups contain from one to six carbon atoms. In another embodiment the alkyl groups contain from one to four carbon atoms.

The term "alkylamino," as used herein, refers to —NHR, wherein R is an alkyl group.

The term "alkylaminocarbonyl," as used herein, refers to an alkylamino group attached to the parent molecular moiety through a carbonyl group.

The term "alkylcarbonyl," as used herein, refers to an alkyl group attached to the parent molecular moiety through a carbonyl group.

The term "alkylsulfonyl," as used herein, refers to an alkyl group attached to the parent molecular moiety through a sulfonyl group.

The term "carbonyl," as used herein, refers to —C(O)—.

The term "carboxamido," as used herein, refers to —C(O)NR$^x$R$^y$, wherein R$^x$ and R$^y$ are independently selected from hydrogen and alkyl.

The term "carboxy," as used herein, refers to —CO$_2$H.

The term "carboxyalkoxy," as used herein, refers to a carboxyalkyl group attached to the parent molecular moiety through an oxygen atom.

The term "carboxyalkyl," as used herein, refers to an alkyl group substituted with one, two, or three carboxy groups.

The term "cyano," as used herein, refers to —CN.

The term "cycloalkyl," as used herein, refers to a saturated monocyclic or bicyclic hydrocarbon ring system having three to seven carbon atoms and zero heteroatoms. Representative examples of cycloalkyl groups include, but are not limited to, cyclopropyl, cyclobutyl, and cyclopentyl.

The term "cycloalkylalkoxy," as used herein, refers to a (cycloalkyl)alkyl group attached to the parent molecular moiety through an oxygen atom.

The term "cycloalkylalkoxycarbonyl," as used herein, refers to a cycloalkylalkoxy group attached to the parent molecular moiety through a carbonyl group.

The term "(cycloalkyl)alkyl," as used herein, refers to an alkyl group substituted with one, two, or three cycloalkyl groups.

The term "cycloalkylcarbonyl," as used herein, refers to a cycloalkyl group attached to the parent molecular moiety through a carbonyl group.

The term "cycloalkyloxy," as used herein, refers to a cycloalkyl group attached to the parent molecular moiety through an oxygen atom.

The term "cycloalkyloxycarbonyl," as used herein, refers to a cycloalkyloxy group attached to the parent molecular moiety through a carbonyl group.

The term "deuteroalkoxy," as used herein, refers to an alkoxy group wherein at least one hydrogen atom is replaced by a deuterium atom.

The term "deuteroalkoxycarbonyl," as used herein, refers to a deuteroalkoxy group attached to the parent molecular moiety through a carbonyl group.

The term "deuteroalkyl," as used herein, refers to an alkyl group wherein at least one hydrogen atom is replaced by a deuterium atom.

The term "deuterohaloalkoxy," as used herein, refers to a haloalkoxy group wherein at least one hydrogen atom is replaced by a deuterium atom.

The term "deuterohaloalkoxycarbonyl," as used herein, refers to a deuterohaloalkoxy group attached to the parent molecular moiety through a carbonyl group.

The term "dialkylamino," as used herein, refers to —NR$^p$R$^q$, wherein R$^p$ and R$^q$ are alkyl groups. The alkyl groups may be the same or different.

The term "dialkylaminocarbonyl," as used herein, refers to a dialkylamino group attached to the parent molecular moiety through a carbonyl group.

The term "dialkylaminocarbonylcarbonyl," as used herein, refers to a dialkylaminocarbonyl group attached to the parent molecular moiety through a carbonyl group.

The terms "halo" and "halogen," as used herein, refer to F, Cl, Br, and I.

The term "haloalkoxy," as used herein, refers to a haloalkyl group attached to the parent molecular moiety through an oxygen atom.

The term "haloalkoxycarbonyl," as used herein, refers to a haloalkoxy group attached to the parent molecular moiety through a carbonyl group.

The term "haloalkyl," as used herein, refers to an alkyl group substituted with one, two, three, or four halogen atoms.

The term "haloalkylamino," as used herein, refers to an alkyl amino group wherein the alkyl is substituted with one, two, three, or four halogen atoms.

The term "haloalkylaminocarbonyl," as used herein, refers to a haloalkylamino group attached to the parent molecular moiety through a carbonyl group.

The term "haloalkylcarbonyl," as used herein, refers to a haloalkyl group attached to the parent molecular moiety through a carbonyl group.

The term "heterocyclyl," as used herein, refers to a four-, five-, six-, or seven-membered ring containing one, two, three, or four heteroatoms independently selected from nitrogen, oxygen, and sulfur. The four-membered ring has zero double bonds, the five-membered ring has zero to two double bonds, and the six- and seven-membered rings have zero to three double bonds. The term "heterocyclyl" also includes bicyclic groups in which the heterocyclyl ring is fused to another monocyclic heterocyclyl group, or a four- to six-membered aromatic or non-aromatic carbocyclic ring; as well as bridged bicyclic groups such as 7-azabicyclo[2.2.1]hept-7-yl, 2-azabicyclo[2.2.2]oc-2-tyl, and 2-azabicyclo[2.2.2]oc-3-tyl. The heterocyclyl groups of the present disclosure can be attached to the parent molecular moiety through any carbon atom or nitrogen atom in the group. Examples of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, thiomorpholinyl, 7-azabicyclo[2.2.1]hept-7-yl, 2-azabicyclo[2.2.2]oc-2-tyl, and 2-azabicyclo[2.2.2]oc-3-tyl.

The term "heterocyclylcarbonyl," as used herein, refers to a heterocyclyl group attached to the parent molecular moiety through a carbonyl group.

The term "heterocyclyloxy," as used herein, refers to a heterocyclyl group attached to the parent molecular moiety through an oxygen atom.

The term "heterocyclyloxycarbonyl," as used herein, refers to a heterocyclyloxy group attached to the parent molecular moiety through a carbonyl group.

The term "hydroxy," as used herein, refers to —OH.

The term "hydroxyalkyl," as used herein, refers to an alkyl group substituted with one, two, or three hydroxy groups.

The term "phenylcarbonyl," as used herein, refers to a phenyl group attached to the parent molecular moiety through a carbonyl group.

The term "phenyloxy," as used herein, refers to a phenyl group attached to the parent molecular moiety through an oxygen atom.

The term "phenyloxycarbonyl," as used herein, refers to a phenyloxy group attached to the parent molecular moiety through a carbonyl group.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable basic functionality with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting an acidic group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine.

Other representative organic amines useful for the formation of base addition salts include ethylenediamine, ethanolamine, diethanolamine, piperidine, and piperazine.

As used herein, the term "anti-HCV activity" means the compound is effective to treat the HCV virus.

The term "compounds of the disclosure", and equivalent expressions, are meant to embrace compounds of formula (I), and pharmaceutically acceptable enantiomers, diastereomers, and salts thereof. Similarly, references to intermediates, are meant to embrace their salts where the context so permits.

The term "patient" includes both human and other mammals.

The term "pharmaceutical composition" means a composition comprising a compound of the disclosure in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in Remington's Pharmaceutical Sciences, 18$^{th}$ ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of patients without excessive toxicity, irritation, allergic response, or other problem or complication commensurate with a reasonable risk/benefit ratio.

The term "sulfonyl," as used herein, refers to —$SO_2$—.

The term "therapeutically effective amount" means the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "treat" and "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

Where used in naming compounds of the present disclosure, the designations P1', P1, P2, P2*, P3, and P4, as used herein, map the relative positions of the amino acid residues of a protease inhibitor binding relative to the binding of the natural peptide cleavage substrate. Cleavage occurs in the natural substrate between P1 and P1' where the nonprime positions designate amino acids starting from the C-terminus end of the peptide natural cleavage site extending towards the N-terminus; whereas, the prime positions emanate from the N-terminus end of the cleavage site designation and extend toward the C-terminus. For example, P1' refers to the first position away from the right hand end of the C-terminus of the cleavage site (i.e. N-terminus first position); whereas P1 starts the numbering from the left hand side of the C-terminus cleavage site, P2: second position from the C-terminus, etc.). (see Berger A. & Schechter I., Transactions of the Royal Society London series (1970), B257, 249-264].

Asymmetric centers exist in the compounds of the present disclosure. For example, the compounds may include P1 cyclopropyl element of formula

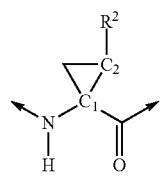

wherein $C_1$ and $C_2$ each represent an asymmetric carbon atom at positions 1 and 2 of the cyclopropyl ring.

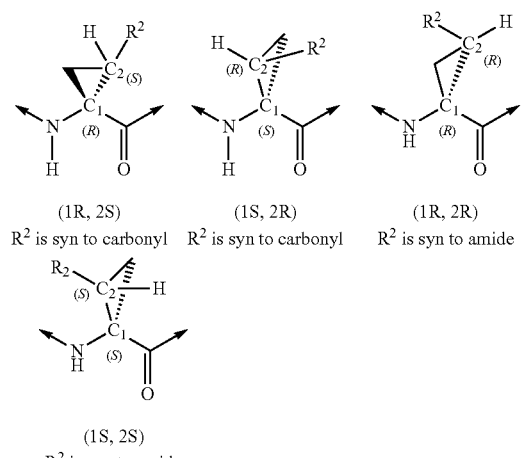

It should be understood that the disclosure encompasses all stereochemical forms, or mixtures thereof, which possess the ability to inhibit HCV protease.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

Certain compounds of the present disclosure may exist in zwitterionic form and the present disclosure includes each zwitterionic form of these compounds and mixtures thereof.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of formula (I), or a pharmaceutically acceptable salt thereof, with one or more pharmaceutically acceptable carriers, diluents, or excipients.

Pharmaceutical formulations may be presented in unit dose forms containing a predetermined amount of active ingredient per unit dose. Dosage levels of between about 0.01 and about 150 milligram per kilogram ("mg/kg") body weight per day, preferably between about 0.05 and about 100 mg/kg body weight per day of the compounds of the disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the disclosure and one or more additional therapeutic and/or prophylactic agent, both the compound and the additional agent can be present in a dose that is less than or equal to the dosage normally administered in a monotherapy regimen. The compositions of this disclosure may be co-formulated with one or more additional therapeutic or prophylactic agents, for example, in the form of a monolithic and/or bi/multi-layer tablet or may be administered separately from the therapeutic or prophylactic agent(s).

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
|---|---|---|---|
| NIM811 | | Cyclophilin Inhibitor | Novartis |
| Zadaxin | | Immuno-modulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts | Antiviral | HCV Inhibitors | Arrow Therapeutics Ltd. |

TABLE 1-continued

| Brand Name | Physiological Class | Type of Inhibitor or Target | Source Company |
|---|---|---|---|
| From WO-2005047288 26 May 2005 | | | |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immuno-suppressant | F. Hoffmann-La Roche LTD, Basel, Switzerland |
| Civacir | Immunosuppressant | HCV IgG immuno-suppressant | Nabi Biopharmaceuticals Inc., Boca Raton, FL |
| Albuferon - α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |

TABLE 1-continued

| Brand Name | Physiological Class | Type of Inhibitor or Target | Source Company |
|---|---|---|---|
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/Valentis |
| Wellferon | Interferon | Lympho-blastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| Boceprevir | Antiviral | serine protease inhibitor | Schering Plough |
| TMS-435 | Antiviral | serine protease inhibitor | Tibotec BVBA, Mechelen, Belgium |
| BI-201335 | Antiviral | serine protease inhibitor | Boehringer Ingelheim Pharma KG, Ingelheim, Germany |
| MK-7009 | Antiviral | serine protease inhibitor | Merck |
| PF-00868554 | Antiviral | replicase inhibitor | Pfizer |
| ANA598 | Antiviral | Non-Nucleoside NS5B Polymerase Inhibitor | Anadys Pharmaceuticals, Inc., San Diego, CA, USA |
| IDX375 | Antiviral | Non-Nucleoside Replicase Inhibitor | Idenix Pharmaceuticals, Cambridge, MA, USA |
| BILB 1941 | Antiviral | NS5B Polymerase Inhibitor | Boehringer Ingelheim Canada Ltd R&D, Laval, QC, Canada |
| PSI-7851 | Antiviral | Nucleoside Polymerase Inhibitor | Pharmasset, Princeton, NJ, USA |
| PSI-7977 | Antiviral | Nucleotide NS5B Polymerase Inhibitor | Pharmasset, Princeton, NJ, USA |

TABLE 1-continued

| Brand Name | Physiological Class | Type of Inhibitor or Target | Source Company |
|---|---|---|---|
| VCH-759 | Antiviral | NS5B Polymerase Inhibitor | ViroChem Pharma |
| INX-189 | Antiviral | Nucleotide NS5B Polymerase Inhibitor | Inhibitex |
| VCH-916 | Antiviral | NS5B Polymerase Inhibitor | ViroChem Pharma |
| GS-9190 | Antiviral | NS5B Polymerase Inhibitor | Gilead |
| Peg-interferon lamda | Antiviral | Interferon | ZymoGenetics/Bristol-Myers Squibb |
| daclatasvir | Antiviral | NS5A inhibitor | Bristol-Myers Squibb |
| BMS-791325 | Antiviral | NS5B Polymerase Inhibitor | Bristol-Myers Squibb |
| ACH-3102 | Antiviral | NS5A inhibitor | Bristol-Myers Squibb |
| BMS-984478 | Antiviral | NS5A inhibitor | Bristol-Myers Squibb |
| asunaprevir | Antiviral | serine protease inhibitor | Bristol-Myers Squibb |

The compounds of the disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having formula (I) when prepared by synthetic processes or by metabolic processes including those occurring in the human or animal body (in vivo) or processes occurring in vitro.

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

The abbreviations used in the present application, including particularly in the illustrative schemes and examples which follow, are well-known to those skilled in the art. Some of the abbreviations used are as follows: THF for tetrahydrofuran; min for minutes; h or hr or hrs for hours; r.t. or RT or Rt for room temprature or retention time (context will dictate); EtOAC or EtOAc for ethyl acetate; TMS for trimethylsilane; DMSO for N,N-dimethylsulfoxide; DCM for dichloromethane; DMF for N,N-dimethylformamide; Me for methyl; DPPA for diphenylphosphoryl azide; Et$_2$O for diethyl ether; Ph for phenyl; DCE for 1,2-dichloroethane; TFA for trifluoroacetic acid; Et$_3$N or TEA for triethylamine; (BOC)$_2$O for di-tert-butyl dicarbonate; and HATU for O-(7-azabenzotriazol-1-yl)-N,N,N',N'-tetramethyluronium phosphate.

The starting materials useful to synthesize the compounds of the present disclosure are known to those skilled in the art and can be readily manufactured or are commercially available.

The following methods set forth below are provided for illustrative purposes and are not intended to limit the scope of the claims. It will be recognized that it may be necessary to prepare such a compound in which a functional group is protected using a conventional protecting group then to remove the protecting group to provide a compound of the present disclosure. The details concerning the use of protecting groups in accordance with the present disclosure are known to those skilled in the art Compounds were named using ChemDraw.

Preparation of 3,3-difluoro-2-methylbutan-2-yl pyridin-2-yl carbonate

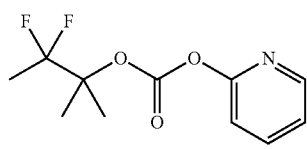 [SMILES: CC(F)(F)C(C)(C)OC(=O)Oc1ccccn1]

Scheme:

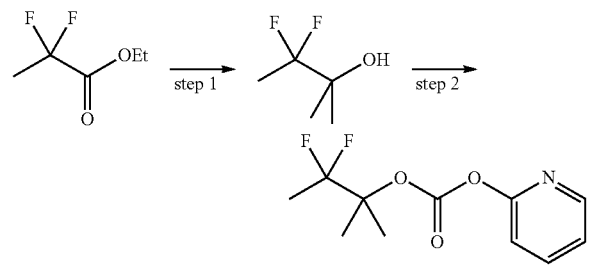

Step 1

Methylmagnesium bromide(24.91 mL, 74.7 mmol) was added dropwise via syringe to a solution of ethyl 2,2-difluoropropanoate (3.44 g, 24.91 mmol) in Diethyl ether (50 mL) at −20° C. and stirred at this temp for 1 hr before warming up to RT. The reaction was quenched with sat. ammonium chloride and extracted with ether. The organic layer was washed with brine, collected, dried over MgSO$_4$, filtered and partially evaporated to give the crude product 3,3-difluoro-2-methylbutan-2-ol(1.84 g, 59.5% yield) as an oil. $^1$H NMR (500 MHz, CDCl$_3$) δ 1.68-1.58 (m, 3H), 1.31 (t, J=1.2 Hz, 6H).

Step 2

To a suspension of sodium hydride, 60% in mineral oil (0.652 g, 16.31 mmol) in THF (25 mL) was added 3,3-difluoro-2-methylbutan-2-ol (1.84 g, 14.82 mmol) at 0° C. After stirring 30 min, the solution was transferred to a solution of di(pyridin-2-yl) carbonate (3.20 g, 14.82 mmol) in THF (25 mL) through a cannula. The formed slurry was stirred at 0° C. for 30 min. The slurry was warmed to rt and stirred for 2 h. The reaction was diluted with EtOAc, washed with brine, dried over MgSO4, filtered, concentrated to give a residue that was purified by Biotage eluting with 10-50% EtOAc in hexanes to afford the desired product 3,3-difluoro-2-methylbutan-2-yl pyridin-2-yl carbonate (500 mg, 13.76%) as an oil that later crystallized to a white solid upon standing. $^1$H NMR (500 MHz, CDCl$_3$) δ 8.43 (ddd, J=4.9, 2.0, 0.7 Hz, 1H), 7.95-7.75 (m, 1H), 7.31-7.24 (m, 1H), 7.15 (dt, J=8.2, 0.8 Hz, 1H), 1.72 (s, 6H), 1.77-1.66 (m, 3H).

Preparation of 1-fluoro-4-methoxyisoquinoline

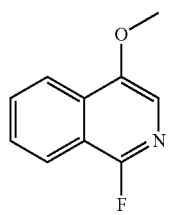

Scheme:

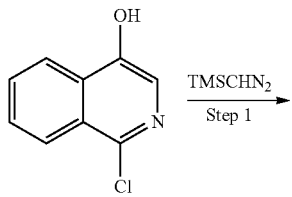

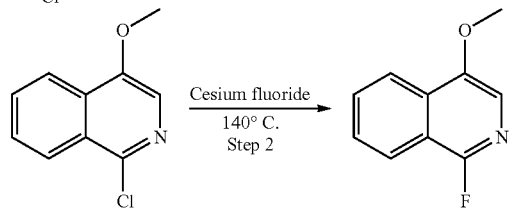

Step 1: Preparation of 1-chloro-4-methoxyisoquinoline

To a solution of 1-chloroisoquinolin-4-ol (5.0 g, 27.8 mmol) in acetonitrile (50 mL) was added TMS-diazomethane (12.73 g, 111.2 mmol) at 0° C. The reaction mixture was allowed to come to room temperature and stirred for 2 h. Solvent was evaporated under reduced pressure to get crude compound. The crude compound was purified by silica gel chromatography to get 1-chloro-4-methoxyisoquinoline (2.5 g, 46.4%) as off-white solid. $^1$H NMR (400 MHz, CD$_3$OD): δ ppm 8.29-8.17 (m, 2H), 7.97 (s, 1H), 7.91-7.82 (m, 2H), 4.05 (s, 3H); MS: MS m/z 194.7 (M$^+$+1).

Step 2: Preparation of 1-Fluoro-4-methoxyisoquinoline

To a solution of 1-chloro-4-methoxyisoquinolin (2.5 g, 12.91 mmol) in DMSO was added cesium fluoride (4.01 g, 25.82 mmol) at room temperature. The reaction vessel (Pressure tube) was sealed and heated at 145° C. for 18 h. The reaction mass was diluted with water and extracted with ethyl acetate. The organic layer was dried over anhydrous Na$_2$SO$_4$ and evaporated under reduced pressure to get crude compound. The crude compound was purified by silica gel chromatography to get desired compound (700 mg, 62%) as a white solid. $^1$H NMR (400 MHz, CD$_3$OD): δ ppm 8.10 (m, 1H), 8.08 (m, 1H), 7.78-7.75 (m, 1H), 7.69-7.65 (m, 1H), 7.49 (m, 1H), 4.04 (s, 3H); $^{19}$F NMR: δ ppm −78.66 (1 F); MS: MS m/z 178.1 (M$^+$+1).

Preparation of 1-fluoro-6-methoxyisoquinoline

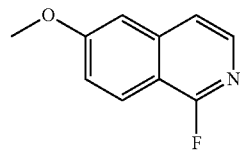

To a 2-5 mL microwave vial was added 1-chloro-6-methoxyisoquinoline (300 mg, 1.55 mmol) and cesium fluoride (941 mg, 6.20 mmol), then DMSO (4 mL) and a small stir bar. The vial was sealed, then irradiated at 200° C. for 40 minutes in a microwave reactor. The reaction mixture was transferred to a 125 mL separatory funnel and was diluted with EtOAc (50 mL). The solution was washed with water:brine (25 mL:25 mL); dried over MgSO$_4$; filtered; then concentrated in vacuo. The residue was transferred subjected to silica gel chromatography (hexanes:EtOAc, 100:0 to 80:20) to afford 1-fluoro-6-methoxyisoquinoline as a white solid (21 mg, 8%). $^1$H-NMR (400 MHz, CDCl$_3$) δ 8.07 (d, J=9.0 Hz, 1H), 7.99 (dd, J=5.8, 1.0 Hz, 1H), 7.42 (dd, J=5.8, 1.5 Hz, 1H), 7.27 (dd, J=9.0, 2.5 Hz, 1H), 7.13 (t, J=2.0 Hz, 1H), 3.97 (s, 3H).

Preparation of 1-fluoro-3,6-dimethoxyisoquinoline

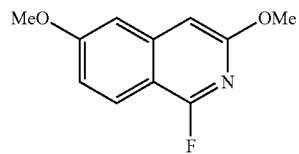 [SMILES: COc1ccc2c(F)nc(OC)cc2c1]

Scheme:

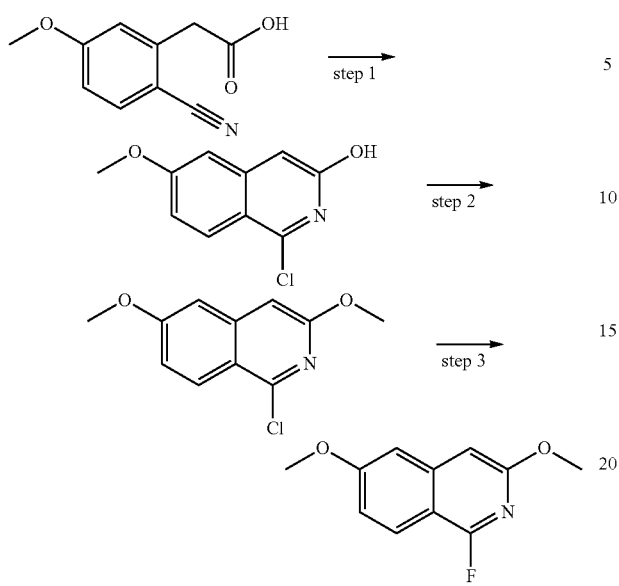

Step 1

2-(2-cyano-5-methoxyphenyl)acetic acid (3.8 g, 19.88 mmol), and SOCl$_2$ (20 mL, 274 mmol) were stirred in dichloromethane (25 mL) at RT. The suspension became a solution over 8 h. The reaction was stirred overnight. The volitile organics were removed under vacuum and the residue was taken up in DCM and filtered. The filtrate was concentrated and then dissolved in 4 N HCl dioxane (30 mL) and transferred to a sealed vessel and heated to 60° C. for 3 h. The reaction was cooled and the solid was collected, washed with dioxane, and dried under vacuum to give the product 1-chloro-6-methoxyisoquinolin-3-ol (3.3 g, 70% yield). $^1$H NMR (400 MHz, CDCl$_3$) δ 8.10 (d, J=9.6 Hz, 1H), 7.12 (dd, J=9.3, 2.5 Hz, 1H), 6.95 (s, 2H), 3.98 (s, 3H).

Step 2

To a mixture of 1-chloro-6-methoxyisoquinolin-3-ol (3.3 g, 15.74 mmol) in DMF (30 mL) was added potassium carbonate (2.61 g, 18.89 mmol) and iodomethane (1.969 mL, 31.5 mmol). It was then stirred at rt overnight. LC/MS showed 2 peaks with the desired mass and also starting material. An additional 1 equ. of MeI, and 1 equ of K$_2$CO$_3$ was added and the reaction warmed to 40° C. for 2 h. LC/MS showed all starting material had been consumed. The reaction was diluted with EtOAc and water. The organic layer was washed with water, brine, dried over sodium sulfate, and concentrated under vacuum. The crude material was purified by silica gel column using 20% EtOAc/Hexanes. The product fractions were collected and the solvent removed under vacuum to give the desired product 1-chloro-3,6-dimethoxyisoquinoline (2.47 g, 70% yield) as a white solid. MS: MS m/z 223.93 (M$^+$+1). $^1$H NMR (400 MHz, CDCl$_3$) δ 8.10 (d, J=9.3 Hz, 1H), 7.08 (dd, J=9.3, 2.5 Hz, 1H), 6.93 (d, J=2.5 Hz, 1H), 6.85 (s, 1H), 4.07-3.99 (m, 3H), 3.95 (s, 3H).

Step 3

To a solution of 1-chloro-3,6-dimethoxyisoquinoline (300 mg, 1.341 mmol) in DMSO (5 mL) was added CsF (408 mg, 2.68 mmol) and heated to 140° C. for 2 hrs. LC/MS showed the desired product. The reaction was diluted with Ethylacteate and washed with water, and brine. The organic phase was collected, dried over MgSO$_4$, and concentrated under vacuum to give the crude product 1-fluoro-3,6-dimethoxy-isoquinoline (250 mg, 90% yield) as a reddish brown solid. $^1$H NMR (400 MHz, CDCl$_3$) δ 7.93 (d, J=9.0 Hz, 1H), 7.03 (dd, J=9.3, 2.3 Hz, 1H), 6.95 (t, J=1.9 Hz, 1H), 6.75 (s, 1H), 4.01-3.96 (m, 3H), 3.96-3.90 (m, 3H). MS: MS m/z 208.07 (M$^+$+1).

Preparation of 1,7-difluoro-6-methoxyisoquinoline

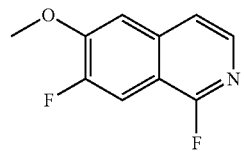

Scheme:

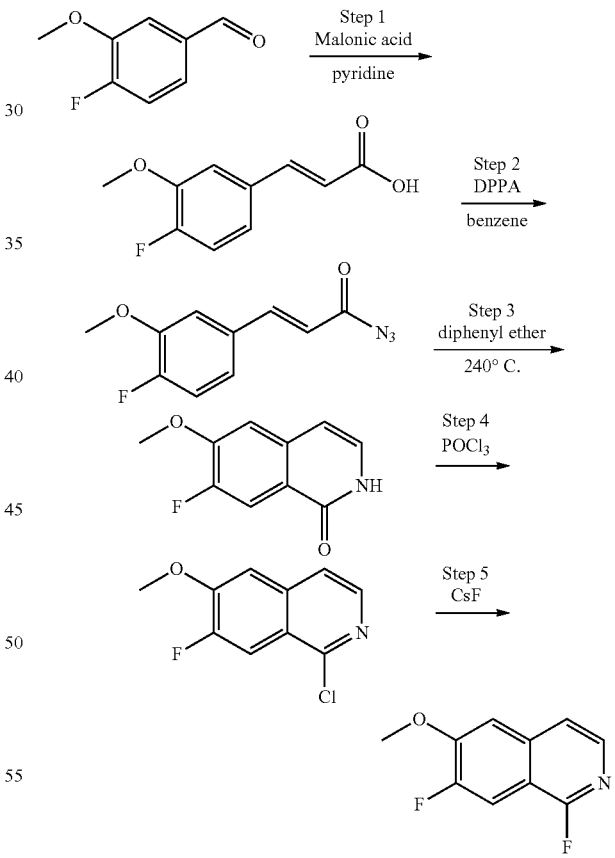

Step 1: Preparation of (E)-3-(4-fluoro-3-methoxyphenyl) acrylic acid

To a solution of 4-fluoro-3-methoxybenzaldehyde (30 g, 195 mmol) in pyridine (134 ml) and Piperidine (4.12 ml) was added malonic acid (30.4 g, 292 mmol) at room temperature. The reaction mass was refluxed for 18 h. The solvent was evaporated under reduced pressure and the residue was acidified with 1.5N HCl solution. The precipitated solid was filtered washed with pet ether to get crude compound (37 g, 97%) as white solid. The crude compound was taken to the next step without further purification. $^1$H NMR (400 MHz, CDCl$_3$): δ ppm 12.37 (s, 1H), 7.59-7.55 (d, J=16 Hz, 1H), 7.53 (s, 1H), 7.26-7.22 (m, 2H), 6.59-6.55 (d, J=16 Hz, 1H), 3.89 (s, 3H); MS: MS m/z 195.0 (M$^+$−1).

Step 2: Preparation of (E)-3-(4-fluoro-3-methoxyphenyl) acryloyl azide

To a solution of (E)-3-(4-fluoro-3-methoxyphenyl) acrylic acid (5 g, 25.5 mmol) in benzene (30 ml) was added triethylamine (5.16 g, 51 mmol) followed by DPPA (7.01 g, 25.5 mmol) at room temperature. The reaction mass was stirred at the same temperature for 18 h. The solvent was evaporated under reduced pressure and the residue was diluted with water and extracted with dichloromethane. The organic layer was dried over anhydrous sodium sulfate, filtered and evaporated to get crude compound. The crude compound was purified by conventional column chromatography (Silica gel, 60-120 mesh) using 10% ethyl acetate in pet ether as mobile phase to get the desire compound as white solid (4 g, 71%). $^1$H NMR (400 MHz, CDCl$_3$): δ ppm 7.70-7.66 (d, J=16 Hz, 1H), 7.12-7.07 (m, 3H), 6.35-6.31 (d, J=16 Hz, 1H), 3.92 (s, 3H).

Step 3: Preparation of 7-fluoro-6-methoxyisoquinolin-1(2H)-one

To a hot (125° C.) diphenyl ether (20 ml) was added (E)-3-(4-fluoro-3-methoxyphenyl) acryloyl azide (4 g, 18.08 mmol) portion wise. The reaction was heated at 250° C. for 4 h. The reaction mass was cooled to room temperature and diluted with pet ether. The precipitated solid was filtered washed with pet ether to get crude compound (3.1 g, 89%). The crude compound was taken to the next step without further purification. MS: MS m/z 194.1 (M$^+$+1).

Step 4: Preparation of 1-chloro-7-fluoro-6-methoxyisoquinoline

A solution of 7-fluoro-6-methoxyisoquinolin-1(2H)-one (3.1 g, 16.05 mmol) in POCl$_3$ (25 ml) was refluxed for 18 h. The solvent was evaporated under reduced pressure and the residue was diluted with cold water. The aqueous solution was basified by solid sodium carbonate and extracted with ethyl acetate. The organic layer was dried over anhydrous sodium sulfate, filtered and evaporated under reduced pressure to get crude compound. The crude compound was purified by silica gel chromatography (20% ethyl acetate in pet ether) to get desired compound (1.9 g, 55%) as off-white solid. $^1$H NMR (400 MHz, CDCl$_3$): δ ppm 8.22-8.20 (d, J=8 Hz, 1H), 7.97-7.94 (m, 1H), 7.49-7.48 (m, 1H), 7.18-7.16 (d, J=8 Hz, 1H), 4.04 (s, 3H); MS: MS m/z 211.7 (M$^+$+1).

Step 5: Preparation of 1,7-difluoro-6-methoxyisoquinoline

To a solution of 1-chloro-7-fluoro-6-methoxyisoquinoline (1.5 g, 7.09 mmol) in DMSO was added cesium fluoride (2.15 g, 14.18 mmol) at room temperature. The reaction vessel (Pressure tube) was sealed and heated at 145° C. for 18 h. The reaction mass was diluted with water and extracted with ethyl acetate. The combined organic layer was dried over anhydrous Na$_2$SO$_4$ and evaporated under reduced pressure to get crude compound. The crude compound was purified by silica gel chromatography to get desired compound (950 mg, 68%) as white solid. $^1$H NMR (400 MHz, CDCl$_3$): δ ppm 8.0-7.98 (m, 1H), 7.77-7.74 (d, J=12 Hz, 1H), 7.42-7.40 (m, 1H), 7.21-7.19 (m, 1H), 4.04 (s, 3H); $^{19}$F NMR: δ ppm −129.05 (1 F), −71.98 (1F); MS: MS m/z 196.1 (M$^+$+1).

Preparation of 1-chloro-7-fluoro-6-methoxyisoquinolin-3-ol

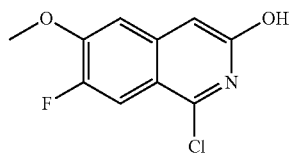

Scheme:

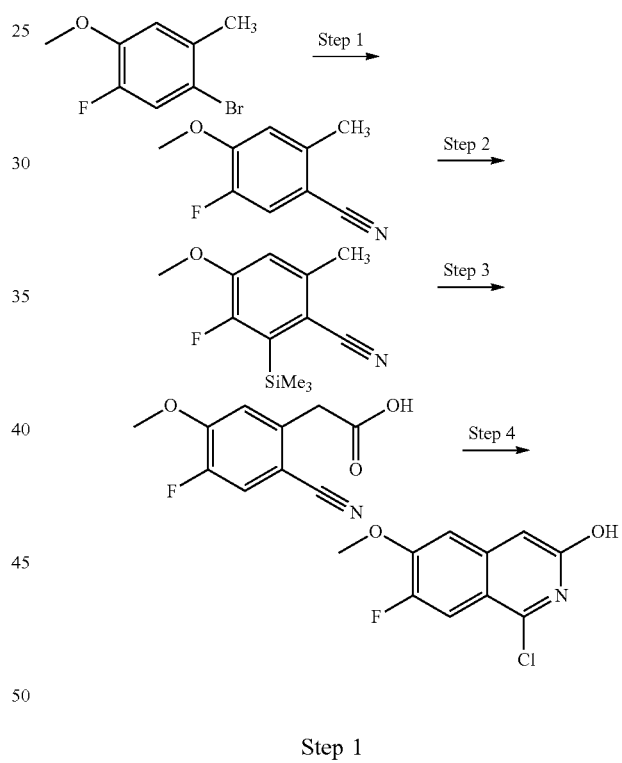

Step 1

To a Schlenk flask equipped with a stir bar was added Pd(OAc)$_2$ (0.307 g, 1.37 mmol) and 2-(dicyclohexylphosphino)-2',4',6'-triisopropylbiphenyl ("XPhos", 1.31 g, 2.74 mmol). The flask was sealed with a rubber septum and then the flask was thrice evacuated and placed under nitrogen atmosphere to establish a N$_2$ atmosphere. To the flask was added dry CH$_2$Cl$_2$ (1mp and Et$_3$N (0.1 mL). The stirred solution was warmed with a heat gun until the solvent condensed on the walls of the flask. The solvent was removed under vacuum with the exclusion of oxygen. To the flask, while under positive nitrogen pressure, was added 1-bromo-5-fluoro-4-methoxy-2-methylbenzene (6.00 g, 27.4 mmol), Na$_2$CO$_3$ (0.363 g, 3.42 mmol), and potassium hexacyanoferrate(II) trihydrate (5.78 g, 13.7 mmol). The flask was thrice evacuated and placed under nitrogen atmosphere. To the flask was added water (20 mL) and acetonitrile (20 mL). The flask was placed in a 70° C. oil bath with stirring for 18 h. The mixture was cooled to room temperature, transferred to a separatory funnel, and then diluted with EtOAc and water. The mixture was shaken; the phases were separated. The organic phase was washed with water; then brine; dried over $MgSO_4$; filtered; and then concentrated in vacuo. The resulting residue was subjected to silica gel chromatography (hexanes:EtOAc, 95:5 to 50:50) to afford 5-fluoro-4-methoxy-2-methylbenzonitrile as a white solid (3.43 g, 76%). $^1$H-NMR (500 MHz, DMSO-$d_6$) δ 7.73 (d, J=11.3 Hz, 1H), 7.28 (d, J=8.4 Hz, 1H), 3.91 (s, 3H), 2.45 (s, 3H).

Step 2

To a round-bottom flask equipped with a stir bar was added THF (50 mL) and N,N-diisopropylamine (2.98 mL, 20.9 mmol). The solution was cooled −78° C. and to the solution was added dropwise n-butyllithium in hexanes (8.36 mL, 20.9 mmol). The solution was stirred for 10 minutes. To the solution was added 5-fluoro-4-methoxy-2-methylbenzonitrile (3.45 g, 20.9 mmol) in THF (15 mL). The solution was stirred for 30 min. To the solution was added dropwise chlorotrimethylsilane (2.64 mL, 20.9 mmol). The solution was stirred for an 60 minutes at −78° C. and then was allowed to warm to room temperature with stirring for 30 minutes. To the solution was carefully added water (80 mL). The mixture was transferred to a separatory funnel and the phases were separated. The aqueous phase was extracted with EtOAc. The combined organics were washed with brine; dried over $Na_2SO_4$; filtered; then concentrated in vacuo to afford 3-fluoro-4-methoxy-6-methyl-2-(trimethylsilyl)benzonitrile as a yellow solid (4.01 g, 81%). $^1$H-NMR (400 MHz, CDCl$_3$) δ 6.84 (d, J=8.3 Hz, 1H), 3.91 (s, 3H), 2.52 (s, 3H), 0.50-0.45 (m, 9H).

Step 3

To a round-bottom flask equipped with a stir bar was added THF (85 mL) and N,N-diisopropylamine (2.65 mL, 18.6 mmol). The solution was cooled to −78° C., then to the solution was added dropwise n-butyllithium in hexanes (7.43 mL, 18.58 mmol). The solution was stirred for 10 min. To the solution was added 3-fluoro-4-methoxy-6-methyl-2-(trimethylsilyl)benzonitrile (4.01 g, 16.9 mmol) in THF (5 mL). The solution was stirred for 30 min. Carbon dioxide gas was then bubbled through the solution until the solution became clear. To the solution was carefully added water (80 mL) and the resulting mixture was allowed to warmed to room temperature. The mixture was transferred to a separatory funnel and was diluted with aq. NaOH (10 N, 40 mL). The mixture was twice washed with Et$_2$O. The aqueous phase was isolated, cooled in a 0° C. bath, and then acidified with concentrated aq. HCl. The resulting mixture was warmed to room temperature and then extracted with EtOAc. The organic phase was collected; dried over Na$_2$SO$_4$; filtered; then concentrated in vacuo to afford the 2-(2-cyano-4-fluoro-5-methoxyphenyl)acetic acid as a white solid (2.16 g, 61%). $^1$H-NMR (400 MHz, CDCl$_3$) δ 7.37 (d, J=10.3 Hz, 1H), 6.98 (d, J=7.8 Hz, 1H), 3.96 (s, 3H), 3.89 (s, 2H).

Step 4

To a round-bottom flask equipped with a stir bar was added 2-(2-cyano-4-fluoro-5-methoxyphenyl)acetic acid (3.34 g, 16.0 mmol) and CH$_2$Cl$_2$. To the mixture was added SOCl$_2$ (5.00 mL, 68.5 mmol). The mixture was stirred at room temperature for 16 h to afford a homogeneous solution. The volatile organics were removed under vacuum and the residue was taken up in CH$_2$Cl$_2$ and filtered. The filtrate was concentrated in vacuo. The residue was dissolved in a solution of HCl in dioxane (4.0N, 30 mL) and then transferred to a bomb flask. The flask was sealed and then heated at 60° C. with stirring for 3 h. The mixture was cooled to room temperature and the solids were collected via filtration. The solids were washed with dioxane and then dried under vacuum to afford 1-chloro-7-fluoro-6-methoxyisoquinolin-3-ol as a colorless solid (1.83 g, 50%). $^1$H-NMR (500 MHz, DMSO-d$_6$) δ 7.76 (d, J=12.0 Hz, 1H), 7.44 (d, J=8.4 Hz, 1H), 6.92 (s, 1H), 3.98 (s, 3H).

Preparation of
1,7-difluoro-3,6-dimethoxyisoquinoline

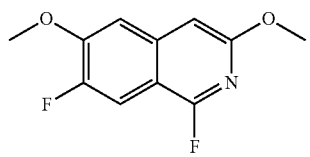

Scheme:

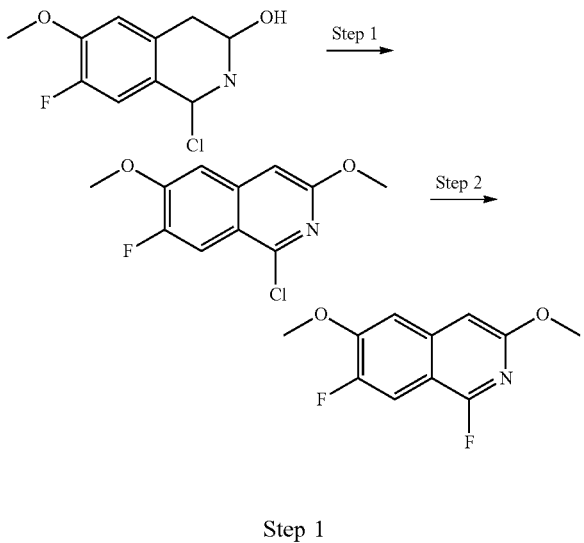

Step 1

To a round-bottom flask equipped with a stir bar and charged with 1-chloro-7-fluoro-6-methoxyisoquinolin-3-ol (138 mg, 0.606 mmol) in DMF (5 mL) was added K$_2$CO$_3$ (168 mg, 1.21 mmol) and iodomethane (0.760 mL, 1.20 mmol). The mixture was stirred at room temperature for 16 h. To the solution was added K$_2$CO$_3$ (84 mg, 0.6 mmol) and iodomethane (0.38 mL, 0.6 mmol). The mixture was stirred at 40° C. for 2 h. The mixture was transferred to a reparatory funnel and was diluted with water; then was extracted with EtOAc. The organic phase was washed with water; then brine; then dried over MgSO$_4$; filtered; then concentrated in vacuo. The resulting residue was subjected to silica gel chromatography (hexanes:EtOAc, 95:5 to 80:20) to afford 1-chloro-7-fluoro-3,6-dimethoxyisoquinoline as a white solid (100 mg, 68%). $^1$H-NMR (500 MHz, DMSO-$d_6$) δ 7.83 (dd, J=11.8, 0.5 Hz, 1H), 7.52 (d, J=8.4 Hz, 1H), 7.18 (s, 1H), 3.99 (s, 3H), 3.91 (s, 3H).

Step 2

To a vial equipped with a stir bar was added 1-chloro-7-fluoro-3,6-dimethoxyisoquinoline (100 mg, 0.414 mmol), CsF (94 mg, 0.62 mmol) and DMSO (2 mL). The mixture was heated at 140° C. with stirring for 2 h. The mixture was transferred to a separatory funnel and was diluted with EtOAc. The mixture was washed with water; then brine. The organic phase was collected; dried over MgSO; filtered; then concentrated under vacuum. The resulting residue was subjected to silica gel chromatography (hexanes:EtOAc, 100:0 to 60:40) to afford 1,7-difluoro-3,6-dimethoxyisoquinoline as a yellow solid (80 mg, 86%). $^1$H-NMR (500 MHz, CDCl$_3$) δ 7.64 (d, J=10.9 Hz, 1H), 7.04 (dd, J=7.8, 1.3 Hz, 1H), 6.79 (s, 1H), 4.04 (s, 3H), 4.00-3.98 (m, 3H).

Preparation of 6,8-difluoro-9-methoxy-2,3-dihydro-1H-pyrano[2,3-c]isoquinoline

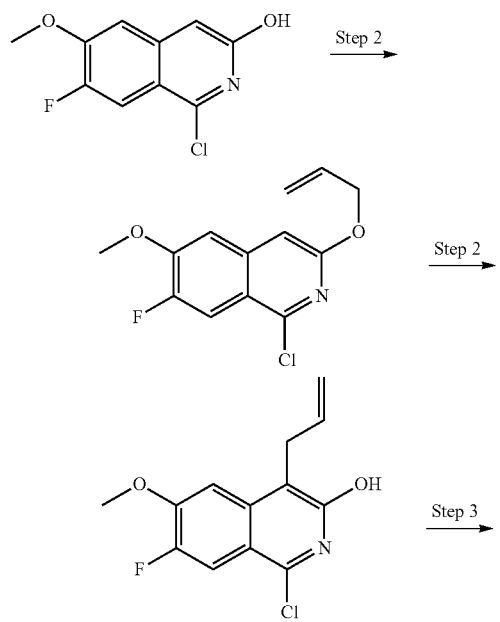

Scheme:

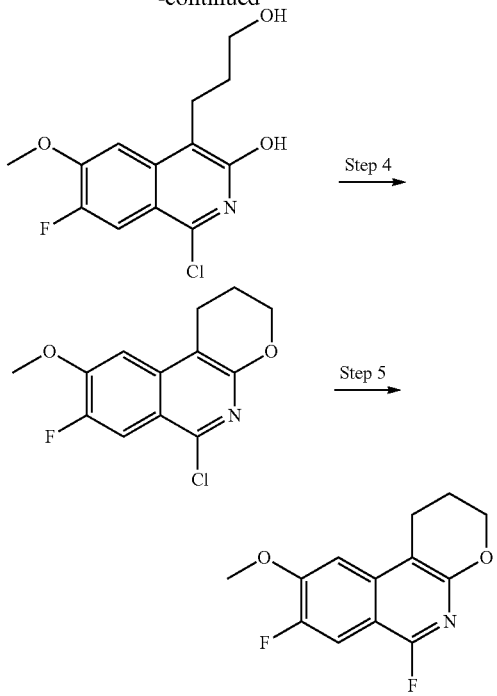

Step 1

To a round-bottom flask equipped with a stir bar and placed under nitrogen atmosphere was added DMF (10 mL) and NaH (60% dispersion in oil, 55.0 mg, 1.38 mmol). The solution was cooled to 0° C. To the solution was added 1-chloro-7-fluoro-6-methoxyisoquinolin-3-ol (285 mg, 1.25 mmol). The solution was stirred for 10 minutes. To the solution was added allylbromide (0.119 mL, 1.38 mmol). The solution was allowed to warm to room temperature with stirring for 1 h. The solution was transferred to a separatory funnel and was diluted with water; then extracted with EtOAc. The organic layer was washed with brine; dried over MgSO$_4$; filtered; and then concentrated in vacuo to afford 3-(allyloxy)-1-chloro-7-fluoro-6-methoxyisoquinoline as a solid (340 mg).

Step 2

To a 2 dram vial equipped with a stir bar was added 3-(allyloxy)-1-chloro-7-fluoro-6-methoxyisoquinoline (all material from step 1, 340 mg, 1.27 mmol) and diethylene glycol dimethyl ether (5 mL). The vial was sealed with a PTFE-lined cap and then placed in a 175° C. heating block with stirring for 16 h. The solution was cooled to room temperature and then was transferred to a separatory funnel and diluted with water. The mixture was thrice extracted and EtOAc. The combined organics were washed with brine; dried over MgSO$_4$; filtered; then concentrated in vacuo to afford 4-allyl-1-chloro-7-fluoro-6-methoxyisoquinolin-3-ol as an orange-brown solid (306 mg, 90% over two steps). $^1$H-NMR (500 MHz, DMSO-$d_6$) δ 11.23 (s, 1H), 7.80 (d, J=11.8 Hz, 1H), 7.30 (d, J=8.4 Hz, 1H), 5.97-5.85 (m, 1H), 5.08-4.98 (m, 2H), 4.00 (s, 3H), 3.66 (d, J=6.1 Hz, 2H).

Step 3

To a round-bottom flask equipped with a stir bar was added 4-allyl-1-chloro-7-fluoro-6-methoxyisoquinolin-3-ol (all material from step 2, 306 mg, 1.14 mmol) and THF (10 mL). To the solution was added 9-Borabicyclo[3.3.1]nonane ("9-BBN", 0.5M in THF, 6.86 mL, 3.43 mmol). The solution was stirred at room temperature until 1H-NMR analysis of a reaction aliquot indicated complete conversion of the alkene starting material. To the solution was added aq. NaOH (3.0 N, 3.43 mL, 10.3 mmol), then and aq. 30% $H_2O_2$ (1.17 mL, 11.4 mmol). The mixture was stirred for 16 h. To the mixture was acidified with via addition of aq. HCl (1.0 N). The mixture was transferred to a separatory funnel and was extracted with EtOAc. The organic phase was washed with brine; dried over $MgSO_4$; filtered; then concentrated in vacuo. The resulting residue was subjected to silica gel chromatography (hexanes:EtOAc, 80:20 to 50:50) to afford 1-chloro-7-fluoro-4-(3-hydroxypropyl)-6-methoxyisoquinolin-3-ol as a white solid (210 mg, 64%). $^1$H-NMR (500 MHz, acetone-$d_6$) δ 9.53 (br. s., 1H), 7.78 (d, J=12.0 Hz, 1H), 7.57 (d, J=8.2 Hz, 1H), 4.08 (s, 3H), 3.61 (br. s., 2H), 3.11-3.04 (m, 2H), 1.92-1.83 (m, 2H).

Step 4

To a round-bottom flask equipped with a stir bar was added $PPh_3$ (347 mg, 1.32 mmol), 1-chloro-7-fluoro-4-(3-hydroxypropyl)-6-methoxyisoquinolin-3-ol (210 mg, 0.735 mmol), and THF (20 mL). The solution was cooled to 0° C., then to the solution was added dropwise diisopropylazodicarboxylate ("DIAD", 0.286 mL, 1.47 mmol). The mixture was allowed to warm to room temperature with stirring for 4 h. The mixture was concentrated in vacuo and the resulting residue was subjected to silica gel purification to afford 6-chloro-8-fluoro-9-methoxy-2,3-dihydro-1H-pyrano[2,3-c]isoquinoline as a yellow solid (171 mg). $^1$H-NMR (500 MHz, $CDCl_3$) δ 7.86 (d, J=11.7 Hz, 1H), 7.01 (d, J=7.9 Hz, 1H), 4.43-4.34 (m, 2H), 4.04 (s, 3H), 2.97 (t, J=6.5 Hz, 2H), 2.22-2.13 (m, 2H).

Step 5

To a vial equipped with a stir bar was added 6-chloro-8-fluoro-9-methoxy-2,3-dihydro-1H-pyrano[2,3-c]isoquinoline (all material from step 4, 171 mg, 0.639 mmol), CsF (146 mg, 0.958 mmol), and DMSO (3 mL). The vial was placed in a 140° C. heating block with stirring for 2 h. The mixture was transferred to a separatory funnel and was diluted with water. The mixture was extracted with EtOAc. The organic phase was washed with water; then brine; then dried over $MgSO_4$; filtered; then concentrated in vacuo. The resulting residue was subjected to silica gel chromatography (hexanes:EtOAc, 100:0 to 60:40) to afford 6,8-difluoro-9-methoxy-2,3-dihydro-1H-pyrano[2,3-c]isoquinoline as a yellow solid (114 mg, 71% over two steps). MS: MS m/z 252.2 ($M^+$+1).

Preparation of 4,6-difluoro-2,7-dimethoxyquinoline

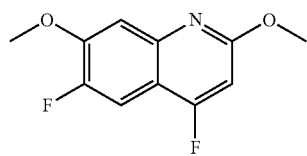

Scheme:

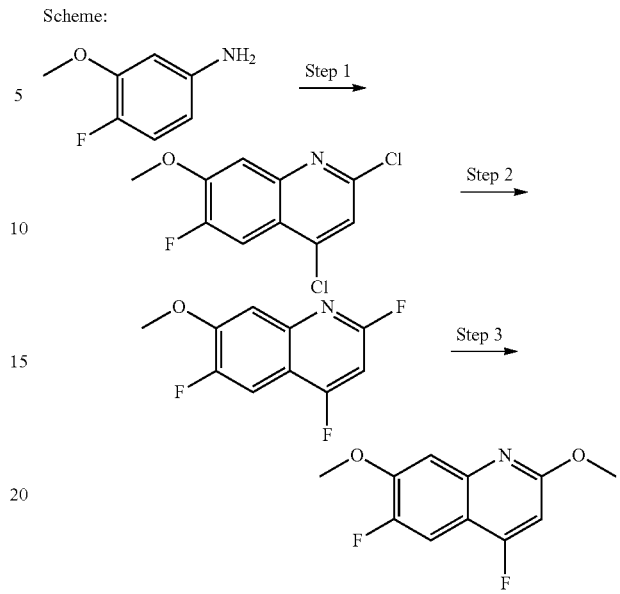

Step 1

To a large round-bottom flask equipped with a stir bar was added 4-fluoro-3-methoxyaniline (4.00 g, 28.3 mmol) and malonic acid (2.95 g, 28.3 mmol). To the flask was added $POCl_3$ (4.76 mL, 101 mmol). The flask was fitted with a bump-trap and then heated to 105° C. After 5 minutes vigorous effervescence and foaming was observed. When the foaming had subsided, to the flask was added $POCl_3$ (4.76 mL, 101 mmol) upon which the mixture slowly became a homogeneous solution. The solution was stirred at 105° C. for 16 h. The solution was cooled to room temperature and then concentrated in vacuo. The resulting oil residue was diluted with $CH_2Cl_2$ and to the mixture was added ice. Once the ice had melted, the flask was placed in a 0° C. bath and to the mixture was added aq. NaOH (10 N) to adjust the aq. phase to pH >8. The mixture was transferred to a separatory funnel and the phases were separated. The organic phase was washed with brine; dried over $MgSO_4$; filtered; then concentrated in vacuo. The resulting residue was subjected to silica gel chromagraphy (hexanes:EtOAc, 95:5 to 80:20) to afford 2,4-dichloro-6-fluoro-7-methoxyquinoline as a white solid (3.7 g, 53%). $^1$H-NMR (500 MHz, $CDCl_3$) δ 7.81 (d, J=11.3 Hz, 1H), 7.46 (d, J=7.9 Hz, 1H), 7.42 (s, 1H), 4.04 (s, 3H).

Step 2

To a round-bottom flask equipped with a stir bar was added 2,4-dichloro-6-fluoro-7-methoxyquinoline (2.00 g, 8.13 mmol), CsF (3.09 g, 20.3 mmol) and DMSO (20 mL). The mixture was stirred at 140° C. for 2 h. The mixture was cooled to room temperature and then transferred to a separatory funnel; then diluted with water. The mixture was extracted with EtOAc. The organic phase was washed with water; then brine; dried over $MgSO_4$; filtered; then concentrated in vacuo to afford as a light-orange solid (1.75 g, 100%). $^1$H-NMR (500 MHz, $CDCl_3$) δ 7.66 (d, J=10.7 Hz, 1H), 7.39 (dd, J=7.6, 1.5 Hz, 1H), 6.72 (dd, J=9.1, 1.5 Hz, 1H), 4.05-4.02 (m, 3H).

Step 3

To a round-bottom flask equipped with a stir bar was added 2,4,6-trifluoro-7-methoxyquinoline (500 mg, 2.35 mmol) and THF (15 mL). To the solution was added NaOMe (25% in MeOH, 2.35 mmol). The solution was stirred at room temperature for 16 h. The solution was transferred to a separatory funnel and was diluted with EtOAc; then washed with brine. The organic solution was dried over MgSO$_4$; filtered; then concentrated in vacuo. The resulting residue was subjected to silica gel chromatography (hexanes:EtOAc. 95:5 to 80:20) to afford 4,6-difluoro-2,7-dimethoxyquinoline as a white solid (268 mg, 51%). NMR Preparation of 4-fluoro-2,7-dimethoxyquinoline

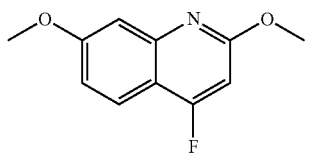

Scheme:

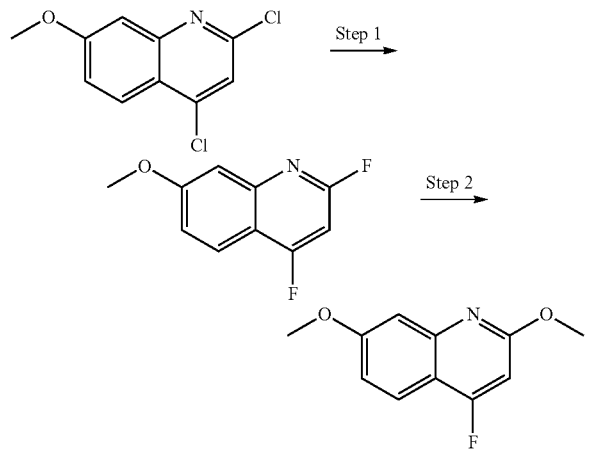

Step 1:

To a round-bottom flask equipped with a stir bar was added 2,4-dichloro-7-methoxyquinoline (905 mg, 3.97 mmol), CsF (1.51 g, 9.92 mmol) and DMSO (20 mL). The mixture was stirred at 140° C. for 2 h. The mixture was allowed to cool to room temperature; then was transferred to a separatory funnel and diluted with water. The mixture was extracted with EtOAc. The organic phase was dried over MgSO$_4$; filtered; then concentrated in vacuo to afford 2,4-difluoro-7-methoxyquinoline as a light-orange solid (706 mg, 91%). MS: MS m/z 196.2 (M$^+$+1).

Step 2

To a round-bottom flask equipped with a stir bar was added 2,4-difluoro-7-methoxyquinoline (all material from step 1, 706 mg, 3.62 mmol) and THF (15 mL). To the solution was added sodium methoxide (25% in methanol, 3.62 mmol). The solution was stirred at room temperature for 16 h. The solution was transferred to a separatory funnel and was diluted with EtOAc; then washed with brine. The organic phase was dried over MgSO$_4$; filtered; then concentrated in vacuo. The resulting residue was subjected to silica gel chromatography (hexanes:EtOAc, 95:5 to 80:20) to afford 4-fluoro-2,7-dimethoxyquinoline as a white solid (381 mg, 1.84 mmol, 51%). $^1$H-NMR (500 MHz, CDCl$_3$) δ 7.83 (d, J=9.0 Hz, 1H), 7.22 (t, J=2.1 Hz, 1H), 7.05 (dd, J=9.0, 2.5 Hz, 1H), 6.45 (d, J=10.7 Hz, 1H), 4.06 (s, 3H), 3.96-3.92 (m, 3H); $^{13}$C-NMR (101 MHz, CDCl$_3$) δ 167.8, 165.2, 164.0 (d, J=14.6 Hz), 161.9, 149.8 (d, J=6.9 Hz), 121.7 (d, J=4.6 Hz), 116.4, 106.5, 106.4, 94.4 (d, J=19.3 Hz), 55.5, 53.7.

After the desired product was eluted from silica gel a second major product was isolated: 2-fluoro-4,7-dimethoxyquinoline as a white solid (222 mg, 30%). $^1$H-NMR (400 MHz, CDCl$_3$) δ 8.00 (d, J=9.0 Hz, 1H), 7.20 (d, J=2.5 Hz, 1H), 7.09 (dd, J=9.0, 2.5 Hz, 1H), 6.26 (s, 1H), 4.06-4.02 (m, 3H), 3.92 (s, 3H); $^{13}$C-NMR (101 MHz, CDCl$_3$) 166.2 (d, J=13.1), 164.4, 162.0, 161.9, 147.9 (d, J=21.6 Hz), 123.2, 117.2 (d, J=2.3 Hz), 114.6, 106.8, 86.5 (d, J=47.0 Hz), 56.1, 55.5.

Preparation of 3-chloro-6-methoxy-2-(trifluoromethyl)quinoxaline

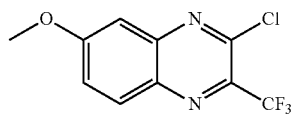 [SMILES: COc1ccc2nc(C(F)(F)F)c(Cl)nc2c1]

Scheme:

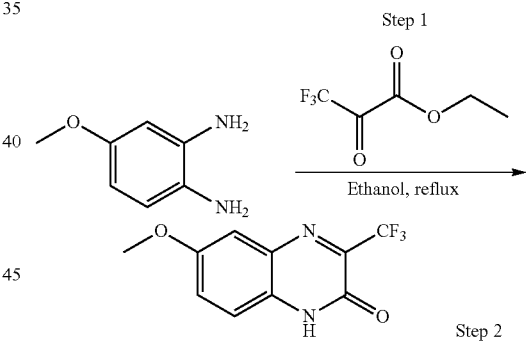

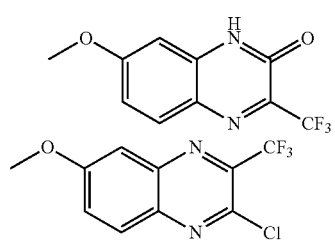

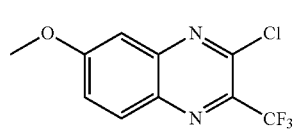

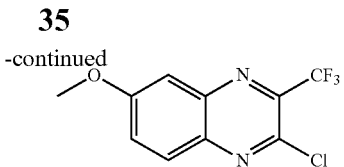

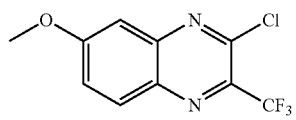

Step 1: Preparation of 6-methoxy-3-(trifluoromethyl)quinoxalin-2(1H)-one and 7-methoxy-3-(trifluoromethyl)quinoxalin-2(1H)-one To a solution of 4-methoxybenzene-1,2-diamine (1 g, 7.24 mmol) in ethanol (10 ml) was added ethyl 3,3,3-trifluoro-2-oxopropanoate (1.23 g, 7.24 mmol)). The reaction mass was heated at reflux for overnight. The solvent was evaporated under reduced pressure and the residue was diluted with ethyl acetate and then evaporated to dryness to get the crude compound. The crude compound was washed with pet ether to get the product (1.55 g, 88% yield) as a mixture of regioisomers (black solid). This crude compound was taken to the next step without separation of isomers. $^1$H NMR (400 MHz, DMSO-$d_6$): δ ppm 12.92 (br, s, 2H), 7.84-7.81 (d, J=12 Hz, 1H), 7.44-7.33 (m, 4H), 7.82 (s, 1H), 3.87 (s, 6H), MS: MS m/z 245.15 (M$^+$+1).

Step 2: Preparation of 2-chloro-6-methoxy-3-(trifluoromethyl)quinoxaline and 3-chloro-6-methoxy-2-(trifluoromethyl)quinoxaline A solution of 6-methoxy-3-(trifluoromethyl)quinoxalin-2(1H)-one & 7-methoxy-3-(trifluoromethyl)quinoxalin-2(1H)-one (0.90 g, 3.69 mmol) in POCl$_3$ (10 ml) was refluxed for 3 h. The solvent was evaporated under reduced pressure and the residue was diluted with cold water. The aqueous solution was basified by solid sodium carbonate and extracted with ethyl acetate. The combine organic layer was dried over anhydrous sodium sulfate, filtered and evaporated under reduced pressure to get crude compound. The crude compound was purified by silica gel chromatography (20% ethyl acetate in pet ether) to get regioisomers as mixture.

Step 3

The mixture of regioisomers were separated by SFC purification to afford 2-chloro-6-methoxy-3-methylquinoxaline (0.51 g, 38.7%) and 3-chloro-6-methoxy-2-methylquinoxaline (required isomer) (0.48 g, 36.5%) as off white solids. 2-chloro-6-methoxy-3-(trifluoromethyl)quinoxaline: $^1$H NMR (400 MHz, DMSO-$d_6$): δ 8.10-8.07 (d, J=12 Hz, 1H), 7.75-7.44 (m, 2H), 3.95 (s, 3H); $^{19}$F-NMR: δ ppm −65.36 (1F) MS: MS m/z 263.10 (M$^+$+1). 3-chloro-6-methoxy-2-(trifluoromethyl)quinoxaline: $^1$H NMR (400 MHz, DMSO-$d_6$): δ 8.11-8.08 (d, J=12 Hz, 1H), 7.78-7.75 (d, J=12 Hz, 1H), 7.68 (s, 1H), 4.00 (s, 3H); $^{19}$F-NMR: δ ppm −65.36 (1F) MS: MS m/z 263.09 (M$^+$+1).

Preparation of (2S,3R)-1-tert-butyl 2-methyl 3-ethylaziridine-1,2-dicarboxylate

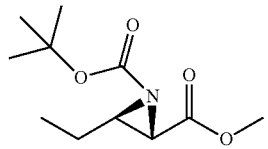 [SMILES: CC[C@@H]1[C@@H](C(=O)OC)N1C(=O)OC(C)(C)C]

Scheme:

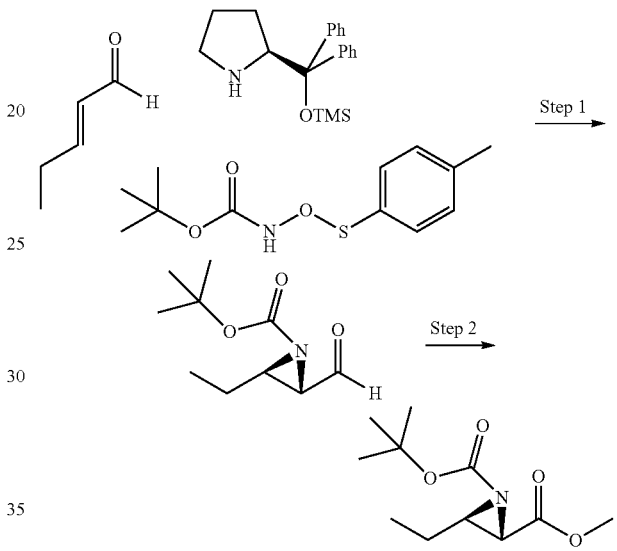

Step 1

To a 500 mL round-bottom flask equipped with a stir bar was added (S)-2-(diphenyl((trimethylsilyl)oxy)methyl)pyrrolidine (2.60 g, 8.00 mmol) and CHCl$_3$ (200 mL). To the solution was added tert-butyl tosylcarbamate (10.9 g, 40.0 mmol). The flask was placed in a room temperature-water bath. To the stirred solution was added sodium acetate (9.84 g, 120 mmol), then (E)-pent-2-enal (4.04 g, 48.0 mmol). The mixture was stirred at room temperature for 40 minutes. The mixture was filtered, washing the filter cake with a small amount of CHCl$_3$. The filtrate was concentrated in vacuo at 30° C. The resulting orange liquid was dissolved in Et$_2$O (400 mL) and transferred to a 1 L separatory funnel. The solution was washed with water:aq. sat. NaHCO$_3$ (200 mL:200 mL). The aqueous phase was extracted with Et$_2$O (100 mL). The combined organics were washed with brine (200 mL); dried over MgSO$_4$; filtered; then concentrated in vacuo to afford (2R,3S)-tert-butyl 2-ethyl-3-formylaziridine-1-carboxylate as a pale orange liquid.

Step 2

The following step was run duplicate. To a 250 mL round-bottom flask equipped with a stir bar was added (2R,3S)-tert-butyl 2-ethyl-3-formylaziridine-1-carboxylate (one-half of the material isolated in step 1, assumed 20 mmol) as a solution in MeOH (100 ml). The solution was cooled to 0° C. To the solution was added sodium cyanide (1.96 g, 40.0 mmol). The solution was stirred for 10 minutes. To the solution was added oxidation-grade MnO₂ (34.8 g, 400 mmol). The mixture was stirred for 10 minutes, then the ice bath was removed and the solution was allowed to warm to room temperature with stirring for 18 hours. The reaction mixture was filtered through a pad of diatomaceous earth (Celite™) and the filter cake was extracted with EtOAc (100 mL). The filtrate was concentrated in vacuo and the resulting orange solid residue was dissolved in water (100 mL) and EtOAc (100 mL) and transferred to a 1 L separatory funnel where the mixture was further diluted with saturated aq. NaCl ("brine", 100 mL) and EtOAc (100 mL). The mixture was shaken and the phases were separated. The aq. phase was extracted with EtOAc (100 mL). The combined organics were washed with brine (100 mL); dried over MgSO₄; filtered; then concentrated in vacuo. The resulting residue was combined with the duplicate run and the combined material was subjected to silica gel chromatography (hexanes:EtOAc, 50:50 to 0:100) to afford (2S,3R)-1-tert-butyl 2-methyl 3-ethylaziridine-1,2-dicarboxylate as a yellow liquid (3.055 g, 33% over two steps). ¹H-NMR (500 MHz, CDCl₃) δ 3.77 (s, 3H), 2.84 (d, J=2.7 Hz, 1H), 2.77 (td, J=6.0, 2.7 Hz, 1H), 1.63-1.52 (m, 2H), 1.47-1.45 (m, 9H), 1.05 (t, J=7.5 Hz, 3H).

Preparation of (2S,3S)-methyl 2-((tert-butoxycarbonyl)amino)-3-((R)-hex-5-en-2-yloxy)pentanoate

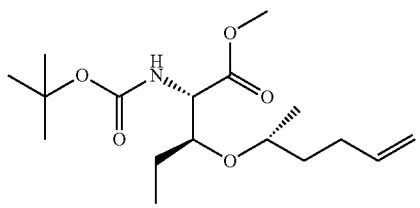 [SMILES: C=CCC[C@@H](C)O[C@@H](CC)[C@H](NC(=O)OC(C)(C)C)C(=O)OC]

To a round-bottom flask equipped with a stir bar was added (2S,3R)-1-tert-butyl 2-methyl 3-ethylaziridine-1,2-dicarboxylate (691, 3.02 mmol) and CH₂Cl₂ (12 mL). To the solution was added (R)-hex-5-en-2-ol (363 mg, 3.62 mmol), then BF₃—OEt₂ (1.0M in CH₂Cl₂, 0.30 mL). The solution was stirred at room temperature for 16 h. The solution was transferred to a separatory funnel and was diluted with CH₂Cl₂, then the solution was washed with aq. saturated NaHCO₃; then brine. The organic phase was dried over Na2SO4; filtered; then concentrated in vacuo. The resulting residue was subjected to silica gel chromatography (hexanes:EtOAc 90:10 to 70:30) to afford (2S,3S)-methyl 2-((tert-butoxycarbonyl)amino)-3-((R)-hex-5-en-2-yloxy)pentanoate as a colorless oil (426 mg, 43%). ¹H-NMR (500 MHz, CDCl₃) δ 5.81 (ddt, J=17.0, 10.4, 6.5 Hz, 1H), 5.19 (d, J=7.7 Hz, 1H), 5.08-5.00 (m, 1H), 4.96 (dd, J=10.2, 1.7 Hz, 1H), 4.50 (dd, J=8.3, 3.5 Hz, 1H), 3.75 (s, 3H), 3.65-3.58 (m, 1H), 3.57-3.50 (m, 1H), 2.19-2.06 (m, 2H), 1.66-1.56 (m, 2H), 1.55-1.38 (m, 11H), 1.13 (d, J=6.1 Hz, 3H), 0.97 (t, J=7.3 Hz, 3H).

Preparation of (2S,4R)-methyl 1-((2S,3S)-2-((tert-butoxycarbonyl)amino)-3-(pent-4-en-1-yloxy)pentanoyl)-4-hydroxypyrrolidine-2-carboxylate

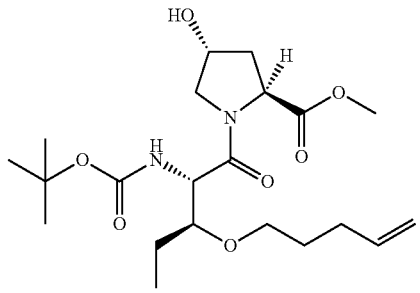 [SMILES: C=CCCCO[C@@H](CC)[C@H](NC(=O)OC(C)(C)C)C(=O)N1C[C@H](O)C[C@H]1C(=O)OC]

To a round-bottom flask equipped with a stir bar was added (2S,3R)-1-tert-butyl 2-methyl 3-ethylaziridine-1,2-dicarboxylate (1.50 g, 6.54 mmol) and CH₂Cl₂ (30 mL). To the solution was added pent-4-en-1-ol (0.676 g, 7.85 mmol), then BF₃—OEt₂ (93 mg, 0.083 mL, 0.65 mmol). The solution was stirred at room temperature for 16 h. The solution was transferred to a separatory funnel and was diluted with CH₂Cl₂. The solution was washed with aq. saturated NaHCO₃; then brine. The organic phase was dried over Na₂SO₄; filtered; then concentrated in vacuo. The resulting residue was subjected to silica gel chromatography (hexane:EtOAc 90:10 to 70:30) to afford (2S,4R)-methyl 1-((2S,3S)-2-((tert-butoxycarbonyl)amino)-3-(pent-4-en-1-yloxy)pentanoyl)-4-hydroxypyrrolidine-2-carboxylate as as an oil (1.06 g, 51%). ¹H-NMR (500 MHz, CDCl₃) δ 5.87-5.76 (m, 1H), 5.20 (d, J=7.9 Hz, 1H), 5.07-5.01 (m, 1H), 4.99-4.95 (m, 1H), 4.54 (dd, J=8.6, 3.9 Hz, 1H), 3.75 (s, 3H), 3.58-3.51 (m, 1H), 3.50-3.44 (m, 2H), 2.17-2.08 (m, 2H), 1.69-1.61 (m, 2H), 1.61-1.54 (m, 2H), 1.46-1.43 (m, 9H), 0.99 (t, J=7.4 Hz, 3H).

Preparation of tert-butyl ((2R,6S,7S,9R,13aS,14aR,16aS,Z)-7-ethyl-2-hydroxy-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate

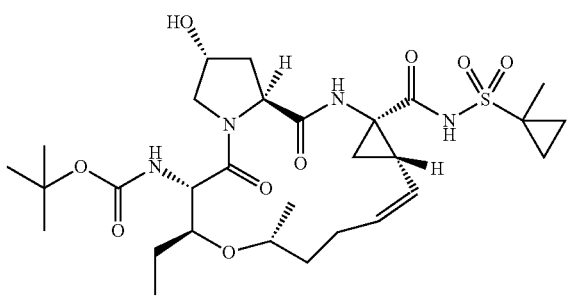 [SMILES: CC[C@@H]1O[C@H](C)CC/C=C\[C@@H]2C[C@@]2(C(=O)NS(=O)(=O)C2(C)CC2)NC(=O)[C@@H]2C[C@@H](O)CN2C(=O)[C@H]1NC(=O)OC(C)(C)C]

Scheme:

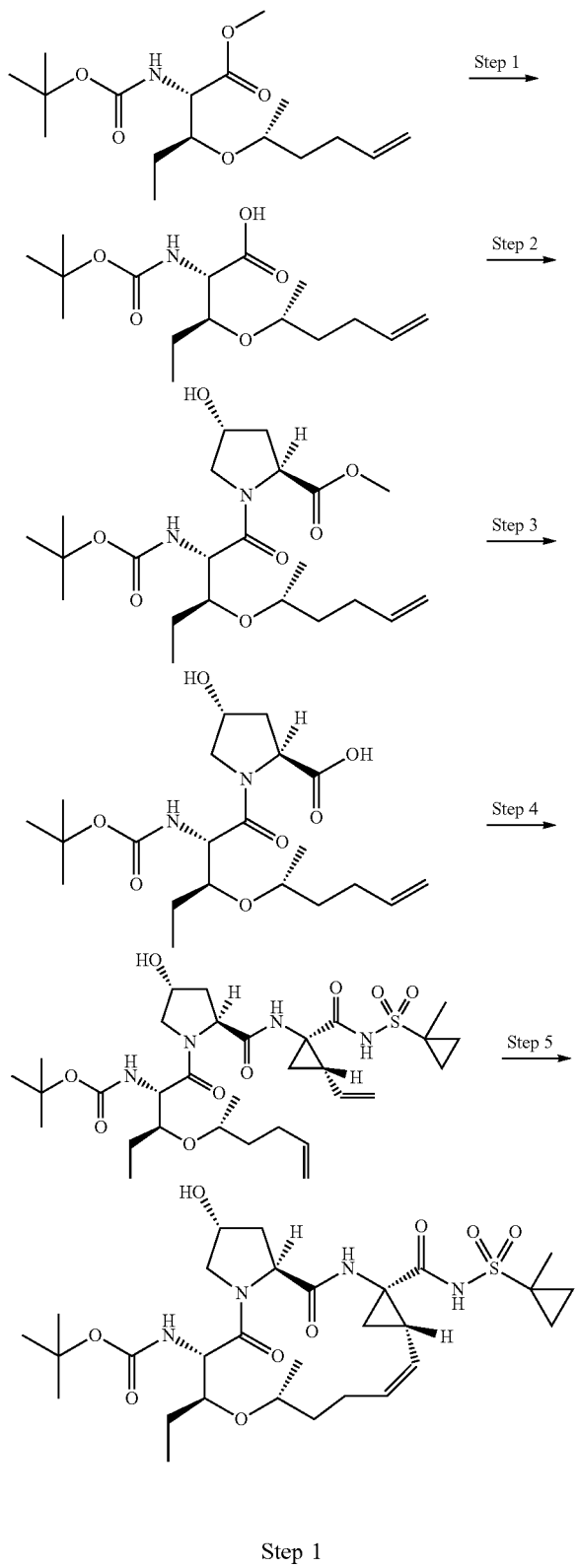

Step 1

To a round-bottom flask equipped with a stir bar was added (2S,3S)-methyl 2-((tert-butoxycarbonyl)amino)-3-((R)-hex-5-en-2-yloxy)pentanoate (458 mg, 1.39 mmol), THF (5 mL) and MeOH (5 mL). To the stirred solution was added aq. LiOH (2.0 M, 2 mL). The mixture was stirred for 16 h, then was concentrated in vacuo to afford an aqueous solution. The solution was acidified with aq. HCl (1 M) and then transferred to a separatory funnel. The mixture was twice extracted with EtOAc. The combined organics were washed with brine; dried over MgSO$_4$; filtered; then concentrated in vacuo to afford (2S,3S)-2-((tert-butoxycarbonyl)amino)-3-((R)-hex-5-en-2-yloxy)pentanoic acid as a white foam (438 mg, 100%).

Step 2

To a round-bottom flask equipped with a stir bar was added (2S,3S)-2-((tert-butoxycarbonyl)amino)-3-(pent-4-en-1-yloxy)pentanoic acid (all material from step 1, 438 mg, 1.39 mmol), (2S,4R)-methyl 4-hydroxypyrrolidine-2-carboxylate-HCl salt (277 mg, 1.53 mmol), 1-[Bis(dimethylamino)methylene]-1H-1,2,3-triazolo[4,5-b]pyridinium 3-oxid hexafluorophosphate ("HATU", 528 mg, 1.39 mmol), and CH$_2$Cl$_2$ (10 mL). To the mixture was added N,N-diisopropylethylamine (0.728 mL, 4.17 mmol). The mixture was stirred at room temperature for 16 h. The reaction mixture was transferred to a separatory funnel and was thrice washed with aq. 1N HCl; then brine. The organic phase was dried over MgSO$_4$; filtered; then concentrated in vacuo to afford (2S,4R)-methyl 1-(2S,3S)-2-((tert-butoxycarbonyl)amino)-3-((R)-hex-5-en-2-yloxy)pentanoyl)-4-hydroxypyrrolidine-2-carboxylate as a yellow oil.

Step 3

To a round-bottom flask equipped with a stir bar was added (2S,4R)-methyl 1-((2S,3S)-2-((tert-butoxycarbonyl)amino)-3-((R)-hex-5-en-2-yloxy)pentanoyl)-4-hydroxypyrrolidine-2-carboxylate (all material from step 2, 1.39 mmol), THF (5 mL) and MeOH (5 mL). To the solution was added aq. lithium hydroxide (2.0 M, 4.51 mmol). The mixture was stirred at room temperature for 16 h; then was concentrated to afford an aqueous solution. This solution was acidified and then transferred to a separatory funnel. The solution was twice extracted with EtOAc. The combined organics were washed with brine; dried over MgSO$_4$; filtered; then concentrated in vacuo to afford (2S,4R)-1-((2S,3S)-2-((tert-butoxycarbonyl)amino)-3-((R)-hex-5-en-2-yloxy)pentanoyl)-4-hydroxypyrrolidine-2-carboxylic acid as a white solid (489 mg).

Step 4

To a round-bottom flask equipped with a stir bar was added (2S,4R)-1-((2S,3S)-2-((tert-butoxycarbonyl)amino)-3-((R)-hex-5-en-2-yloxy)pentanoyl)-4-hydroxypyrrolidine-2-carboxylic acid (all material from step 3, 489 mg, 1.14 mmol), (1R,2S)-1-amino-N-((1-methylcyclopropyl)sulfonyl)-2-vinylcyclopropanecarboxamide-trifluoroacetic acid salt (450 mg, 1.26 mmol), HATU (456 mg, 1.20 mmol) and DCM (10 mL). To the stirred solution was added N,N-diisopropylethylamine (0.80 mL, 4.56 mmol). The mixture was stirred for 16 h and then was transferred to a separatory funnel. The mixture was thrice washed with aq. 1N HCl; then brine. The solution was dried over MgSO$_4$; filtered; then concentrated in vacuo to afford tert-butyl ((2S,3S)-3-((R)-hex-5-en-2-yloxy)-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-1-oxopentan-2-yl)carbamate as a light-orange solid foam (569 mg).

Step 5

To a round-bottom flask equipped with a stir bar was added tert-butyl ((2S,3S)-3-((R)-hex-5-en-2-yloxy)-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-1-oxopentan-2-yl)carbamate (all material from step 4, 569 mg, 0.869 mmol) and DCE (100 mL). The solution was sparged with nitrogen for 30 min. and then to the solution was added (1,3-Bis-(2,4,6-trimethylphenyl)-2-imidazolidinylidene)dichloro(o-isopropoxyphenylmethylene)ruthenium ("Hoveyda-Grubbs Catalyst 2nd Generation", 27 mg, 0.043 mmol). The solution was stirred at 80° C. for 2 h and then cooled to 45° C. and stirred for 3 days. The solution was concentrated in vacuo and the resulting residue was subjected to silica gel purification (hexanes:acetone 80:20 to 40:60). The product containing fractions were pooled; concentrated; and re-subjected to silica gel chromatography (hexanes:acetone 80:20 to 40:60) to afford tert-butyl ((2R,6S,7S,9R,13aS,14aR,16aS,Z)-7-ethyl-2-hydroxy-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate as a light-brown solid foam (90 mg, 10% over 5 steps). $^1$H-NMR (500 MHz, CD$_3$OD) δ 8.93 (s, 1H), 5.61 (td, J=10.1, 6.2 Hz, 1H), 5.03 (t, J=10.3 Hz, 1H), 4.58 (br. s., 1H), 4.47-4.37 (m, 2H), 3.92 (br. s., 2H), 3.86-3.79 (m, 1H), 3.58-3.49 (m, 1H), 2.75 (q, J=9.5 Hz, 1H), 2.64-2.52 (m, 1H), 2.23-2.11 (m, 2H), 1.92-1.80 (m, 2H), 1.75 (dd, J=8.5, 5.5 Hz, 1H), 1.66-1.60 (m, 1H), 1.59-1.52 (m, 2H), 1.49 (s, 4H), 1.43 (s, 9H), 1.41-1.32 (m, 2H), 1.15 (d, J=6.3 Hz, 3H), 0.95 (t, J=7.4 Hz, 3H), 0.88-0.84 (m, 2H).

Preparation of tert-butyl ((2R,6S,7S,9R,13aS,14aR,16aS,Z)-14a-((cyclopropylsulfonyl)carbamoyl)-7-ethyl-2-hydroxy-9-methyl-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate

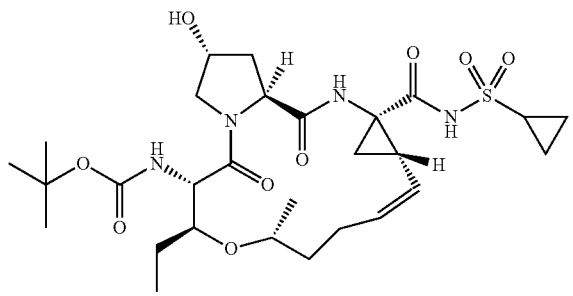 [SMILES: CC[C@@H]1O[C@H](C)CC/C=C\[C@@H]2C[C@@]2(C(=O)NS(=O)(=O)C2CC2)NC(=O)[C@@H]2C[C@@H](O)CN2C(=O)[C@H]1NC(=O)OC(C)(C)C]

Scheme:

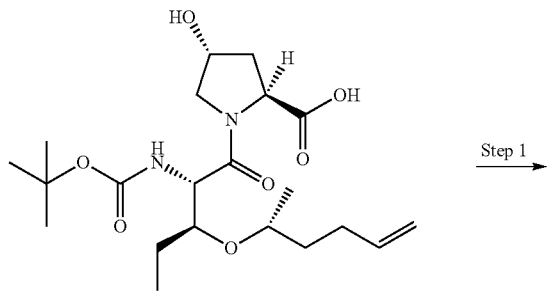

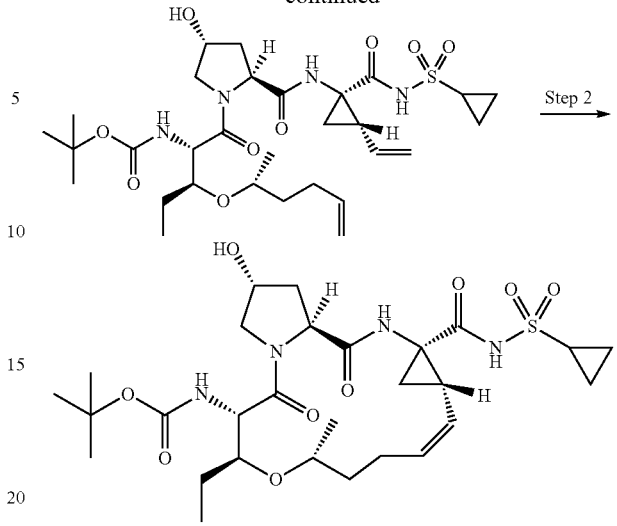

Step 1

To a round-bottom flask equipped with a stir bar was added (2S,4R)-1-((2S,3S)-2-((tert-butoxycarbonyl)amino)-3-((R)-hex-5-en-2-yloxy)pentanoyl)-4-hydroxypyrrolidine-2-carboxylic acid (700 mg, 1.63 mmol), (1R,2S)-1-amino-N-(cyclopropylsulfonyl)-2-vinylcyclopropanecarboxamide-p-toluenesulfonic acid salt (723 mg, 1.80 mmol), HATU (652 mg, 1.72 mmol) and CH$_2$Cl$_2$ (10 mL). To the mixture was added N,N-diisopropylethylamine (1.14 mL, 6.53 mmol). The mixture was stirred for 16 h. The mixture was transferred to a separatory funnel and was thrice washed with aq. 1N HCl; then brine. The organic solution was dried over MgSO$_4$; filtered; then concentrated in vacuo. The resulting residue was subjected to silica gel chromatography (hexanes:acetone 95:5 to 60:40) to afford tert-butyl ((2S,3S)-1-((2S,4R)-2-(((1R,2S)-1-((cyclopropylsulfonyl)carbamoyl)-2-vinylcyclopropyl)carbamoyl)-4-hydroxypyrrolidin-1-yl)-3-((R)-hex-5-en-2-yloxy)-1-oxopentan-2-yl)carbamate as a white solid foam (755 mg, 1.18 mmol, 72%).

Step 2

To a round-bottom flask equipped with a stir bar was added tert-butyl ((2S,3S)-1-((2S,4R)-2-(((1R,2S)-1-((cyclopropylsulfonyl)carbamoyl)-2-vinylcyclopropyl)carbamoyl)-4-hydroxypyrrolidin-1-yl)-3-((R)-hex-5-en-2-yloxy)-1-oxopentan-2-yl)carbamate (755 mg, 1.178 mmol) and DCE (120 mL). The solution was sparged with nitrogen for 30 min. and then to the solution was added Hoveyda-Grubbs Catalyst 2nd Generation (37 mg, 0.059 mmol). The solution was stirred at 80° C. for 4 h. The reaction solution was cooled to room temperature and then was concentrated in vacuo. The resulting residue was subjected to C$_{18}$ chromatography (water with 0.1% TFA: acetonitrile with 0.1% TFA 60:40 to 0:100) to afford tert-butyl ((2R,6S,7S,9R,13aS,14aR,16aS,Z)-14a-((cyclopropylsulfonyl)carbamoyl)-7-ethyl-2-hydroxy-9-methyl-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate as a brown solid foam (393 mg, 54%). $^1$H-NMR (500 MHz, CD$_3$OD) δ 8.87 (s, 1H), 5.60 (td, J=10.2, 6.1 Hz, 1H), 5.08 (t, J=10.2 Hz, 1H), 4.57 (br. s., 1H), 4.46-4.36 (m, 2H), 3.91 (d, J=2.8 Hz, 2H), 3.85-3.79 (m, 1H), 3.58-3.50 (m, 1H), 2.96-2.86

(m, 1H), 2.74 (q, J=9.3 Hz, 1H), 2.63-2.51 (m, 1H), 2.27-2.11 (m, 2H), 1.90-1.79 (m, 2H), 1.76 (dd, J=8.5, 5.5 Hz, 1H), 1.73-1.63 (m, 1H), 1.61-1.47 (m, 4H), 1.42 (s, 8H), 1.30 (ddt, J=9.9, 7.1, 4.8 Hz, 1H), 1.16 (d, J=6.3 Hz, 3H), 1.14-0.98 (m, 5H), 0.95 (t, J=7.4 Hz, 3H).

Preparation of tert-butyl ((2R,6S,7S,9R,13aS,14aR,16aS,Z)-7-ethyl-14a-(((1-(fluoromethyl)cyclopropyl)sulfonyl)carbamoyl)-2-hydroxy-9-methyl-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate

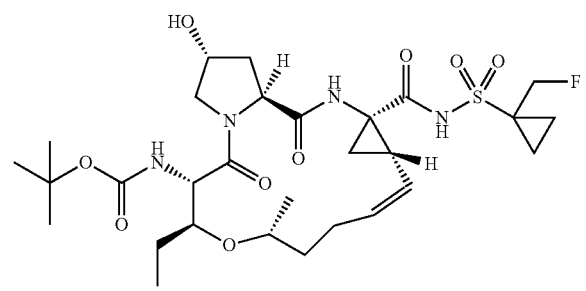 [SMILES: CC[C@@H]1O[C@H](C)CC/C=C\[C@@H]2C[C@@]2(C(=O)NS(=O)(=O)C2(CF)CC2)NC(=O)[C@@H]2C[C@@H](O)CN2C(=O)[C@H]1NC(=O)OC(C)(C)C]

Scheme :

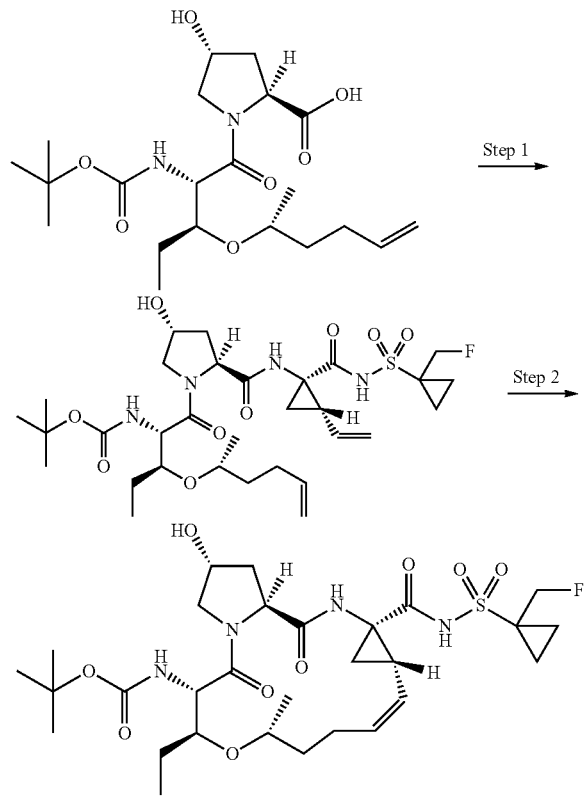

Step 1

To a round-bottom flask equipped with a stir bar was added was added (2S,4R)-1-((2S,3S)-2-((tert-butoxycarbonyl)amino)-3-((R)-hex-5-en-2-yloxy)pentanoyl)-4-hydroxypyrrolidine-2-carboxylic acid (700 mg, 1.63 mmol), (1R,2S)-1-amino-N-((1-(fluoromethyl)cyclopropyl)sulfonyl)-2-vinylcyclopropanecarboxamide-trifluoroacetic acid salt (676 mg, 1.80 mmol), HATU (652 mg, 1.72 mmol) and $CH_2Cl_2$ (10 mL). To the mixture was added N,N-diisopropylethylamine (1.14, 6.53 mmol). The mixture was stirred at room temperature for 16 h. The reaction mixture was transferred to a separatory funnel and was thrice washed with aq. 1N HCl; then brine. The organic phase was dried over $MgSO_4$; filtered; then concentrated in vacuo. The resulting residue was subjected to silica gel chromatography (hexanes:acetone 95:5 to 60:40) to afford tert-butyl ((2S,3S)-1-((2S,4R)-2-(((1R,2S)-1-(((1-(fluoromethyl)cyclopropyl)sulfonyl)carbamoyl)-2-vinylcyclopropyl)carbamoyl)-4-hydroxypyrrolidin-1-yl)-3-((R)-hex-5-en-2-yloxy)-1-oxopentan-2-yl)carbamate as a white solid foam (559 mg, 51%).

Step 2

To a round-bottom flask equipped with a stir bar was added tert-butyl ((2S,3S)-1-((2S,4R)-2-(((1R,2S)-1-(((1-(fluoromethyl)cyclopropyl)sulfonyl)carbamoyl)-2-vinylcyclopropyl)carbamoyl)-4-hydroxypyrrolidin-1-yl)-3-((R)-hex-5-en-2-yloxy)-1-oxopentan-2-yl)carbamate (559 mg, 0.831 mmol) and DCE (90 mL). The solution was sparged with nitrogen for 30 min. and then to the solution was added Hoveyda-Grubbs Catalyst 2nd Generation (26 mg, 0.042 mmol). The solution was stirred at 80° C. for 16 h. The solution was concentrated in vacuo and the resulting residue was subjected to $C_{18}$ chromatography (water with 0.1% TFA:acetonitrile with 0.1% TFA, 60:40 to 0:100) to afford tert-butyl ((2R,6S,7S,9R,13aS,14aR,16aS,Z)-7-ethyl-14a-(((1-(fluoromethyl)cyclopropyl)sulfonyl)carbamoyl)-2-hydroxy-9-methyl-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate as a brown solid foam (120 mg, 22%). $^1$H NMR (500 MHz, $CD_3OD$) δ 8.91 (s, 1H), 5.60 (td, J=10.0, 6.5 Hz, 1H), 5.03 (t, J=10.3 Hz, 1H), 4.61-4.55 (m, J=11.2 Hz, 2H), 4.49 (d, J=11.2 Hz, 1H), 4.43 (d, J=9.9 Hz, 1H), 4.38 (t, J=7.8 Hz, 1H), 3.96-3.87 (m, 2H), 3.82 (d, J=12.1 Hz, 1H), 3.53 (dq, J=9.4, 6.5 Hz, 1H), 2.71 (q, J=9.4 Hz, 1H), 2.61-2.50 (m, 1H), 2.23-2.13 (m, 2H), 1.84 (dd, J=10.9, 6.8 Hz, 2H), 1.74-1.60 (m, 5H), 1.59-1.54 (m, 2H), 1.54-1.46 (m, 2H), 1.43 (s, 9H), 1.26-1.20 (m, 2H), 1.16 (d, J=6.3 Hz, 3H), 0.95 (t, J=7.4 Hz, 3H).

Preparation of tert-butyl ((2R,6S,7S,13aS,14aR,16aS,Z)-7-ethyl-2-hydroxy-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate

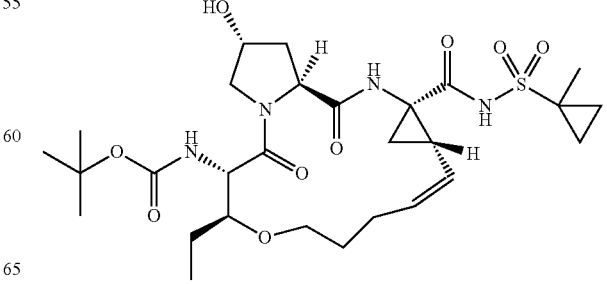

Scheme:

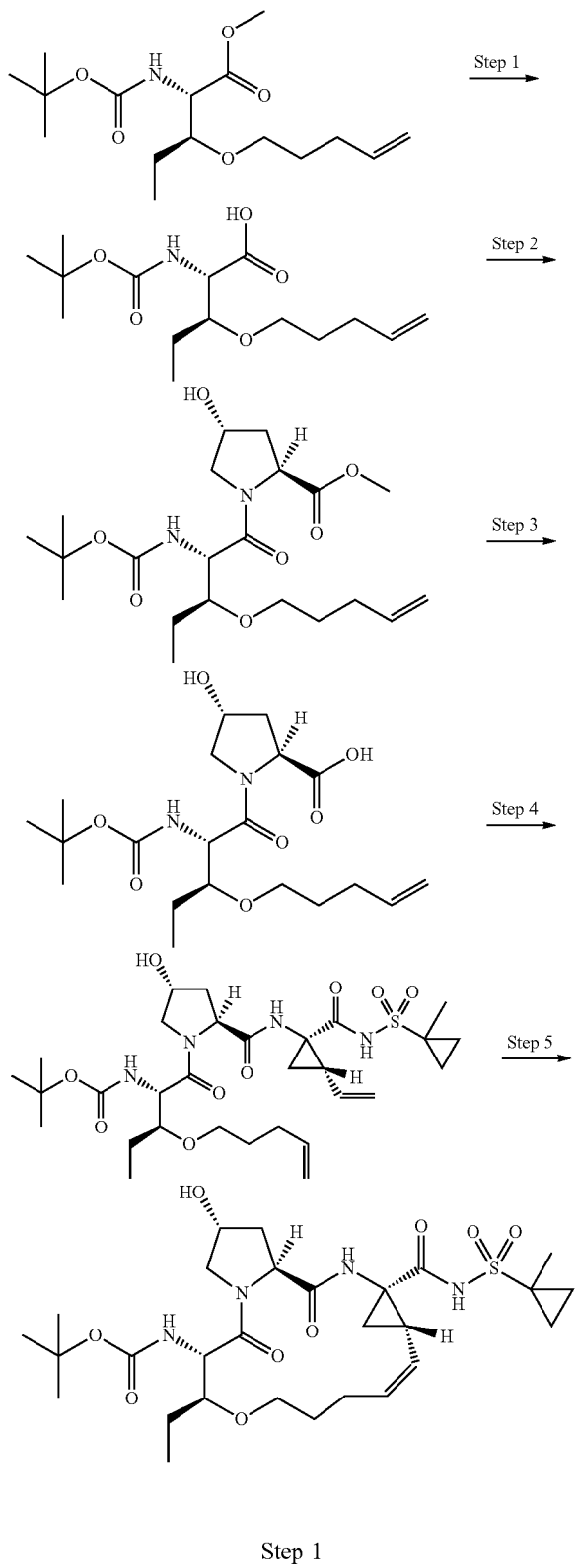

Step 1

To a round-bottom flask equipped with a stir bar was added (2S,3S)-methyl 2-((tert-butoxycarbonyl)amino)-3-(pent-4-en-1-yloxy)pentanoate (1.06 g, 3.36 mmol), THF (10 mL) and MeOH (10 mL). To the solution was added aq. LiOH (1.0 M, 5.04 mL). The mixture was stirred for 16 h at room temperature. The mixture was concentrated in vacuo, and the resulting aqueous solution was acidified with aq HCl (1.0 M) and then transferred to a separatory funnel. The solution was twice extracted with EtOAc and the combined organics were dried over MgSO$_4$; filtered; then concentrated in vacuo to afford (2S,3S)-2-((tert-butoxycarbonyl)amino)-3-(pent-4-en-1-yloxy)pentanoic acid as a colorless solid foam (1.00 g, 99% yield).

Step 2

To a round-bottom flask equipped with a stir bar was added (2S,3S)-2-((tert-butoxycarbonyl)amino)-3-(pent-4-en-1-yloxy)pentanoic acid (all material from step 1, 1.00 g, 3.32 mmol), (2S,4R)-methyl 4-hydroxypyrrolidine-2-carboxylate-HCl salt (0.663 g, 3.65 mmol), HATU (1.26 g, 3.32 mmol) and CH$_2$Cl$_2$ (30 mL). To the mixture was added N,N-diisopropylethylamine (1.75 mL, 9.95 mmol). The mixture was stirred at room temperature for 16 h. The mixture was transferred to a separatory funnel and was thrice washed with aq. HCl (1M); then brine. The organic solution was dried over MgSO$_4$; filtered; then concentrated in vacuo to afford (2S,4R)-methyl 1-((2S,3S)-2-((tert-butoxycarbonyl)amino)-3-(pent-4-en-1-yloxy)pentanoyl)-4-hydroxypyrrolidine-2-carboxylate as a yellow oil (1.53 g).

Step 3

To a round-bottom flask equipped with a stir bar was added (2S,4R)-methyl 1-((2S,3S)-2-((tert-butoxycarbonyl)amino)-3-(pent-4-en-1-yloxy)pentanoyl)-4-hydroxypyrrolidine-2-carboxylate (all material from step 2, 1.53 g, 3.57 mmol), THF (10 mL) and MeOH (10 mL). To the solution was added aq. LiOH (1.0 M, 5.36 mL). The mixture was stirred at room temperatuer for 16 h; then was concentrated in vacuo to afford an aqueous solution. The solution was acidified with aq HCl (1M) and then transferred to a separatory funnel. The solution was twice extracted with EtOAc. The combined organics were dried over MgSO$_4$; filtered; then concentrated in vacuo to afford (2S,4R)-1-((2S,3S)-2-((tert-butoxycarbonyl)amino)-3-(pent-4-en-1-yloxy)pentanoyl)-4-hydroxypyrrolidine-2-carboxylic acid as a white solid (1.28 g, 86% over two steps).

Step 4

To a round-bottom flask equipped with a stir bar was added (2S,4R)-1-((2S,3S)-2-((tert-butoxycarbonyl)amino)-3-(pent-4-en-1-yloxy)pentanoyl)-4-hydroxypyrrolidine-2-carboxylic acid (½ of material from step 3, 600 mg, 1.45 mmol), (1R,2S)-1-amino-N-((1-methylcyclopropyl)sulfonyl)-2-vinylcyclopropanecarboxamide-trifluoroacetic acid salt (571 mg, 1.59 mmol), HATU (578 mg, 1.52 mmol) and CH$_2$Cl$_2$ (10 mL). To the mixture was added N,N-diisopropylethylamine (1.01 mL, 5.79 mmol). The mixture was stirred at room temperature for 16 h. The mixture was transferred to a separatory funnel and was thrice washed with aq. HCl (1M); then brine. The organic solution was dried over MgSO$_4$; filtered; then concentrated in vacuo. The resulting residue was subjected to silica gel chromatography (hexanes:acetone, 94:6 to 60:40) to afford tert-butyl ((2S,3S)-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-1-oxo-3-(pent-4-en-1-yloxy)pentan-2-yl)carbamate as a colorless solid foam (480 mg, 52%). MS: MS m/z 641.5 (M$^+$+1).

Step 5

To a round-bottom flask equipped with a stir bar was added tert-butyl ((2S,3S)-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-1-oxo-3-(pent-4-en-1-yloxy)pentan-2-yl)carbamate (all material from step 4, 480 mg, 0.749 mmol) and DCE (100 mL). The solution was sparged with nitrogen for 30 minutes. To the solution was added Hoveyda-Grubbs Catalyst 2nd Generation (23 mg, 0.037 mmol). The solution was stirred at 80° C. for 2 h, then was cooled to 45° C. and was stirred for 3 days. The solution was concentrated in vacuo and the resulting residue was subjected to $C_{18}$ chromatography (water with 0.1% TFA: acetonitrile with 0.1% TFA, 60:40 to 0:100) to afford tert-butyl ((2R,6S,7S,13aS,14aR,16aS,Z)-7-ethyl-2-hydroxy-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate as a brown solid foam (100 mg, 22%). MS: MS m/z 613.4 (M$^+$+1).

Preparation of Compound 1001

Compound 1001

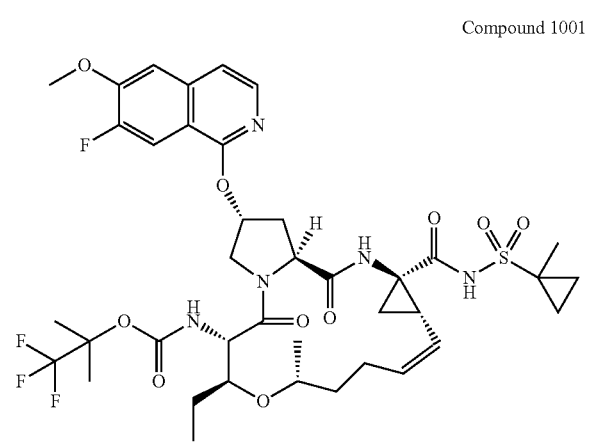 [SMILES: CC[C@@H]1O[C@H](C)CC/C=C\[C@@H]2C[C@@]2(C(=O)NS(=O)(=O)C2(C)CC2)NC(=O)[C@@H]2C[C@@H](Oc3nccc4cc(OC)c(F)cc34)CN2C(=O)[C@H]1NC(=O)OC(C)(C)C(F)(F)F]

Scheme:

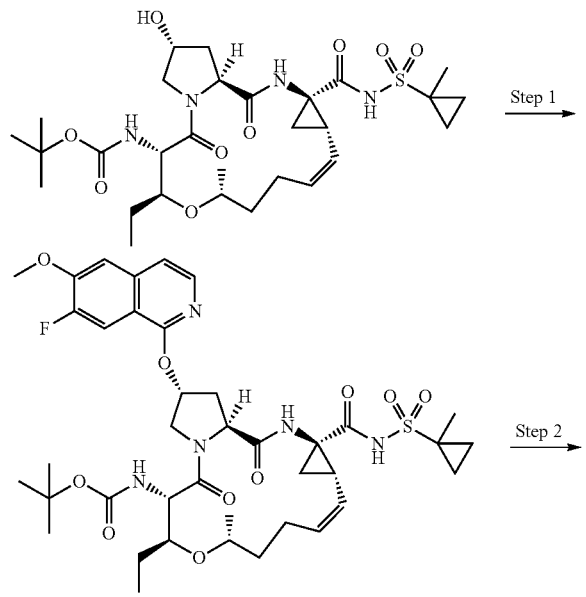

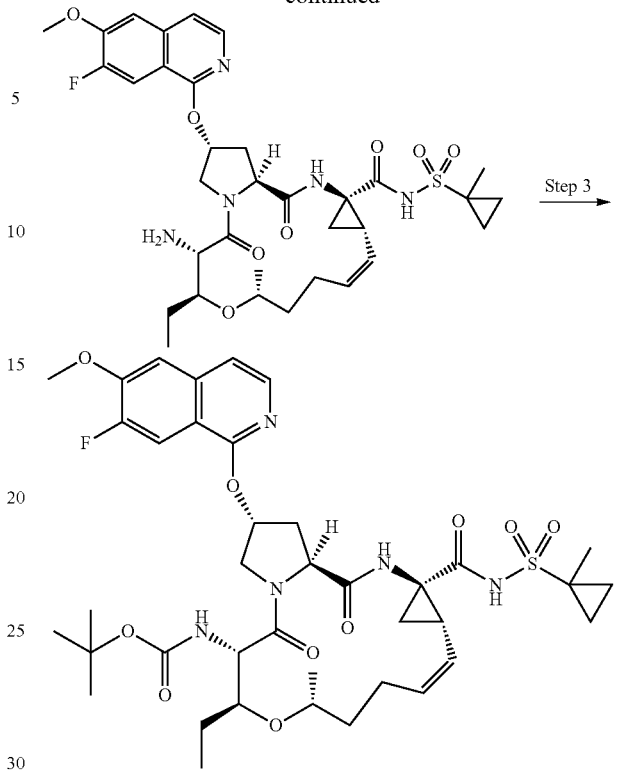

Step 1

To a vial equipped with a stir bar was added tert-butyl ((2R,6S,7S,9R,13aS,14aR,16aS,Z)-7-ethyl-2-hydroxy-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate (25 mg, 0.040 mmol), 1-chloro-7-fluoro-6-methoxyisoquinoline (9.3 mg, 0.044 mmol) and DMSO (1 mL). The mixture was sonicated for 5 min. To the solution was added potassium tert-butoxide (22 mg, 0.20 mmol). The solution was stirred at room temperature for 2 h and then was diluted with aq. HCl (2N) and transferred to a separatory funnel. The mixture was extracted with EtOAc; washed with brine; dried over MgSO$_4$; then concentrated in vacuo to afford tert-butyl ((2R,6S,7S,9R,13aS,14aR,16aS,Z)-7-ethyl-2-((7-fluoro-6-methoxyisoquinolin-1-yl)oxy)-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate.

Step 2

To a vial equipped with a stir bar and charged with tert-butyl ((2R,6S,7S,9R,13aS,14aR,16aS,Z)-7-ethyl-2-(7-fluoro-6-methoxyisoquinolin-1-yl)oxy)-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate (all material from step 1, 0.04 mmol) was added CH$_2$Cl$_2$, then trifluoroacetic acid (1.0 ml, 13 mmol). The solution was stirred for 1 h. The solution was concentrated in vacuo to afford (2R,6S,7S,9R,13aS,14aR,16aS,Z)-6-amino-7-ethyl-2-((7-fluoro-6-methoxyisoquinolin-1-yl)oxy)-9-methyl-N-((1-methylcyclopropyl)sulfonyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecine-14a-carboxamide as the trifluoroacetic acid salt.

Step 3

To a vial equipped with a stir bar and charged with (2R,6S,7S,9R,13aS,14aR,16aS,Z)-6-amino-7-ethyl-2-((7-fluoro-6-methoxyisoquinolin-1-yl)oxy)-9-methyl-N-((1-methylcyclopropyl)sulfonyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecine-14a-carboxamide-trifluoroacetic acid salt (all material from step 2, 0.04 mmol) was added CH$_2$Cl$_2$ (1 mL) and pyridin-2-yl (1,1,1-trifluoro-2-methylpropan-2-yl) carbonate (12 mg, 0.049 mmol). To the solution was added N,N-diisopropylethylamine (0.036 mL, 0.21 mmol). The reaction was stirred for 1 h and then the solvent was removed in vacuo. The resulting residue was subjected to C$_{18}$ HPLC purification (water with 0.1% TFA:MeCN with 0.1% TFA) to afford Compound 1001 as a white solid (14.7 mg, 41% yield over 3 steps).

Compound 1001: 1,1,1-trifluoro-2-methylpropan-2-yl ((2R,6S,7S,9R,13aS,14aR,16aS,Z)-7-ethyl-2-(7-fluoro-6-methoxyisoquinolin-1-yl)oxy)-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl) carbamate. $^1$H-NMR (400 MHz, CD$_3$OD) δ 8.93 (s, 1H), 7.94 (d, J=6.0 Hz, 1H), 7.76 (d, J=11.5 Hz, 1H), 7.38 (d, J=8.3 Hz, 1H), 7.29 (d, J=5.5 Hz, 1H), 5.90 (br. s., 1H), 5.62 (td, J=10.0, 6.5 Hz, 1H), 5.06 (t, J=10.2 Hz, 1H), 4.64-4.54 (m, 2H), 4.35 (d, J=10.0 Hz, 1H), 4.12 (dd, J=11.7, 3.6 Hz, 1H), 4.02 (s, 3H), 3.93-3.86 (m, 1H), 3.60-3.48 (m, 1H), 2.82 (q, J=9.4 Hz, 1H), 2.75-2.65 (m, 1H), 2.65-2.55 (m, 1H), 2.45 (ddd, J=13.8, 9.7, 4.4 Hz, 1H), 1.94-1.81 (m, 2H), 1.77 (dd, J=8.7, 5.6 Hz, 1H), 1.74-1.68 (m, 1H), 1.68-1.62 (m, 1H), 1.58 (dd, J=9.5, 5.5 Hz, 2H), 1.52 (s, 3H), 1.43 (s, 3H), 1.42-1.35 (m, 4H), 1.17 (d, J=6.3 Hz, 3H), 1.11 (s, 3H), 0.91 (t, J=7.2 Hz, 3H), 0.89-0.85 (m, 1H); MS: MS m/z 857.5 (M$^+$+1).

Preparation of Compound 1002

Compound 1002 was prepared using 1-fluoro-3,6-dimethoxyisoquinoline and the intermediates described above and by following the general procedure described for the synthesis of Compound 1001.

Compound 1002: 1,1,1-trifluoro-2-methylpropan-2-yl ((2R,6S,7S,9R,13aS,14aR,16aS,Z)-2-((3,6-dimethoxyisoquinolin-1-yl)oxy)-7-ethyl-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl) carbamate. $^1$H-NMR (400 MHz, CD$_3$OD) δ 8.95 (s, 1H), 7.92 (d, J=9.0 Hz, 1H), 7.02 (d, J=2.3 Hz, 1H), 6.86 (dd, J=9.0, 2.3 Hz, 1H), 6.55 (s, 1H), 5.88 (br. s., 1H), 5.62 (td, J=10.2, 6.3 Hz, 1H), 5.06 (t, J=10.3 Hz, 1H), 4.64-4.54 (m, 2H), 4.38 (d, J=10.0 Hz, 1H), 4.17 (dd, J=11.5, 3.8 Hz, 1H), 3.98 (s, 3H), 3.95-3.90 (m, 1H), 3.89 (s, 3H), 3.55 (td, J=6.6, 2.9 Hz, 1H), 2.80 (q, J=9.3 Hz, 1H), 2.70 (dd, J=13.7, 7.4 Hz, 1H), 2.66-2.51 (m, 1H), 2.45 (ddd, J=13.9, 9.5, 4.5 Hz, 1H), 1.93-1.80 (m, 2H), 1.77 (dd, J=8.5, 5.5 Hz, 1H), 1.75-1.62 (m, 2H), 1.57 (dd, J=9.5, 5.8 Hz, 1H), 1.54-1.48 (m, 4H), 1.46 (s, 3H), 1.45-1.35 (m, 4H), 1.17 (d, J=6.3 Hz, 3H), 1.09 (s, 3H), 0.91 (t, J=7.4 Hz, 3H), 0.89-0.85 (m, 2H).

Preparation of Compound 1003

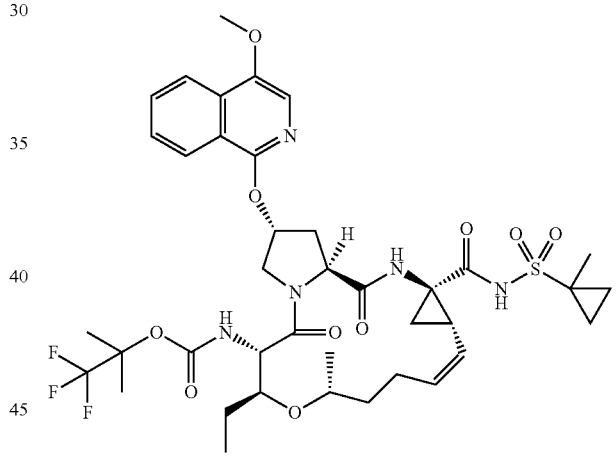

Compound 1003

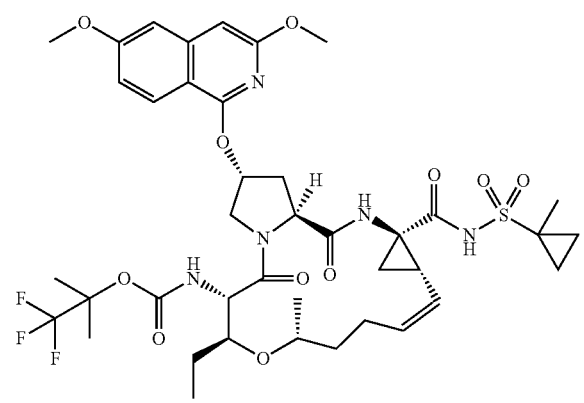

Compound 1002

Compound 1003 was prepared using 1-fluoro-4-methoxyisoquinoline and the intermediates described above and by following the general procedure described for the synthesis of Compound 1001.

Compound 1003: 1,1,1-trifluoro-2-methylpropan-2-yl ((2R,6S,7S,9R,13aS,14aR,16aS,Z)-7-ethyl-2-(4-methoxyisoquinolin-1-yl)oxy)-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate.
$^1$H-NMR (400 MHz, CD$_3$OD) δ 8.95 (s, 1H), 8.19-8.09 (m, 2H), 7.73 (ddd, J=8.3, 7.0, 1.3 Hz, 1H), 7.63-7.54 (m, 2H), 5.85 (br. s., 1H), 5.62 (td, J=10.0, 6.4 Hz, 1H), 5.06 (t, J=10.3 Hz, 1H), 4.66-4.56 (m, 2H), 4.36 (d, J=10.0 Hz, 1H), 4.13 (dd, J=11.8, 3.5 Hz, 1H), 4.02 (s, 3H), 3.93-3.83 (m, 1H), 3.55 (td, J=6.7, 3.0 Hz, 1H), 2.81 (q, J=9.4 Hz, 1H), 2.71 (dd, J=13.6, 7.3 Hz, 1H), 2.64-2.54 (m, 1H), 2.44 (ddd, J=13.9, 9.7, 4.3 Hz, 1H), 1.94-1.80 (m, 2H), 1.77 (dd, J=8.5, 5.5 Hz, 1H), 1.75-1.62 (m, 2H), 1.62-1.54 (m, 2H), 1.52 (s, 3H), 1.51-1.42 (m, 2H), 1.42-1.35 (m, 4H), 1.17 (d, J=6.3 Hz, 3H), 0.96 (s, 3H), 0.93-0.86 (m, 5H); MS: MS m/z 838.5 (M⁺+1).

Preparation of Compound 1004

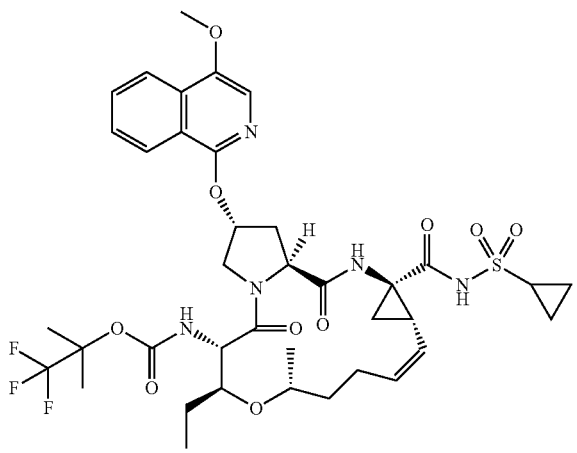

Compound 1004

Compound 1004 was prepared using 1-fluoro-4-methoxy-isoquinoline and the intermediates described above and by following the general procedure described for the synthesis of Compound 1001.

Compound 1004: 1,1,1-trifluoro-2-methylpropan-2-yl ((2R,6S,7S,9R,13aS,14aR,16aS,Z)-14a-((cyclopropylsulfonyl)carbamoyl)-7-ethyl-2-((4-methoxyisoquinolin-1-yl)oxy)-9-methyl-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. ¹H-NMR (500 MHz, DMSO-d₆) δ 8.65 (br. s., 1H), 8.05 (d, J=8.5 Hz, 2H), 7.86 (d, J=9.2 Hz, 1H), 7.79 (t, J=7.5 Hz, 1H), 7.65-7.58 (m, 2H), 5.76 (br. s., 1H), 5.50 (d, J=8.5 Hz, 1H), 5.31 (br. s., 1H), 4.40 (t, J=8.2 Hz, 1H), 4.28 (d, J=11.0 Hz, 1H), 4.15 (t, J=9.3 Hz, 1H), 3.98 (br. s., 1H), 3.95 (s, 3H), 3.81 (br. s., 1H), 2.89 (s, 1H), 2.82 (br. s., 1H), 2.73 (s, 1H), 2.55 (d, J=2.1 Hz, 1H), 2.31 (br. s., 2H), 1.81 (br. s., 1H), 1.77 (br. s., 1H), 1.65 (br. s., 2H), 1.59-1.48 (m, 3H), 1.38 (br. s., 3H), 1.28 (br. s., 1H), 1.23 (br. s., 1H), 1.06 (d, J=5.8 Hz, 3H), 0.99 (br. s., 3H), 0.91 (br. s., 3H), 0.80 (t, J=7.0 Hz, 3H); MS: MS m/z 824.7 (M⁺+1).

Preparation of Compound 1005

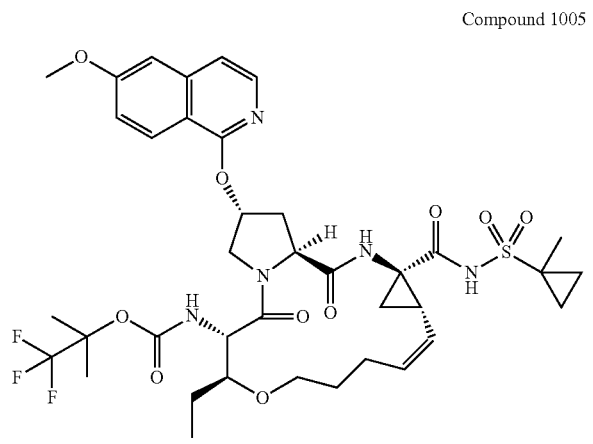 [SMILES: CC[C@@H]1O[C@H](C)CC/C=C\[C@@H]2C[C@@]2(C(=O)NS(=O)(=O)C2(C)CC2)NC(=O)[C@@H]2C[C@@H](Oc3nccc4cc(OC)ccc34)CN2C(=O)[C@H]1NC(=O)OC(C)(C)C(F)(F)F]

Compound 1005

Compound 1005 was prepared using 1-fluoro-6-methoxy-isoquinoline and the intermediates described above and by following the general procedure described for the synthesis of Compound 1001.

Compound 1005: 1,1,1-trifluoro-2-methylpropan-2-yl ((2R,6S,7S,13aS,14aR,16aS,Z)-7-ethyl-2-(6-methoxyisoquinolin-1-yl)oxy)-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. ¹H-NMR (500 MHz, DMSO-d₆) δ 8.58-8.18 (m, 1H), 8.00-7.89 (m, 4H), 7.32-7.28 (m, 2H), 7.17-7.13 (m, 1H), 5.81 (br. s., 1H), 5.56-5.50 (m, 1H), 5.29 (br. s., 1H), 4.45 (t, J=8.2 Hz, 1H), 4.27 (d, J=11.0 Hz, 1H), 4.21-4.14 (m, 1H), 4.05 (d, J=7.6 Hz, 1H), 3.89 (s, 3H), 3.72 (d, J=10.1 Hz, 1H), 2.40 (br. s., 1H), 2.24 (br. s., 1H), 2.15-2.03 (m, 3H), 1.69 (br. s., 1H), 1.59 (d, J=8.9 Hz, 3H), 1.52 (br. s., 2H), 1.37 (s, 3H), 1.40 (s, 3H), 1.28 (br. s., 2H), 1.18 (d, J=10.1 Hz, 2H), 1.03 (s, 3H), 0.81 (t, J=7.3 Hz, 3H), 0.67 (br. s., 2H); MS: MS m/z 824.6 (M⁺+1).

Preparation of Compound 1006

Compound 1006

Compounds 1006 was prepared using 1-fluoro-6-methoxyisoquinoline and the intermediates described above and by following the general procedure described for the synthesis of Compound 1001.

Compound 1006: 1,1,1-trifluoro-2-methylpropan-2-yl ((2R,6S,7S,9R,13aS,14aR,16aS,Z)-7-ethyl-2-(6-methoxyisoquinolin-1-yl)oxy)-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate.
¹H-NMR (500 MHz, DMSO-d₆) δ 8.88 (br. s., 1H), 7.99-7.88 (m, 3H), 7.33-7.29 (m, 2H), 7.14 (dd, J=9.0, 2.3 Hz, 1H), 5.84 (br. s., 1H), 5.56-5.49 (m, 1H), 5.16 (br. s., 1H), 4.44 (t, J=8.4 Hz, 1H), 4.30 (d, J=11.6 Hz, 1H), 4.16 (t, J=9.6 Hz, 1H), 3.99 (d, J=8.2 Hz, 1H), 3.89 (s, 4H), 3.85 (d, J=9.2 Hz, 1H), 3.47 (d, J=4.0 Hz, 2H), 2.65-2.54 (m, 2H), 2.38 (br. s., 1H), 2.36-2.28 (m, 1H), 1.82 (d, J=6.1 Hz, 1H), 1.73-1.63 (m, 1H), 1.57 (d, J=8.2 Hz, 2H), 1.45 (br. s., 1H), 1.40 (d, J=4.0 Hz, 6H), 1.34-1.22 (m, 3H), 1.09-1.04 (m, 6H), 0.81 (t, J=7.2 Hz, 5H); MS: MS m/z 838.7 (M⁺+1).

Preparation of Compound 1007

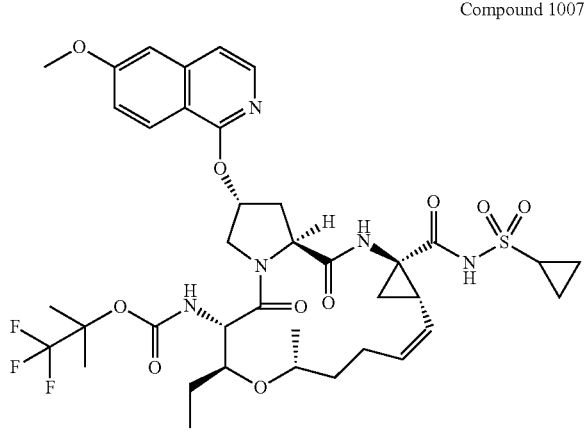 [SMILES: CC[C@@H]1O[C@H](C)CC/C=C\[C@@H]2C[C@@]2(C(=O)NS(=O)(=O)C2CC2)NC(=O)[C@@H]2C[C@@H](Oc3nccc4cc(OC)ccc34)CN2C(=O)[C@H]1NC(=O)OC(C)(C)C(F)(F)F]

Compound 1007

Compound 1007 was prepared using 1-fluoro-6-methoxyisoquinoline and the intermediates described above and by following the general procedure described for the synthesis of Compound 1001.

Compound 1007: 1,1,1-trifluoro-2-methylpropan-2-yl ((2R,6S,7S,9R,13aS,14aR,16aS,Z)-14a-((cyclopropylsulfonyl)carbamoyl)-7-ethyl-2-((6-methoxyisoquinolin-1-yl)oxy)-9-methyl-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H-NMR (500 MHz, DMSO-$d_6$) δ 11.59-10.46 (m, 1H), 8.84 (br. s., 1H), 7.98 (d, J=6.1 Hz, 1H), 7.91 (d, J=9.2 Hz, 1H), 7.69 (d, J=11.3 Hz, 1H), 7.55 (d, J=8.2 Hz, 1H), 7.35 (d, J=6.1 Hz, 1H), 5.82 (br. s., 1H), 5.55-5.49 (m, 1H), 5.17 (br. s., 1H), 4.44-4.38 (m, 1H), 4.30 (d, J=11.6 Hz, 1H), 4.16 (t, J=9.6 Hz, 1H), 3.98 (s, 3H), 3.95 (d, J=7.9 Hz, 2H), 3.85 (d, J=9.8 Hz, 1H), 2.89 (d, J=3.7 Hz, 1H), 2.67 (br. s., 1H), 2.61-2.54 (m, 1H), 2.42 (br. s., 1H), 2.33-2.27 (m, 1H), 1.82 (d, J=6.4 Hz, 1H), 1.71 (br. s., 1H), 1.62-1.50 (m, 4H), 1.43 (s, 3H), 1.42-1.35 (m, 1H), 1.35-1.27 (m, 2H), 1.14 (s, 3H), 1.07 (d, J=6.1 Hz, 3H), 0.97 (br. s., 2H), 0.81 (t, J=7.5 Hz, 3H); MS: MS m/z 842.7 (M$^+$+1).

Preparation of Compound 1008

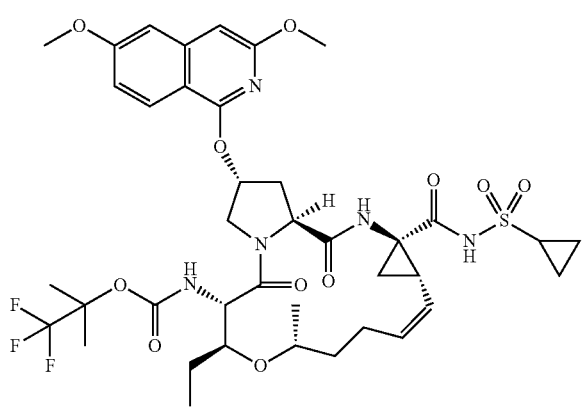

Compound 1008

Compound 1008 was prepared using 1-fluoro-3,6-dimethoxyisoquinoline and the intermediates described above and by following the general procedure described for the synthesis of Compound 1001.

Compound 1008: 1,1,1-trifluoro-2-methylpropan-2-yl ((2R,6S,7S,9R,13aS,14aR,16aS,Z)-14a-((cyclopropylsulfonyl)carbamoyl)-2-((3,6-dimethoxyisoquinolin-1-yl)oxy)-7-ethyl-9-methyl-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H-NMR (500 MHz, DMSO-$d_6$) δ 11.23 (s, 1H), 8.83 (br. s., 1H), 7.91 (d, J=9.2 Hz, 1H), 7.85 (d, J=9.2 Hz, 1H), 7.13 (s, 1H), 6.89 (d, J=9.2 Hz, 1H), 6.61 (s, 1H), 5.77 (br. s., 1H), 5.55-5.49 (m, 1H), 5.19 (br. s., 1H), 4.39 (t, J=8.1 Hz, 1H), 4.29 (d, J=11.0 Hz, 1H), 4.17 (t, J=9.5 Hz, 1H), 4.00 (d, J=7.6 Hz, 1H), 3.85 (s, 5H), 3.89 (s, 4H), 2.88 (d, J=8.5 Hz, 1H), 2.62-2.55 (m, 1H), 2.44-2.28 (m, 2H), 1.83 (br. s., 1H), 1.70 (br. s., 1H), 1.60-1.51 (m, 3H), 1.44 (s, 3H), 1.43-1.34 (m, 2H), 1.30 (d, J=11.9 Hz, 1H), 1.15 (s, 3H), 1.07 (d, J=6.1 Hz, 3H), 0.96 (br. s., 3H), 0.81 (t, J=7.2 Hz, 3H); MS: MS m/z 854.8 (M$^+$+1).

Preparation of Compound 1009

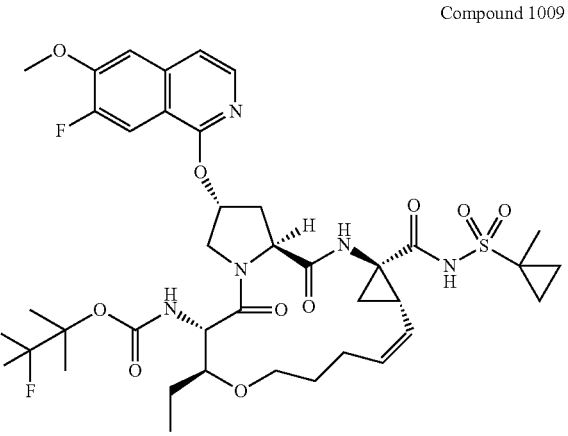

Compound 1009

Compound 1009 was prepared using 1,7-difluoro-6-methoxyisoquinoline and the intermediates described above and by following the general procedure described for the synthesis of Compound 1001.

Compound 1009: 1,1,1-trifluoro-2-methylpropan-2-yl ((2R,6S,7S,13aS,14aR,16aS,Z)-7-ethyl-2-(7-fluoro-6-methoxyisoquinolin-1-yl)oxy)-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate.
$^1$H-NMR (500 MHz, DMSO-$d_6$) δ 7.96 (d, J=5.8 Hz, 1H), 7.92 (d, J=9.2 Hz, 1H), 7.70 (d, J=11.3 Hz, 1H), 7.54 (d, J=8.5 Hz, 1H), 7.34 (d, J=5.8 Hz, 1H), 5.79 (br. s., 1H), 5.55-5.48 (m, 1H), 5.27 (br. s., 1H), 4.51-4.43 (m, 1H), 4.27 (d, J=11.3 Hz, 1H), 4.17 (t, J=9.6 Hz, 1H), 4.03 (d, J=7.9 Hz, 1H), 3.97 (s, 3H), 3.72 (d, J=9.5 Hz, 1H), 3.53 (br. s., 1H), 3.24 (br. s., 1H), 2.37 (br. s., 1H), 2.24 (br. s., 1H), 2.08 (br. s., 1H), 1.69 (br. s., 1H), 1.57 (d, J=6.1 Hz, 3H), 1.50 (d, J=14.6 Hz, 1H), 1.40 (s, 3H), 1.36 (s, 4H), 1.31 (br. s., 1H), 1.24 (d, J=14.0 Hz, 2H), 1.18 (d, J=10.7 Hz, 1H), 1.08 (s, 3H), 0.80 (t, J=7.2 Hz, 3H), 0.67 (br. s., 2H); MS: MS m/z 842.9 (M$^+$+1).

Preparation of Compound 1010

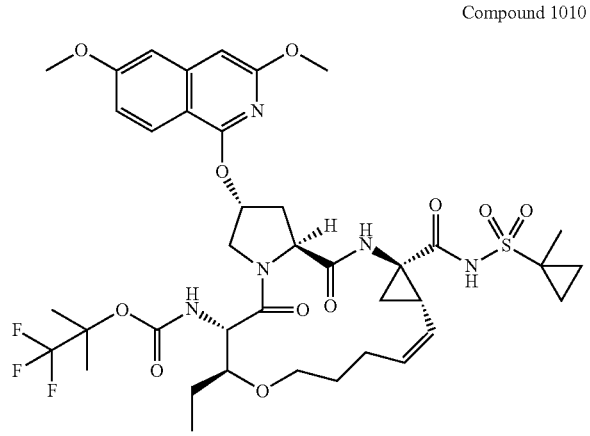

Compound 1010

Compound 1010 was prepared using 1-fluoro-3,6-dimethoxyisoquinoline and the intermediates described above and by following the general procedure described for the synthesis of Compound 1001.

Compound 1010: 1,1,1-trifluoro-2-methylpropan-2-yl ((2R,6S,7S,13aS,14aR,16aS,Z)-2-((3,6-dimethoxyisoquinolin-1-yl)oxy)-7-ethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H-NMR (500 MHz, DMSO-$d_6$) δ 8.62 (s, 1H), 7.93 (d, J=9.2 Hz, 1H), 7.85 (d, J=8.9 Hz, 1H), 7.13 (d, J=2.1 Hz, 1H), 6.89 (dd, J=9.2, 2.1 Hz, 1H), 6.61 (s, 1H), 5.77 (br. s., 1H), 5.55 (q, J=8.7 Hz, 1H), 5.21 (br. s., 1H), 4.44 (t, J=8.2 Hz, 1H), 4.29 (d, J=11.3 Hz, 1H), 4.18 (t, J=9.8 Hz, 1H), 4.05 (d, J=8.5 Hz, 1H), 3.91-3.84 (m, 8H), 3.73 (d, J=9.2 Hz, 1H), 3.24 (br. s., 1H), 2.38 (br. s., 2H), 2.17 (br. s., 1H), 2.07 (br. s., 1H), 1.70 (br. s., 1H), 1.63-1.51 (m, 4H), 1.43 (s, 3H), 1.38 (s, 3H), 1.33 (br. s., 2H), 1.23 (br. s., 2H), 1.11 (s, 3H), 0.81 (t, J=7.2 Hz, 3H), 0.74 (br. s., 2H); MS: MS m/z 854.8 (M$^+$+1).

Preparation of Compound 1011

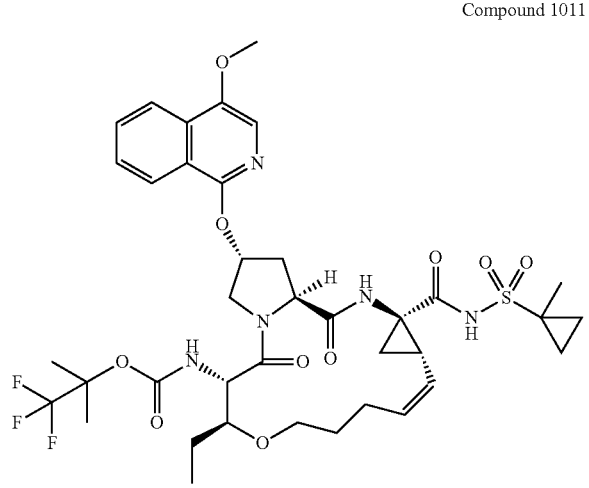 [SMILES: CC[C@@H]1OCCC/C=C\[C@@H]2C[C@@]2(C(=O)NS(=O)(=O)C2(C)CC2)NC(=O)[C@@H]2C[C@@H](Oc3ncc(OC)c4ccccc34)CN2C(=O)[C@H]1NC(=O)OC(C)(C)C(F)(F)F]

Compound 1011

Compound 1011 was prepared using 1-fluoro-4-methoxyisoquinoline and the intermediates described above and by following the general procedure described for the synthesis of Compound 1001.

Compound 1011: 1,1,1-trifluoro-2-methylpropan-2-yl ((2R,6S,7S,13aS,14aR,16aS,Z)-7-ethyl-2-(4-methoxyisoquinolin-1-yl)oxy)-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H-NMR (500 MHz, DMSO-$d_6$) δ 8.58 (br. s., 1H), 8.04 (d, J=8.2 Hz, 2H), 7.88 (d, J=9.2 Hz, 1H), 7.78 (t, J=7.5 Hz, 1H), 7.68-7.59 (m, 2H), 5.76 (br. s., 1H), 5.53 (d, J=9.2 Hz, 1H), 5.21 (br. s., 1H), 4.48-4.43 (m, 1H), 4.27 (d, J=11.3 Hz, 1H), 4.17-4.13 (m, 1H), 4.02 (d, J=8.9 Hz, 1H), 3.97-3.92 (m, 3H), 3.71 (d, J=9.5 Hz, 1H), 3.52 (br. s., 1H), 3.23 (br. s., 1H), 2.54 (br. s., 1H), 2.36 (br. s., 1H), 2.07 (br. s., 1H), 1.58 (br. s., 2H), 1.46 (br. s., 2H), 1.37 (br. s., 7H), 1.31 (br. s., 3H), 1.23 (d, J=10.7 Hz, 2H), 0.94 (s, 3H), 0.79 (t, J=7.2 Hz, 4H), 0.72 (br. s., 2H); MS: MS m/z 824.8 (M$^+$+1).

Preparation of Compound 1012

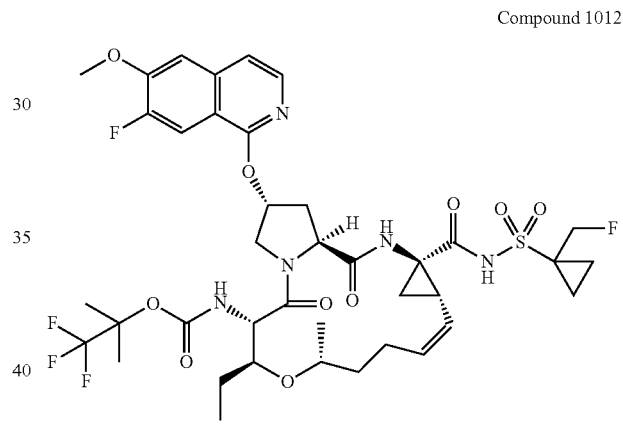

Compound 1012

Compound 1012 was prepared using 1,7-difluoro-6-methoxyisoquinoline and the intermediates described above and by following the general procedure described for the synthesis of Compound 1001.

Compound 1012: 1,1,1-trifluoro-2-methylpropan-2-yl ((2R,6S,7S,9R,13aS,14aR,16aS,Z)-7-ethyl-2-(7-fluoro-6-methoxyisoquinolin-1-yl)oxy)-14a-(((1-(fluoromethyl)cyclopropyl)sulfonyl)carbamoyl)-9-methyl-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H-NMR (500 MHz, DMSO-$d_6$) δ 11.66-10.74 (m, 1H), 9.12-8.58 (m, 1H), 7.98 (d, J=5.8 Hz, 1H), 7.93 (d, J=9.2 Hz, 1H), 7.69 (d, J=11.3 Hz, 1H), 7.55 (d, J=8.2 Hz, 1H), 7.36 (d, J=5.8 Hz, 1H), 5.82 (br. s., 1H), 5.51 (d, J=7.3 Hz, 1H), 5.15 (br. s., 1H), 4.87-4.68 (m, 1H), 4.61 (d, J=10.4 Hz, 1H), 4.41 (t, J=8.1 Hz, 1H), 4.29 (d, J=11.0 Hz, 1H), 4.16 (t, J=9.6 Hz, 1H), 4.00-3.98 (m, 3H), 3.97-3.94 (m, 1H), 3.85 (d, J=9.2 Hz, 1H), 2.55 (br. s., 1H), 2.39 (br. s., 1H), 2.31 (t, J=9.5 Hz, 1H), 1.81 (br. s., 1H), 1.70 (br. s., 1H), 1.62 (br. s., 1H), 1.52 (d, J=7.9 Hz, 2H), 1.48-1.46 (m, 1H), 1.43 (s, 4H), 1.39 (d, J=8.5 Hz, 1H), 1.31 (d, J=12.2 Hz, 2H), 1.23 (br. s., 2H), 1.15 (s, 3H), 1.07 (d, J=6.1 Hz, 3H), 0.81 (t, J=7.3 Hz, 4H); MS: MS m/z 874.8 (M$^+$+1).

Preparation of Compound 1013

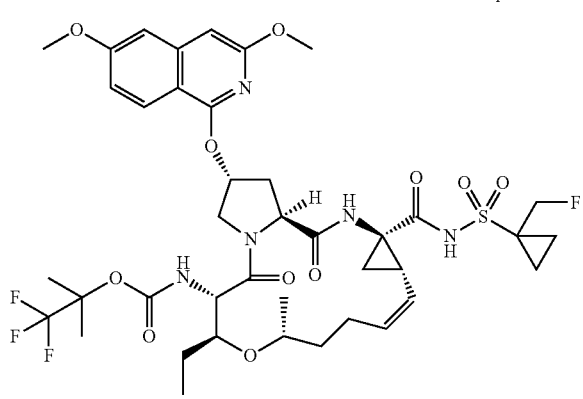

Compound 1013

Compound 1013 was prepared using 1-fluoro-3,6-dimethoxyisoquinoline and the intermediates described above and by following the general procedure described for the synthesis of Compound 1001.

Compound 1013: 1,1,1-trifluoro-2-methylpropan-2-yl ((2R,6S,7S,9R,13aS,14aR,16aS,Z)-2-((3,6-dimethoxyisoquinolin-1-yl)oxy)-7-ethyl-14a-(((1-(fluoromethyl)cyclopropyl)sulfonyl)carbamoyl)-9-methyl-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H-NMR (500 MHz, DMSO-d$_6$) δ 11.32 (s, 1H), 9.11-8.59 (m, 1H), 7.92 (d, J=9.2 Hz, 1H), 7.85 (d, J=9.2 Hz, 1H), 7.14 (s, 1H), 6.89 (d, J=9.2 Hz, 1H), 6.61 (s, 1H), 5.77 (br. s., 1H), 5.51 (d, J=7.6 Hz, 1H), 4.86-4.67 (m, 1H), 4.65-4.55 (m, 1H), 4.40 (t, J=8.2 Hz, 1H), 4.29 (d, J=11.0 Hz, 1H), 4.20-4.14 (m, 1H), 4.01 (d, J=8.5 Hz, 1H), 3.86 (s, 4H), 3.89 (s, 4H), 2.55 (br. s., 1H), 2.34 (d, J=9.2 Hz, 2H), 1.83 (br. s., 1H), 1.69 (br. s., 1H), 1.52 (br. s., 3H), 1.45 (s, 4H), 1.43-1.34 (m, 2H), 1.29 (br. s., 2H), 1.23 (br. s., 1H), 1.15 (s, 3H), 1.06 (d, J=5.8 Hz, 4H), 0.82 (t, J=7.3 Hz, 4H); MS: MS m/z 886.9 (M$^+$+1).

Preparation of Compound 1014

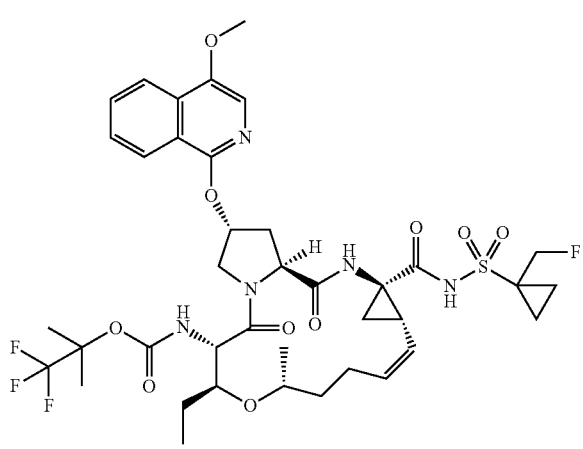

Compound 1014

Compound 1014 was prepared using 1-fluoro-4-methoxyisoquinoline and the intermediates described above and by following the general procedure described for the synthesis of Compound 1001.

Compound 1014: 1,1,1-trifluoro-2-methylpropan-2-yl ((2R,6S,7S,9R,13aS,14aR,16aS,Z)-7-ethyl-14a-(((1-(fluoromethyl)cyclopropyl)sulfonyl)carbamoyl)-2-(4-methoxyisoquinolin-1-yl)oxy)-9-methyl-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H-NMR (500 MHz, DMSO-d$_6$) δ 11.37 (s, 1H), 8.94 (d, J=11.6 Hz, 1H), 8.05 (d, J=8.5 Hz, 2H), 7.89 (d, J=9.5 Hz, 1H), 7.79 (t, J=7.8 Hz, 1H), 7.66-7.60 (m, 2H), 5.78 (br. s., 1H), 5.51 (br. s., 1H), 4.87-4.67 (m, 1H), 4.52 (br. s., 1H), 4.42 (t, J=7.9 Hz, 1H), 4.30 (d, J=9.5 Hz, 1H), 4.15 (t, J=9.6 Hz, 1H), 3.99 (br. s., 1H), 3.96 (s, 4H), 3.85 (br. s., 1H), 2.55 (br. s., 1H), 2.31 (br. s., 1H), 1.83 (br. s., 1H), 1.68 (br. s., 1H), 1.52 (d, J=8.5 Hz, 3H), 1.49-1.44 (m, 2H), 1.39 (s, 4H), 1.37-1.34 (m, 1H), 1.30 (br. s., 1H), 1.25 (br. s., 2H), 1.07 (d, J=5.8 Hz, 4H), 1.02 (s, 3H), 0.81 (t, J=7.3 Hz, 4H); MS: MS m/z 856.8 (M$^+$+1).

Preparation of Compound 1015

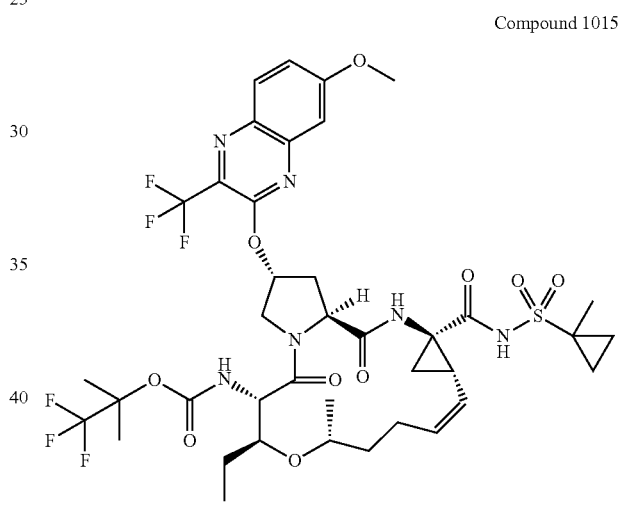

Compound 1015

Compound 1015 was prepared using 3-chloro-6-methoxy-2-(trifluoromethyl)quinoxaline and the intermediates described above and by following the general procedure described for the synthesis of Compound 1001.

Compound 1015: 1,1,1-trifluoro-2-methylpropan-2-yl ((2R,6S,7S,9R,13aS,14aR,16aS,Z)-7-ethyl-2-((7-methoxy-3-(trifluoromethyl)quinoxalin-2-yl)oxy)-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H-NMR (500 MHz, DMSO-d$_6$) δ 8.88 (br. s., 1H), 7.76 (d, J=9.2 Hz, 1H), 7.57 (d, J=9.5 Hz, 1H), 7.16 (dd, J=9.2, 2.4 Hz, 1H), 7.09 (s, 1H), 5.69 (br. s., 1H), 5.32-5.24 (m, 1H), 4.81 (br. s., 1H), 4.15 (t, J=8.4 Hz, 1H), 4.04 (d, J=11.6 Hz, 1H), 3.82-3.76 (m, 1H), 3.74-3.69 (m, 3H), 3.58 (d, J=9.8 Hz, 1H), 3.23-3.16 (m, 1H), 2.39 (br. s., 1H), 2.33 (dd, J=13.4, 6.7 Hz, 1H), 2.21-2.05 (m, 2H), 1.58 (br. s., 1H), 1.40 (br. s., 1H), 1.31 (d, J=10.1 Hz, 3H), 1.22 (br. s., 1H), 1.14 (s, 3H), 1.12-1.05 (m, 2H), 1.02 (s, 5H), 0.98 (br. s., 1H), 0.83-0.77 (m, 6H), 0.61 (br. s., 1H), 0.56 (d, J=7.0 Hz, 1H), 0.49 (t, J=7.3 Hz, 3H); MS: MS m/z 907.7 (M$^+$+1).

Preparation of Compound 1016

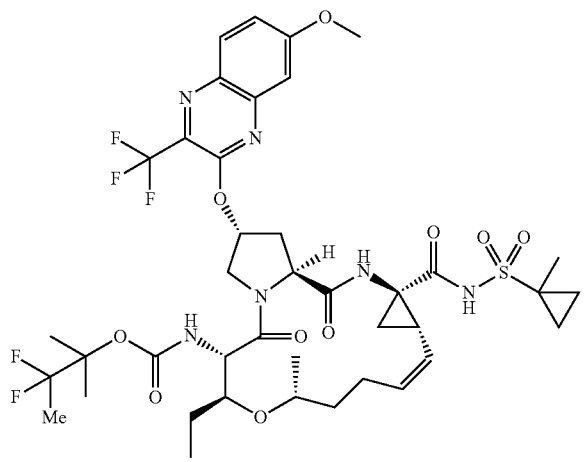

Compound 1016

Compound 1016 was prepared using 3-chloro-6-methoxy-2-(trifluoromethyl)quinoxaline and the intermediates described above and by following the general procedure described for the synthesis of Compound 1001.

Compound 1016: 3,3-difluoro-2-methylbutan-2-yl ((2R,6S,7S,9R,13aS,14aR,16aS,Z)-7-ethyl-2-((7-methoxy-3-(trifluoromethyl)quinoxalin-2-yl)oxy)-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H-NMR (500 MHz, DMSO-$d_6$) δ 11.16 (br. s., 1H), 9.16 (br. s., 1H), 8.01 (d, J=9.2 Hz, 1H), 7.63 (d, J=9.8 Hz, 1H), 7.41 (dd, J=9.3, 2.6 Hz, 1H), 7.34 (d, J=2.7 Hz, 1H), 5.94 (br. s., 1H), 5.56-5.50 (m, 1H), 5.03 (br. s., 1H), 4.44-4.38 (m, 1H), 4.31 (d, J=11.6 Hz, 1H), 4.10-4.01 (m, 2H), 4.01-3.94 (m, 4H), 3.81 (d, J=11.0 Hz, 1H), 2.73 (s, 1H), 2.58 (dd, J=13.7, 6.7 Hz, 1H), 2.40-2.27 (m, 1H), 1.84 (br. s., 1H), 1.67 (d, J=7.6 Hz, 1H), 1.62-1.56 (m, 2H), 1.51 (t, J=19.7 Hz, 3H), 1.40 (s, 3H), 1.38-1.21 (m, 5H), 1.16 (s, 3H), 1.05 (d, J=6.1 Hz, 3H), 0.90 (s, 6H), 0.75 (t, J=7.3 Hz, 3H); MS: MS m/z 903.9 (M$^+$+1).

Preparation of Compound 1017

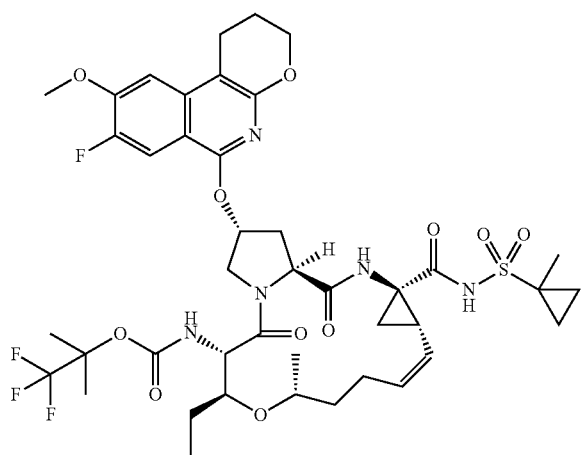

Compound 1017

Compound 1017 was prepared using 6,8-difluoro-9-methoxy-2,3-dihydro-1H-pyrano[2,3-c]isoquinoline and the intermediates described above and by following the general procedure described for the synthesis of Compound 1001.

Compound 1017: 1,1,1-trifluoro-2-methylpropan-2-yl ((2R,6S,7S,9R,13aS,14aR,16aS,Z)-7-ethyl-2-((8-fluoro-9-methoxy-2,3-dihydro-1H-pyrano[2,3-c]isoquinolin-6-yl)oxy)-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H-NMR (500 MHz, DMSO-$d_6$) δ 11.08 (s, 1H), 8.89 (br. s., 1H), 7.93 (d, J=9.2 Hz, 1H), 7.59 (d, J=11.6 Hz, 1H), 7.17 (d, J=8.2 Hz, 1H), 5.69 (br. s., 1H), 5.55-5.49 (m, 1H), 5.13 (br. s., 1H), 4.44-4.37 (m, 1H), 4.31-4.22 (m, 3H), 4.15 (t, J=9.5 Hz, 1H), 3.99 (s, 3H), 3.95-3.90 (m, 1H), 3.85 (d, J=9.2 Hz, 1H), 2.95-2.87 (m, 1H), 2.85 (br. s., 2H), 2.61-2.53 (m, 1H), 2.41 (br. s., 1H), 2.26 (t, J=9.5 Hz, 1H), 2.07-1.98 (m, 2H), 1.82 (br. s., 1H), 1.69 (br. s., 1H), 1.65-1.51 (m, 3H), 1.44 (s, 3H), 1.39 (s, 5H), 1.31 (br. s., 1H), 1.26 (br. s., 2H), 1.19-1.12 (m, 4H), 1.06 (d, J=6.1 Hz, 3H), 0.81 (t, J=7.3 Hz, 4H); MS: MS m/z 912.8 (M$^+$+1).

Preparation of Compound 1018

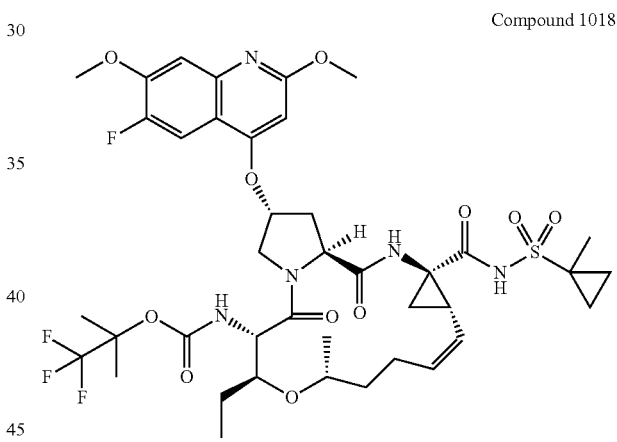

Compound 1018

Compound 1018 was prepared using 4,6-difluoro-2,7-dimethoxyquinoline and the intermediates described above and by following the general procedure described for the synthesis of Compound 1001.

Compound 1018: 1,1,1-trifluoro-2-methylpropan-2-yl ((2R,6S,7S,9R,13aS,14aR,16aS,Z)-7-ethyl-2-((6-fluoro-2,7-dimethoxyquinolin-4-yl)oxy)-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H-NMR (500 MHz, DMSO-$d_6$) δ 11.09 (br. s., 1H), 9.04 (br. s., 1H), 7.85 (d, J=9.8 Hz, 1H), 7.51 (d, J=11.9 Hz, 1H), 7.27 (d, J=7.6 Hz, 1H), 6.44 (br. s., 1H), 5.52 (br. s., 1H), 5.41 (br. s., 1H), 5.02 (br. s., 1H), 4.38 (br. s., 1H), 4.33 (d, J=10.7 Hz, 2H), 4.13 (br. s., 2H), 3.92 (br. s., 6H), 2.66 (br. s., 1H), 2.56 (br. s., 2H), 2.39 (br. s., 1H), 2.22 (br. s., 1H), 1.82 (br. s., 1H), 1.69 (br. s., 1H), 1.57 (br. s., 1H), 1.51 (br. s., 2H), 1.41-1.35 (m, 8H), 1.26 (br. s., 3H), 1.09-1.01 (m, 6H), 0.86 (br. s., 2H), 0.78 (br. s., 3H); MS: MS m/z 886.9 (M$^+$+1).

Preparation of Compound 1019

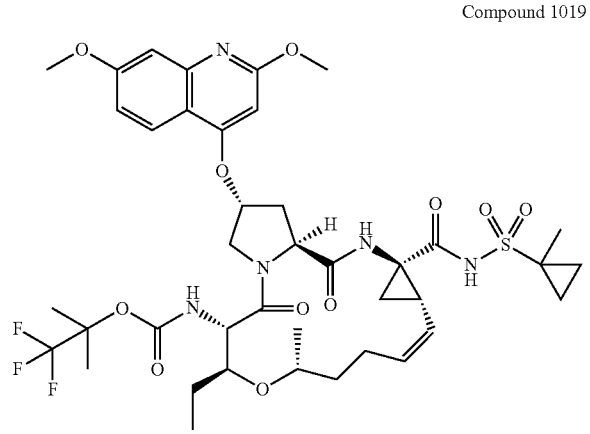 [SMILES: CC[C@@H]1O[C@H](C)CC/C=C\[C@@H]2C[C@@]2(C(=O)NS(=O)(=O)C2(C)CC2)NC(=O)[C@@H]2C[C@@H](Oc3cc(OC)nc4cc(OC)ccc34)CN2C(=O)[C@H]1NC(=O)OC(C)(C)C(F)(F)F]

Compound 1019

Compound 1019 was prepared using 4-fluoro-2,7-dimethoxyquinoline and the intermediates described above and by following the general procedure described for the synthesis of Compound 1001.

Compound 1019: 1,1,1-trifluoro-2-methylpropan-2-yl ((2R,6S,7S,9R,13aS,14aR,16aS,Z)-2-((2,7-dimethoxyquinolin-4-yl)oxy)-7-ethyl-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate.

$^1$H-NMR (500 MHz, DMSO-$d_6$) δ 11.12 (br. s., 1H), 9.08 (br. s., 1H), 7.92 (d, J=9.5 Hz, 1H), 7.79 (d, J=8.9 Hz, 1H), 7.11 (br. s., 1H), 6.91 (d, J=8.2 Hz, 1H), 6.39 (s, 1H), 5.54 (d, J=7.9 Hz, 1H), 5.42 (br. s., 1H), 5.02 (br. s., 1H), 4.36 (d, J=10.7 Hz, 2H), 4.15 (t, J=9.0 Hz, 1H), 3.94 (s, 4H), 3.85 (br. s., 4H), 2.71 (d, J=8.9 Hz, 1H), 2.59 (br. s., 1H), 2.41 (br. s., 1H), 2.23 (br. s., 1H), 1.84 (br. s., 1H), 1.70 (br. s., 1H), 1.59 (br. s., 1H), 1.52 (br. s., 2H), 1.40 (s, 4H), 1.42 (s, 3H), 1.37-1.20 (m, 4H), 1.10 (br. s., 3H), 1.06 (d, J=5.5 Hz, 3H), 0.89 (br. s., 2H), 0.80 (t, J=6.9 Hz, 3H); MS: MS m/z 868.5 (M$^+$+1).

Preparation of Compound 1020

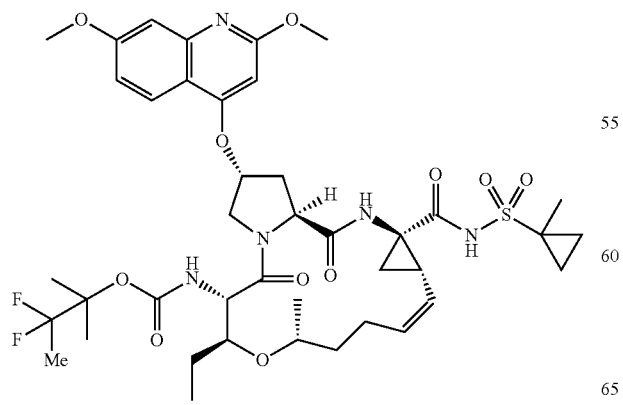

Compound 1020

Compound 1020 was prepared using 4-fluoro-2,7-dimethoxyquinoline and the intermediates described above and by following the general procedure described for the synthesis of Compound 1001.

Compound 1020: 3,3-difluoro-2-methylbutan-2-yl ((2R,6S,7S,9R,13aS,14aR,16aS,Z)-2-((2,7-dimethoxyquinolin-4-yl)oxy)-7-ethyl-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate.

$^1$H-NMR (500 MHz, DMSO-$d_6$) δ 11.12 (br. s., 1H), 9.05 (br. s., 1H), 7.79 (d, J=9.2 Hz, 1H), 7.72 (d, J=9.2 Hz, 1H), 7.12 (br. s., 1H), 6.91 (d, J=8.9 Hz, 1H), 6.39 (br. s., 1H), 5.53 (br. s., 1H), 5.42 (br. s., 1H), 5.03 (br. s., 1H), 4.38 (br. s., 2H), 4.17 (t, J=9.9 Hz, 1H), 3.94 (s, 4H), 3.86 (s, 5H), 2.73 (br. s., 1H), 2.58 (br. s., 1H), 2.24 (br. s., 1H), 1.86 (br. s., 1H), 1.71 (br. s., 1H), 1.59 (br. s., 1H), 1.56-1.47 (m, 4H), 1.46 (br. s., 2H), 1.40 (br. s., 4H), 1.33 (br. s., 3H), 1.23 (br. s., 3H), 1.07 (d, J=5.5 Hz, 3H), 1.03 (br. s., 3H), 0.89 (br. s., 2H), 0.82 (t, J=7.2 Hz, 3H); MS: MS m/z 864.7 (M$^+$+1).

Preparation of intermediate 7-chloro-2,3-dihydro-[1,4]dioxino[2,3-f]isoquinoline

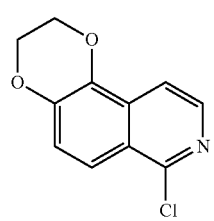 [SMILES: Clc1nccc2c3c(ccc12)OCCO3]

Scheme

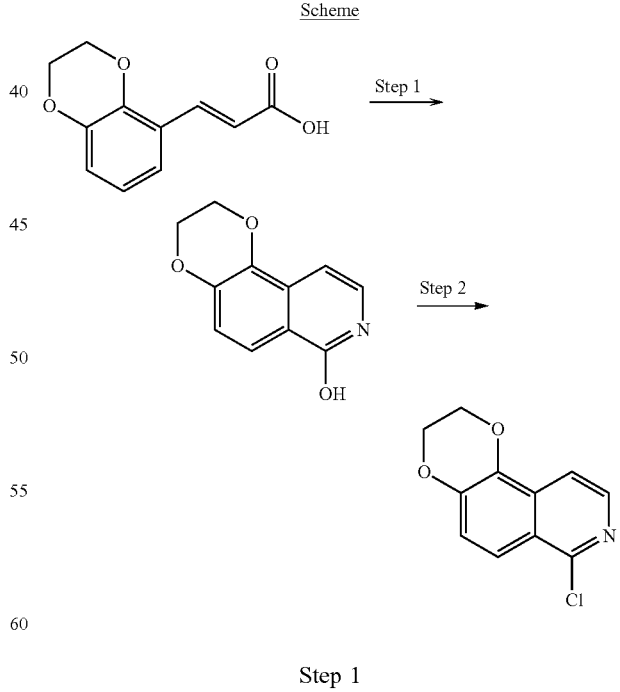

Step 1

(E)-3-(2,3-dihydrobenzo[b][1,4]dioxin-5-yl)acrylic acid (5 g, 24.25 mmol), diphenylphosphoryl azide (4.96 mL, 23.04 mmol), and Et$_3$N (6.76 mL, 48.5 mmol) were dissolved in benzene and stirred for 16 h. The solution was concentrated under vacuum and the residue was purified by silica gel chromatography using 20% EtOAc/hexanes to give 4.5 g of (E)-3-(2,3-dihydrobenzo[b][1,4]dioxin-5-yl) acryloyl azide as a yellow solid, which was taken into PhCH$_2$Ph (50 mL). The resulting solution was slowly heated to 80° C. for 1 h and then to reflux for 3 h. After cooling to rt, the solid was collected washing with benzene to give 3.5 g of the desired product 2,3-dihydro-[1,4]dioxino[2,3-f] isoquinolin-7-ol as a solid. $^1$H NMR (400 MHz, CD$_3$OD) δ ppm 4.37 (m, 4H), 6.83 (d, J=7.09 Hz, 1H), 7.02 (d, J=8.80 Hz, 1H), 7.12 (d, J=7.34 Hz, 1H), 7.79 (d, J=8.80 Hz, 1H); MS: (M+H)$^+$ 204.

Step 2

A solution of 2,3-dihydro-[1,4]dioxino[2,3-f]isoquinolin-7-ol (5 g, 24.61 mmol) in POCl$_3$ (50 mL) was refluxed for 14 h. After Concentration, the residue was taken into the mixture of DCM and 4N NaOH solution. The organic phase was collected and dried over sodium sulfate, filtered, then concentrated under vacuum. The crude material was purified by silica gel chromatography using 20% EtOAc/Hexanes as eluent to give 4 g of the desired product 7-chloro-2,3-dihydro-[1,4]dioxino[2,3-f]isoquinoline as a solid. $^1$H NMR (400 Hz, CDCl$_3$) δ ppm 4.42 (m, 4H), 7.24 (d, J=9.05 Hz, 1H), 7.77 (d, J=5.87 Hz, 1H), 7.84 (d, J=9.05 Hz, 1H), 8.18 (d, J=5.87 Hz, 1H); MS: (M+H)$^+$ 222.

Preparation of intermediate 1-chloro-3-(5-isopropoxypyridin-2-yl)-6-methoxyisoquinoline

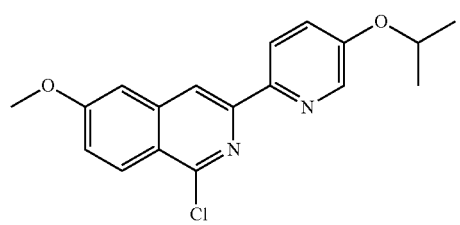 [SMILES: COc1ccc2c(Cl)nc(-c3ccc(OC(C)C)cn3)cc2c1]

Step 1

To a solution of N,N-diethyl-4-methoxy-2-methylbenzamide (4.43 g, 20 mmol) in THF (100 ml) at −78° C., tert-butyllithium 1.7 M in pentane (17.65 ml, 30.0 mmol) solution was added dropwise. The reaction mixture was stirred for 0.5 h before addition of 5-isopropoxypicolinonitrile (3.41 g, 21.00 mmol) in THF (2 mL). The resulting solution was warmed to rt and stirred for 16 h. The reaction mixture was quenched with water, neutralized with 1 N HCl. The precipitated solid (5 g) was collected and washed with water to give 4 g of the product 3-(5-isopropoxypyridin-2-yl)-6-methoxyisoquinolin-1-ol as a white solid. MS: MS m/z 311.11 (M$^+$+1).

Step 2

A solution of 3-(5-isopropoxypyridin-2-yl)-6-methoxyisoquinolin-1-ol (4 g, 12.89 mmol) in POCl$_3$ (20 mL) was refluxed for 2 hs. After concentration, the residue was taken into the mixture of DCM and 4N NaOH solution. The organic phase was collected and dried over sodium sulfate, filtered, then concentrated under vacuum. The crude material was purified by silica gel chromatography using CH$_2$Cl$_2$ as eluent to give 3.4 g of the desired product 1-chloro-3-(5-isopropoxypyridin-2-yl)-6-methoxyisoquinoline as a solid. $^1$H NMR (400 MHz, CHLOROFORM-d) δ ppm 8.49 (s, 1H), 8.39 (d, J=8.8 Hz, 1H), 8.33 (d, J=2.5 Hz, 1H), 8.19 (d, J=9.1 Hz, 1H), 7.29 (dd, J=8.8, 3.0 Hz, 1H), 7.23 (dd, J=6.8, 2.5 Hz, 1H), 7.16 (d, J=2.3 Hz, 1H), 4.65 (spt, J=6.0 Hz, 1H), 3.94 (s, 3H), 1.38 (d, J=6.3 Hz, 6H).

Preparation of 1-chloro-7-fluoro-4-methoxyisoquinoline

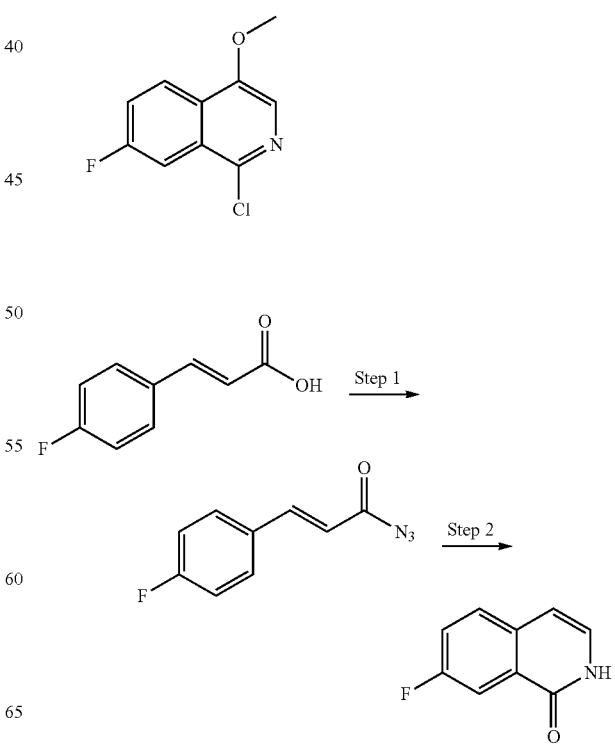

Scheme

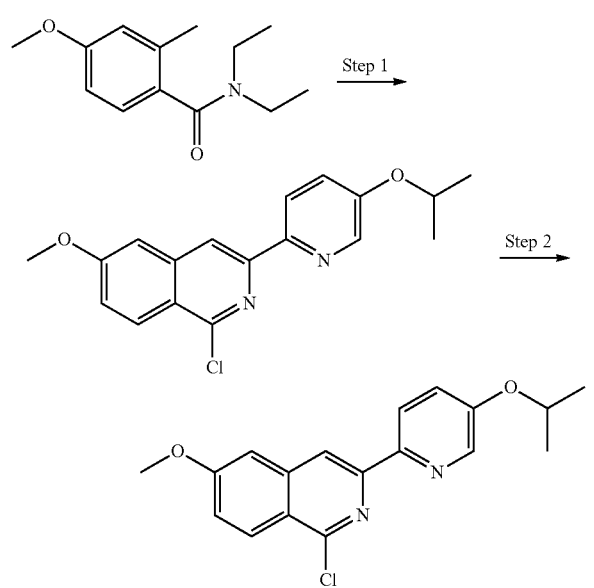

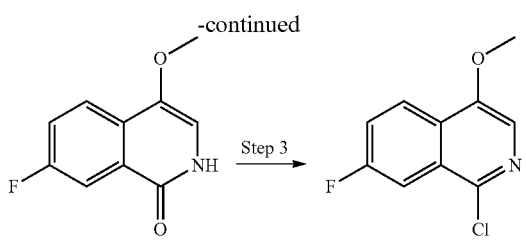

Step 1

To a solution of (E)-3-(4-fluorophenyl) acrylic acid (25 g, 150 mmol) in benzene (120 mL) was added triethylamine (30.5 g, 301 mmol) followed by DPPA (41.4 g, 150 mmol) at room temperature. The reaction mass was stirred at the same temperature for 18 h. The solvent was evaporated under reduced pressure and the residue was diluted with water and extracted with dichloromethane. The organic layer was dried over anhydrous sodium sulfate, filtered and evaporated to get crude compound. The crude compound was purified by conventional column chromatography (silica gel, 60-120 mesh) using 10% ethyl acetate in pet ether as mobile phase to get the desired compound as a white solid (26 g, 90%). $^1$H NMR (400 MHz, CDCl$_3$): δ ppm 7.73-7.69 (d, J=16 Hz, 1H), 7.55-7.51 (m, 2H), 7.11-7.07 (m, 2H), 6.36-6.32 (d, J=16 Hz, 1H).

Step 2

To a hot (125° C.) diphenyl ether (25 ml) was added (E)-3-(4-fluorophenyl) acryloyl azide (5 g, 26.2 mmol) portion wise. The reaction was heated at 250° C. for 4 h. The reaction mass was cooled to room temperature and diluted with pet ether. The precipitated solid was filtered washed with pet ether to get crude compound (2.45 g, 57%). The crude compound was taken to the next step without further purification. $^1$H NMR (400 MHz, CD$_3$OD): δ ppm 7.96-7.93 (m, 1H), 7.76-7.72 (m, 1H), 7.56-7.51 (m, 1H), 7.18-7.16 (m, 1H), 6.72-6.70 (m, 1H); MS: MS m/z 164.1 (M$^+$+1).

Step 3

To a solution of 7-fluoroisoquinolin-1(2H)-one (11 g, 67.4 mmol) in methanol was added iodozobenzenediacetate (21.7 g, 67.4 mmol) followed by methane sulphonic acid (7.78 g, 81 mmol) at room temperature. The reaction mass was heated at reflux for 3 h. The solvent was evaporated and the residue was diluted with cold water. The precipitated solid was filtered and washed with water to get crude compound (11 g, 84%) as light red color solid. $^1$H NMR (400 MHz, CD$_3$OD): δ ppm 8.06-8.04 (m, 1H), 7.96-7.93 (m, 1H), 7.62-7.54 (m, 2H), 6.74 (s, 1H), 3.89 (s, 3H); MS: MS m/z 194.1 (M$^+$+1).

Step 4

A solution of 7-fluoro-4-methoxyisoquinolin-1(2H)-one (11 g, 56.9 mmol) in POCl$_3$ (100 ml) was refluxed for 18 h. The solvent was evaporated under reduced pressure and the residue was diluted with cold water. The aqueous solution was basified by solid sodium carbonate and extracted with ethyl acetate. The combine organic layer was dried over anhydrous sodium sulfate, filtered and evaporated under reduced pressure to get crude compound. The crude compound was purified by silica gel chromatography (20% ethyl acetate in pet ether) to get desired compound (2.9 g, 24%) as off-white solid. $^1$H NMR (400 MHz, CDCl$_3$): δ ppm 8.36-8.32 (m, 1H), 7.93-7.90 (m, 1H), 7.88 (s, 1H), 7.70-7.65 (m, 1H), 4.11 (s, 3H); MS: MS m/z 212.1 (M$^+$+1).

Preparation of 1,7-difluoro-4-methoxyisoquinoline

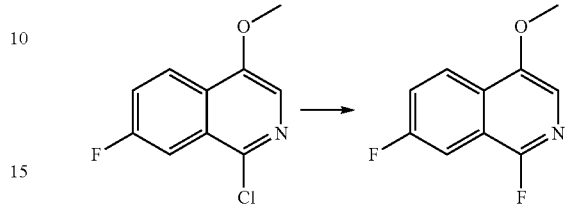

To a solution of 1-chloro-7-fluoro-4-methoxyisoquinoline (3.7 g, 17.48 mmol) in DMSO was added cesium fluoride (10.26 g, 69.9 mmol) at room temperature. The reaction vessel (pressure tube) was sealed and heated at 145° C. for 18 h. The reaction mass was diluted with water and extracted with ethyl acetate. The combined organic layer was dried over anhydrous Na$_2$SO$_4$ and evaporated under reduced pressure to get crude compound. The crude compound was purified by silica gel chromatography to get desired compound (1.7 g, 49%) as white solid. $^1$H NMR (400 MHz, CD$_3$OD): δ ppm 8.20-8.18 (m, 1H), 7.69-7.66 (m, 1H), 7.54-7.47 (m, 1H), 7.46 (s, 1H), 4.04 (s, 3H); $^{19}$F NMR: δ ppm 109.65 (1F), −78.53 (1F); MS: MS m/z 196.1 (M$^+$+1)

Preparation of 1,7-difluoro-5-methoxyisoquinoline

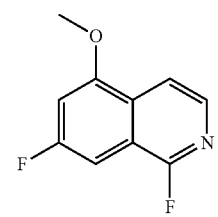

Scheme

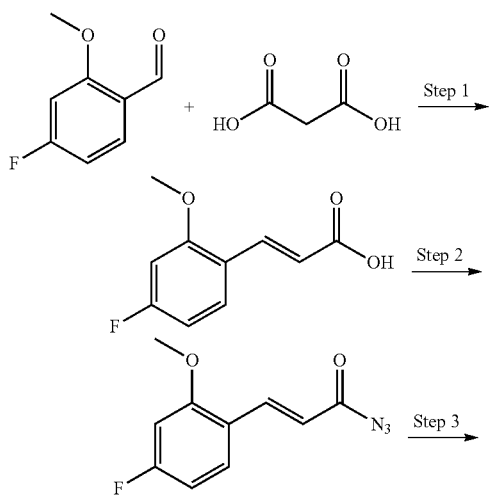

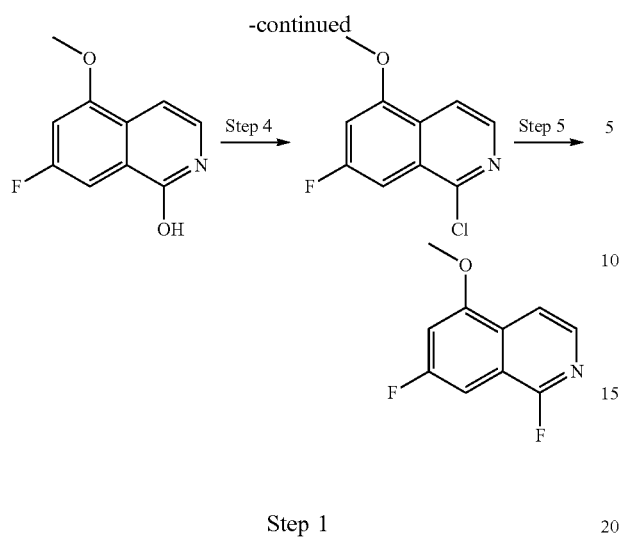

for 4 h. The reaction was diluted with EtOAc and washed with water, and brine. The organic phase was collected, dried over sodium sulfate, and concentrated under vacuum to give 1,7-difluoro-5-methoxyisoquinoline (340 mg, 105% yield) which was not purified further. MS m/z 196.1 (M$^+$+1).

Preparation of 1-fluoro-4-ethoxyisoquinoline

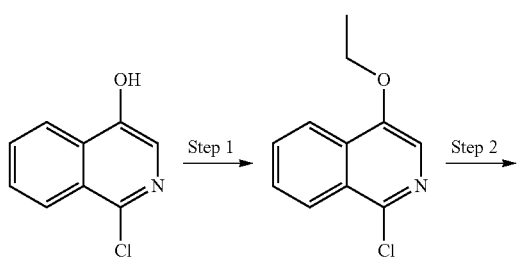

Step 1

A solution of 4-fluoro-2-methoxybenzaldehyde (1.0 g, 6.49 mmol) and malonic acid (1.350 g, 12.98 mmol) in pyridine (10 mL) was refluxed for 16 h. After concentration the residue was taken into water. The solid was filtered, washed with water, then dried to give (E)-3-(4-fluoro-2-methoxyphenyl)acrylic acid (1.22 g, 96% yield). $^1$H NMR (400 MHz, CHLOROFORM-d) δ ppm 8.03 (d, J=16.1 Hz, 1H), 7.53 (dd, J=8.5, 6.8 Hz, 1H), 6.75-6.65 (m, 2H), 6.52 (d, J=16.1 Hz, 1H), 3.92 (s, 3H).

Step 2

(E)-3-(4-fluoro-2-methoxyphenyl)acrylic acid (1.22 g, 6.22 mmol), diphenylphosphinyl azide (1.273 mL, 5.91 mmol), and Et3N (1.734 mL, 12.44 mmol) were dissolved in benzene and stirred for 16 h. The solution was concentrated under vacuum and the residue was purified by silica gel chromatography using 20% EtOAc/hexanes to give (E)-3-(4-fluoro-2-methoxyphenyl)acryloyl azide (1.0 g, 73% yield).

Step 3

A mixture of (E)-3-(4-fluoro-2-methoxyphenyl)acryloyl azide (1 g, 4.52 mmol) in PhCH$_2$Ph (5 mL) was slowly heated to 80° C. for 1 h and then to reflux for 3 h. After cooling to RT, the solid was collected and washed with benzene to give 7-fluoro-5-methoxyisoquinolin-1-ol (383 mg, 46% yield). MS m/z 194.2 (M$^+$+1).

Step 4

A solution of 7-fluoro-5-methoxyisoquinolin-1-ol (383 mg, 1.983 mmol) in POCl$_3$ (2772 μl, 29.7 mmol) was refluxed (90° C.) for 4 h. The reaction mixture was concentrated. The residue was dissolved in DCM and the pH was adjusted to 7 with 4N NaOH. The organic phase was collected and dried over sodium sulfate, filtered, then concentrated under vacuum to give 1-chloro-7-fluoro-5-methoxyisoquinoline (399 mg, 95% yield).

Step 5

To a solution of 1-chloro-7-fluoro-5-methoxyisoquinoline (350 mg, 1.654 mmol) in DMSO (3 mL), was added CsF (502 mg, 3.31 mmol) and the mixture was heated to 140° C.

Step 1

To a solution of 1-chloroisoquinolin-4-ol (1.0 g, 5.5 mmol) in acetonitrile (10 mL) was added K$_2$CO$_3$ (2.3 g, 16.7 mmol) followed by ethyl iodide (0.87 ml, 11.0 mmol) at room temperature. The reaction mixture was stirred at room temperature for overnight. The solvent was evaporated under reduced pressure and the residue was diluted with water and extracted with ethyl acetate. The combined organic layer was dried over anhydrous Na$_2$SO$_4$ and evaporated under reduced pressure to get crude compound. The crude compound was purified by silica gel chromatography to get 1-chloro-4-ethoxyisoquinoline (0.7 g, 62%) as off-white solid. $^1$H NMR (400 MHz, CD$_3$OD): δ ppm 8.26-8.24 (m, 2H), 7.79 (s, 1H), 7.76-7.26 (m, 2H), 4.29-4.24 (q, J=6.8 Hz, 2H), 1.58-1.54 (t, J=6.8 Hz, 3H); MS: MS m/z 207.7 (M$^+$+1).

Step 2

To a solution of 1-chloro-4-ethoxyisoquinolin (4.8 g, 23.12 mmol) in DMSO was added cesium fluoride (6.9 g, 46.24 mmol) at room temperature. The reaction vessel (pressure tube) was sealed and heated at 145° C. for 18 h. The reaction mass was diluted with water and extracted with ethyl acetate. The organic layer was dried over anhydrous Na$_2$SO$_4$ and evaporated under reduced pressure to get crude compound. The crude compound was purified by silica gel chromatography to get desired compound (2.6 g, 58.8%) as white solid. MS: MS m/z 192.3 (M$^+$+1).

Preparation of 6-chloro-2,3-dihydro-1H-pyrano[2,3-c]isoquinoline

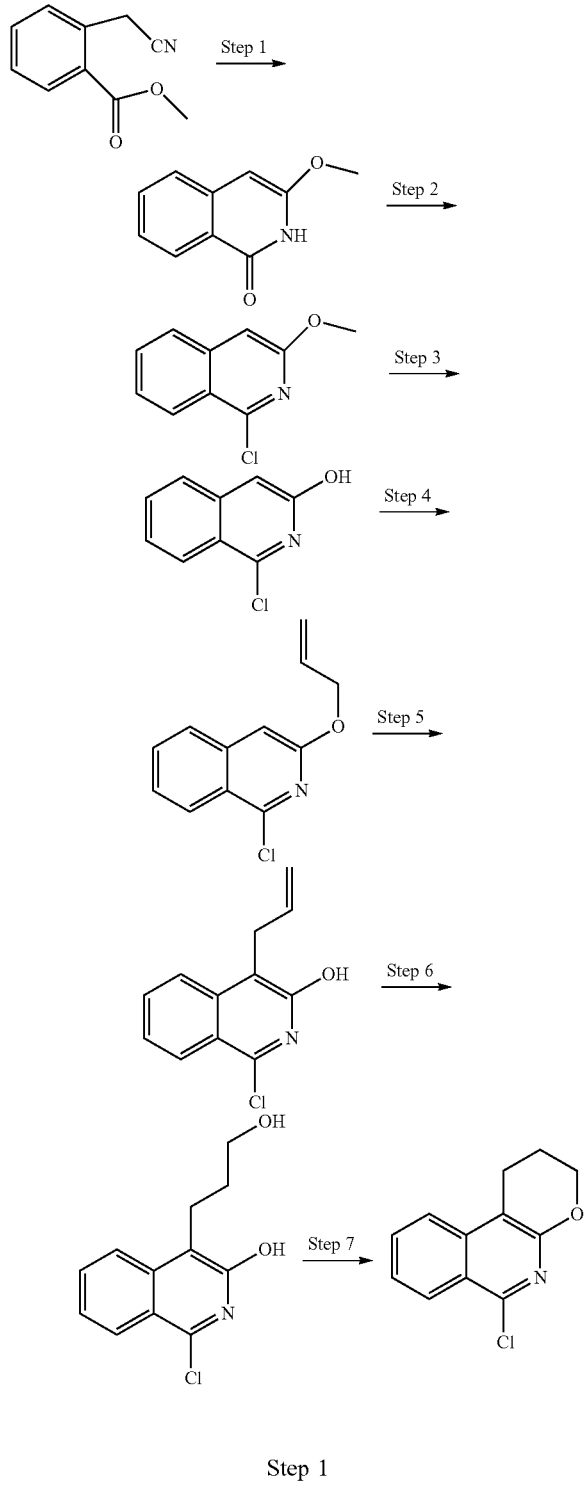

Step 1

A mixture of methyl 2-(cyanomethyl)benzoate (3.50 g, 20 mmol) and sodium methoxide (10 mL, 25% wt in methanol) in 35 mL MeOH was heated to reflux under nitrogen for 3 h. While still hot, the solution was acidified with 1N HCl solution until the green solution turned to yellow color and a lot of white solid precipitated out. After cooling, the precipitated product was collected by filtration, washed with water and dried to yield the desired product 3-methoxyisoquinolin-1(2H)-one as a white solid (2.8 g, 80%). MS: MS m/z 176.1 (M$^+$+1).

Step 2

3-methoxyisoquinolin-1(2H)-one (2.8 g, 16.0 mmol) in POCl$_3$ (10 mL) was heated to reflux for 3 h then evaporated in vacuo. The residue was poured into iced NaHCO$_3$ solution (50 mL). The product was extracted with EtOAc for 2 times. The organic layer was washed with brine, dried over MgSO$_4$, filtered, evaporated. The residue was purified by flash chromatography with 20% then 40% of EtOAc/hexane to afford 1.36 g (44%) of the desired product 1-chloro-3-methoxyisoquinoline as a white solid. $^1$H NMR (400 MHz, CHLOROFORM-d) δ 8.29-8.16 (d, J=8.3 Hz, 1H), 7.72 (d, J=8.3 Hz, 1H), 7.63 (ddd, J=8.3, 6.8, 1.1 Hz, 1H), 7.47 (ddd, J=8.5, 7.0, 1.1 Hz, 1H), 6.98 (s, 1H), 4.05 (s, 3H); MS: MS m/z 194.0 (M$^+$+1).

Step 3

Dissolve 1-chloro-3-methoxyisoquinoline (850 mg, 4.39 mmol) in DCM (5 mL) and cool down the solution to −78° C. BBr$_3$ (17.6 mL, 1M, 17.6 mmol) in DCM solution was then added to the reaction. The reaction was warmed up to r.t slowly and run for 5 h. Cool down the reaction mixture to −78° C. and quench with 1N NaOH until PH=7. The product was extracted with EtOAc. EtOA$_C$ layer was washed with brine, dried and concentrated. The crude material 1-chloroisoquinolin-3-ol (800 mg, 100%) was used directly for the next step reaction. $^1$H NMR (400 MHz, CHLOROFORM-d) δ 8.23 (d, J=9.5 Hz, 1H), 7.73 (d, J=8.5 Hz, 1H), 7.66 (ddd, J=8.3, 6.8, 1.1 Hz, 1H), 7.47 (ddd, J=8.4, 6.9, 1.3 Hz, 1H), 7.04 (s, 1H).

Step 4

To a stirring solution of NaH (0.267 g, 6.68 mmol) in DMF (10 mL) at 0° C. was added 1-chloroisoquinolin-3-ol (0.80 g, 4.45 mmol). The mixture was stirred at 0° C. for 10 mins before the addition of allyl bromide (0.65 g, 5.35 mmol) dropwise. The reaction mixture was stirred at r.t for 1 h. The reaction mixture was diluted with ethyl acetate and then quenched with 1N HCl solution. The organic layer was washed with brine, dried over MgSO$_4$, filtered and evaporated to get the crude material. The material was purified by flash chromatography with 10%-20% of EtOAc/hexane to afford 3-(allyloxy)-1-chloroisoquinoline (670 mg, 69% yield) as a solid. MS: MS m/z 220.1 (M$^+$+1).

Step 5

3-(allyloxy)-1-chloroisoquinoline (670 mg, 3.05 mmol) was dissolved in diglyme (5 mL) and heated to 180° C. for 2 h. The reaction was cooled down to rt before adding EtOAc and water. Washed EtOAc layer with water then brine solution. The organic layer was then dried and concentrated. The residue was purified by flash chromatography with 20% of EtOAc/hexane to afford 4-allyl-1-chloroisoquinolin-3-ol (370 mg, 55%) as product. MS: MS m/z 220.1 (M$^+$ 1).

Step 6

To a stirred solution of 4-allyl-1-chloroisoquinolin-3-ol (370 mg, 1.68 mmol) in dry THF (5 mL) at room temperature was added 0.5 M in THF solution of 9-BBN (10.11 mL, 5.05 mmol) and the mixture was stirred for overnight. 3N NaOH (5.05 mL, 15.16 mmol) and H₂O₂ (1.56 mL, 16.84 mmol) were the added to the mixture. The mixture was stirred for 45 min before quenching with saturated NaCl solution. 1 N HCl was then added to the solution to adjust PH<7. The reaction was extracted with EtOAc. The organic layer was washed with brine, dried and concentrated to afford a yellow oil that was chromatographed using 20-40% EtOAc/hexane to obtain 1-chloro-4-(3-hydroxypropyl)isoquinolin-3-ol (300 mg, 75%) as product. MS: MS m/z 238.0 (M⁺+1).

Step 7

To a solution of triphenylphosphine (596 mg, 2.27 mmol) and 1-chloro-4-(3-hydroxypropyl)isoquinolin-3-ol (300 mg, 1.26 mmol) in THF (5 mL) at 0° C. was added diisoprpyl azodicarboxylate (0.50 mL, 2.52 mmol) dropwise. The resulting solution was stirred for 4 h at r.t. After concentration of solvent, the residue was purified by Biotage eluting with 0%-20% ethyl acetate in hexane to give the desired product 6-chloro-2,3-dihydro-1H-pyrano[2,3-c]isoquinoline (280 mg, 100%) as a white solid. ¹H NMR (400 MHz, CHLOROFORM-d) δ 8.25 (dd, J=17.3, 8.3 Hz, 1H), 7.84-7.76 (m, 1H), 7.74-7.68 (m, 1H), 7.56-7.46 (m, 1H), 4.42 (dd, J=5.6, 4.9 Hz, 2H), 3.05 (q, J=6.4 Hz, 2H), 2.27-2.03 (m, 2H); MS: MS m/z 220.0 (M⁺1).

Preparation of 6-chloro-9-methoxy-2,3-dihydro-1H-pyrano[2,3-c]isoquinoline

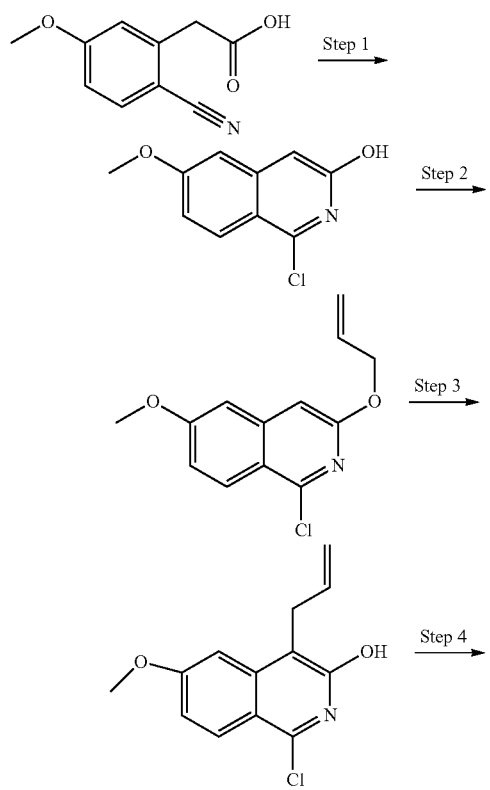

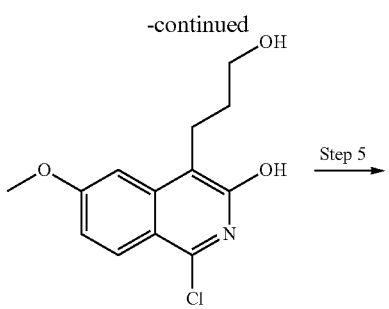

Step 5

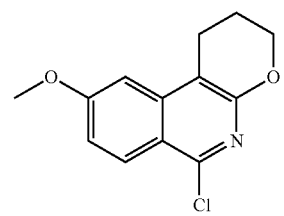

Step 1

2-(2-cyano-5-methoxyphenyl)acetic acid (3.8 g, 19.88 mmol), and SOCl₂ (20 mL, 274 mmol) were stirred in dichloromethane (25 mL) at RT. The suspension became a solution over 8 h. The reaction was stirred overnight. The volatile organics were removed under vacuum and the residue was taken up in DCM and filtered. The filtrate was concentrated and then dissolved in 4 N HCl in dioxane (30 mL) and transferred to a sealed vessel and heated to 60° C. for 3 h. The reaction was cooled and the solid was collected, washed with dioxane, and dried under vacuum to give the product 1-chloro-6-methoxyisoquinolin-3-ol (3.3 g, 70% yield). ¹H NMR (400 MHz, CHLOROFORM-d) δ 8.10 (d, J=9.6 Hz, 1H), 7.12 (dd, J=9.3, 2.5 Hz, 1H), 6.95 (s, 2H), 3.98 (s, 3H).

Step 2-5

6-chloro-9-methoxy-2,3-dihydro-1H-pyrano[2,3-c]isoquinoline was then prepared using the similar procedure described for synthesizing 6-chloro-2,3-dihydro-1H-pyrano[2,3-c]isoquinoline. 1-chloro-6-methoxyisoquinolin-3-ol was used as starting material in step 2 instead of 1-chloroisoquinolin-3-ol. ¹H NMR (400 MHz, CHLOROFORM-d) δ 8.16 (d, J=9.0 Hz, 1H), 7.10 (dd, J=9.3, 2.3 Hz, 1H), 6.96 (d, J=2.3 Hz, 1H), 4.46-4.29 (m, 2H), 3.98 (s, 3H), 2.97 (t, J=6.5 Hz, 2H), 2.19 (dd, J=5.9, 4.6 Hz, 2H); MS: MS m/z 250.0 (M⁺+1).

Preparation of intermediate 6-ethoxy-1,7-difluoroisoquinoline

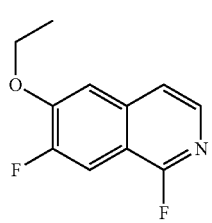

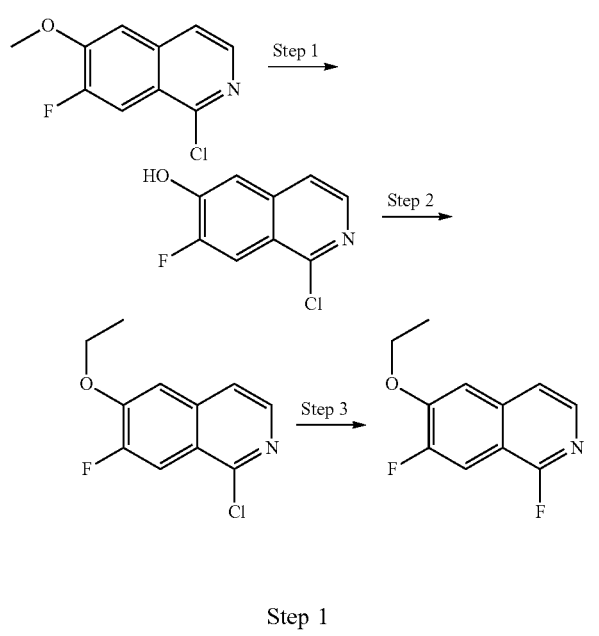

Step 1

To a solution of 1-chloro-7-fluoro-6-methoxyisoquinoline (1.7 g, 8.03 mmol) in CH$_2$Cl$_2$ (5 mL) at room temperature was added BBr$_3$ (24.10 mL, 24.10 mmol) via syringe. The reaction mixture was stirred at room temperature for 18 h. The reaction mixture was cooled to −78° C. and quenched with 1 ml of MeOH. After concentration, the residue was taken into water, the solid was collected washing with water to give 500 mg of the desired product 1-chloro-7-fluoroisoquinolin-6-ol.

Step 2

A mixture of 1-chloro-7-fluoroisoquinolin-6-ol (1.186 g, 6 mmol), bromoethane (1.308 g, 12.00 mmol), and K$_2$CO$_3$ (2.488 g, 18.00 mmol) in acetone (20 mL) was refluxed for 16 h. After filtration washing with acetone, the filtrate was concentrated and purified by Biotage eluting with 10-20% ethyl acetate in hexane to give 1.1 g of the product 1-chloro-6-ethoxy-7-fluoroisoquinoline as a solid. MS: MS m/z 226.03 (M$^+$+1).

Step 3

To a solution of 1-chloro-6-ethoxy-7-fluoroisoquinoline (1.128 g, 5 mmol) in DMSO (10 mL) was added CsF (1.519 g, 10.00 mmol) and heated to 140° C. for 4 hrs. The reaction was diluted with ethylacteate and washed with water, and brine. The organic phase was collected, dried over sodium sulfate, and concentrated under vacuum to give the crude product which was purified by silica gel chromatography using a gradient of 5-25% EtOAc in hexanes. The product fractions were collected and the solvent removed under vacuum to give 1.1 g of the desired product 6-ethoxy-1,7-difluoroisoquinoline. $^1$H NMR (400 MHz, CHLOROFORM-d) δ 8.00 (d, J=5.5 Hz, 1H), 7.77 (dd, J=10.8, 0.5 Hz, 1H), 7.41 (dd, J=5.8, 1.3 Hz, 1H), 7.21 (dd, J=7.8, 1.8 Hz, 1H), 4.28 (q, J=7.0 Hz, 2H), 1.59 (t, J=7.0 Hz, 3H). MS: MS m/z 210.03 (M$^+$ 1).

Preparation of
1,1-difluoro-2-methylpropan-2-ylpyridin-2-yl
carbonate

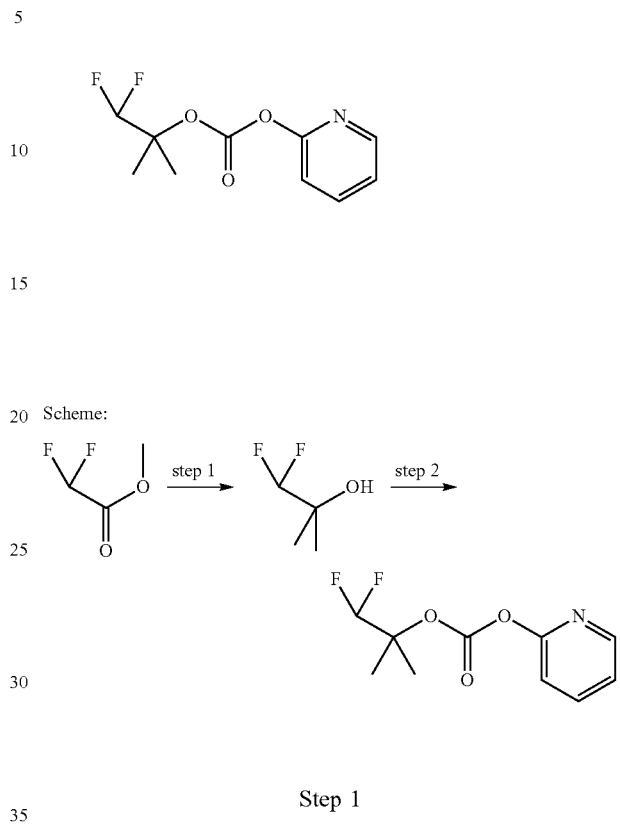

Scheme:

Step 1

Methylmagnesium bromide (2.53 mL, 7.60 mmol) was added dropwise via syringe to a solution of methyl 2,2-difluoroacetate (0.398 g, 3.62 mmol) in diethyl ether (10 mL) at −20° C. and stirred at this temp for 1 hr before warming up to RT. The reaction was quenched 4N HCl and extracted with a small portion of Et$_2$O. The organic layer was washed with brine, collected, dried over MgSO$_4$, filtered and concentrated to give a residue that was used in the next step as it was.

Step 2

To a suspension of sodium hydride, 60% in mineral oil (0.145 g, 3.62 mmol) in THF (50 mL) was added 1,1-difluoro-2-methylpropan-2-ol (0.399 g, 3.62 mmol) in THF (1 mL) from Step 1 at 0° C. After stirring 30 min, to the solution was added with a solution of di(pyridin-2-yl) carbonate (0.783 g, 3.62 mmol) in THF (50 mL) through a cannula. The formed slurry was stirred at 0° C. for 30 min. The slurry was warmed to rt and stirred for 2 h. The reaction was diluted with EtOAc, washed with brine, dried over MgSO$_4$, filtered, concentrated to give a residue that was purified by Biotage eluting with 20% EtOAc in hexanes to afford 400 mg of the desired product 1,1-difluoro-2-methylpropan-2-ylpyridin-2-yl carbonate as an oil. $^1$H NMR (400 MHz, CHLOROFORM-d) δ 8.47-8.39 (m, 1H), 7.91-7.74 (m, 1H), 7.32-7.23 (m, 1H), 7.14 (dt, J=8.2, 0.8 Hz, 1H), 6.22-5.89 (m, 1H), 1.65 (t, J=1.5 Hz, 6H).

Preparation of Intermediate (2S,3S)-2-((tert-butoxy-carbonyl)amino)-3-((R)-hex-5-en-2-yloxy)butanoic acid

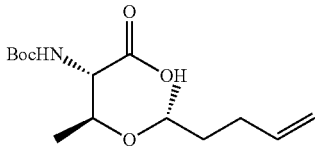 [SMILES: C=CCC[C@H]1OC(=O)[C@@H](NC(=O)OC(C)(C)C)[C@H](C)O1]

Scheme:

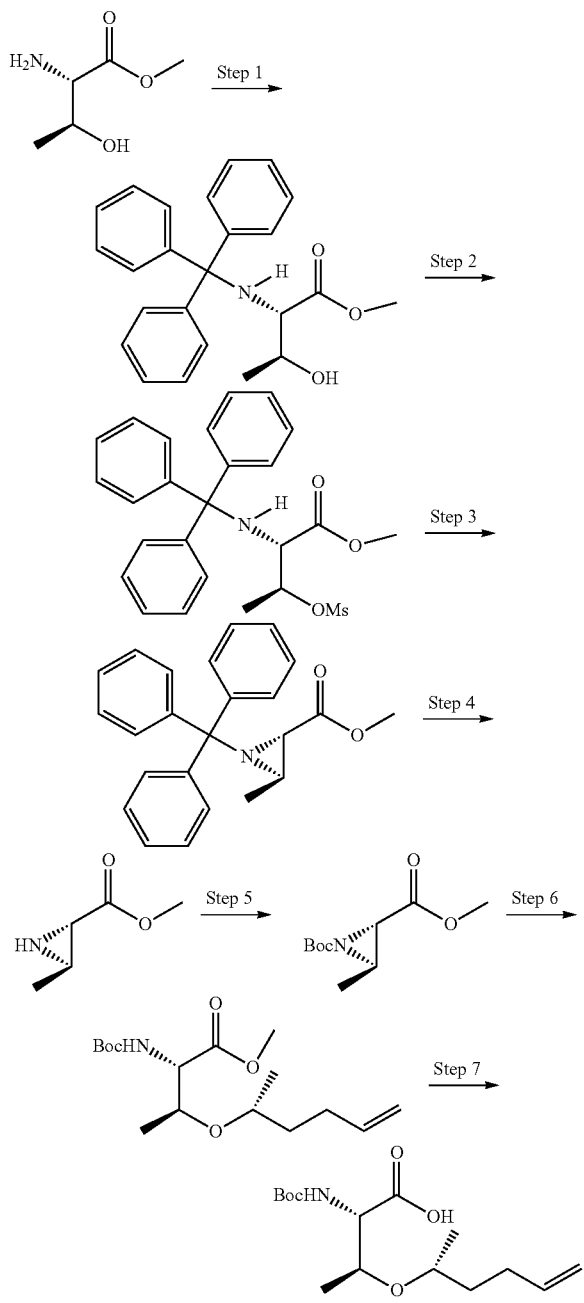

Step 1

(2S,3S)-methyl 2-amino-3-hydroxybutanoate, HCl (2.3 g, 13.56 mmol), trityl chloride (4.16 g, 14.92 mmol) and triethylamine (5.67 mL, 40.7 mmol) were stirred in DCM (50 mL) for 16 h. The reaction was diluted with EtOAc and washed with 10% citric acid solution. The organic layer was collected, dried over sodium sulfate, and concentrated under vacuum. The crude material was purified by silica gel chromatography using a gradient of 20-50% EtOAc in hexanes. The product fractions were collected and the solvent removed under vacuum to give 4.2 g (78%) (2S,3S)-methyl 3-hydroxy-2-(tritylamino)butanoate as a solid. MS: MS m/z 398.0 ($M^+$+Na).

Step 2

(2S,3S)-methyl 3-hydroxy-2-(tritylamino)butanoate (4.46 g, 11.88 mmol) was dissolved in DCM (29.7 ml) and cooled to 0° C. Ms-Cl (1.018 ml, 13.07 mmol) was added to the cooled solution followed by the dropwise addition of TEA (2.483 ml, 17.82 mmol). The reaction was allowed to stir for 1 h. The reaction was diluted with DCM and washed with 10% Citric acid solution. The organic layer was collected, dried over sodium sulfate, filtered, and concentrated under vacuum. The crude (2S,3S)-methyl 3-((methylsulfonyl)oxy)-2-(tritylamino)butanoate 4.8 g was used in the next step without further purification. MS: MS m/z 476.1 ($M^+$+Na).

Step 3

(2S,3S)-methyl 3-((methylsulfonyl)oxy)-2-(tritylamino) butanoate (4.83 g, 10.65 mmol), and TEA (2.97 ml, 21.30 mmol) were dissolved in THF (7.10 ml) and the mixture was refluxed for 36 h. The reaction was diluted with EtOAc and washed with 10% citric acid, then saturated sodium bicarbonate solution, followed by brine. The organic layer was collected, dried over sodium sulfate, filtered, and solvent removed under vacuum. The crude material was purified by silica gel chromatography using 20% EtOAc/Hexanes as eluent. The product fractions were collected and the solvent removed under vacuum to give 3.1 g (81%) (2S,3R)-methyl 3-methyl-1-tritylaziridine-2-carboxylate. $^1$H NMR (400 MHz, CHLOROFORM-d) δ 7.58-7.46 (m, 6H), 7.35-7.17 (m, 9H), 3.72 (s, 3H), 3.00 (qd, J=6.2, 2.3 Hz, 1H), 2.37 (d, J=2.3 Hz, 1H), 0.62 (d, J=6.0 Hz, 3H); MS: MS m/z 380.1 ($M^+$+Na).

Step 4

(2S,3R)-methyl 3-methyl-1-tritylaziridine-2-carboxylate (3.1 g, 8.67 mmol) was stirred in TFA (12 ml, 156 mmol), MeOH (6 mL), and DCM (6 mL) at 0° C. for 2 h. The solvent was removed under vacuum and the crude oil was partitioned between $Et_2O$ and water. The $Et_2O$ layer was discarded and the aquious layer was made alkaline by addition of solid sodium bicarbonate. The solution was then saturated with sodium chloride and extracted with $Et_2O$ 4×50 mL. The combined $Et_2O$ layers were dried over sodium sulfate, filtered, and concentrated under vacuum giving caution to the product (2S,3R)-methyl 3-methylaziridine-2-carboxylate being of low molecular weight. The product was carried to the next step without further purification. $^1$H NMR (400 MHz, CHLOROFORM-d) δ 3.78 (s, 3H), 2.36-2.29 (m, 2H), 2.10 (br. s, 1H), 1.26 (d, J=5.3 Hz, 3H).

Step 5

(2S,3R)-methyl 3-methylaziridine-2-carboxylate (1.5 g, 13.03 mmol) and Et₃N (3.63 mL, 26.1 mmol) were dissolved in DCM (15 mL) and cooled to 0° C. BOC₂O (4.54 mL, 19.54 mmol) was added and the reaction was allowed to warm to RT and stirred for 16 h. The reaction was diluted with saturated sodium bicarbonate solution and stirred vigorously for 10 min. The organic phase was collected, washed with brine, dried over sodium sulfate, and concentrated under vacuum. The crude material was purified by silica gel chromatography using a gradient of 10-40% EtOAc in hexanes. The product fractions were collected and the solvent removed under vacuum to give 720 mg (25%) (2S,3R)-1-tert-butyl 2-methyl 3-methylaziridine-1,2-dicarboxylate. ¹H NMR (400 MHz, CHLOROFORM-d) δ 3.77 (s, 3H), 2.87-2.81 (m, 1H), 2.80 (d, J=2.5 Hz, 1H), 1.47 (s, 9H), 1.34 (d, J=5.5 Hz, 3H).

Step 6

(2S,3R)-1-tert-butyl 2-methyl 3-methylaziridine-1,2-dicarboxylate (500 mg, 2.323 mmol) was dissolved in DCM (12 ml) at RT. BF₃.OEt₂ (2 drops) was added to the mixture and the reaction was stirred for 16 h. BF₃.OEt₂ (another 2 drops) was added to the reaction and it was stirred for an additional 6 h. The reaction was diluted with DCM and washed with saturated sodium bicarbonate solution, followed by brine. The organic layer was collected, dried over sodium sulfate, and concentrated under vacuum. The crude material was purified by silica gel chromatography using a gradient of 10-30% EtOAc in hexanes. The product fractions were collected and dried under vacuum to give 400 mg (55%) (2S,3S)-methyl 2-((tert-butoxycarbonyl)amino)-3-((R)-hex-5-en-2-yloxy)butanoate as an oil. ¹H NMR (400 MHz, CHLOROFORM-d) δ 5.81 (ddt, J=17.1, 10.3, 6.5 Hz, 1H), 5.24 (d, J=8.5 Hz, 1H), 5.04 (dq, J=17.2, 1.6 Hz, 1H), 4.99-4.94 (m, 1H), 4.39 (dd, J=8.5, 4.0 Hz, 1H), 3.89-3.81 (m, 1H), 3.76 (s, 3H), 3.53 (sxt, J=6.1 Hz, 1H), 2.20-2.00 (m, 2H), 1.65-1.54 (m, 1H), 1.50-1.39 (m, 10H), 1.19 (d, J=6.5 Hz, 3H), 1.14 (d, J=6.0 Hz, 3H); MS: MS m/z 338.2 (M⁺+Na).

Step 7

(2S,3S)-methyl 2-((tert-butoxycarbonyl)amino)-3-((R)-hex-5-en-2-yloxy)butanoate (2000 mg, 6.34 mmol) was dissolved in THF (8 mL), and MeOH (8 mL). Water (8 mL) and LiOH (607 mg, 25.4 mmol) were added to the solution which was then stirred for 16 h. The volatiles were removed under vacumm and the resulting aqueous residue was diluted with water and EtOAc. The aqueous layer acidified with 1 N HCl and was extracted with ethyl acetate (2 X). The combined organic layers were washed with brine solution, dried over Na₂SO₄, and concentrated to give 1.74 g (91%) (2S,3S)-2-((tert-butoxycarbonyl)amino)-3-((R)-hex-5-en-2-yloxy)butanoic acid as an oil. ¹H NMR (400 MHz, CHLOROFORM-d) δ 5.81 (ddt, J=17.0, 10.3, 6.6 Hz, 1H), 5.26 (d, J=7.3 Hz, 1H), 5.04 (dq, J=17.3, 1.6 Hz, 1H), 4.97 (dq, J=10.2, 1.5 Hz, 1H), 4.40 (br. s., 1H), 3.91 (br. s., 1H), 3.57 (sxt, J=6.3 Hz, 1H), 2.20-2.02 (m, 2H), 1.69-1.57 (m, 1H), 1.50-1.43 (m, 10H), 1.26 (d, J=6.5 Hz, 3H), 1.16 (d, J=6.0 Hz, 3H); MS: MS m/z 347.2 (M⁺+2Na).

Preparation of tert-butyl ((2R,6S,7S,9R,13aS,14aR,16a5,Z)-2-hydroxy-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate

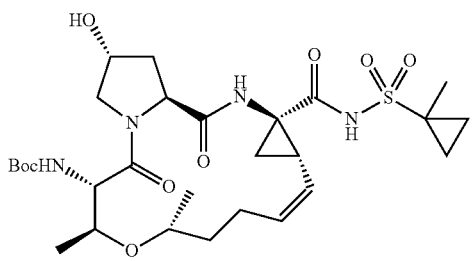 [SMILES: C[C@@H]1CC/C=C\[C@@H]2C[C@@]2(C(=O)NS(=O)(=O)C2(C)CC2)NC(=O)[C@@H]2C[C@@H](O)CN2C(=O)[C@@H](NC(=O)OC(C)(C)C)[C@H](C)O1]

Scheme

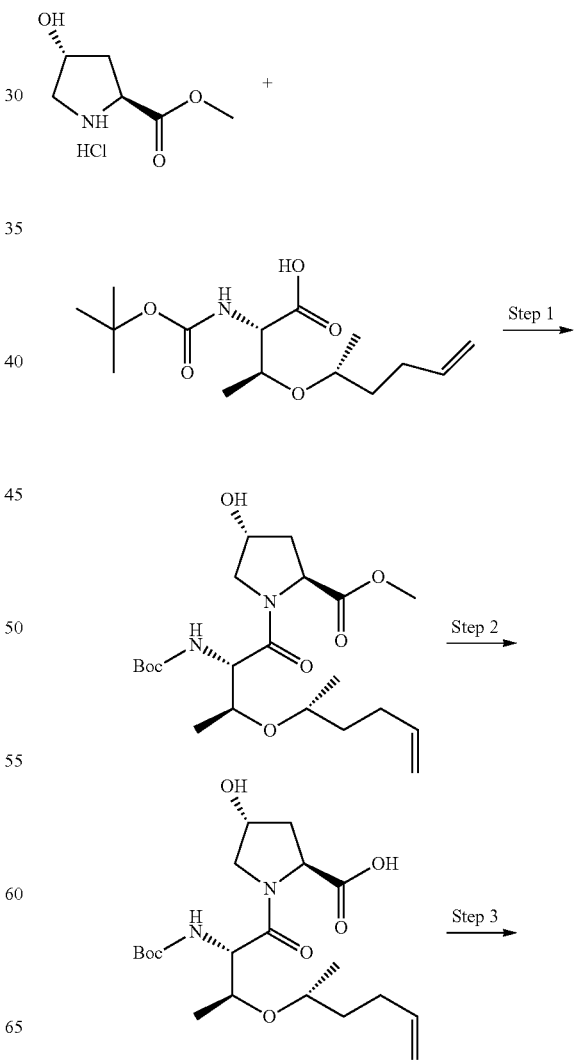

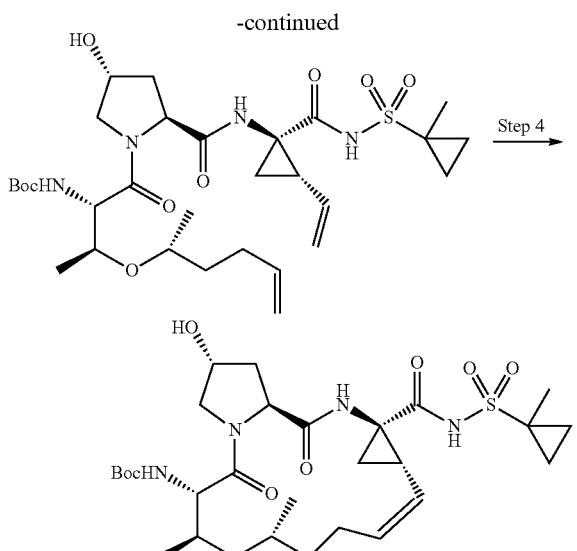

Step 1

HATU (2.63 g, 6.93 mmol) was added to a solution of (2S,4R)-methyl 4-hydroxypyrrolidine-2-carboxylate, HCl (1.153 g, 6.35 mmol), (2S,3S)-2-((tert-butoxycarbonyl) amino)-3-((R)-hex-5-en-2-yloxy)butanoic acid (1.74 g, 5.77 mmol), and Et₃N (3.22 mL, 23.09 mmol) in DCM (30 mL) and was stirred at RT for 16 h. The reaction was diluted with DCM and washed with 1 N HCl (3×), followed by brine. The organic layer was collected, dried over sodium sulfate, and concentrated under vacuum to give (2S,4R)-methyl 1-((2S,3S)-2-((tert-butoxycarbonyl)amino)-3-((R)-hex-5-en-2-yloxy)butanoyl)-4-hydroxypyrrolidine-2-carboxylate which was used in the next step without further purification. MS: MS m/z 429.2 (M$^+$+1).

Step 2

(2S,4R)-methyl 1-((2S,3S)-2-((tert-butoxycarbonyl) amino)-3-((R)-hex-5-en-2-yloxy)butanoyl)-4-hydroxypyrrolidine-2-carboxylate (2.5 g, 5.83 mmol) was dissolved in THF (8 mL). Water (8 mL) and LiOH (0.559 g, 23.34 mmol) were added to the solution which was then stirred for 16 h. The volitiles were removed under vacuumm and the resulting aqueous residue was diluted with water, and extracted with EtOAc. The aqueous layer was acidified with 1 N HCl and extracted with ethyl acetate. Combined organic layers were washed with brine solution, dried over Na₂SO₄, concentrated to give 2.29 g (95%) (2S,4R)-1-((2S,3S)-2-((tert-butoxycarbonyl)amino)-3-((R)-hex-5-en-2-yloxy)butanoyl)-4-hydroxypyrrolidine-2-carboxylic acid. MS: MS m/z 415.2 (M$^+$+1).

Step 3

HATU (1.761 g, 4.63 mmol) was added to a solution of (2S,4R)-1-((2S,3S)-2-((tert-butoxycarbonyl)amino)-3-((R)-hex-5-en-2-yloxy)butanoyl)-4-hydroxypyrrolidine-2-carboxylic acid (1.6 g, 3.86 mmol), (1R,2S)-1-amino-N-((1-methylcyclopropyl)sulfonyl)-2-vinylcyclopropanecarboxamide, HCl (1.192 g, 4.25 mmol), and Hunig'sBase (2.70 mL, 15.44 mmol) in DCM (20 mL) and was stirred at RT for overnight. The reaction was diluted with DCM, washed with 1N HCl (3×) and then brine. The organic phase was collected and dried over sodium sulfate, anc concentrated under vacuum. The crude material was purified by silica gel chromatography using 20-60% Acetone in hexanes. The product fractions were collected and the solvent removed under vacuum to give 2.0 g (81%) tert-butyl ((2S,3S)-3-((R)-hex-5-en-2-yloxy)-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-1-oxobutan-2-yl)carbamate. MS: MS m/z 641.4 (M$^+$+1).

Step 4

A solution of tert-butyl ((2S,3S)-3-((R)-hex-5-en-2-yloxy)-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-1-oxobutan-2-yl)carbamate (2 g, 3.12 mmol) in DCE (390 ml) was sparged with nitrogen for 30 min. and then Hoveyda-Grubbs catalyst 2nd generation (0.098 g, 0.156 mmol) was added and the reaction heated to 80° C. for 2 h. The reaction was concentrated and purified by flash chromatography on the Biotage (20-60% Acetone in hexanes) to give 450 mg (24%) tert-butyl ((2R,6S,7S,9R,13aS,14aR,16aS,Z)-2-hydroxy-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. ¹H NMR (400 MHz, DMSO-d₆) δ 11.26 (s, 1H), 9.08 (s, 1H), 7.25 (d, J=9.8 Hz, 1H), 5.62-5.48 (m, 1H), 5.19 (d, J=3.3 Hz, 1H), 4.94 (t, J=10.3 Hz, 1H), 4.44 (br. s., 1H), 4.26 (t, J=7.9 Hz, 1H), 4.00 (t, J=9.8 Hz, 1H), 3.88-3.65 (m, 2H), 3.61-3.40 (m, 2H), 2.76-2.64 (m, 1H), 2.11-0.82 (m, 30H); MS: MS m/z 613.3 (M$^+$+1).

Preparation of Intermediate tert-butyl ((2R,6S,7S,9R,13aS,14aR,16aS,Z)-14a-(((1-(fluoromethyl)cyclopropyl)sulfonyl)carbamoyl)-2-hydroxy-7,9-dimethyl-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate

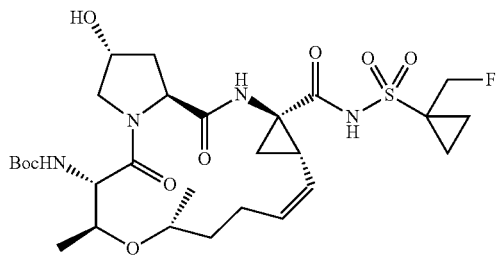 [SMILES: C[C@@H]1CC/C=C\[C@@H]2C[C@@]2(C(=O)NS(=O)(=O)C2(CF)CC2)NC(=O)[C@@H]2C[C@@H](O)CN2C(=O)[C@@H](NC(=O)OC(C)(C)C)[C@H](C)O1]

Intermediate tert-butyl ((2R,6S,7S,9R,13aS,14aR,16aS,Z)-14a-(((1-(fluoromethyl)cyclopropyl)sulfonyl)carbamoyl)-2-hydroxy-7,9-dimethyl-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate was prepared according to the method described for the synthesis of intermediate tert-butyl ((2R,6S,7S,9R,13aS,14aR,16aS,Z)-2-hydroxy-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate except that (1R, 2S)-1-amino-N-((1-(fluoromethyl)cyclopropyl)sulfonyl)-2-vinylcyclopropanecarboxamide, HCl was used instead of (1R,2S)-1-amino-N-((1-methylcyclopropyl)sulfonyl)-2-vinylcyclopropanecarboxamide, HCl in step 3.

Step 3

Modifications: 1.26 g (1R,2S)-1-amino-N-((1-(fluoromethyl)cyclopropyl)sulfonyl)-2-vinylcyclopropanecarboxamide, HCl used, 2.0 g product tert-butyl ((2S,3S)-1-((2S,4R)-2-(((1R,2S)-1-(((1-(fluoromethyl)cyclopropyl)sulfonyl)carbamoyl)-2-vinylcyclopropyl)carbamoyl)-4-hydroxypyrrolidin-1-yl)-3-((R)-hex-5-en-2-yloxy)-1-oxobutan-2-yl)carbamate was obtained (78% yield); MS: MS m/z 659.4 (M$^+$+1).

Step 4

Modifications: 1.50 g tert-butyl ((2S,3S)-1-((2S,4R)-2-(((1R,2S)-1-(((1-(fluoromethyl)cyclopropyl)sulfonyl)carbamoyl)-2-vinylcyclopropyl)carbamoyl)-4-hydroxypyrrolidin-1-yl)-3-((R)-hex-5-en-2-yloxy)-1-oxobutan-2-yl)carbamate used, 782 mg tert-butyl ((2R,6S,7S,9R,13a5,14aR,16aS,Z)-14a-(((1-(fluoromethyl)cyclopropyl)sulfonyl)carbamoyl)-2-hydroxy-7,9-dimethyl-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate was obtained (55% yield). $^1$H NMR (400 MHz, DMSO-d$_6$) δ 11.46 (s, 1H), 9.02 (s, 1H), 7.24 (d, J=9.8 Hz, 1H), 5.63-5.47 (m, 1H), 5.17 (d, J=3.3 Hz, 1H), 4.96 (t, J=10.3 Hz, 1H), 4.89-4.69 (m, 1H), 4.64-4.39 (m, 2H), 4.24 (t, J=7.8 Hz, 1H), 3.99 (t, J=9.7 Hz, 1H), 3.87-3.65 (m, 2H), 3.59-3.39 (m, 2H), 2.76-2.61 (m, 1H), 2.48-2.33 (m, 1H), 2.09-1.91 (m, 2H), 1.89-1.73 (m, 1H), 1.63-0.99 (m, 23H); MS: MS m/z 631.3 (M$^+$+1).

Preparation of Compound 2001

Compound 2001

Scheme:

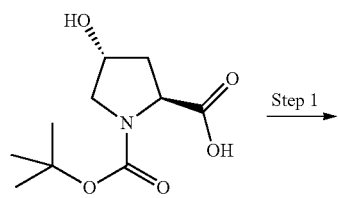

Step 1

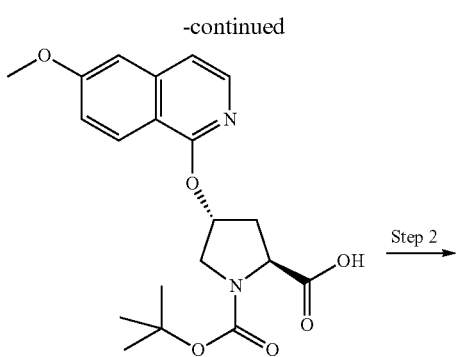

Step 2

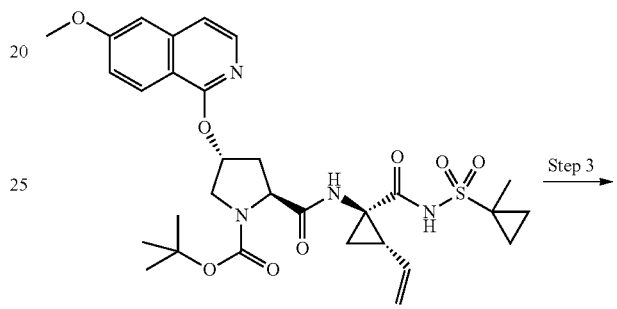

Step 3

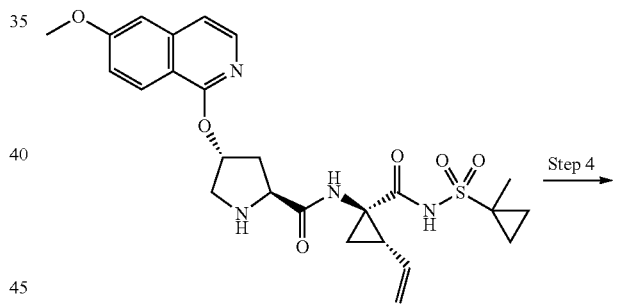

Step 4

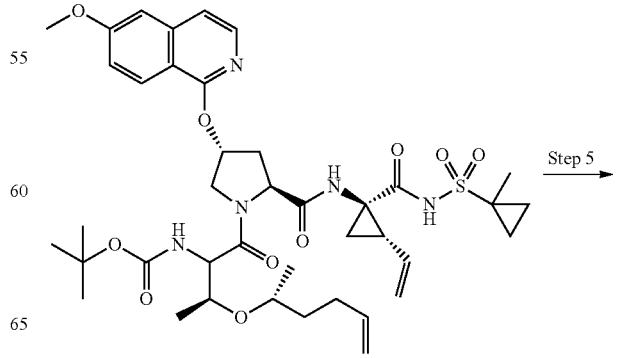

Step 5

-continued

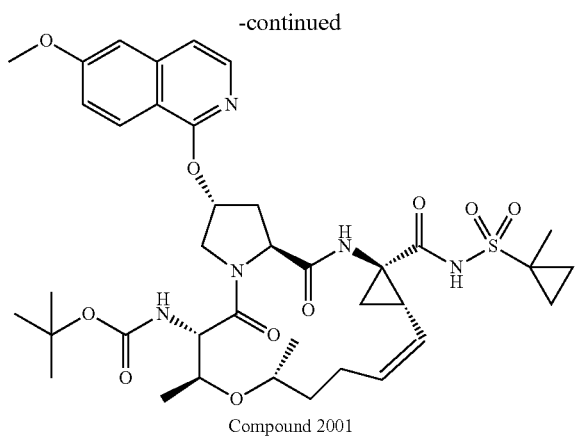

Compound 2001

Step 1

A mixture of (2S,4R)-1-(tert-butoxycarbonyl)-4-hydroxypyrrolidine-2-carboxylic acid (11.94 g, 51.6 mmol), 1-chloro-6-methoxyisoquinoline (10 g, 51.6 mmol), and potassium 2-methylpropan-2-olate (17.37 g, 154.8 mmol) in DMSO (10 mL) where stirred overnight. The reaction was quenched with water, diluted with EtOAc and acidified with 1N HCl. The organic phase was collected and dried over sodium sulfate, then concentrated under vacuum to give 15 g (75%) (2S,4R)-1-(tert-butoxycarbonyl)-4-((4-methoxyisoquinolin-1-yl)oxy)pyrrolidine-2-carboxylic acid as a solid. MS: MS m/z 389.2 (M$^+$+H).

Step 2

HATU (295 mg, 0.777 mmol) was added to a solution of (2S,4R)-1-(tert-butoxycarbonyl)-4-((6-methoxyisoquinolin-1-yl)oxy)pyrrolidine-2-carboxylic acid (252 mg, 0.648 mmol), (1R,2S)-1-amino-N-((1-methylcyclopropyl)sulfonyl)-2-vinylcyclopropanecarboxamide, HCl (200 mg, 0.712 mmol), and Et$_3$N (0.361 mL, 2.59 mmol) in DCM (5 mL) and was stirred at RT for 16 h. The reaction mixture was concentrated under vacuum and purified by silica gel chromatography using 20% Acetone in hexanes. The product fractions were collected and the solvent removed under vacuum to give 350 mg (88%) (2S,4R)-tert-butyl 4-((6-methoxyisoquinolin-1-yl)oxy)-2-(((1R,2S)-1-(((1-methylcyclopropyl)sulfonyl)carbamoyl)-2-vinylcyclopropyl)carbamoyl)pyrrolidine-1-carboxylate. MS: MS m/z 389.2 (M$^+$+H).

Step 3

A solution of (2S,4R)-tert-butyl 4-((6-methoxyisoquinolin-1-yl)oxy)-2-(((1R,2S)-1-(((1-methylcyclopropyl)sulfonyl)carbamoyl)-2-vinylcyclopropyl)carbamoyl)pyrrolidine-1-carboxylate (204 mg, 0.332 mmol) and hydrogen chloride, 4 M in dioxane (4 mL) was stirred for 2 h. Concentration under vacuum gave 183 mg crude (2S,4R)-4-((6-methoxyisoquinolin-1-yl)oxy)-N-((1R,2S)-1-(((1-methylcyclopropyl)sulfonyl)carbamoyl)-2-vinylcyclopropyl)pyrrolidine-2-carboxamide as the HCl salt which was used in the next step as is.

Step 4

HATU (151 mg, 0.398 mmol) was added to a solution of (2S,4R)-4-((6-methoxyisoquinolin-1-yl)oxy)-N-((1R,2S)-1-(((1-methylcyclopropyl)sulfonyl)carbamoyl)-2-vinylcyclopropyl)pyrrolidine-2-carboxamide, HCl (183 mg, 0.332 mmol), (2S,3S)-2-((tert-butoxycarbonyl)amino)-3-((R)-hex-5-en-2-yloxy)butanoic acid (100 mg, 0.332 mmol), and Et$_3$N (0.185 mL, 1.327 mmol) in DCM (220 mL) and was stirred at RT for 16 h. The reaction mixture was concentrated under vacuum and purified by silica gel chromatography using 20% Acetone in hexanes. The product fractions were collected and the solvent removed under vacuum to give 231 mg (87%) tert-butyl ((3S)-3-((R)-hex-5-en-2-yloxy)-1-((2S,4R)-4-((6-methoxyisoquinolin-1-yl)oxy)-2-(((1R,2S)-1-(((1-methylcyclopropyl)sulfonyl)carbamoyl)-2-vinylcyclopropyl)carbamoyl)pyrrolidin-1-yl)-1-oxobutan-2-yl)carbamate. MS: MS m/z 798.4 (M$^+$+H).

Step 5

A solution of tert-butyl ((3S)-3-((R)-hex-5-en-2-yloxy)-1-((2S,4R)-4-((6-methoxyisoquinolin-1-yl)oxy)-2-(((1R,2S)-1-(((1-methylcyclopropyl)sulfonyl)carbamoyl)-2-vinylcyclopropyl)carbamoyl)pyrrolidin-1-yl)-1-oxobutan-2-yl)carbamate (231 mg, 0.289 mmol) in DCE (40 mL) was sparged with nitrogen for 30 min. and then Hoveyda-Grubbs Catalyst 2nd Generation (9.10 mg, 0.014 mmol) was added and the reaction heated to 80° C. for 2 h. The reaction was concentrated and The crude material was purified via preparative LC/MS with the following conditions: Column: Waters X Bridge C18, 19×200 mm, 5-μm particles; Guard Column: Waters X Bridge C18, 19×10 mm, 5-μm particles; Mobile Phase A: water with 20-mM ammonium acetate; Mobile Phase B: 95:5 acetonitrile:water with 20-mM ammonium acetate; Gradient: 50-100% B over 13 minutes, then a 4-minute hold at 100% B; Flow: 20 mL/min. Fractions containing the desired product were combined and dried via centrifugal evaporation to give 64 mg (30%) tert-butyl ((2R,6S,7S,9R,13aS,14aR,16aS,Z)-2-((6-methoxyisoquinolin-1-yl)oxy)-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (500 MHz, DMSO-d$_6$) δ 11.19 (s, 1H), 9.05 (br. s., 1H), 8.02 (d, J=9.2 Hz, 1H), 7.96 (d, J=5.8 Hz, 1H), 7.36-7.26 (m, 2H), 7.15 (dd, J=9.2, 2.4 Hz, 1H), 5.84 (br. s., 1H), 5.60-5.50 (m, 1H), 5.02 (t, J=10.2 Hz, 1H), 4.43 (t, J=8.2 Hz, 1H), 4.31 (d, J=11.3 Hz, 1H), 4.02-3.94 (m, 2H), 3.91 (s, 3H), 3.85-3.77 (m, 1H), 3.51-3.42 (m, 1H), 2.85-2.71 (m, 1H), 2.62-2.55 (m, J=7.0 Hz, 1H), 2.34-2.23 (m, 1H), 1.89-1.78 (m, 1H), 1.66-1.58 (m, 1H), 1.57-1.23 (m, 9H), 1.18-1.03 (m, 16H), 0.96-0.85 (m, 2H); MS: MS m/z 770.5 (M$^+$+1).

Preparation of Compound 2002

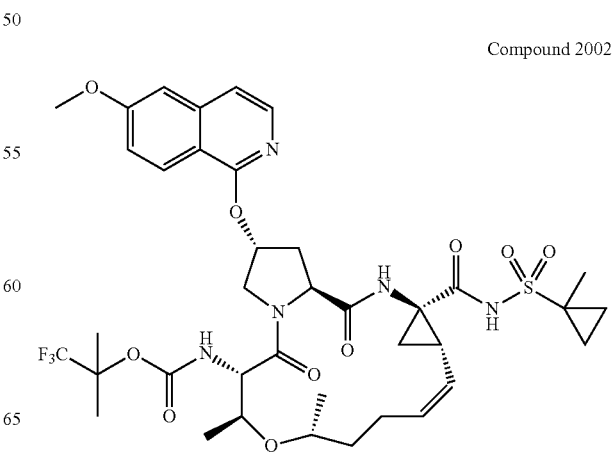

Compound 2002

Scheme

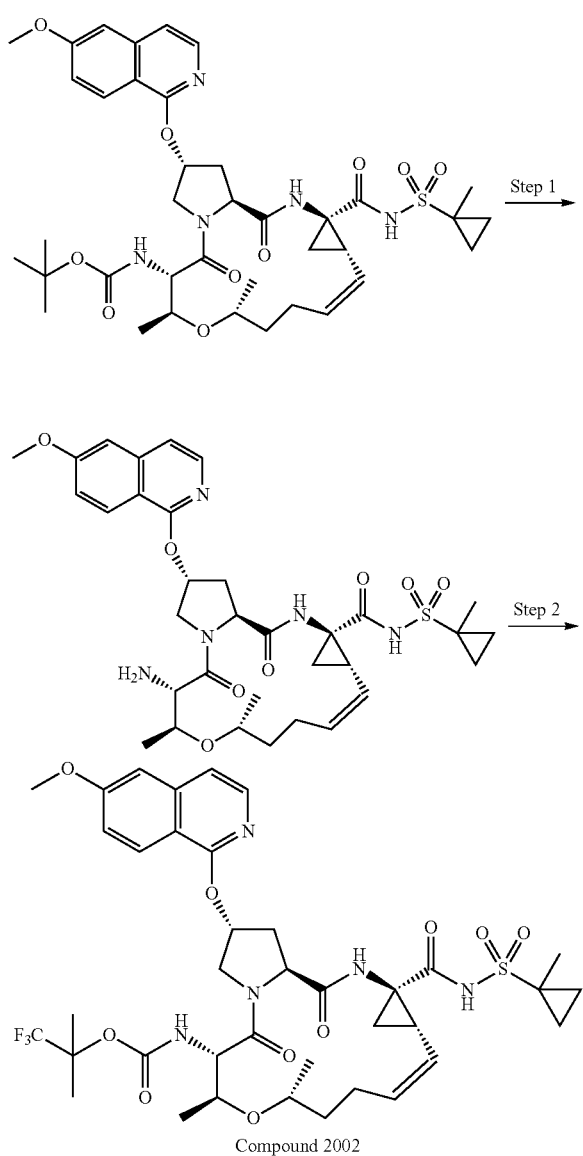

Compound 2002

Step 1 tert-butyl ((2R,6S,7S,9R,13aS,14aR,16aS,Z)-2-((6-methoxyisoquinolin-1-yl)oxy)-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate (54 mg, 0.070 mmol) was dissolved in DCM and TFA (1 ml, 12.98 mmol) was added. The reaction was stirred for 1 h. The solvent was removed under vacuum to give 55 mg (100%) crude (2R,6S,7S,9R,13aS,14aR,16aS,Z)-6-amino-2-((6-methoxyisoquinolin-1-yl)oxy)-7,9-dimethyl-N-((1-methylcyclopropyl)sulfonyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecine-14a-carboxamide as the TFA salt which was used in the next step as is. MS: MS m/z 670.3 (M$^+$+1).

Step 2

A solution of (2R,6S,7S,9R,13aS,14aR,16aS,Z)-6-amino-2-((6-methoxyisoquinolin-1-yl)oxy)-7,9-dimethyl-N-((1-methylcyclopropyl)sulfonyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecine-14a-carboxamide, TFA (55 mg, 0.070 mmol) and pyridin-2-yl (1,1,1-trifluoro-2-methylpropan-2-yl) carbonate (20.98 mg, 0.084 mmol) in CH$_2$Cl$_2$ (1 mL) was added N-ethyl-N-isopropylpropan-2-amine (0.061 mL, 0.351 mmol). The reaction was stirred for 16 h. The solvent was removed under vacuum and the crude material was purified via preparative LC/MS with the following conditions: Column: Waters X Bridge C18, 19×200 mm, 5-μm particles; Guard Column: Waters X Bridge C18, 19×10 mm, 5-μm particles; Mobile Phase A: water with 20-mM ammonium acetate; Mobile Phase B: 95:5 acetonitrile:water with 20-mM ammonium acetate; Gradient: 50-90% B over 12 minutes, then a 5-minute hold at 100% B; Flow: 20 mL/min. Fractions containing the desired product were combined and dried via centrifugal evaporation to give 30 mg (52%) 1,1,1-trifluoro-2-methylpropan-2-yl ((2R,6S,7S,9R,13aS,14aR,16aS,Z)-2-((6-methoxyisoquinolin-1-yl)oxy)-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (400 MHz, METHANOL-d$_4$) δ 8.09 (d, J=9.0 Hz, 1H), 7.92 (d, J=6.0 Hz, 1H), 7.27 (d, J=6.0 Hz, 1H), 7.21 (d, J=2.3 Hz, 1H), 7.12 (dd, J=9.2, 2.4 Hz, 1H), 5.89 (br. s., 1H), 5.70-5.57 (m, 1H), 5.16-5.02 (m, 1H), 4.68-4.49 (m, 2H), 4.18-4.10 (m, 2H), 3.95 (s, 3H), 3.93-3.83 (m, 1H), 3.62-3.52 (m, 1H), 2.89-2.58 (m, 3H), 2.52-2.39 (m, 1H), 1.97-1.85 (m, 1H), 1.78 (dd, J=8.5, 5.5 Hz, 1H), 1.72-1.01 (m, 20H), 0.96-0.84 (m, 2H); MS: MS m/z 824.5 (M$^+$+1).

Preparation of Compound 2003

Compound 2003

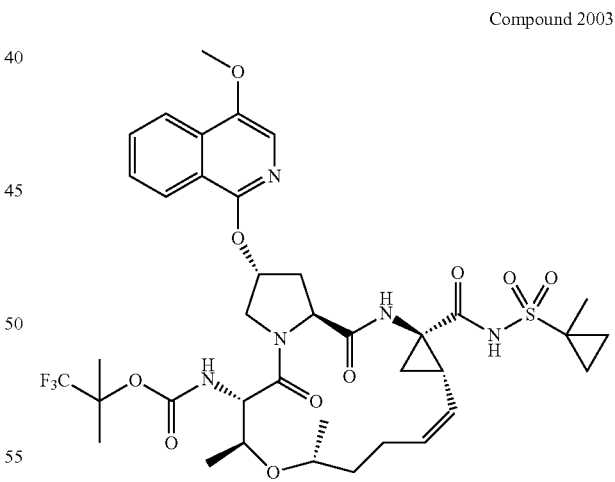

Compound 2003 was prepared using the intermediates described herein and by following the general procedure described for the synthesis of Compound 2002: Compound 2003: 1,1,1-trifluoro-2-methylpropan-2-yl ((2R,6S,7S,9R,13aS,14aR,16aS,Z)-2-((4-methoxyisoquinolin-1-yl)oxy)-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate; $^1$H NMR (500 MHz, DMSO-d$_6$) δ 11.20 (s, 1H), 9.09 (s, 1H), 8.08 (d, J=3.4

Hz, 1H), 8.07 (d, J=3.7 Hz, 1H), 7.92 (d, J=9.2 Hz, 1H), 7.85-7.77 (m, 1H), 7.66 (s, 1H), 7.64 (t, J=8.1 Hz, 1H), 5.80 (br. s., 1H), 5.60-5.51 (m, 1H), 5.02 (t, J=10.4 Hz, 1H), 4.48 (t, J=8.4 Hz, 1H), 4.29 (d, J=11.3 Hz, 1H), 4.01-3.91 (m, 5H), 3.87-3.80 (m, 1H), 3.51-3.43 (m, 1H), 2.77 (q, J=9.5 Hz, 1H), 2.61 (dd, J=13.3, 6.6 Hz, 1H), 2.35-2.26 (m, 1H), 1.90-1.78 (m, 1H), 1.67-1.59 (m, 1H), 1.58-1.24 (m, 12H), 1.11-1.03 (m, 9H), 0.91 (br. s., 2H); MS: MS m/z 824.5 (M+ +1).

Preparation of Compound 2004

Compound 2004

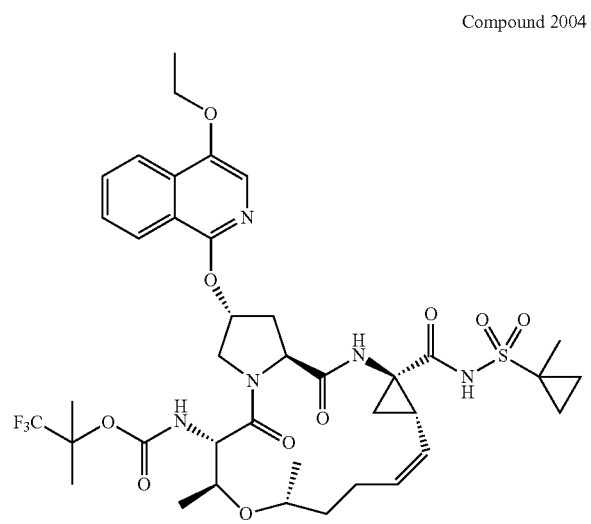 [SMILES: CCOc1cnc(O[C@@H]2C[C@H]3C(=O)N[C@]4(C(=O)NS(=O)(=O)C5(C)CC5)C[C@H]4/C=C\CC[C@@H](C)O[C@@H](C)[C@H](NC(=O)OC(C)(C)C(F)(F)F)C(=O)N3C2)c2ccccc12]

Compound 2004 was prepared using the intermediates described herein and by following the general procedure described for the synthesis of Compound 2002:

Compound 2004: 1,1,1-trifluoro-2-methylpropan-2-yl ((2R,6S,7S,9R,13aS,14aR,16aS,Z)-2-((4-ethoxyisoquinolin-1-yl)oxy)-7,9-dimethyl-14a-(((1-methylcyclopropyl)sulfonyl)carbamoyl)-5,16-dioxo-2,3,5,6,7,9,10,11,13a,14,14a, 15,16,16a-tetradecahydro-1H-cyclopropa[i]pyrrolo[1,2-e][1,5,8]oxadiazacyclopentadecin-6-yl)carbamate; $^1$H NMR (500 MHz, DMSO-d$_6$) δ 11.19 (s, 1H), 9.08 (s, 1H), 8.08 (d, J=4.9 Hz, 1H), 8.07 (d, J=4.6 Hz, 1H), 7.92 (d, J=9.2 Hz, 1H), 7.80 (t, J=7.6 Hz, 1H), 7.66 (s, 1H), 7.63 (t, J=8.1 Hz, 1H), 5.79 (br. s., 1H), 5.59-5.50 (m, 1H), 5.02 (t, J=10.4 Hz, 1H), 4.53-4.44 (m, 1H), 4.29 (d, J=12.2 Hz, 1H), 4.21 (q, J=6.9 Hz, 2H), 4.00-3.92 (m, 2H), 3.87-3.79 (m, 1H), 3.50-3.43 (m, 1H), 2.77 (q, J=9.2 Hz, 1H), 2.60 (dd, J=12.8, 6.7 Hz, 1H), 2.35-2.27 (m, 1H), 1.89-1.79 (m, 1H), 1.67-1.59 (m, 1H), 1.57-1.24 (m, 15H), 1.12-1.04 (m, 9H), 0.91 (br. s., 2H); MS: MS m/z 824.5 (M+ +1).

Preparation of Compound 2005

Compound 2005

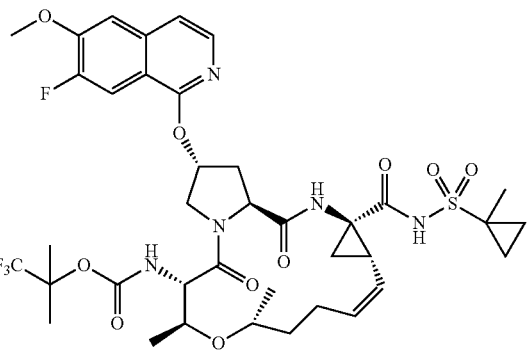

Scheme

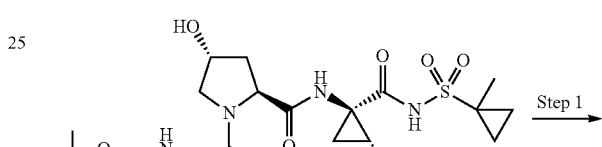

Step 1

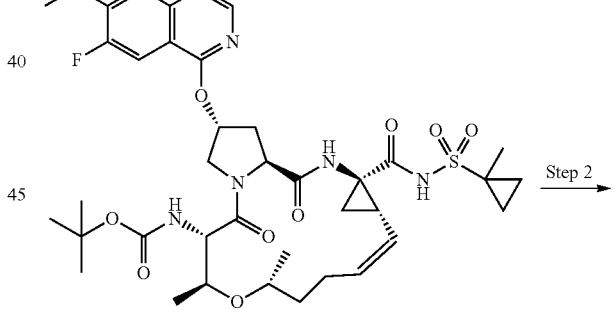

Step 2

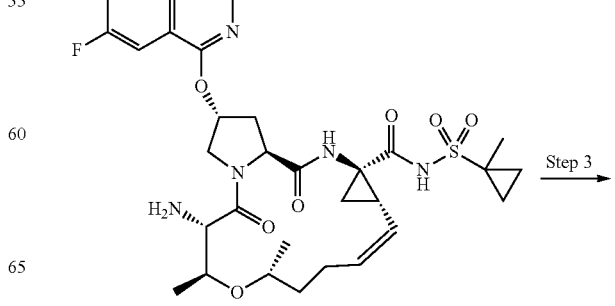

Step 3

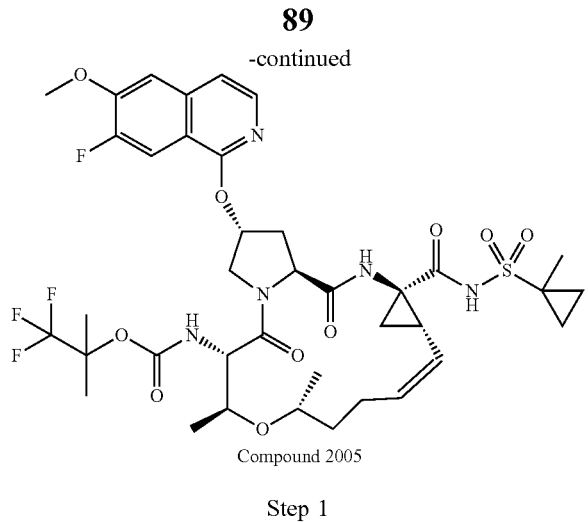

Compound 2005

Step 1

To a mixture of tert-butyl ((2R,6S,7S,9R,13aS,14aR,16aS,Z)-2-hydroxy-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate (40 mg, 0.065 mmol),1,7-difluoro-6-methoxyisoquinoline (14.01 mg, 0.072 mmol), and potassium tert-butoxide (36.6 mg, 0.326 mmol) was added DMSO (5 mL) and then sonicated for 15 min. The resulting solution was stirred for 4 h. The reaction was quenched with water, acidified with 6 N HCl, extracted with EtOAc, washed with brine, dried over MgSO$_4$, and concentrated to give tert-butyl ((2R,6S,7S,9R,13aS,14aR,16aS,Z)-2-((7-fluoro-6-methoxyisoquinolin-1-yl)oxy)-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate which was used in the next step without further purification. MS: MS m/z 788.6 (M$^+$+1).

Step 2 tert-butyl ((2R,6S,7S,9R,13aS,14aR,16aS,Z)-2-((7-fluoro-6-methoxyisoquinolin-1-yl)oxy)-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate (70 mg, 0.089 mmol) was dissolved in DCM and TFA (1 ml, 12.98 mmol) was added. The reaction was stirred for 1 h. The solvent was removed under vacuum to give 71 mg (100%) (2R,6S,7S,9R,13aS,14aR,16aS,Z)-6-amino-2-((7-fluoro-6-methoxyisoquinolin-1-yl)oxy)-7,9-dimethyl-N-((1-methylcyclopropyl)sulfonyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecine-14a-carboxamide, TFA which was used in the next step as is. MS: MS m/z 788.6 (M$^+$+1).

Step 3

A solution of (2R,6S,7S,9R,13aS,14aR,16aS,Z)-6-amino-2-((7-fluoro-6-methoxyisoquinolin-1-yl)oxy)-7,9-dimethyl-N-((1-methylcyclopropyl)sulfonyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecine-14a-carboxamide, TFA (35.7 mg, 0.0445 mmol) and pyridin-2-yl (1,1,1-trifluoro-2-methylpropan-2-yl) carbonate (13.31 mg, 0.053 mmol) in CH$_2$Cl$_2$ (1 mL) was added N-ethyl-N-isopropylpropan-2-amine (0.039 mL, 0.223 mmol). The reaction was stirred for 16 h. The solvent was removed under vacuum and the crude material was purified via preparative LC/MS with the following conditions: Column: Waters X Bridge C18, 19×200 mm, 5-µm particles; Guard Column: Waters X Bridge C18, 19×10 mm, 5-µm particles; Mobile Phase A: water with 20-mM ammonium acetate; Mobile Phase B: 95:5 acetonitrile:water with 20-mM ammonium acetate; Gradient: 50-100% B over 13 minutes, then a 4-minute hold at 100% B; Flow: 20 mL/min. Fractions containing the desired product were combined and dried via centrifugal evaporation to give 15.4 mg (41%) 1,1,1-trifluoro-2-methylpropan-2-yl ((2R,6S,7S,9R,13aS,14aR,16aS,Z)-2-((7-fluoro-6-methoxyisoquinolin-1-yl)oxy)-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (500 MHz, DMSO-d$_6$) δ 11.17 (br. s, 1H), 9.05 (br. s., 1H), 7.96 (d, J=5.8 Hz, 1H), 7.90 (d, J=8.9 Hz, 1H), 7.71 (d, J=11.3 Hz, 1H), 7.54 (d, J=8.2 Hz, 1H), 7.35 (d, J=5.8 Hz, 1H), 5.81 (br. s., 1H), 5.60-5.48 (m, 1H), 5.16-4.93 (m, 1H), 4.45 (t, J=8.5 Hz, 1H), 4.25 (d, J=10.4 Hz, 1H), 4.02-3.90 (m, 4H), 3.86-3.76 (m, 1H), 2.80-2.53 (m, 2H), 2.33-2.22 (m, 1H), 1.88-1.74 (m, 1H), 1.66-0.75 (m, 27H); MS: MS m/z 824.5 (M$^+$+1).

Preparation of Compound 2006

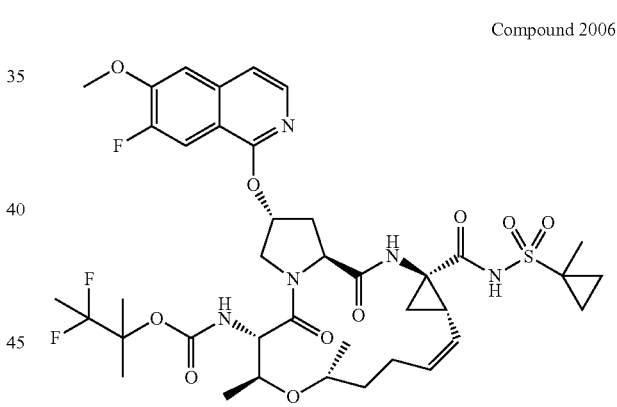

Compound 2006

Compound 2006 was prepared using the intermediates described herein and by following the general procedure described for the synthesis of Compound 2005:

Compound 2006: 3,3-difluoro-2-methylbutan-2-yl ((2R,6S,7S,9R,13aS,14aR,16aS,Z)-2-((7-fluoro-6-methoxyisoquinolin-1-yl)oxy)-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (500 MHz, DMSO-d$_6$) δ 11.16 (br. s., 1H), 9.04 (br. s., 1H), 7.96 (d, J=5.8 Hz, 1H), 7.73-7.65 (m, 2H), 7.55 (d, J=8.2 Hz, 1H), 7.35 (d, J=5.8 Hz, 1H), 5.83 (br. s., 1H), 5.59-5.47 (m, 1H), 5.02 (br. s., 1H), 4.51-4.40 (m, 1H), 4.25 (d, J=11.6 Hz, 1H), 4.03-3.89 (m, 5H), 3.79 (dd, J=9.6, 5.6 Hz, 1H), 2.73 (br. s., 1H), 2.63-2.53 (m, 1H), 2.36-2.22 (m, 1H), 1.88-1.76 (m, 1H), 1.66-1.19 (m, 17H), 1.07 (dd, J=8.4, 6.3 Hz, 6H), 1.00 (s, 3H), 0.93-0.83 (m, 2H); MS: MS m/z 838.8 (M$^+$+1).

Preparation of Compound 2007

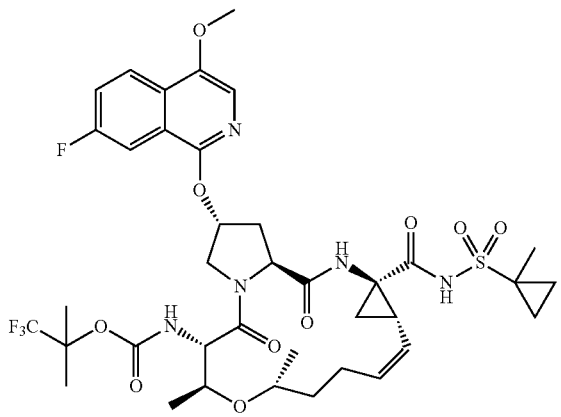

Compound 2007

Compound 2007 was prepared using the intermediates described herein and by following the general procedure described for the synthesis of Compound 2005:

Compound 2007: 1,1,1-trifluoro-2-methylpropan-2-yl ((2R,6S,7S,9R,13aS,14aR,16aS,Z)-2-((7-fluoro-4-methoxyisoquinolin-1-yl)oxy)-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. MS: MS m/z 842.8 (M$^+$+1).

Preparation of Compound 2008

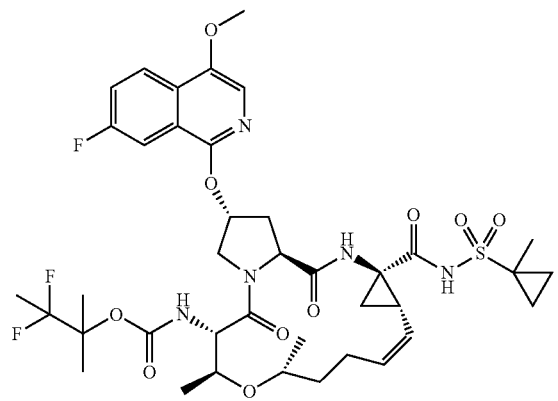

Compound 2008

Compound 2008 was prepared using the intermediates described herein and by following the general procedure described for the synthesis of Compound 2005:

Compound 2008: 3,3-difluoro-2-methylbutan-2-yl ((2R,6S,7S,9R,13aS,14aR,16aS,Z)-2-((7-fluoro-4-methoxyisoquinolin-1-yl)oxy)-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[1,2-e][1,5,8]oxadiazacyclopentadecin-6-yl)carbamate. $^1$H NMR (500 MHz, DMSO-d$_6$) δ 11.18 (br. s., 1H), 9.05 (br. s., 1H), 8.13 (dd, J=9.0, 5.3 Hz, 1H), 7.76-7.59 (m, 4H), 5.77 (br. s., 1H), 5.60-5.45 (m, 1H), 5.01 (br. s., 1H), 4.52-4.42 (m, 1H), 4.26 (d, J=11.6 Hz, 1H), 4.00-3.88 (m, 5H), 3.85-3.72 (m, 1H), 2.85-2.70 (m, 1H), 2.63-2.53 (m, 1H), 2.34-2.22 (m, 1H), 1.88-1.77 (m, 1H), 1.67-1.57 (m, 1H), 1.56-1.18 (m, 16H), 1.06 (d, J=4.9 Hz, 6H), 0.97-0.80 (m, 5H); MS: MS m/z 838.8 (M$^+$+1).

Preparation of Compound 2009

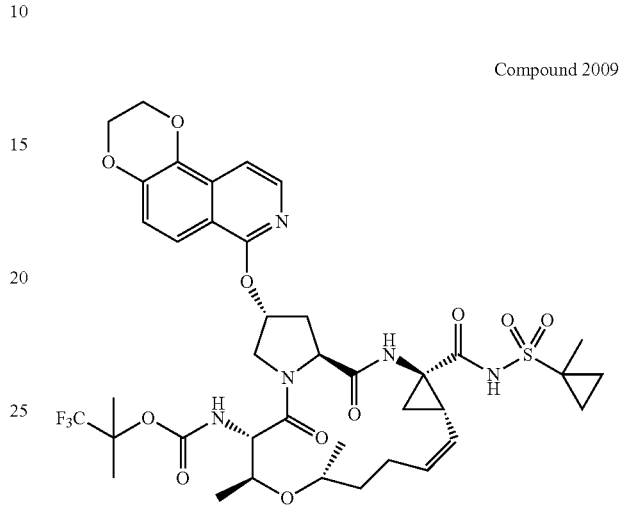

Compound 2009

Compound 2009 was prepared using the intermediates described herein and by following the general procedure described for the synthesis of Compound 2005:

Compound 2009: 1,1,1-trifluoro-2-methylpropan-2-yl ((2R,6S,7S,9R,13aS,14aR,16aS,Z)-2-((2,3-dihydro-[1,4]dioxino[2,3-f]isoquinolin-7-yl)oxy)-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. MS: MS m/z 852.7 (M$^+$+1).

Preparation of Compound 2010

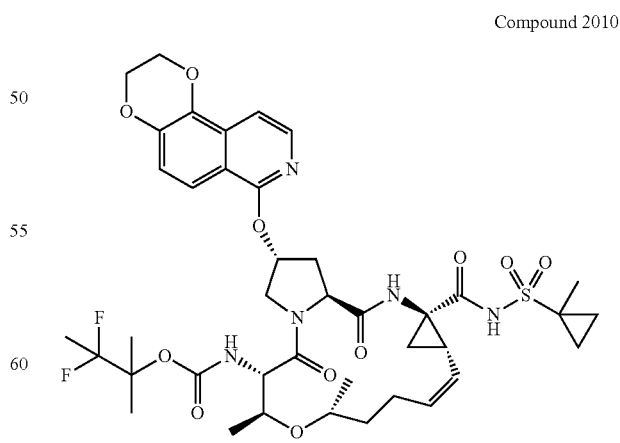

Compound 2010

Compound 2010 was prepared using the intermediates described herein and by following the general procedure described for the synthesis of Compound 2005:

Compound 2010: 3,3-difluoro-2-methylbutan-2-yl ((2R,6S,7S,9R,13aS,14aR,16aS,Z)-2-((2,3-dihydro[1,4]dioxino[2,3-f]isoquinolin-7-yl)oxy)-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (500 MHz, DMSO-$d_6$) δ 7.94 (d, J=5.8 Hz, 1H), 7.66 (d, J=9.2 Hz, 1H), 7.59 (d, J=8.9 Hz, 1H), 7.37 (d, J=6.1 Hz, 1H), 7.11 (d, J=9.2 Hz, 1H), 5.82 (br. s., 1H), 5.52 (d, J=6.1 Hz, 1H), 5.10 (br. s., 1H), 4.49-4.32 (m, 5H), 4.21 (d, J=11.6 Hz, 1H), 4.03-3.88 (m, 2H), 3.83-3.74 (m, 1H), 2.69-2.53 (m, 2H), 2.34-2.24 (m, 1H), 1.88-1.76 (m, 1H), 1.65-1.17 (m, 17H), 1.06 (d, J=3.4 Hz, 6H), 0.95 (s, 3H), 0.88-0.77 (m, 2H); MS: MS m/z 848.7 (M$^+$+1).

Preparation of Compound 2011

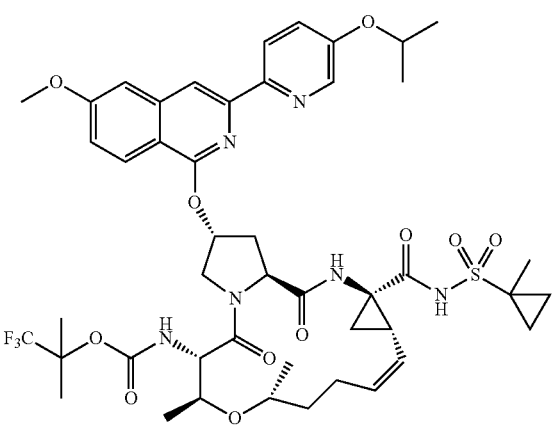

Compound 2011

Compound 2011 was prepared using the intermediates described herein and by following the general procedure described for the synthesis of Compound 2005:

Compound 2011: 1,1,1-trifluoro-2-methylpropan-2-yl ((2R,6S,7S,9R,13a5,14aR,16aS,Z)-2-((3-(5-isopropoxypyridin-2-yl)-6-methoxyisoquinolin-1-yl)oxy)-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (500 MHz, DMSO-$d_6$) δ 8.40-8.30 (m, 2H), 8.23 (s, 1H), 7.99 (d, J=9.2 Hz, 1H), 7.91 (d, J=8.9 Hz, 1H), 7.55 (d, J=9.2 Hz, 1H), 7.43 (br. s., 1H), 7.12 (d, J=9.2 Hz, 1H), 6.00 (br. s., 1H), 5.59-5.49 (m, 1H), 5.09 (br. s., 1H), 4.85-4.71 (m, 1H), 4.47 (t, J=7.9 Hz, 1H), 4.31 (d, J=10.4 Hz, 1H), 4.07 (d, J=8.9 Hz, 1H), 4.00-3.93 (m, 1H), 3.90 (s, 3H), 3.85-3.78 (m, 1H), 2.71-2.61 (m, 1H), 2.45-2.32 (m, 1H), 1.88-1.76 (m, 1H), 1.64-1.20 (m, 20H), 1.13-1.01 (m, 10H), 0.84 (br. s., 2H); MS: MS m/z 959.8 (M$^+$+1).

Preparation of Compound 2012

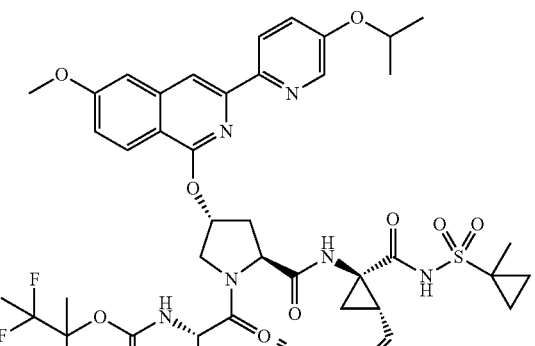

Compound 2012

Compound 2012 was prepared using the intermediates described herein and by following the general procedure described for the synthesis of Compound 2005:

Compound 2012: 3,3-difluoro-2-methylbutan-2-yl ((2R,6S,7S,9R,13a5,14aR,16aS,Z)-2-((3-(5-isopropoxypyridin-2-yl)-6-methoxyisoquinolin-1-yl)oxy)-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (500 MHz, DMSO-$d_6$) δ 8.36 (d, J=8.9 Hz, 1H), 8.33 (br. s, 1H), 8.23 (s, 1H), 7.99 (d, J=9.2 Hz, 1H), 7.70 (d, J=9.5 Hz, 1H), 7.56 (d, J=8.2 Hz, 1H), 7.44 (s, 1H), 7.12 (d, J=8.9 Hz, 1H), 6.00 (br. s., 1H), 5.59-5.46 (m, J=6.7 Hz, 1H), 5.10 (br. s., 1H), 4.78 (dt, J=12.1, 6.2 Hz, 1H), 4.47 (t, J=8.1 Hz, 1H), 4.29 (d, J=11.3 Hz, 1H), 4.08 (d, J=7.9 Hz, 1H), 4.02-3.95 (m, 1H), 3.90 (s, 3H), 3.84-3.76 (m, 1H), 2.71-2.61 (m, 1H), 2.43-2.33 (m, 1H), 1.88-1.77 (m, 1H), 1.63-1.21 (m, 23H), 1.10-1.03 (m, 7H), 0.99 (s, 3H), 0.84 (br. s., 2H); MS: MS m/z 955.8 (M$^+$+1).

Preparation of Compound 2013

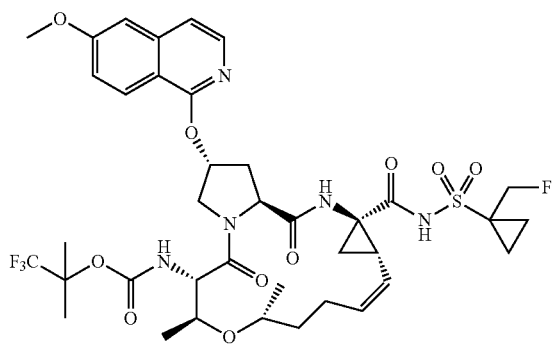

Compound 2013

Compound 2013 was prepared using the intermediates described herein and by following the general procedure described for the synthesis of Compound 2005:

Compound 2013: 1,1,1-trifluoro-2-methylpropan-2-yl ((2R,6S,7S,9R,13a5,14aR,16aS,Z)-14a-(((1-(fluoromethyl)

cyclopropyl)sulfonyl)carbamoyl)-2-((6-methoxyisoquinolin-1-yl)oxy)-7,9-dimethyl-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (500 MHz, DMSO-$d_6$) δ 11.38 (br. s, 1H), 8.95 (br. s, 1H), 7.98 (d, J=9.2 Hz, 1H), 7.93 (d, J=5.5 Hz, 1H), 7.86 (d, J=8.9 Hz, 1H), 7.33-7.27 (m, 2H), 7.13 (dd, J=9.3, 2.0 Hz, 1H), 5.80 (br. s., 1H), 5.56-5.45 (m, 1H), 5.10 (br. s., 1H), 4.86-4.67 (m, 1H), 4.63-4.47 (m, 1H), 4.41 (t, J=8.1 Hz, 1H), 4.21 (d, J=10.4 Hz, 1H), 4.01-3.91 (m, 2H), 3.88 (s, 3H), 3.83-3.77 (m, 1H), 2.59-2.53 (m, 1H), 2.45-2.34 (m, 1H), 2.34-2.25 (m, 1H), 1.85-1.74 (m, 1H), 1.65-0.96 (m, 22H); MS: MS m/z 842.7 (M$^+$+1).

Preparation of Compound 2014

Compound 2014

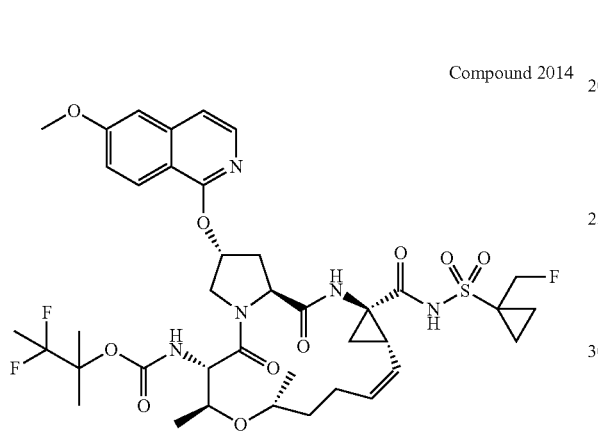

Compound 2014 was prepared using the intermediates described herein and by following the general procedure described for the synthesis of Compound 2005:

Compound 2014: 3,3-difluoro-2-methylbutan-2-yl ((2R,6S,7S,9R,13aS,14aR,16aS,Z)-14a-(((1-(fluoromethyl)cyclopropyl)sulfonyl)carbamoyl)-2-((6-methoxyisoquinolin-1-yl)oxy)-7,9-dimethyl-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. MS: MS m/z 838.7 (M$^+$+1).

Preparation of Compound 2015

Compound 2015

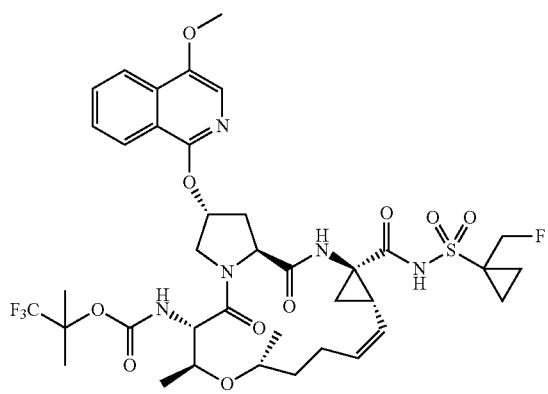

Compound 2015 was prepared using the intermediates described herein and by following the general procedure described for the synthesis of Compound 2005:

Compound 2015: 1,1,1-trifluoro-2-methylpropan-2-yl ((2R,6S,7S,9R,13a5,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. MS: MS m/z 842.7 (M$^+$+1).

Preparation of Compound 2016

Compound 2016

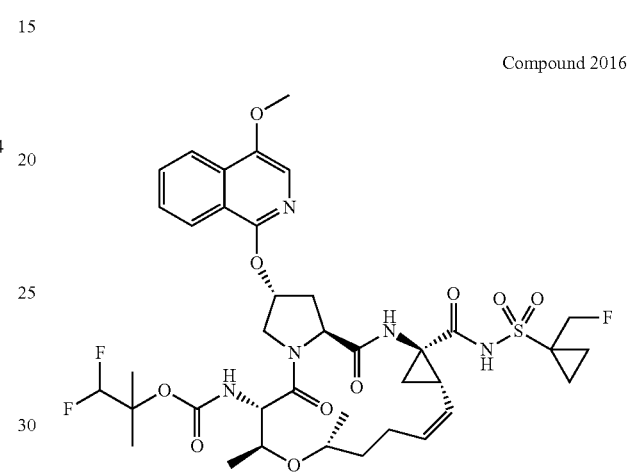

Compound 2016 was prepared using the intermediates described herein and by following the general procedure described for the synthesis of Compound 2005:

Compound 2016: 1,1-difluoro-2-methylpropan-2-yl ((2R,6S,7S,9R,13aS,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. MS: MS m/z 824.8 (M$^+$+1).

Preparation of Compound 2017

Compound 2017

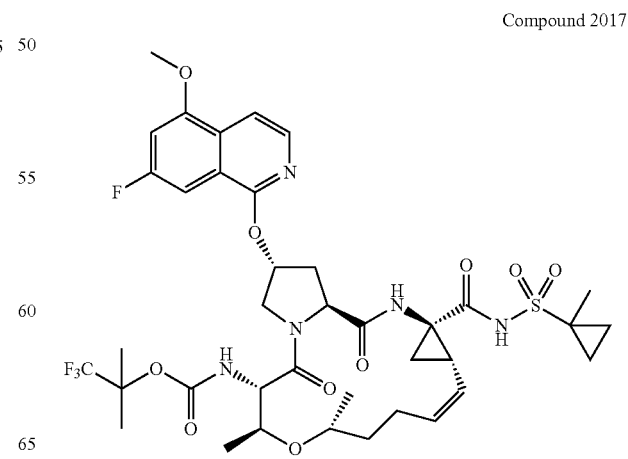

Compound 2017 was prepared using the intermediates described herein and by following the general procedure described for the synthesis of Compound 2005:

Compound 2017: 1,1,1-trifluoro-2-methylpropan-2-yl ((2R,6S,7S,9R,13aS,14aR,16aS,Z)-2-((7-fluoro-5-methoxyisoquinolin-1-yl)oxy)-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (500 MHz, DMSO-d$_6$) δ 11.16 (br. s., 1H), 9.06 (br. s, 1H), 8.00 (d, J=5.8 Hz, 1H), 7.92 (d, J=8.5 Hz, 1H), 7.51 (d, J=6.1 Hz, 1H), 7.26 (d, J=8.9 Hz, 1H), 7.22 (d, J=11.3 Hz, 1H), 5.87-5.81 (m, 1H), 5.58-5.48 (m, 1H), 5.05 (br. s., 1H), 4.46 (t, J=8.4 Hz, 1H), 4.30 (d, J=11.3 Hz, 1H), 4.00 (s, 3H), 3.98-3.90 (m, 2H), 3.86-3.78 (m, 1H), 2.64-2.56 (m, 1H), 2.35-2.26 (m, 1H), 1.86-1.75 (m, 1H), 1.64-1.22 (m, 14H), 1.12 (s, 3H), 1.10-1.04 (m, 7H), 0.87 (br. s., 2H); MS: MS m/z 842.7 (M$^+$+1).

Preparation of Compound 2018

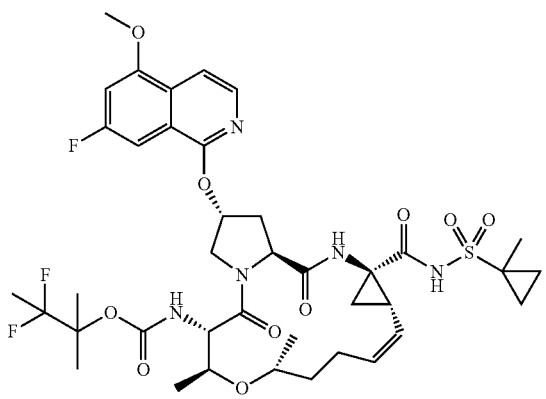

Compound 2018

Compound 2018 was prepared using the intermediates described herein and by following the general procedure described for the synthesis of Compound 2005:

Compound 2018: 3,3-difluoro-2-methylbutan-2-yl ((2R,6S,7S,9R,13aS,14aR,16aS,Z)-2-((7-fluoro-5-methoxyisoquinolin-1-yl)oxy)-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (500 MHz, DMSO-d$_6$) δ 8.94 (br. s., 1H), 8.00 (d, J=6.1 Hz, 1H), 7.69 (d, J=9.2 Hz, 1H), 7.51 (d, J=5.8 Hz, 1H), 7.26 (d, J=9.5 Hz, 1H), 7.22 (d, J=11.0 Hz, 1H), 5.84 (br. s., 1H), 5.61-5.45 (m, 1H), 5.08 (br. s., 1H), 4.51-4.40 (m, 1H), 4.27 (d, J=11.3 Hz, 1H), 4.06-3.90 (m, 5H), 3.85-3.74 (m, 1H), 2.65-2.54 (m, 1H), 2.36-2.26 (m, 1H), 1.88-1.74 (m, 1H), 1.65-1.20 (m, 17H), 1.11-1.03 (m, 7H), 0.98 (s, 3H), 0.84 (br. s., 2H); MS: MS m/z 838.7 (M$^+$+1).

Preparation of Compound 2019

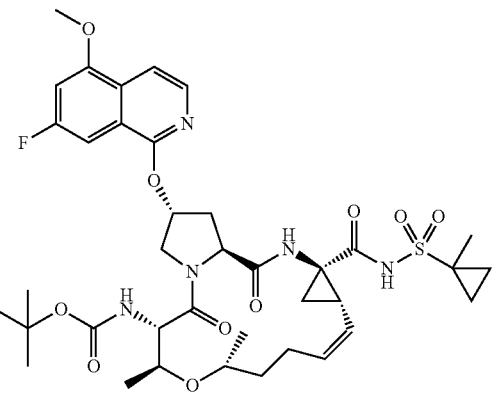

Compound 2019

Compound 2019 was prepared using the intermediates described herein and by following the general procedure described for the synthesis of Compound 2005:

Compound 2019: 1,1-difluoro-2-methylpropan-2-yl ((2R,6S,7S,9R,13aS,14aR,16aS,Z)-2-((7-fluoro-5-methoxyisoquinolin-1-yl)oxy)-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (500 MHz, DMSO-d$_6$) δ 8.87 (br. s., 1H), 8.00 (d, J=5.8 Hz, 1H), 7.76 (d, J=8.9 Hz, 1H), 7.51 (d, J=6.1 Hz, 1H), 7.27 (d, J=7.6 Hz, 1H), 7.22 (d, J=11.0 Hz, 1H), 6.00-5.70 (m, 2H), 5.58-5.47 (m, 1H), 5.12 (br. s., 1H), 4.45 (t, J=8.1 Hz, 1H), 4.33 (d, J=11.3 Hz, 1H), 4.00 (s, 3H), 3.97-3.88 (m, 2H), 3.85-3.75 (m, 1H), 2.70-2.54 (m, 2H), 2.36-2.27 (m, 1H), 1.85-1.72 (m, J=4.0 Hz, 1H), 1.64-1.02 (m, 22H), 0.82 (br. s., 2H); MS: MS m/z 824.6 (M$^+$+1).

Preparation of Compound 2020

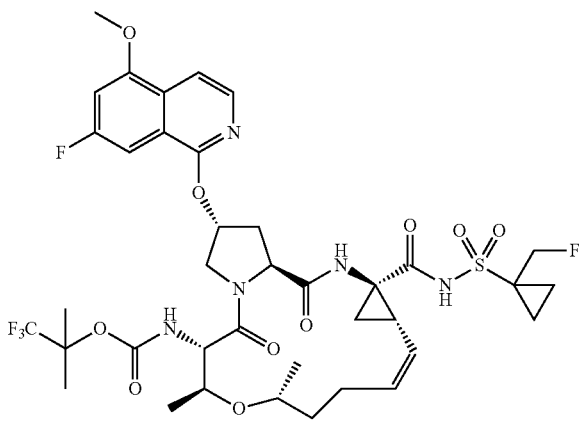

Compound 2020

Compound 2020 was prepared using the intermediates described herein and by following the general procedure described for the synthesis of Compound 2005:

Compound 2020: 1,1,1-trifluoro-2-methylpropan-2-yl ((2R,6S,7S,9R,13aS,14aR,16aS,Z)-2-((7-fluoro-5- methoxyisoquinolin-1-yl)oxy)-14a-(((1-(fluoromethyl)cyclopropyl)sulfonyl)carbamoyl)-7,9-dimethyl-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (500 MHz, DMSO-$d_6$) δ 11.38 (br. s, 1H), 8.93 (br. s, 1H), 8.00 (d, J=6.1 Hz, 1H), 7.91 (d, J=8.9 Hz, 1H), 7.51 (d, J=5.8 Hz, 1H), 7.26 (d, J=8.2 Hz, 1H), 7.22 (d, J=11.3 Hz, 1H), 5.82 (br. s., 1H), 5.56-5.46 (m, 1H), 5.10 (br. s., 1H), 4.87-4.69 (m, 1H), 4.65-4.48 (m, 1H), 4.42 (t, J=8.2 Hz, 1H), 4.27 (d, J=10.1 Hz, 1H), 4.00 (s, 3H), 3.98-3.89 (m, 2H), 3.85-3.77 (m, 1H), 2.61-2.53 (m, 1H), 2.47-2.39 (m, 1H), 2.36-2.26 (m, 1H), 1.79 (br. s., 1H), 1.62-1.00 (m, 22H); MS: MS m/z 860.7 (M$^+$+1).

Preparation of Compound 2021

Compound 2021

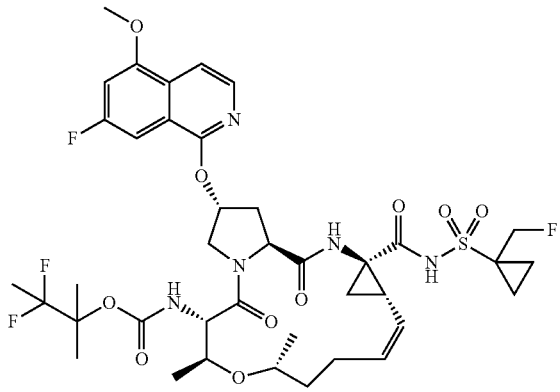

Compound 2021 was prepared using the intermediates described herein and by following the general procedure described for the synthesis of Compound 2005:

Compound 2021: 3,3-difluoro-2-methylbutan-2-yl ((2R,6S,7S,9R,13aS,14aR,16aS,Z)-2-((7-fluoro-5-methoxyisoquinolin-1-yl)oxy)-14a-(((1-(fluoromethyl)cyclopropyl)sulfonyl)carbamoyl)-7,9-dimethyl-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. MS: MS m/z 856.7 (M$^+$+1).

Preparation of Compound 2022

Compound 2022

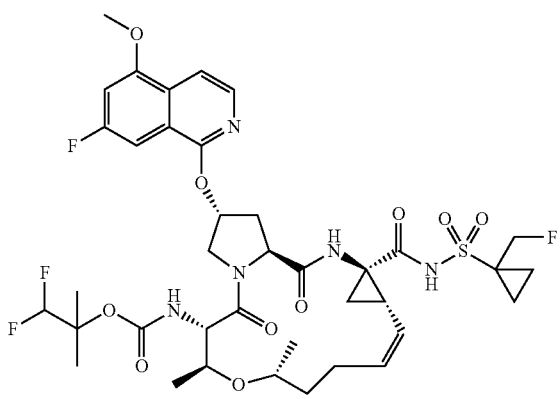

Compound 2022 was prepared using the intermediates described herein and by following the general procedure described for the synthesis of Compound 2005:

Compound 2022: 1,1-difluoro-2-methylpropan-2-yl ((2R,6S,7S,9R,13aS,14aR,16aS,Z)-2-((7-fluoro-5-methoxyisoquinolin-1-yl)oxy)-14a-(((1-(fluoromethyl)cyclopropyl)sulfonyl)carbamoyl)-7,9-dimethyl-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. MS: MS m/z 824.6 (M$^+$+1).

Preparation of Compound 2301

Compound 2301

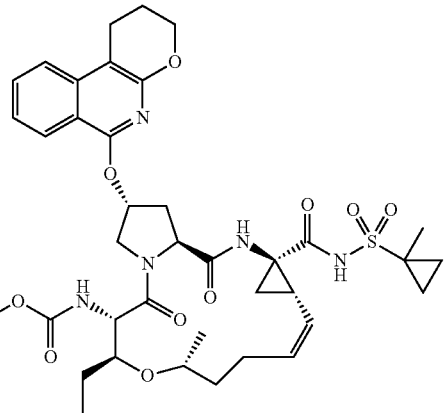

Compound 2301 was prepared using 6-chloro-2,3-dihydro-1H-pyrano[2,3-c]isoquinoline and the intermediates described above and by following the general procedure described for the synthesis of Compound 1001.

Compounds 2301: 3,3-difluoro-2-methylbutan-2-yl ((2R,6S,7S,9R,13aS,14aR,16aS,Z)-2-((2,3-dihydro-1H-pyrano[2,3-c]isoquinolin-6-yl)oxy)-7-ethyl-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (500 MHz, DMSO-$d_6$) δ 11.27 (br. s., 1H), 9.06 (br. s., 1H), 7.99 (d, J=7.9 Hz, 1H), 7.79-7.64 (m, 3H), 7.39-7.25 (m, 1H), 5.73 (br. s., 1H), 5.58-5.46 (m, 1H), 5.04 (m, 1H), 4.47-4.37 (m, 1H), 4.32 (d, J=11.0 Hz, 1H), 4.27 (d, J=5.2 Hz, 2H), 4.16 (t, J=9.6 Hz, 1H), 3.96 (d, J=7.9 Hz, 1H), 3.84 (m, 1H), 2.93-2.81 (m, 2H), 2.79-2.70 (m, 1H), 2.64-2.40 (m, 5H), 2.27 (t, J=9.8 Hz, 1H), 2.09-1.99 (m, 2H), 1.86 (m, 1H), 1.70 (m, 1H), 1.59 (d, J=6.7 Hz, 1H), 1.56-1.44 (m, 4H), 1.44-1.36 (m, 4H), 1.30 (m, 4H), 1.07 (d, J=6.1 Hz, 4H), 0.94 (m, 4H), 0.88-0.71 (m, 4H); MS: MS m/z 860.8 (M$^+$+1).

Preparation of Compound 2302

Compound 2302

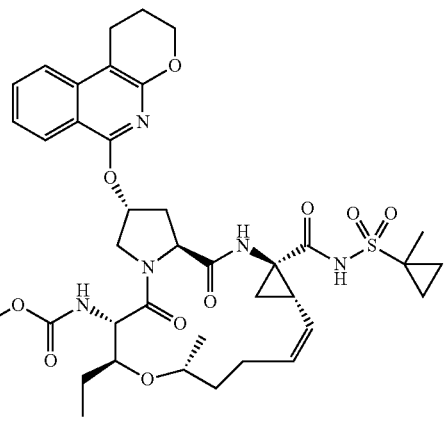

Compound 2302 was prepared using 6-chloro-2,3-dihydro-1H-pyrano[2,3-c]isoquinoline and the intermediates described above and by following the general procedure described for the synthesis of Compound 1001.

Compounds 2302: 1,1,1-trifluoro-2-methylpropan-2-yl ((2R,6S,7S,9R,13aS,14aR,16aS,Z)-2-((2,3-dihydro-1H-pyrano[2,3-c]isoquinolin-6-yl)oxy)-7-ethyl-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (500 MHz, DMSO-d$_6$) δ 11.27 (br. s., 1H), 9.06 (br. s., 1H), 7.99 (d, J=8.2 Hz, 1H), 7.88 (d, J=9.2 Hz, 1H), 7.80-7.63 (m, 2H), 7.33 (t, J=7.5 Hz, 1H), 5.72 (br. s., 1H), 5.60-5.44 (m, 1H), 5.13 (m, 1H), 4.42 (t, J=8.2 Hz, 1H), 4.32 (d, J=11.0 Hz, 1H), 4.29-4.20 (m, 2H), 4.14 (t, J=9.8 Hz, 1H), 3.95 (d, J=8.5 Hz, 1H), 3.84 (d, J=8.5 Hz, 2H), 2.92-2.79 (m, 2H), 2.68-2.53 (m, 2H), 2.37 (m, 1H), 2.28 (t, J=9.5 Hz, 1H), 2.03 (d, J=5.5 Hz, 2H), 1.83 (m, 1H), 1.68 (m, 1H), 1.58 (m, 2H), 1.52 (dd, J=9.0, 5.0 Hz, 2H), 1.40 (m, 6H), 1.36-1.21 (m, 3H), 1.06 (m, 3H), 1.00 (s, 3H), 0.86-0.66 (m, 5H); MS: MS m/z 864.7 (M$^+$+1).

Preparation of Compound 2303

Compound 2303

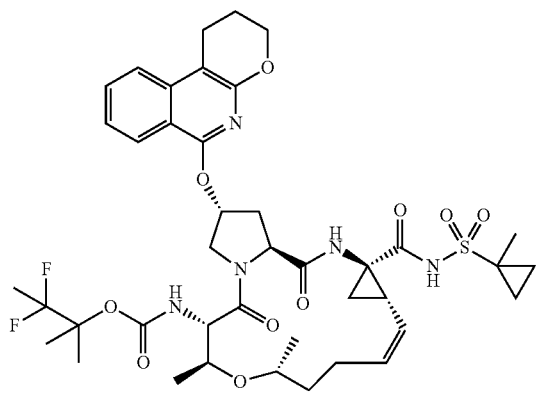

Compound 2303 was prepared using 6-chloro-2,3-dihydro-1H-pyrano[2,3-c]isoquinoline and the intermediates described above and by following the general procedure described for the synthesis of Compound 2005.

Compounds 2303: 3,3-difluoro-2-methylbutan-2-yl ((2R,6S,7S,9R,13aS,14aR,16aS,Z)-2-((2,3-dihydro-1H-pyrano[2,3-c]isoquinolin-6-yl)oxy)-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (500 MHz, DMSO-d$_6$) δ 11.27 (br. s., 1H), 9.06 (br. s., 1H), 8.00 (d, J=7.9 Hz, 1H), 7.77-7.57 (m, 3H), 7.33 (t, J=7.2 Hz, 1H), 5.72 (br. s., 1H), 5.58-5.47 (m, 1H), 5.12 (m, 1H), 4.42 (t, J=8.4 Hz, 1H), 4.31-4.16 (m, 3H), 4.01-3.87 (m, 2H), 3.84-3.71 (m, 1H), 2.93-2.78 (m, 2H), 2.61-2.49 (m, 4H), 2.46 (m, 1H), 2.28 (t, J=9.6 Hz, 1H), 2.03 (d, J=4.9 Hz, 2H), 1.82 (m, 1H), 1.58 (m, 1H), 1.54-1.35 (m, 9H), 1.30 (m, 2H), 1.25 (d, J=10.7 Hz, 2H), 1.06 (d, J=5.8 Hz, 3H), 1.06 (d, J=5.2 Hz, 3H), 0.94 (s, 3H), 0.82 (m, 2H); MS: MS m/z 846.8 (M$^+$+1).

Preparation of Compound 2304

Compound 2304

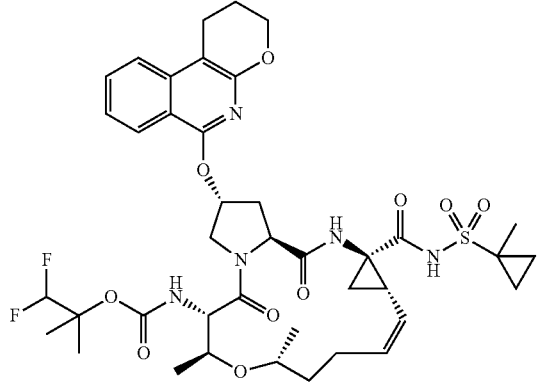

Compound 2304 was prepared using 6-chloro-2,3-dihydro-1H-pyrano[2,3-c]isoquinoline and the intermediates described above and by following the general procedure described for the synthesis of Compound 2005.

Compounds 2304: 1,1-difluoro-2-methylpropan-2-yl ((2R,6S,7S,9R,13aS,14aR,16aS,Z)-2-((2,3-dihydro-1H-pyrano[2,3-c]isoquinolin-6-yl)oxy)-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (500 MHz, DMSO-d$_6$) δ 11.27 (br. s., 1H), 9.06 (br. s., 1H), 8.01 (d, J=8.2 Hz, 1H), 7.80-7.65 (m, 3H), 7.34 (t, J=7.3 Hz, 1H), 5.68 (m, 2H), 5.57-5.46 (m, 1H), 5.14 (br. s., 1H), 4.47-4.36 (m, 1H), 4.35-4.21 (m, 3H), 4.01-3.87 (m, 2H), 3.79 (dd, J=9.6, 6.0 Hz, 1H), 2.92-2.78 (m, 2H), 2.55 (m, 3H), 2.33-2.25 (m, 2H), 2.09-2.00 (m, 2H), 1.57 (m, 1H), 1.55-1.47 (m, 2H), 1.39 (s, 3H), 1.31 (d, J=12.8 Hz, 2H), 1.23 (m, 2H), 1.12-1.02 (m, 12H), 0.80 (m, 2H); MS: MS m/z 832.8 (M$^+$+1).

Preparation of Compound 2305

Compound 2305

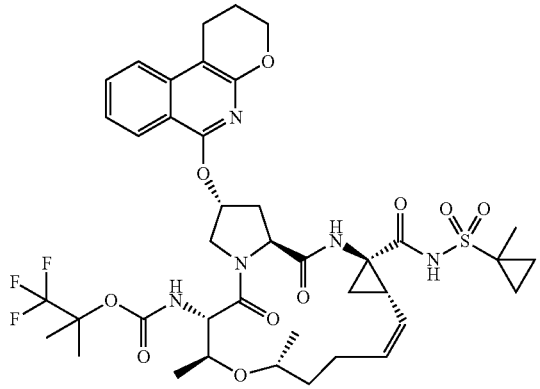

Compound 2305 was prepared using 6-chloro-2,3-dihydro-1H-pyrano[2,3-c]isoquinoline and the intermediates described above and by following the general procedure described for the synthesis of Compound 2005.

Compounds 2305: 1,1,1-trifluoro-2-methylpropan-2-yl ((2R,6S,7S,9R,13aS,14aR,16aS,Z)-2-((2,3-dihydro-1H-pyrano[2,3-c]isoquinolin-6-yl)oxy)-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (500 MHz, DMSO-$d_6$) δ 11.27 (br. s., 1H), 9.06 (br. s., 1H), 7.76 (d, J=8.2 Hz, 1H), 7.63 (d, J=8.9 Hz, 1H), 7.53-7.38 (m, 2H), 7.09 (t, J=7.3 Hz, 1H), 5.46 (br. s., 1H), 5.28 (d, J=7.0 Hz, 1H), 4.84 (m, 1H), 4.18 (t, J=8.1 Hz, 1H), 4.01 (s, 3H), 3.78-3.65 (m, 2H), 3.56 (m, 1H), 2.60 (d, J=6.7 Hz, 2H), 2.40-2.19 (m, 4H), 2.03 (m, 1H), 1.78 (d, J=5.2 Hz, 2H), 1.56 (m, 1H), 1.34-0.96 (m, 10H), 0.81-0.78 (m, 10H), 0.59 (m, 3H); MS: MS m/z 850.8 (M$^+$+1).

Preparation of Compound 2306

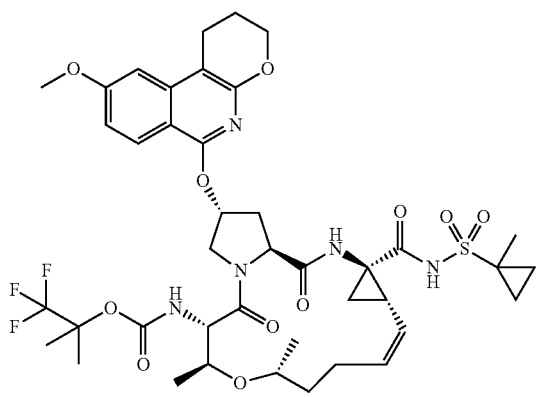

Compound 2306

Compound 2306 was prepared using 6-chloro-9-methoxy-2,3-dihydro-1H-pyrano[2,3-c]isoquinoline and the intermediates described above and by following the general procedure described for the synthesis of Compound 2005.

Compounds 2306: 1,1,1-trifluoro-2-methylpropan-2-yl ((2R,6S,7S,9R,13aS,14aR,16aS,Z)-2-((9-methoxy-2,3-dihydro-1H-pyrano[2,3-c]isoquinolin-6-yl)oxy)-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (500 MHz, DMSO-$d_6$) δ 11.27 (br. s., 1H), 9.06 (br. s., 1H), 7.90 (dd, J=8.5, 3.7 Hz, 2H), 7.00 (br. s., 1H), 6.92 (d, J=8.9 Hz, 1H), 5.69 (br. s., 1H), 5.52 (d, J=5.8 Hz, 1H), 5.08 (br. s., 1H), 4.45-4.35 (m, 1H), 4.24 (d, J=4.6 Hz, 3H), 3.99-3.86 (m, 6H), 3.82 (d, J=6.1 Hz, 1H), 2.81 (d, J=5.5 Hz, 2H), 2.67 (m, 1H), 2.55 (s, 3H), 2.26 (t, J=9.9 Hz, 1H), 2.03 (d, J=5.2 Hz, 2H), 1.81 (m, 1H), 1.59 (m, 1H), 1.51 (m, 2H), 1.40 (m, 3H), 1.43 (s, 3H), 1.35-1.21 (m, 2H), 1.12 (s, 3H), 1.06 (t, J=6.1 Hz, 6H), 0.85 (m, 2H); MS: MS m/z 880.8 (M$^+$+1).

Preparation of Compound 2307

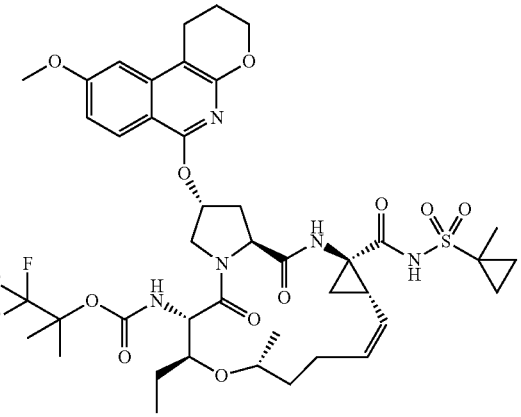

Compound 2307

Compound 2307 was prepared using 6-chloro-9-methoxy-2,3-dihydro-1H-pyrano[2,3-c]isoquinoline and the intermediates described above and by following the general procedure described for the synthesis of Compound 1001.

Compounds 2307: 1,1,1-trifluoro-2-methylpropan-2-yl ((2R,6S,7S,9R,13aS,14aR,16aS,Z)-7-ethyl-2-((9-methoxy-2,3-dihydro-1H-pyrano[2,3-c]isoquinolin-6-yl)oxy)-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (400 MHz, METHANOL-$d_4$) δ 7.97 (d, J=9.0 Hz, 1H), 6.99 (d, J=2.3 Hz, 1H), 6.90 (dd, J=9.2, 2.4 Hz, 1H), 5.83-5.74 (m, 1H), 5.61 (td, J=9.9, 6.5 Hz, 1H), 5.11 (t, J=10.0 Hz, 1H), 4.68-4.50 (m, 2H), 4.39-4.28 (m, 3H), 4.08 (dd, J=11.8, 3.5 Hz, 1H), 3.93 (m, 4H), 3.54 (td, J=6.4, 3.0 Hz, 1H), 2.87 (td, J=6.4, 3.3 Hz, 2H), 2.83-2.74 (m, 1H), 2.71-2.63 (m, 2H), 2.61-2.51 (m, 1H), 2.41 (ddd, J=13.9, 9.9, 4.3 Hz, 1H), 2.18-2.08 (m, 2H), 1.91-1.79 (m, 2H), 1.78-1.55 (m, 4H), 1.51 (s, 4H), 1.43 (s, 5H), 1.16 (d, J=6.3 Hz, 3H), 1.04 (s, 3H), 0.94-0.84 (m, 4H); MS: MS m/z 895.0 (M$^+$+1).

Preparation of Compound 2308

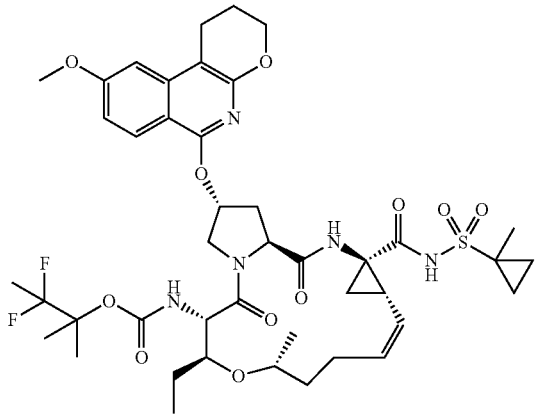

Compound 2308

Compound 2308 was prepared using 6-chloro-9-methoxy-2,3-dihydro-1H-pyrano[2,3-c]isoquinoline and the intermediates described above and by following the general procedure described for the synthesis of Compound 1001.

Compounds 2308: 3,3-difluoro-2-methylbutan-2-yl ((2R,6S,7S,9R,13aS,14aR,16aS,Z)-7-ethyl-2-((9-methoxy-2,3-dihydro-1H-pyrano[2,3-c]isoquinolin-6-yl)oxy)-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (500 MHz, DMSO-$d_6$) δ 11.27 (br. s., 1H), 9.06 (br. s., 1H), 7.88 (d, J=8.9 Hz, 1H), 7.70 (d, J=9.8 Hz, 1H), 7.00 (s, 1H), 6.94-6.87 (m, 1H), 5.70 (br. s., 1H), 5.57-5.49 (m, 1H), 5.10 (m, 1H), 4.40 (t, J=8.2 Hz, 1H), 4.25 (m, 3H), 4.16 (t, J=9.8 Hz, 1H), 3.95 (d, J=7.9 Hz, 1H), 3.90 (m, 4H), 3.83 (d, J=9.2 Hz, 1H), 3.48 (d, J=4.3 Hz, 1H), 2.81 (d, J=5.2 Hz, 2H), 2.73 (m, 1H), 2.55 (m, 1H), 2.43 (m, 1H), 2.27 (t, J=9.5 Hz, 1H), 2.03 (m, 2H), 1.85 (m, 1H), 1.69 (m, 1H), 1.58 (m, 2H), 1.55-1.43 (m, 4H), 1.40 (m, 3H), 1.33 (m, 3H), 1.27 (m, 2H), 1.07 (d, J=6.1 Hz, 3H), 1.02 (s, 3H), 0.82 (t, J=7.2 Hz, 6H); MS: MS m/z 890.9 (M$^+$+1).

Preparation of Compound 2309

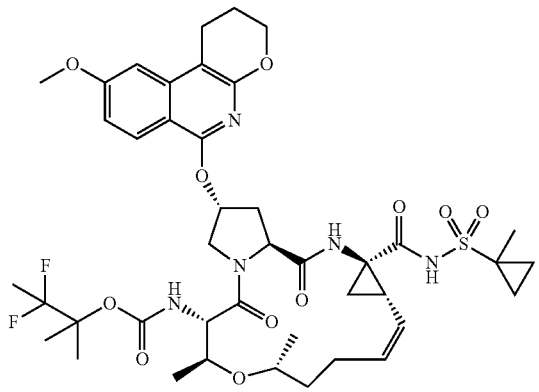

Compound 2309

Compound 2309 was prepared using 6-chloro-9-methoxy-2,3-dihydro-1H-pyrano[2,3-c]isoquinoline and the intermediates described above and by following the general procedure described for the synthesis of Compound 2005.

Compounds 2309: 3,3-difluoro-2-methylbutan-2-yl ((2R,6S,7S,9R,13aS,14aR,16aS,Z)-2-((9-methoxy-2,3-dihydro-1H-pyrano[2,3-c]isoquinolin-6-yl)oxy)-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (500 MHz, DMSO-$d_6$) δ 11.27 (br. s., 1H), 9.06 (br. s., 1H), 7.90 (d, J=8.9 Hz, 1H), 7.69 (d, J=9.2 Hz, 1H), 7.01 (d, J=1.8 Hz, 1H), 6.92 (d, J=9.2 Hz, 1H), 5.70 (br. s., 1H), 5.52 (d, J=7.3 Hz, 1H), 5.09 (br. s., 1H), 4.40 (t, J=8.4 Hz, 1H), 4.29-4.11 (m, 3H), 3.99-3.85 (m, 5H), 3.79 (dd, J=9.6, 6.0 Hz, 1H), 3.45 (m, 1H), 2.81 (d, J=6.1 Hz, 2H), 2.55 (s, 1H), 2.27 (t, J=9.5 Hz, 1H), 2.03 (d, J=3.7 Hz, 2H), 1.83 (br. s., 1H), 1.63-1.55 (m, 1H), 1.53-1.37 (m, 9H), 1.34 (s, 3H), 1.26 (d, J=9.8 Hz, 2H), 1.18 (d, J=11.9 Hz, 1H), 1.09-0.99 (m, 9H), 0.83 (br. s., 3H); MS: MS m/z 876.9 (M$^+$+1).

Preparation of Compound 2310

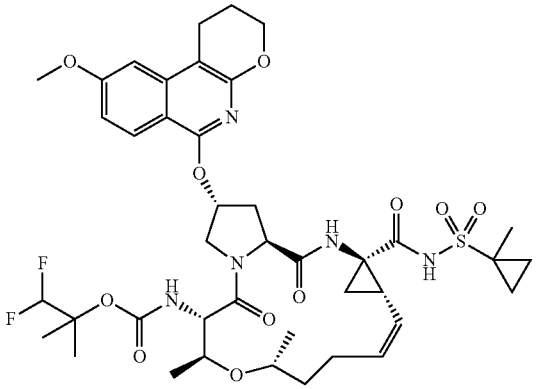

Compound 2310

Compound 2310 was prepared using 6-chloro-9-methoxy-2,3-dihydro-1H-pyrano[2,3-c]isoquinoline and the intermediates described above and by following the general procedure described for the synthesis of Compound 2005.

Compounds 2310: 1,1-difluoro-2-methylpropan-2-yl ((2R,6S,7S,9R,13aS,14aR,16aS,Z)-2-((9-methoxy-2,3-dihydro-1H-pyrano[2,3-c]isoquinolin-6-yl)oxy)-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (500 MHz, DMSO-$d_6$) δ 11.27 (br. s., 1H), 9.06 (br. s., 1H), 7.90 (d, J=8.9 Hz, 1H), 7.76 (d, J=9.2 Hz, 1H), 7.00 (br. s., 1H), 6.93 (d, J=9.2 Hz, 1H), 6.02-5.66 (m, 4H), 5.57-5.43 (m, 1H), 5.13 (br. s., 1H), 4.40 (t, J=8.2 Hz, 1H), 4.25 (m, 3H), 3.99-3.86 (m, 5H), 3.83-3.74 (m, 1H), 3.45 (m, 1H), 2.81 (d, J=6.4 Hz, 2H), 2.56-2.48 (m, 2H), 2.28 (d, J=10.4 Hz, 1H), 2.03 (d, J=5.5 Hz, 2H), 1.80 (m, 1H), 1.57 (m, 1H), 1.55-1.46 (m, 2H), 1.39 (s, 3H), 1.35-1.19 (m, 4H), 1.15 (m, 2H), 1.12-1.03 (m, 8H), 0.81 (m, 2H); MS: MS m/z 862.9 (M$^+$+1).

Preparation of Compound 2311

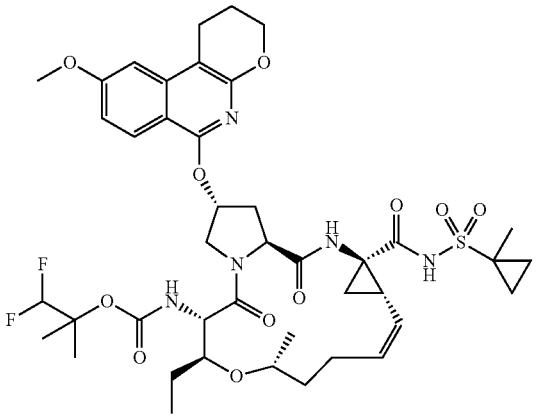

Compound 2311

Compound 2311 was prepared using 6-chloro-9-methoxy-2,3-dihydro-1H-pyrano[2,3-c]isoquinoline and the intermediates described above and by following the general procedure described for the synthesis of Compound 1001.

Compounds 2311: 1,1-difluoro-2-methylpropan-2-yl ((2R,6S,7S,9R,13aS,14aR,16aS,Z)-7-ethyl-2-((9-methoxy-2,3-dihydro-1H-pyrano[2,3-c]isoquinolin-6-yl)oxy)-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (400 MHz, METHANOL-$d_4$) δ 7.97 (d, J=9.0 Hz, 1H), 6.99 (d, J=2.3 Hz, 1H), 6.91 (dd, J=9.0, 2.3 Hz, 1H), 5.87-5.55 (m, 2H), 5.10 (m, 1H), 4.71-4.51 (m, 3H), 4.38-4.25 (m, 3H), 4.07 (dd, J=12.0, 3.3 Hz, 1H), 3.96-3.77 (m, 4H), 3.53 (d, J=2.8 Hz, 1H), 2.90-2.73 (m, 3H), 2.73-2.54 (m, 2H), 2.41 (ddd, J=14.0, 10.1, 4.3 Hz, 1H), 2.19-2.04 (m, 2H), 1.88-1.79 (m, 1H), 1.78-1.54 (m, 4H), 1.51 (s, 3H), 1.44-1.26 (m, 4H), 1.16 (d, J=6.3 Hz, 3H), 1.10 (m, 6H), 0.97-0.77 (m, 5H); MS: MS m/z 876.9 (M$^+$+1).

Preparation of Compound 2601

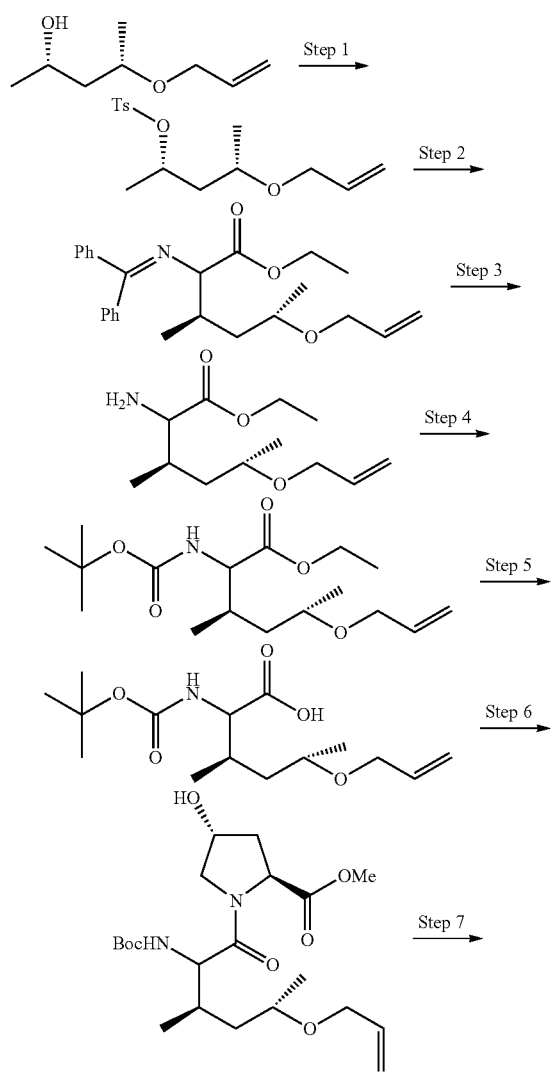

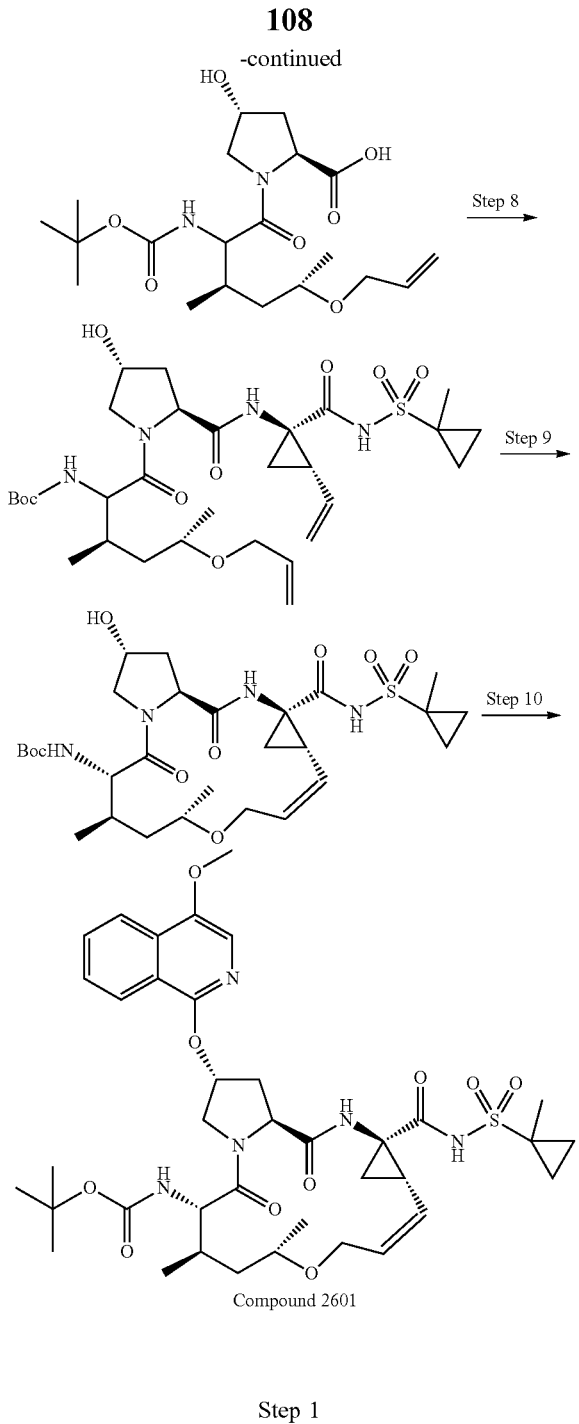

Compound 2601

Step 1

To a solution of (2S,4S)-4-(allyloxy)pentan-2-ol (2, 13.87 mmol) and Tosyl-Cl (5.29 g, 27.7 mmol) in CH$_2$Cl$_2$ (20 mL) was added Tosyl-Cl (5.29 g, 27.7 mmol) at 0° C. The formed was stirred at rt overnight. Quenched with iced water, extracted with EtOAc. The organic layer was washed with 1M HCl, saturated NaHCO$_3$, and brine, dried over MgSO$_4$, filtered, evaporated. 2.4 g of the product (2S,4S)-4-(allyloxy)pentan-2-yl 4-methylbenzenesulfonate was obtained as a lightly colored oil. $^1$H NMR (400 MHz, CHLOROFORM-d) δ 7.82 (d, J=8.3 Hz, 2H), 7.38-7.33 (m, 2H), 5.94-5.82 (m, 1H), 5.25 (dq, J=17.1, 1.7 Hz, 1H), 5.15 (dq, J=10.3, 1.4 Hz, 1H), 4.93 (dqd, J=9.4, 6.3, 2.9 Hz, 1H), 3.95 (ddt, J=12.2, 6.0, 1.3 Hz, 1H), 3.63 (ddt, J=12.2, 5.4, 1.5 Hz, 1H), 3.46

(dqd, J=9.4, 6.2, 2.9 Hz, 1H), 2.46 (s, 3H), 1.78-1.69 (m, 1H), 1.67-1.58 (m, 1H), 1.26 (d, J=6.5 Hz, 3H), 1.11 (d, J=6.3 Hz, 3H).

Step 2

To a light yellow solution of (2S,4S)-4-(allyloxy)pentan-2-yl 4-methylbenzenesulfonate (2.4 g, 8.04 mmol) and ethyl 2-((diphenylmethylene)amino)acetate (2.150 g, 8.04 mmol) in PhCH$_3$ (20 mL) was added LiHMDS (9.65 mL, 9.65 mmol) dropwise. It was slightly exothemic. The formed dark brown solution was heated to gentle reflux for overnight. The formed light brown slurry was queched with water, extracted with EtOAc. The organic layer was washed with water and brine, dried over MgSO$_4$, filtrated, and concentrated in vacuo to afford 3.17 g of the desired product (with impurities) (3R,5S)-ethyl 5-(allyloxy)-2-((diphenylmethylene)amino)-3-methylhexanoate as a dark red oil. Crude material was taken directly onto next step.

Step 3

A mixture of (3R,5S)-ethyl 5-(allyloxy)-2-((diphenylmethylene)amino)-3-methylhexanoate (3.17 g, 8.06 mmol) in diethyl ether (50 mL) and 1M HCl (16.11 mL, 16.11 mmol) was stirred at rt for 16 h. The reaction was extracted with ether. The aqueous layer was adjusted to pH=8 using sat. sodium bicarbonate addition carefully. It was then extracted with EtOAc, dried over MgSO$_4$, filtered and concentrated to obtaina red oil (1.1 g) that will be used in the next step as it is.

Step 4

A mixture of (3R,5S)-ethyl 5-(allyloxy)-2-amino-3-methylhexanoate (1.1 g, 4.80 mmol), di-tert-butyl dicarbonate (1.256 g, 5.76 mmol) and Et$_3$N (1.337 mL, 9.59 mmol) in DCM (10 mL) was stirred at rt for overnight. It was washed with 1M HCl(2×) and then brine. The organic layer was collected, dried over MgSO$_4$, filtered and evaporated to give the product (3R,5S)-ethyl 5-(allyloxy)-2-((tert-butoxycarbonyl)amino)-3-methylhexanoate (1.5 g, 4.55 mmol, 95% yield) as a red oil that will be used in the next step as it is.

Step 5

NaOH (0.767 g, 19.18 mmol) was added to a solution of (3R,5S)-ethyl 5-(allyloxy)-2-((tert-butoxycarbonyl)amino)-3-methylhexanoate (1.58 g, 4.80 mmol) in water (10 mL) and MeOH (20 mL) and was stirred at RT for overnight. The reaction was partially evaporated to remove most of the solvent then diluted with 2M HCl and extracted with EtOAc (2×). The organic layer was washed with brine, collected, dried over MgSO$_4$, filtered and evaporated to give the final product (3R,5S)-5-(allyloxy)-2-((tert-butoxycarbonyl)amino)-3-methylhexanoic acid (1.4 g, 4.65 mmol, 97% yield) as an orange viscous oil. MS: MS m/z 324.15 (M$^+$+23).

Step 6

HATU (6.36 g, 16.72 mmol) was added to a solution of (2S,4R)-methyl 4-hydroxypyrrolidine-2-carboxylate, HCl (2.78 g, 15.33 mmol), (3R,5S)-5-(allyloxy)-2-((tert-butoxycarbonyl)amino)-3-methylhexanoic acid (4.2 g, 13.94 mmol) and Hunig'sBase (7.30 mL, 41.8 mmol) in DCM (100 mL) and stirred at r.t. overnight. The reaction was washed with 1N HCl (3×) and then brine. The organics were dried with magnesium sulfate, filtered and evaporated to give the crude product. The crude material was purified by flash chromatography on the Biotage (25-75% EtOAc in hexane) to give 5.1 of a mixture of thediastereomers (2S,4R)-methyl 1-((3R,5S)-5-(allyloxy)-2-((tert-butoxycarbonyl)amino)-3-methylhexanoyl)-4-hydroxypyrrolidine-2-carboxylate. MS: MS m/z 451.15 (M$^+$+23).

Step 7

To solution of (2S,4R)-methyl 1-((3R,5S)-5-(allyloxy)-2-((tert-butoxycarbonyl)amino)-3-methylhexanoyl)-4-hydroxypyrrolidine-2-carboxylate (5.14 g, 12 mmol) in MeOH (10 mL) and THF (10.00 mL) was added the solution of LiOH (1.150 g, 48.0 mmol) in water (10.00 mL). The reaction mixture was stirred at rt for overnight. After removing the volatiles under vacumm, the aqueous layer was neutralised with 1.5 N HCl, and extracted with ethyl acetate. Combined organic layers was washed with brine solution, dried over Na$_2$SO$_4$, concentrated to give 4.2 g of the product (2S,4R)-1-((3R,5S)-5-(allyloxy)-2-((tert-butoxycarbonyl)amino)-3-methylhexanoyl)-4-hydroxypyrrolidine-2-carboxylic acid as yellow solid. MS: MS m/z 437.14 (M$^+$+23).

Step 8

HATU (1.825 g, 4.80 mmol) was added to a solution of (2S,4R)-1-((3R,5S)-5-(allyloxy)-2-((tert-butoxycarbonyl)amino)-3-methylhexanoyl)-4-hydroxypyrrolidine-2-carboxylic acid (1.658 g, 4 mmol), (1R,2S)-1-amino-N-((1-methylcyclopropyl)sulfonyl)-2-vinylcyclopropanecarboxamide, HCl (1.348 g, 4.80 mmol), and Hunig'sBase (2.79 ml, 16.00 mmol) in DCM (20 ml) and was stirred at RT for overnight. The reaction was washed with 1N HCl (3×) and then brine and evaporated on rotovap to get the product tert-butyl ((3R,5S)-5-(allyloxy)-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-3-methyl-1-oxohexan-2-yl)carbamate (1.5 g, 2.341 mmol, 58.5% yield) as a light orange foam. MS: MS m/z 663.24 (M$^+$+23).

Step 9

A solution of tert-butyl ((3R,5S)-5-(allyloxy)-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-3-methyl-1-oxohexan-2-yl)carbamate (32.0 mg, 0.05 mmol) in DCE (10 mL) was sparged with nitrogen for 30 min. and then Hoveyda-Grubbs Catalyst 2nd Generation (1.886 mg, 3.00 µmol) was added and the reaction heated to 80° C. for 2 hrs then cooled down to 45° C. and stirred at this temp for over the weekend. The reaction was concentrated and purified by flash chromatography on the Biotage (20-60% Acetone in hexanes) to give the final product contaminated with ruthenium catalyst as a light brown crispy foam that was purified by prep HPLC to give 12 mg of the desired product tert-butyl ((2R,6S,7R,9S,13a5,14aR,16aS,Z)-2-hydroxy-7,9-dimethyl-14a-(((1-methylcyclopropyl)sulfonyl)carbamoyl)-5,16-dioxo-2,3,5,6,7,8,9,11,13a,14,14a,15,16,16a-tetradecahydro-1H-cyclopropa[e]pyrrolo[2,1-i][1,7,10]oxadiazacyclopentadecin-6-yl)carbamate as a sloid. MS: MS m/z 613.34 (M$^+$+1).

Step 10

To a mixture of tert-butyl ((2R,6S,7R,9S,13aS,14aR,16aS,Z)-2-hydroxy-7,9-dimethyl-14a-(((1-methylcyclopropyl)sulfonyl)carbamoyl)-5,16-dioxo-2,3,5,6,7,8,9,11,13a, 14,14a,15,16,16a-tetradecahydro-1H-cyclopropa[e]pyrrolo[2,1-i][1,7,10]oxadiazacyclopentadecin-6-yl)carbamate (30.6 mg, 0.05 mmol),1-fluoro-4-methoxyisoquinoline (10.63 mg, 0.060 mmol), and tert-BuOK(28.1 mg, 0.250 mmol) was added DMSO (5 mL) and then sonicated for 15 min. The resulting solution was stirred for 4 h. The reaction was quenched with water, acidified with 6 N HCl, extracted with EtOAc, washed with brine, dried over MgSO₄. After concentration, the residue was purified by prep HPLC to give 10.3 mg of compound 2601.

Compound 2601: tert-butyl ((2R,6S,7R,9S,13aS,14aR,16aS,Z)-2-((4-methoxyisoquinolin-1-yl)oxy)-7,9-dimethyl-14a-(((1-methylcyclopropyl)sulfonyl)carbamoyl)-5,16-dioxo-2,3,5,6,7,8,9,11,13a,14,14a,15,16,16a-tetradecahydro-1H-cyclopropa[e]pyrrolo[2,1-i][1,7,10]oxadiazacyclopentadecin-6-yl)carbamate. MS: MS m/z 770.5 (M⁺+1).

Preparation of Compound 2602

Compound 2602

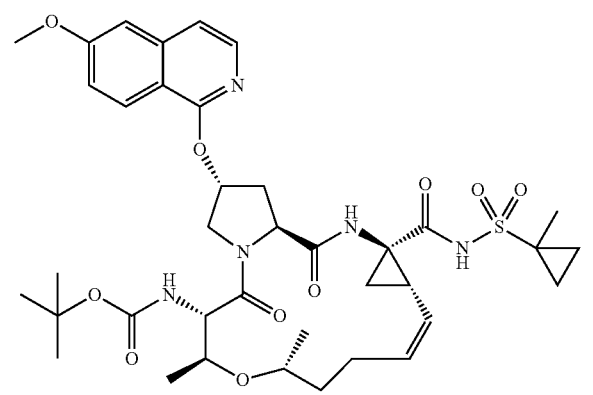

Compound was prepared using the intermediates described herein and by following the general procedure described for the synthesis of Compound 2001: Compound 2602: tert-butyl ((2R,6S,7R,9S,13aS,14aR,16aS,Z)-2-((6-methoxyisoquinolin-1-yl)oxy)-7,9-dimethyl-14a-(((1-methylcyclopropyl)sulfonyl)carbamoyl)-5,16-dioxo-2,3,5,6,7,8,9,11,13a,14,14a,15,16,16a-tetradecahydro-1H-cyclopropa[e]pyrrolo[2,1-i][1,7,10]oxadiazacyclopentadecin-6-yl)carbamate. MS: MS m/z 770.6 (M⁺+1).

Preparation of Compound 2603

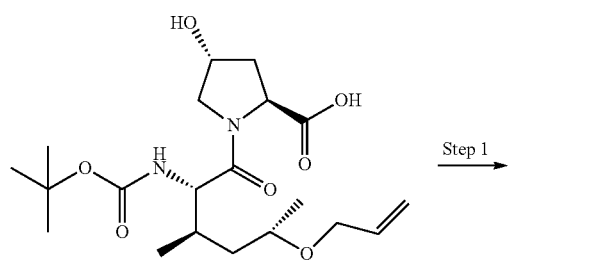

Step 1

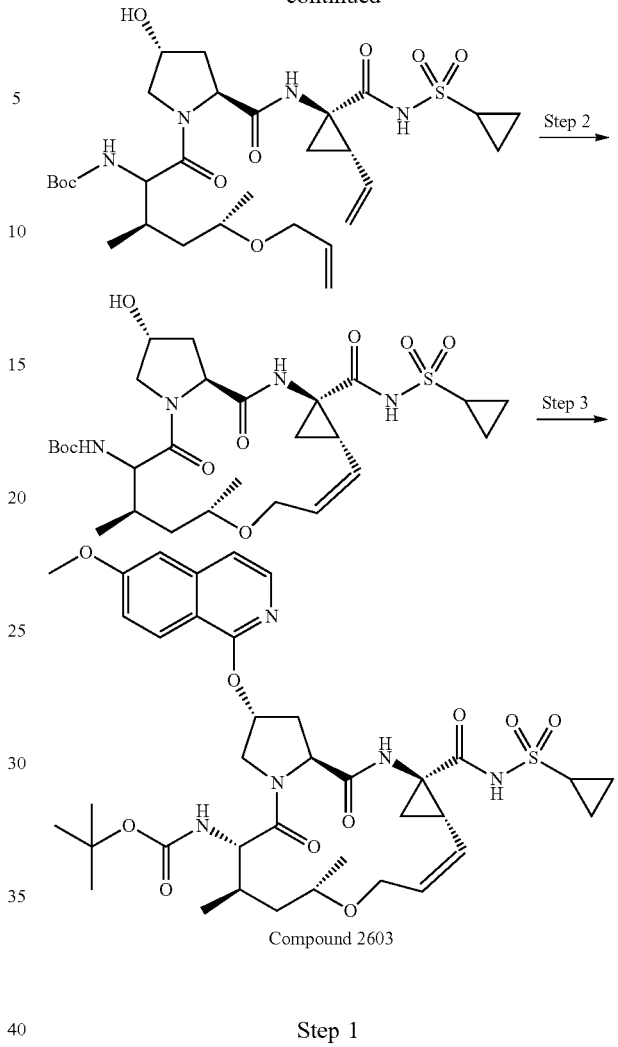

Step 1

HATU (1.506 g, 3.96 mmol) was added to a solution of (2S,4R)-1-((3R,5S)-5-(allyloxy)-2-((tert-butoxycarbonyl)amino)-3-methylhexanoyl)-4-hydroxypyrrolidine-2-carboxylic acid (1.368 g, 3.3 mmol), (1R,2S)-1-amino-N-(cyclopropylsulfonyl)-2-vinylcyclopropanecarboxamide, p-toluenesulfonate salt (1.457 g, 3.63 mmol), and Hunig'sBase (2.305 ml, 13.20 mmol) in DCM (20 ml) and was stirred at RT for overnight. The reaction was washed with 1N HCl (3×) and then brine and evaporated on rotovap to get the final product tert-butyl ((3R,5S)-5-(allyloxy)-1-((2S,4R)-2-(((1R,2S)-1-((cyclopropylsulfonyl)carbamoyl)-2-vinylcyclopropyl)carbamoyl)-4-hydroxypyrrolidin-1-yl)-3-methyl-1-oxohexan-2-yl)carbamate (1.5 g, 2.393 mmol, 72.5% yield) as a light orange foam. MS: MS m/z 649.2 (M⁺+23).

Step 2

A solution of tert-butyl ((2S,3R,5S)-5-(allyloxy)-1-((2S,4R)-2-(((1R,2S)-1-((cyclopropylsulfonyl)carbamoyl)-2-vinylcyclopropyl)carbamoyl)-4-hydroxypyrrolidin-1-yl)-3-methyl-1-oxohexan-2-yl)carbamate (31.3 mg, 0.05 mmol) in DCE (500 mL) was sparged with nitrogen for 30 min. and then Hoveyda-Grubbs Catalyst 2nd Generation (1.886 mg, 3.00 μmol) was added and the reaction heated to 80° C. for 2 hrs, then cooled down to 45° C. and stirred at this temp for over the weekend. The reaction was concentrated and purified by flash chromatography on the Biotage (20-60% Acetone in hexanes) to give the final product contaminated with ruthenium catalyst as a light brown crispy foam that was purified by prep HPLC to give 24.6 mg of the desired product as a solid. MS: MS m/z 599.4 (M$^+$+1).

Step 3

To a mixture of tert-butyl ((2R,6S,7R,9S,13a5,14aR,16aS,Z)-14a-((cyclopropylsulfonyl)carbamoyl)-2-hydroxy-7,9-dimethyl-5,16-dioxo-2,3,5,6,7,8,9,11,13a,14,14a,15,16,16a-tetradecahydro-1H-cyclopropa[e]pyrrolo[2,1-i][1,7,10]oxadiazacyclopentadecin-6-yl)carbamate (29.9 mg, 0.05 mmol),1-chloro-6-methoxyisoquinoline (11.62 mg, 0.060 mmol), and tert-BuOK (28.1 mg, 0.250 mmol) was added DMSO (5 mL) and then sonicated for 15 min. The resulting solution was stirred for 4 h. The reaction was quenched with water, acidified with 6 N HCl, extracted with EtOAc, washed with brine, dried over MgSO$_4$. After concentration, the residue was purified by prep HPLC to give 13.5 mg of the product as a solid.

Compound 2603: tert-butyl ((2R,6S,7R,9S,13a5,14aR,16aS,Z)-14a-((cyclopropylsulfonyl)carbamoyl)-2-((6-methoxyisoquinolin-1-yl)oxy)-7,9-dimethyl-5,16-dioxo-2,3,5,6,7,8,9,11,13a,14,14a,15,16,16a-tetradecahydro-1H-cyclopropa[e]pyrrolo[2,1-i][1,7,10]oxadiazacyclopentadecin-6-yl)carbamate. MS: MS m/z 756.4 (M$^+$+1).

Preparation of Compound 2604

Compound 2604

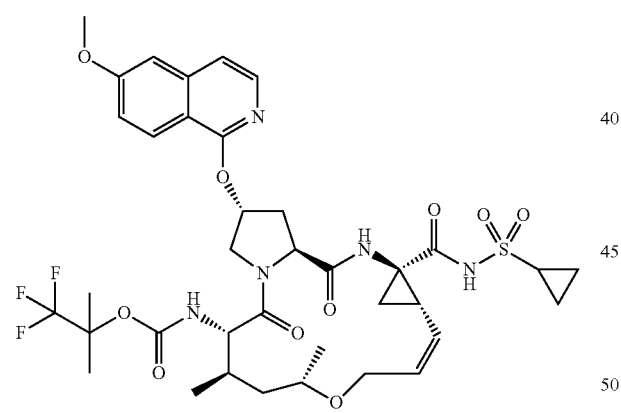

Compound was prepared using the intermediates described herein and by following the general procedure described for the synthesis of Compound 2002: Compound 2604: 1,1,1-trifluoro-2-methylpropan-2-yl ((2R,6S,7R,9S,13aS,14aR,16aS,Z)-14a-((cyclopropylsulfonyl)carbamoyl)-2-((6-methoxyisoquinolin-1-yl)oxy)-7,9-dimethyl-5,16-dioxo-2,3,5,6,7,8,9,11,13a,14,14a,15,16,16a-tetradecahydro-1H-cyclopropa[e]pyrrolo[2,1-i][1,7,10]oxadiazacyclopentadecin-6-yl)carbamate. $^1$H NMR (400 MHz, METHANOL-d$_4$) δ 8.08 (d, J=9.0 Hz, 1H), 7.91 (d, J=6.0 Hz, 1H), 7.25 (d, J=5.8 Hz, 1H), 7.19 (d, J=2.3 Hz, 1H), 7.11 (dd, J=9.2, 2.4 Hz, 1H), 5.84 (br. s., 1H), 5.71-5.49 (m, 2H), 4.70-4.55 (m, 2H), 4.25 (dd, J=11.4, 6.7 Hz, 1H), 4.07 (dd, J=11.5, 3.0 Hz, 1H), 3.96-3.87 (m, 5H), 3.50 (q, J=5.0 Hz, 1H), 2.94-2.85 (m, 1H), 2.77-2.45 (m, 3H), 1.99 (dd, J=12.9, 5.1 Hz, 2H), 1.78 (dd, J=8.4, 5.1 Hz, 1H), 1.62 (dd, J=9.5, 5.0 Hz, 1H), 1.37 (s, 3H), 1.29-1.05 (m, 7H), 1.00-0.92 (m, 7H). MS: MS m/z 810.4 (M$^+$+1).

Preparation of Compound 2605

Compound 2605

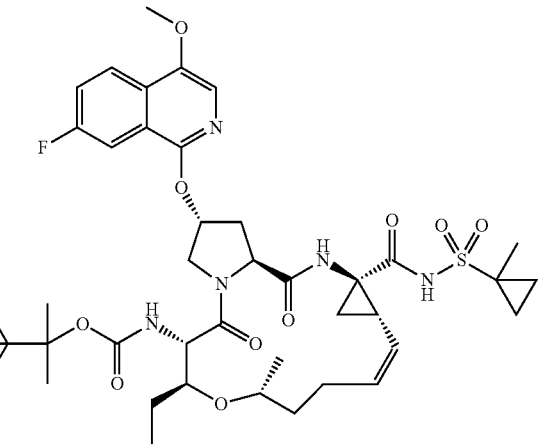

Compounds 2605 was prepared using the intermediates described herein and by following the general procedure described for the synthesis of Compound 1001:

Compound 2605: 3,3-difluoro-2-methylbutan-2-yl ((2R,6S,7S,9R,13aS,14aR,16aS,Z)-7-ethyl-2-((7-fluoro-4-methoxyisoquinolin-1-yl)oxy)-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. MS: MS m/z 852.7 (M$^+$+1).

Preparation of Compound 2606

Compound 2606

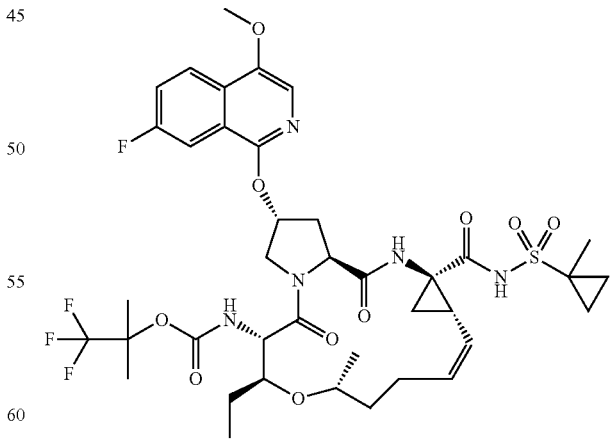

Compounds 2606 was prepared using the intermediates described herein and by following the general procedure described for the synthesis of Compound 1001:

Compound 2606: 1,1,1-trifluoro-2-methylpropan-2-yl ((2R,6S,7S,9R,13aS,14aR,16aS,Z)-7-ethyl-2-(7-fluoro-4- methoxyisoquinolin-1-yl)oxy)-9-methyl-14a-(((1-methyl-cyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (500 MHz, DMSO-d$_6$) δ 11.16 (br. s., 1H), 9.05 (br. s., 1H), 8.13 (dd, J=9.2, 5.2 Hz, 1H), 7.92 (d, J=8.9 Hz, 1H), 7.75-7.61 (m, 3H), 5.79 (br. s., 1H), 5.54 (d, J=7.0 Hz, 1H), 5.05 (br.s., 1H), 4.46 (br. s., 1H), 4.33 (d, J=11.3 Hz, 1H), 4.14 (t, J=9.6 Hz, 1H), 3.97 (s, 4H), 3.86 (d, J=9.2 Hz, 1H), 3.47 (br. s., 1H), 2.74 (s, 1H), 2.58 (br. s., 1H), 2.29 (br. s., 1H), 1.89-1.21 (m, 16H), 1.11-1.03 (m, 6H), 0.96-0.76 (m, 5H). MS: MS m/z 856.7 (M$^+$+1).

Preparation of Compound 2607

Compound 2607

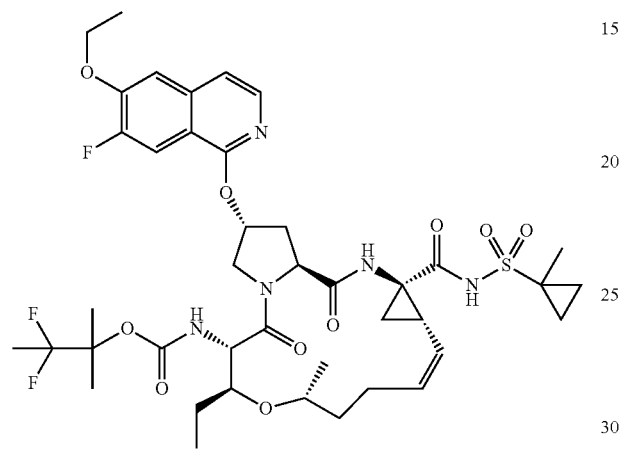

Compounds 2607 was prepared using the intermediates described herein and by following the general procedure described for the synthesis of Compound 1001:

Compound 2607: 3,3-difluoro-2-methylbutan-2-yl ((2R,6S,7S,9R,13 aS,14aR,16aS,Z)-2-((6-ethoxy-7-fluoroisoquinolin-1-yl)oxy)-7-ethyl-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (500 MHz, DMSO-d$_6$) δ 11.16 (br. s., 1H), 9.03 (br. s., 1H), 7.97 (d, J=5.8 Hz, 1H), 7.74-7.66 (m, 2H), 7.54 (d, J=8.5 Hz, 1H), 7.34 (d, J=5.8 Hz, 1H), 5.84 (br. s., 1H), 5.59-5.48 (m, 1H), 5.03 (br. s., 1H), 4.49-4.42 (m, 1H), 4.33 (d, J=11.3 Hz, 1H), 4.26 (q, J=6.9 Hz, 2H), 4.17 (t, J=9.5 Hz, 1H), 3.97 (d, J=8.5 Hz, 1H), 3.84 (d, J=9.5 Hz, 1H), 3.48 (br. s., 1H), 2.79 (br. s., 1H), 2.58 (d, J=6.7 Hz, 1H), 2.29 (t, J=9.6 Hz, 1H), 1.86 (br. s., 1H), 1.78-1.21 (m, 21H), 1.08 (d, J=6.1 Hz, 3H), 1.01 (s, 3H), 0.89 (br. s., 2H), 0.82 (t, J=7.3 Hz, 3H). MS: MS m/z 866.7 (M$^+$+1).

Preparation of Compound 2608

Compound 2608

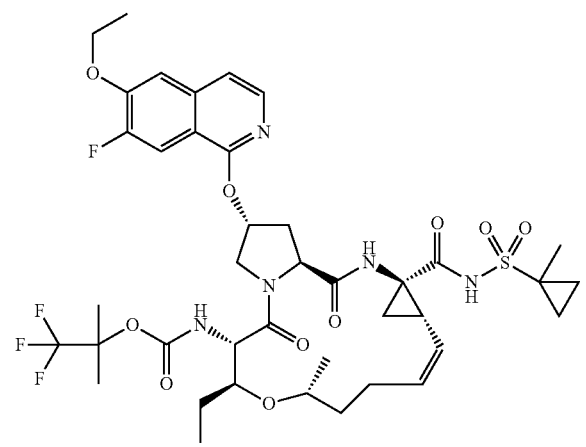

Compounds 2608 was prepared using the intermediates described herein and by following the general procedure described for the synthesis of Compound 1001:

Compound 2608: 1,1,1-trifluoro-2-methylpropan-2-yl ((2R,6S,7S,9R,13aS,14aR,16aS,Z)-2-((6-ethoxy-7-fluoroisoquinolin-1-yl)oxy)-7-ethyl-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (500 MHz, DMSO-d$_6$) δ 11.15 (br. s., 1H), 9.03 (br. s., 1H), 8.02-7.91 (m, 2H), 7.69 (d, J=11.3 Hz, 1H), 7.54 (d, J=8.2 Hz, 1H), 7.34 (d, J=5.8 Hz, 1H), 5.83 (br. s., 1H), 5.59-5.50 (m, 1H), 5.03 (br. s., 1H), 4.50-4.42 (m, 1H), 4.33 (d, J=11.6 Hz, 1H), 4.26 (q, J=6.8 Hz, 2H), 4.16 (t, J=9.6 Hz, 1H), 3.96 (d, J=8.2 Hz, 1H), 3.87 (d, J=8.9 Hz, 1H), 3.47 (br. s., 1H), 2.74 (s, 1H), 2.62-2.55 (m, 1H), 2.29 (t, J=9.9 Hz, 1H), 1.89-1.21 (m, 19H), 1.15 (s, 3H), 1.07 (d, J=6.4 Hz, 3H), 0.89 (br. s., 2H), 0.82 (t, J=7.3 Hz, 3H). MS: MS m/z 870.7 (M$^+$+1).

Preparation of Compound 2609

Compound 2609

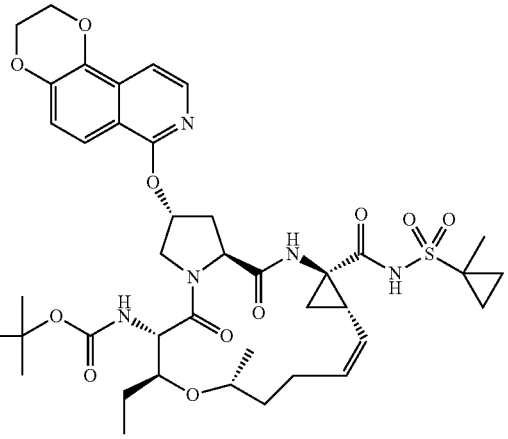

Compounds 2609 was prepared using the intermediates described herein and by following the general procedure described for the synthesis of Compound 1001:

Compound 2609: 3,3-difluoro-2-methylbutan-2-yl ((2R,6S,7S,9R,13aS,14aR,16aS,Z)-2-((2,3-dihydro-[1,4]dioxino[2,3-f]isoquinolin-7-yl)oxy)-7-ethyl-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (500 MHz, DMSO-d$_6$) δ 11.17 (br. s., 1H), 9.06 (br. s., 1H), 7.96 (d, J=6.1 Hz, 1H), 7.68 (d, J=9.5 Hz, 1H), 7.59 (d, J=9.2 Hz, 1H), 7.38 (d, J=6.1 Hz, 1H), 7.12 (d, J=9.2 Hz, 1H), 5.84 (br. s., 1H), 5.61-5.47 (m, 1H), 5.02 (br. s., 1H), 4.48-4.27 (m, 6H), 4.21-4.12 (m, 1H), 4.01-3.94 (m, 1H), 3.83 (d, J=9.2 Hz, 1H), 3.46 (d, J=6.7 Hz, 1H), 2.83-2.71 (m, 1H), 2.58 (dd, J=13.1, 7.0 Hz, 1H), 2.29 (t, J=9.8 Hz, 1H), 1.90-1.21 (m, 19H), 1.07 (d, J=6.1 Hz, 3H), 0.97-0.74 (m, 8H). MS: MS m/z 862.6 (M$^+$+1).

Preparation of Compound 2610

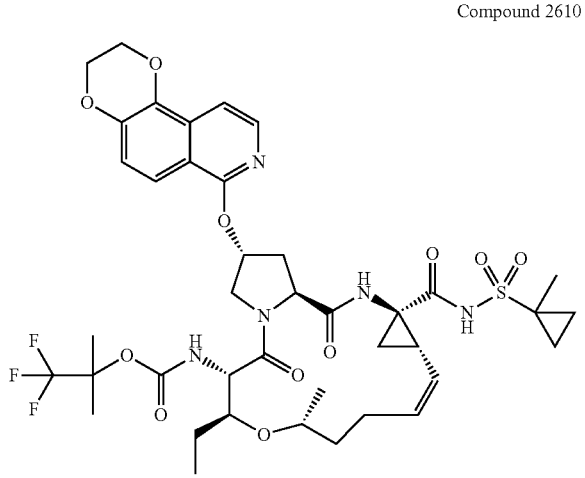 [SMILES: CC[C@@H]1O[C@H](C)CC/C=C\[C@@H]2C[C@@]2(C(=O)NS(=O)(=O)C2(C)CC2)NC(=O)[C@@H]2C[C@@H](Oc3nccc4c5c(ccc34)OCCO5)CN2C(=O)[C@H]1NC(=O)OC(C)(C)C(F)(F)F]

Compound 2610

Compounds 2610 was prepared using the intermediates described herein and by following the general procedure described for the synthesis of Compound 1001:

Compound 2610: 1,1,1-trifluoro-2-methylpropan-2-yl ((2R,6S,7S,9R,13aS,14aR,16aS,Z)-2-((2,3-dihydro-[1,4]dioxino[2,3-f]isoquinolin-7-yl)oxy)-7-ethyl-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (500 MHz, DMSO-d$_6$) δ 11.16 (br. s., 1H), 9.07 (br. s., 1H), 7.96 (d, J=6.1 Hz, 1H), 7.88 (d, J=9.2 Hz, 1H), 7.59 (d, J=8.9 Hz, 1H), 7.37 (d, J=5.8 Hz, 1H), 7.11 (d, J=8.9 Hz, 1H), 5.84 (br. s., 1H), 5.59-5.48 (m, 1H), 5.02 (br. s., 1H), 4.49-4.27 (m, 7H), 4.13 (t, J=9.5 Hz, 1H), 3.97 (d, J=7.9 Hz, 1H), 3.85 (d, J=9.2 Hz, 1H), 2.73 (s, 1H), 2.56 (d, J=6.7 Hz, 1H), 2.29 (t, J=9.8 Hz, 1H), 1.84 (br. s., 1H), 1.76-1.21 (m, 15H), 1.10-0.99 (m, 6H), 0.92-0.74 (m, 5H). MS: MS m/z 866.7 (M$^+$+1).

Preparation of Compound 2611

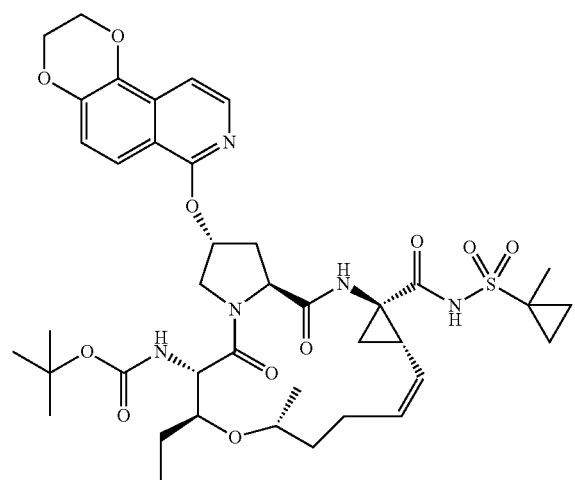

Compound 2611

Compounds 2611 was prepared using the intermediates described herein and by following the Step 10 general procedure described for the synthesis of Compound 2601:

Compound 2611: tert-butyl ((2R,6S,7S,9R,13aS,14aR,16aS,Z)-2-((2,3-dihydro-[1,4]dioxino[2,3-f]isoquinolin-7-yl)oxy)-7-ethyl-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (400 MHz, METHANOL-d$_4$) δ 7.90 (d, J=6.0 Hz, 1H), 7.69 (d, J=9.0 Hz, 1H), 7.43 (d, J=6.0 Hz, 1H), 7.04 (d, J=9.0 Hz, 1H), 5.88 (br. s., 1H), 5.59 (td, J=10.0, 6.4 Hz, 1H), 5.13 (br. s., 1H), 4.63-4.52 (m, 2H), 4.45-4.35 (m, 5H), 4.14 (dd, J=11.7, 3.6 Hz, 1H), 3.87 (d, J=9.8 Hz, 1H), 3.59-3.51 (m, 1H), 2.82-2.38 (m, 3H), 1.92-1.34 (m, 13H), 1.21-1.09 (m, 12H), 0.96-0.83 (m, 5H). MS: MS m/z 812.7 (M$^+$+1).

Preparation of Compound 2612

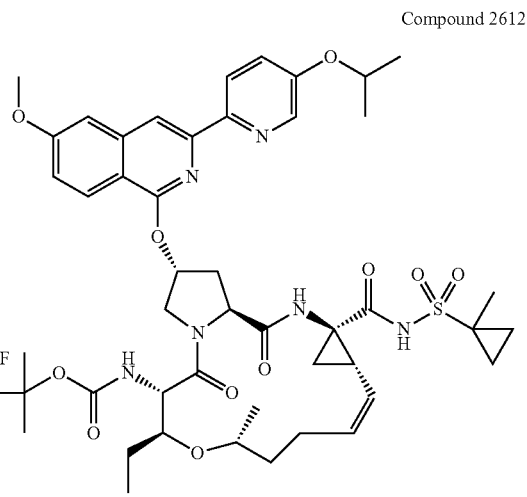

Compound 2612

Compounds 2612 was prepared using the intermediates described herein and by following the general procedure described for the synthesis of Compound 1001:

Compound 2612:1 1,1,1-trifluoro-2-methylpropan-2-yl ((2R,6S,7S,9R,13aS,14aR,16aS,Z)-7-ethyl-2-((3-(5-isopropoxypyridin-2-yl)-6-methoxyisoquinolin-1-yl)oxy)-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (400 MHz, METHANOL-d$_4$) δ 8.41 (d, J=8.8 Hz, 1H), 8.26 (d, J=2.8 Hz, 1H), 8.13-8.03 (m, 2H), 7.53 (dd, J=8.9, 2.9 Hz, 1H), 7.27 (d, J=2.5 Hz, 1H), 7.09 (dd, J=9.2, 2.4 Hz, 1H), 6.07 (br. s., 1H), 5.66-5.57 (m, 1H), 5.21-5.07 (m, 1H), 4.76 (dt, J=12.0, 6.0 Hz, 1H), 4.66-4.57 (m, 1H), 4.40 (d, J=10.0 Hz, 1H), 4.26 (dd, J=11.5, 4.0 Hz, 1H), 3.99-3.88 (m, 4H), 3.63-3.51 (m, 1H), 2.82-2.69 (m, 2H), 2.55 (ddd, J=13.7, 9.2, 4.6 Hz, 2H), 1.97-1.35 (m, 22H), 1.21-1.08 (m, 6H), 0.98-0.80 (m, 5H). MS: MS m/z 974.0 (M$^+$+1).

Preparation of Compound 2613

Compound 2613

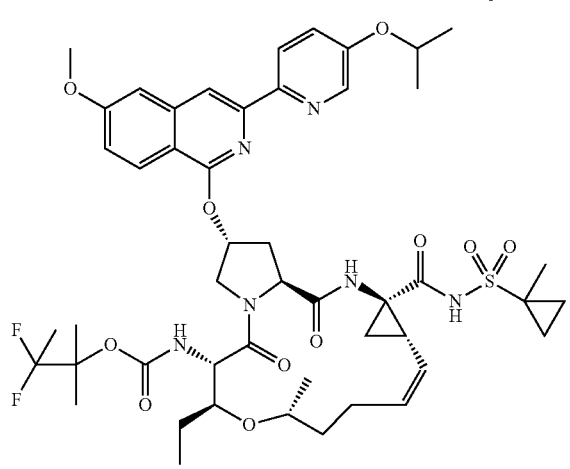

Compounds 2613 was prepared using the intermediates described herein and by following the general procedure described for the synthesis of Compound 1001:

Compound 2613: 3,3-difluoro-2-methylbutan-2-yl ((2R,6S,7S,9R,13aS,14aR,16aS,Z)-7-ethyl-2-((3-(5-isopropoxypyridin-2-yl)-6-methoxyisoquinolin-1-yl)oxy)-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. MS: MS m/z 970.0 (M$^+$+1).

Preparation of Compound 2614

Compound 2614

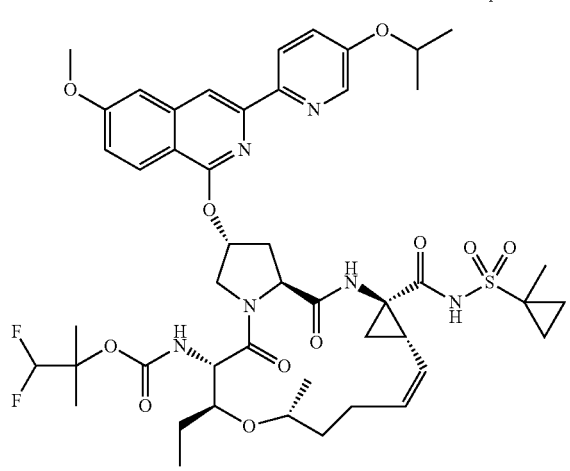

Compounds 2614 was prepared using the intermediates described herein and by following the general procedure described for the synthesis of Compound 1001:

Compound 2614: 1,1-difluoro-2-methylpropan-2-yl ((2R,6S,7S,9R,13aS,14aR,16aS,Z)-7-ethyl-2-(3-(5-isopropoxypyridin-2-yl)-6-methoxyisoquinolin-1-yl)oxy)-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. MS: MS m/z 955.9 (M$^+$+1).

Preparation of Compound 2615

Compound 2615

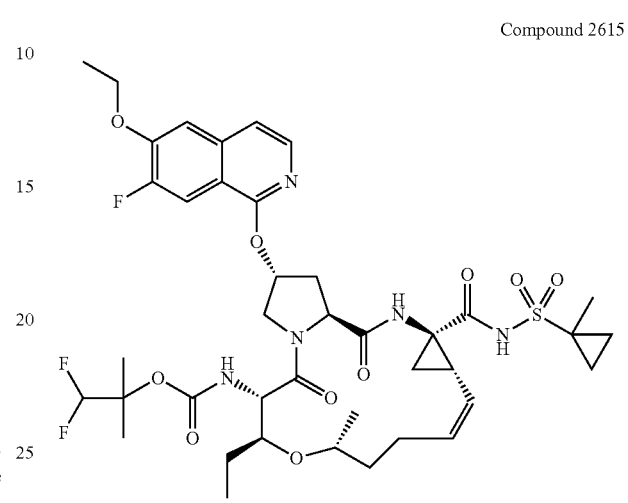

Compounds 2615 was prepared using the intermediates described herein and by following the general procedure described for the synthesis of Compound 1001:

Compound 2615: 1,1-difluoro-2-methylpropan-2-yl ((2R,6S,7S,9R,13 aS,14aR,16aS,Z)-2-((6-ethoxy-7-fluoroisoquinolin-1-yl)oxy)-7-ethyl-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (500 MHz, DMSO-d$_6$) δ 7.96 (d, J=5.8 Hz, 1H), 7.76 (d, J=9.2 Hz, 1H), 7.69 (d, J=11.6 Hz, 1H), 7.53 (d, J=7.9 Hz, 1H), 7.33 (d, J=5.8 Hz, 1H), 5.99-5.73 (m, 2H), 5.57-5.48 (m, 1H), 5.06 (br. s., 1H), 4.49-4.34 (m, 2H), 4.28-4.21 (m, 2H), 4.14 (t, J=9.6 Hz, 1H), 3.95 (d, J=8.5 Hz, 1H), 3.85 (d, J=9.5 Hz, 1H), 2.73 (s, 1H), 2.62-2.53 (m, 2H), 2.29 (t, J=9.5 Hz, 1H), 1.88-1.21 (m, 21H), 1.17-1.04 (m, 9H), 0.90-0.75 (m, 5H). MS: MS m/z 852.7 (M$^+$+1).

Preparation of Compound 2616

Compound 2616

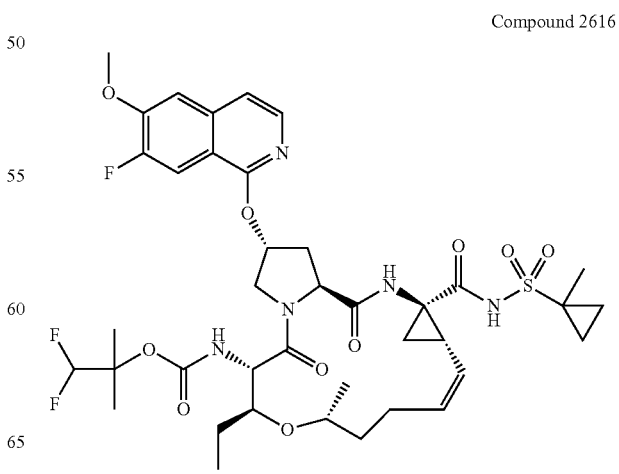

Compounds 2616 was prepared using the intermediates described herein and by following the general procedure described for the synthesis of Compound 1001:

Compound 2616: 1,1-difluoro-2-methylpropan-2-yl ((2R,6S,7S,9R,13aS,14aR,16aS,Z)-7-ethyl-2-(7-fluoro-6-methoxyisoquinolin-1-yl)oxy)-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (500 MHz, DMSO-$d_6$) δ 7.98 (d, J=5.8 Hz, 1H), 7.76 (d, J=9.2 Hz, 1H), 7.70 (d, J=11.6 Hz, 1H), 7.55 (d, J=8.5 Hz, 1H), 7.35 (d, J=6.1 Hz, 1H), 5.99-5.72 (m, 2H), 5.57-5.47 (m, 1H), 5.06 (br. s., 1H), 4.45 (t, J=8.1 Hz, 1H), 4.37 (d, J=11.0 Hz, 1H), 4.13 (t, J=9.5 Hz, 1H), 4.00-3.91 (m, 4H), 3.84 (d, J=8.5 Hz, 1H), 2.73 (s, 1H), 2.61-2.53 (m, 1H), 2.29 (t, J=9.6 Hz, 1H), 1.88-1.02 (m, 22H), 0.91-0.76 (m, 5H). MS: MS m/z 838.8 (M$^+$+1).

Preparation of Compound 2617

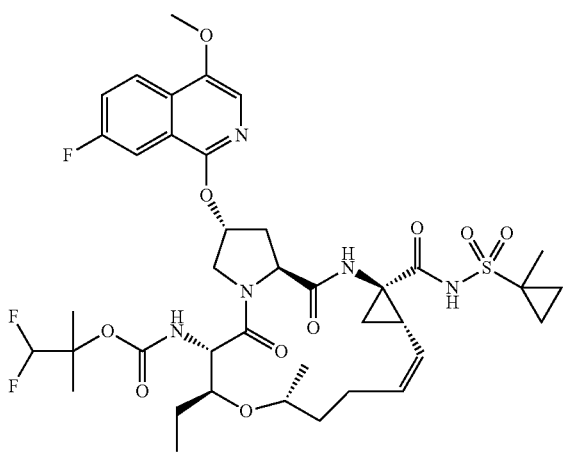

Compound 2617

Compounds 2617 was prepared using the intermediates described herein and by following the general procedure described for the synthesis of Compound 1001:

Compound 2617: 1,1-difluoro-2-methylpropan-2-yl ((2R,6S,7S,9R,13aS,14aR,16aS,Z)-7-ethyl-2-((7-fluoro-4-methoxyisoquinolin-1-yl)oxy)-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (500 MHz, DMSO-$d_6$) δ 8.13 (dd, J=9.0, 5.3 Hz, 1H), 7.77-7.62 (m, 4H), 5.99-5.72 (m, 2H), 5.59-5.48 (m, 1H), 5.06 (br. s., 1H), 4.50-4.34 (m, 2H), 4.13 (t, J=9.8 Hz, 1H), 4.01-3.92 (m, 4H), 3.84 (d, J=9.5 Hz, 1H), 2.73 (s, 1H), 2.62-2.54 (m, 1H), 2.29 (t, J=9.6 Hz, 1H), 1.89-0.98 (m, 22H), 0.91-0.73 (m, 5H). MS: MS m/z 838.9 (M$^+$+1).

Preparation of Compound 2618

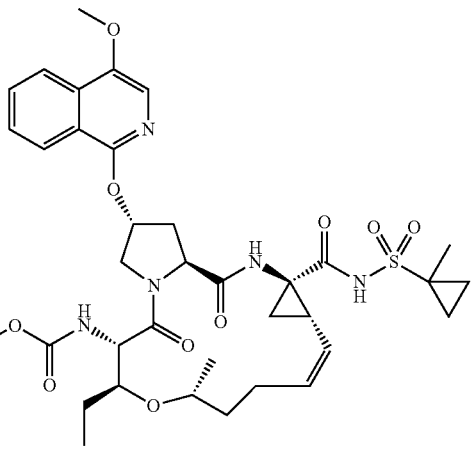

Compound 2618

Compounds 2618 was prepared using the intermediates described herein and by following the general procedure described for the synthesis of Compound 1001:

Compound 2618: 1,1-difluoro-2-methylpropan-2-yl ((2R,6S,7S,9R,13aS,14aR,16aS,Z)-7-ethyl-2-((4-methoxyisoquinolin-1-yl)oxy)-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H NMR (500 MHz, DMSO-$d_6$) δ 8.06 (d, J=8.2 Hz, 2H), 7.82-7.71 (m, 2H), 7.67-7.59 (m, 2H), 6.01-5.72 (m, 2H), 5.57-5.47 (m, 1H), 5.16 (br. s., 1H), 4.46-4.33 (m, 2H), 4.15 (t, J=9.6 Hz, 1H), 4.01-3.93 (m, 4H), 3.84 (d, J=10.1 Hz, 1H), 2.66-2.53 (m, 2H), 2.46-2.26 (m, 2H), 1.88-0.97 (m, 22H), 0.80 (t, J=7.2 Hz, 5H). MS: MS m/z 820.8 (M$^+$+1).

Biological Studies

HCV NS3/4A protease complex enzyme assays and cell-based HCV replicon assays were utilized in the present disclosure, and were prepared, conducted and validated as follows:

Generation of Recombinant HCV NS3/4A Protease Complex

HCV NS3 protease complexes, derived from the BMS strain, H77 strain or J4L6S strain, were generated, as described below. These purified recombinant proteins were generated for use in a homogeneous assay (see below) to provide an indication of how effective compounds of the present disclosure would be in inhibiting HCV NS3 proteolytic activity.

Serum from an HCV-infected patient was obtained from Dr. T. Wright, San Francisco Hospital. An engineered full-length cDNA (compliment deoxyribonucleic acid) template of the HCV genome (BMS strain) was constructed from DNA fragments obtained by reverse transcription-PCR (RT-PCR) of serum RNA (ribonucleic acid) and using primers selected on the basis of homology between other genotype 1a strains. From the determination of the entire genome sequence, a genotype 1a was assigned to the HCV isolate according to the classification of Simmonds et al. (See P Simmonds, K A Rose, S Graham, S W Chan, F McOmish, B C Dow, E A Follett, P L Yap and H Marsden, *J. Clin. Microbiol.*, 31(6), 1493-1503 (1993)). The amino acid sequence of the nonstructural region, NS2-5B, was shown to be >97% identical to HCV genotype 1a (H77) and 87% identical to genotype 1b (J4L6S). The infectious clones, H77 (1a genotype) and J4L6S (1b genotype) were obtained from R. Purcell (NIH) and the sequences are published in Genbank (AAB67036, see Yanagi, M., Purcell, R. H., Emerson, S. U. and Bukh, *J. Proc. Natl. Acad. Sci. U.S.A.* 94(16), 8738-8743 (1997); AF054247, see Yanagi, M., St Claire, M., Shapiro, M., Emerson, S. U., Purcell, R. H. and Bukh, J., *Virology* 244 (1), 161-172. (1998)).

The H77 and J4L6S strains were used for production of recombinant NS3/4A protease complexes. DNA encoding the recombinant HCV NS3/4A protease complex (amino acids 1027 to 1711) for these strains was manipulated as described by P. Gallinari et al. (see Gallinari P, Paolini C, Brennan D, Nardi C, Steinkuhler C, De Francesco R. *Biochemistry.* 38(17):5620-32, (1999)). Briefly, a three-lysine solubilizing tail was added at the 3'-end of the NS4A coding region. The cysteine in the P1 position of the NS4A-NS4B cleavage site (amino acid 1711) was changed to a glycine to avoid the proteolytic cleavage of the lysine tag. Furthermore, a cysteine to serine mutation was introduced by PCR at amino acid position 1454 to prevent the autolytic cleavage in the NS3 helicase domain. The variant DNA fragment was cloned in the pET21b bacterial expression vector (Novagen) and the NS3/4A complex was expressed in *Escherichia. coli* strain BL21 (DE3) (Invitrogen) following the protocol described by P. Gallinari et al. (see Gallinari P, Brennan D, Nardi C, Brunetti M, Tomei L, Steinkuhler C, De Francesco R., *J Virol.* 72(8):6758-69 (1998)) with modifications. Briefly, the NS3/4A protease complex expression was induced with 0.5 millimolar (mM) Isopropyl β-D-1-thiogalactopyranoside (IPTG) for 22 hours (h) at 20° C. A typical fermentation (1 Liter (L)) yielded approximately 10 grams (g) of wet cell paste. The cells were resuspended in lysis buffer (10 mL/g) consisting of 25 mM N-(2-Hydroxyethyl)Piperazine-N'-(2-Ethane Sulfonic acid) (HEPES), pH 7.5, 20% glycerol, 500 mM Sodium Chloride (NaCl), 0.5% Triton X-100, 1 microgram/milliliter ("µg/mL") lysozyme, 5 mM Magnesium Chloride ($MgCl_2$), 1 µg/ml DnaseI, 5 mM β-Mercaptoethanol (βME), Protease inhibitor-Ethylenediamine Tetraacetic acid (EDTA) free (Roche), homogenized and incubated for 20 minutes (min) at 4° C. The homogenate was sonicated and clarified by ultra-centrifugation at 235000 g for 1 hour (h) at 4° C. Imidazole was added to the supernatant to a final concentration of 15 mM and the pH adjusted to 8.0. The crude protein extract was loaded on a Nickel-Nitrilotriacetic acid (Ni-NTA) column pre-equilibrated with buffer B (25 mM HEPES, pH 8.0, 20% glycerol, 500 mM NaCl, 0.5% Triton X-100, 15 mM imidazole, 5 mM βME). The sample was loaded at a flow rate of 1 mL/min. The column was washed with 15 column volumes of buffer C (same as buffer B except with 0.2% Triton X-100). The protein was eluted with 5 column volumes of buffer D (same as buffer C except with 200 mM Imidazole).

NS3/4A protease complex-containing fractions were pooled and loaded on a desalting column Superdex-5200 pre-equilibrated with buffer D (25 mM HEPES, pH 7.5, 20% glycerol, 300 mM NaCl, 0.2% Triton X-100, 10 mM βME). Sample was loaded at a flow rate of 1 mL/min. NS3/4A protease complex-containing fractions were pooled and concentrated to approximately 0.5 mg/ml. The purity of the NS3/4A protease complexes, derived from the BMS, H77 and J4L6S strains, were judged to be greater than 90% by SDS-PAGE and mass spectrometry analyses. The enzyme was stored at −80° C., thawed on ice and diluted prior to use in assay buffer.

FRET Peptide Assay to Monitor HCV NS3/4A Proteolytic Activity

The purpose of this in vitro assay was to measure the inhibition of HCV NS3 protease complexes, derived from the BMS strain, H77 strain or J4L6S strain, as described above, by compounds of the present disclosure. This assay provides an indication of how effective compounds of the present disclosure would be in inhibiting HCV NS3 proteolytic activity.

In order to monitor HCV NS3/4A protease activity, an NS3/4A peptide substrate was used. The substrate was RET S1 (Resonance Energy Transfer Depsipeptide Substrate; AnaSpec, Inc. cat #22991)(FRET peptide), described by Taliani et al. in *Anal. Biochem.* 240(2):60-67 (1996). The sequence of this peptide is loosely based on the NS4A/NS4B natural cleavage site for the HCV NS3 protease except there is an ester linkage rather than an amide bond at the cleavage site. The peptide also contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent.

The peptide substrate was incubated with one of the three recombinant NS3/4A protease complexes, in the absence or presence of a compound of the present disclosure. The inhibitory effects of a compound were determined by monitoring the formation of fluorescent reaction product in real time using a Cytofluor Series 4000.

The reagents were as follow: HEPES and Glycerol (Ultrapure) were obtained from GIBCO-BRL. Dimethyl Sulfoxide (DMSO) was obtained from Sigma. β-Mercaptoethanol was obtained from Bio Rad.

Assay buffer: 50 mM HEPES, pH 7.5; 0.15 M NaCl; 0.1% Triton; 15% Glycerol; 10 mM βME. Substrate: 2 µM final concentration (from a 2 mM stock solution in DMSO stored at −20° C.). HCV NS3/4A protease type 1a (1b), 2-3 nM final concentration (from a 5 µM stock solution in 25 mM HEPES, pH 7.5, 20% glycerol, 300 mM NaCl, 0.2% Triton-X100, 10 mM βME). For compounds with potencies approaching the assay limit, the assay was made more sensitive by adding 50 µg/ml Bovine Serum Albumin (Sigma) to the assay buffer and reducing the end protease concentration to 300 pM.

The assay was performed in a 96-well polystyrene black plate from Falcon. Each well contained 25 µl NS3/4A protease complex in assay buffer, 50 µl of a compound of the present disclosure in 10% DMSO/assay buffer and 25 µl substrate in assay buffer. A control (no compound) was also prepared on the same assay plate. The enzyme complex was mixed with compound or control solution for 1 min before initiating the enzymatic reaction by the addition of substrate. The assay plate was read immediately using the Cytofluor Series 4000 (Perspective Biosystems). The instrument was set to read an emission of 340 nm and excitation of 490 nm at 25° C. Reactions were generally followed for approximately 15 min.

The percent inhibition was calculated with the following equation:

$$100-[(\delta F_{inh}/\delta F_{con}) \times 100]$$

where δF is the change in fluorescence over the linear range of the curve. A non-linear curve fit was applied to the inhibition-concentration data, and the 50% effective concentration ($IC_{50}$) was calculated by the use of Excel XLfit software using the equation, $y=A+((B-A)/(1+((C/x)\hat{}D)))$.

Compounds of the present disclosure, which were tested against more than one type of NS3/4A complex, were found to have similar inhibitory properties though the compounds uniformly demonstrated greater potency against the 1b strains as compared to the 1a strains.

Generation of HCV Replicon

An HCV replicon whole cell system was established as described by Lohmann V, Korner F, Koch J, Herian U, Theilmann L, Bartenschlager R., Science 285(5424):110-3 (1999) and modified to introduce a luciferase reporter, as first described by Krieger et al (Krieger N, Lohmann V, and Bartenschlager R, *J. Virol.* 75(10):4614-4624 (2001)). CDNA encoding a humanized form of the Renilla luciferase gene and a linker sequence fused directly to the 3'-end of the luciferase gene were introduced into the replicon construct using an Ascl restriction site located in core, directly upstream of the neomycin marker gene. The adaptive mutation at position 1179 (serine to isoleucine) was also introduced (Blight K J, Kolykhalov, A A, Rice, C M, *Science* 290(5498):1972-1974). A stable cell line constitutively expressing this HCV replicon construct was generated by first linearizing plasmid DNAs with ScaI. RNA transcripts were synthesized in vitro using the T7 MegaScript transcription kit (Ambion, Austin, Tex.) according to manufacturer's directions. In vitro transcripts of the cDNA were transfected into the human hepatoma cell line, HUH-7. Selection for cells constitutively expressing the HCV replicon was achieved in the presence of the selectable marker, neomycin (G418). Resulting cell lines were characterized for positive and negative strand RNA production and protein production over time.

A stable HCV replicon luciferase reporter cell line representing the genotype 1a H77 strain (Yanagi M, Purcell R H, Emerson S U, et al. Transcripts from a single full-length cDNA clone of hepatitis C virus are infectious when directly transfected into the liver of a chimpanzee. Proc Natl Acad Sci USA 1997; 94(16):8738-8743) was generated as described previously for the genotype 1b(Con1) replicon luciferase cell line. The replicon construct was modified by introducing mutations were introduced into the genes encoding the NS3 helicase domain (proline replaced by leucine at position 1496) and NS5A (serine to isoleucine at position 2204) to improve replication in cell culture.

HCV Replicon Luciferase Reporter Assay

HCV replicon luciferase assays were developed to monitor the inhibitory effects of compounds described in the disclosure on HCV genotypes 1a and 1b viral replication. HUH-7 cells, constitutively expressing the HCV replicon, were grown in Dulbecco's Modified Eagle Media (DMEM) (Gibco-BRL) containing 10% Fetal calf serum (FCS) (Sigma) and 1 mg/mL G418 (Gibco-BRL). Compounds were serially diluted 3 folds in DMSO for a twenty-point titration and subsequently transferred to sterile 384-well tissue-culture treated plates (Corning cat #3571). The plates were then seeded with 50 μL of cells at a density of 3.0×10³ cells/well in DMEM containing 4% FCS (final DMSO concentration at 0.5%). After 3 days incubation at 37° C., cells were analyzed for Renilla Luciferase activity using the EnduRen as substrate (Promega cat #E6485). The EnduRen substrate was diluted in DMEM and then added to the plates to a final concentration of 7.5 μM. The plates were incubated for 2 hrs at 37° C. and then read immediately for 30 seconds with Viewlux Imager (PerkinElmer) using a luminescence program. To assess cytotoxicity of compounds, $CC_{50}$ values were generated by multiplexing the EnduRen-containing plates with Cell Titer-Blue (Promega, cat # G8082). Cell-Titer Blue (3 μL) was added to each well and incubated for 8 hrs at 37° C. The fluorescence signal from each well was read, with an excitation wavelength at 525/10 nm and an emission wavelength of 598/10 nm, using the Viewlux Imager.

The $EC_{50}$ values for compounds were calculated by using a four-parameter logistic equation:

$$y=A+((B-A)/(1+((C/x)\hat{}D))),$$

where A and B denotes minimal and maximal % inhibition, respectively, C is the $EC_{50}$, D is the hill slope and x represents compound concentration.

Table 2 shows the EC50 values of representative compounds of the present disclosure. Ranges are as follows: A=0.10 nM-0.50 nM; B=0.51 nM-1.00 nM; C=1.01 nM-5.00 nM; D=5.01 nM-35.00 nM; E=35.01 nM-620 nM.

TABLE 2

| Compound Number | LE_1a (EC50, nM) | LE_1a (EC50, range) | LE_1b (EC50, nM) | LE_1b (EC50, range) |
|---|---|---|---|---|
| 1001 | 1.26 | C | 0.47 | A |
| 1002 | | B | | A |
| 1003 | | B | | A |
| 1004 | | B | | A |
| 1005 | | C | | B |
| 1006 | | C | | A |
| 1007 | | C | | B |
| 1008 | 0.41 | A | 0.28 | A |
| 1009 | | C | | C |
| 1010 | | B | | C |
| 1011 | | B | | B |
| 1012 | | C | | C |
| 1013 | | C | | C |
| 1014 | | C | | C |
| 1015 | | A | | A |
| 1016 | | A | | A |
| 1017 | | B | | B |
| 1018 | | C | | B |
| 1019 | | C | | A |
| 1020 | | C | | B |
| 2001 | | C | | C |
| 2002 | | B | | A |
| 2003 | | B | | A |
| 2004 | | B | | A |
| 2005 | | C | | A |
| 2006 | | C | | A |
| 2007 | 0.63 | B | 0.24 | A |
| 2008 | | B | | A |
| 2009 | | C | | B |
| 2010 | | C | | B |
| 2011 | | B | | A |
| 2012 | | A | | A |
| 2013 | | C | | B |
| 2014 | 2.38 | C | 0.66 | B |
| 2015 | | C | | B |
| 2016 | | C | | B |
| 2017 | 0.89 | B | 0.42 | A |
| 2018 | | B | | A |
| 2019 | | C | | B |
| 2020 | | C | | B |

TABLE 2-continued

| Compound Number | LE_1a (EC50, nM) | LE_1a (EC50, range) | LE_1b (EC50, nM) | LE_1b (EC50, range) |
|---|---|---|---|---|
| 2021 | | C | | B |
| 2022 | | C | | C |
| 2301 | | B | | A |
| 2302 | | B | | A |
| 2303 | | B | | B |
| 2304 | 0.49 | A | 0.64 | B |
| 2305 | | B | | B |
| 2306 | | A | | A |
| 2307 | | A | | A |
| 2308 | | A | | A |
| 2309 | | B | | B |
| 2310 | | A | | A |
| 2311 | | A | | A |
| 2601 | | C | | C |
| 2602 | | C | | C |
| 2603 | 9.08 | D | 6.64 | D |
| 2604 | | D | | C |
| 2605 | | B | | A |
| 2606 | | B | | A |
| 2607 | | B | | A |
| 2608 | | B | | A |
| 2609 | | C | | B |
| 2610 | | C | | B |
| 2611 | | C | | B |
| 2612 | | C | | C |
| 2613 | | C | | A |
| 2614 | | | | |
| 2615 | | B | | B |
| 2616 | | C | | C |
| 2617 | | A | | B |
| 2618 | | A | | A |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (I)

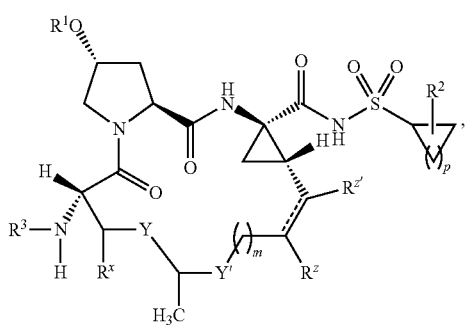

(I)

or a pharmaceutically acceptable salt thereof, wherein
p is 1;
----- is a double bond;
m is 1;
$R^1$ is selected from

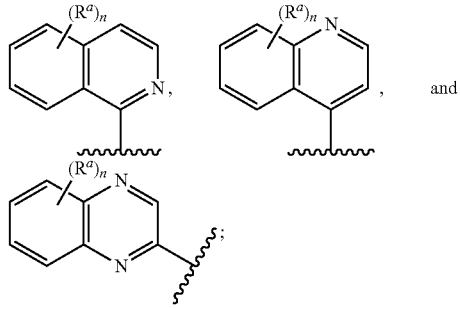

each $R^a$ is independently selected from alkenyloxy, alkoxy, alkoxyalkoxy, alkoxycarbonyl, alkyl, benzodioxanyl, carboxamido, carboxy, carboxyalkoxy, cyano, cycloalkyl, cycloalkylalkoxy, cycloalkyloxy, deuteroalkoxy, dialkylamino, halo, haloalkyl, haloalkoxy, haloalkoxycarbonyl, hydroxy, imidazolyl, morpholinyl, oxazolyl, phenyl, piperazinyl, pyrazolyl, pyridinyl, pyrrolidinyl, thiazolyl, and —$NR^qR^{q'}$, wherein the imidazolyl, the morpholinyl, the oxazolyl, the phenyl, the piperazinyl, the pyridinyl, the pyrrolidinyl, and the thiazolyl are optionally substituted with one group selected from alkoxy, alkyl, halo, haloalkoxy, and haloalkyl; and wherein two adjacent $R^a$ groups, together with the carbon atoms to which they are attached, can optionally form a ring selected from dioxanyl and pyranyl;

$R^x$ is selected from methyl and ethyl;
$R^z$ and $R^{z'}$ are hydrogen;
$R^2$ is selected from hydrogen, alkyl, deuteroalkyl, halo, haloalkoxy, haloalkyl, and hydroxyalkyl;
$R^3$ is selected from hydrogen, alkoxyalkoxycarbonyl, alkoxycarbonyl, alkylaminocarbonyl, alkylcarbonyl, cycloalkylalkoxycarbonyl, cycloalkylcarbonyl, cycloalkyloxycarbonyl, deuteroalkoxycarbonyl, deuterohaloalkoxycarbonyl, dialkylaminocarbonyl, dialkylaminocarbonylcarbonyl, haloalkoxycarbonyl, haloalkylaminocarbonyl, haloalkylcarbonyl, phenylcarbonyl, and phenyloxycarbonyl, wherein the cycloalkyl part of the cycloalkylalkoxycarbonyl, the cycloalkylcarbonyl, and the cycloalkyloxycarbonyl and the phenyl part of the phenylcarbonyl and the phenyloxycarbonyl, is optionally substituted with one, two, or three groups independently selected from alkyl, alkylamino, alkylcarbonyl, cycloalkyl, dialkylamino, halo, haloalkoxy, and haloalkyl;
one of $R^q$ and $R^{q'}$ is selected from hydrogen and alkyl and the other is selected from alkylcarbonyl and phenylcarbonyl; and
one of Y and Y' is oxygen and the other is $CH_2$.

2. A compound of claim 1, or a pharmaceutically acceptable salt thereof, wherein $R^2$ is selected from alkyl and haloalkyl.

3. A compound of claim 1, or a pharmaceutically acceptable salt thereof, wherein $R^3$ is selected from alkoxycarbonyl and haloalkoxycarbonyl.

4. A compound selected from
1,1,1-trifluoro-2-methylpropan-2-yl ((2R,6S,7S,9R,13aS, 14aR,16aS,Z)-7-ethyl-2-((7-fluoro-6-methoxyisoquinolin-1-yl)oxy)-9-methyl-14a-(((1-methylcyclopropyl) sulfonyl)carbamoyl)-5,16-dioxo-2,3,5,6,7,9,10,11,13a, 14,14a,15,16,16a-tetradecahydro-1H-cyclopropa[i]pyrrolo[1,2-e][1,5,8]oxadiazacyclopentadecin-6-yl)carbamate;

1,1,1-trifluoro-2-methylpropan-2-yl ((2R,6S,7S,9R,13aS,14aR,16aS,Z)-2-((3,6-dimethoxyisoquinolin-1-yl)oxy)-7-ethyl-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate;

1,1,1-trifluoro-2-methylpropan-2-yl ((2R,6S,7S,9R,13aS,14aR,16aS,Z)-7-ethyl-2-((4-methoxyisoquinolin-1-yl)oxy)-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate;

1,1,1-trifluoro-2-methylpropan-2-yl ((2R,6S,7S,9R,13aS,14aR,16aS,Z)-14a-((cyclopropylsulfonyl)carbamoyl)-7-ethyl-2-((4-methoxyisoquinolin-1-yl)oxy)-9-methyl-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate;

1,1,1-trifluoro-2-methylpropan-2-yl ((2R,6S,7S,13aS,14aR,16aS,Z)-7-ethyl-2-((6-methoxyisoquinolin-1-yl)oxy)-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate;

1,1,1-trifluoro-2-methylpropan-2-yl ((2R,6S,7S,9R,13aS,14aR,16aS,Z)-7-ethyl-2-((6-methoxyisoquinolin-1-yl)oxy)-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate]oxadiazacyclopentadecin-6-yl)carbamate;

1,1,1-trifluoro-2-methylpropan-2-yl ((2R,6S,7S,9R,13aS,14aR,16aS,Z)-14a-((cyclopropylsulfonyl)carbamoyl)-7-ethyl-2-((6-methoxyisoquinolin-1-yl)oxy)-9-methyl-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate;

1,1,1-trifluoro-2-methylpropan-2-yl ((2R,6S,7S,9R,13aS,14aR,16aS,Z)-14a-((cyclopropylsulfonyl)carbamoyl)-2-((3,6-dimethoxyisoquinolin-1-yl)oxy)-7-ethyl-9-methyl-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate;

1,1,1-trifluoro-2-methylpropan-2-yl ((2R,6S,7S,13aS,14aR,16aS,Z)-7-ethyl-2-((7-fluoro-6-methoxyisoquinolin-1-yl)oxy)-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate;

1,1,1-trifluoro-2-methylpropan-2-yl ((2R,6S,7S,13aS,14aR,16aS,Z)-2-((3,6-dimethoxyisoquinolin-1-yl)oxy)-7-ethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate;

1,1,1-trifluoro-2-methylpropan-2-yl ((2R,6S,7S,13aS,14aR,16aS,Z)-7-ethyl-2-((4-methoxyisoquinolin-1-yl)oxy)-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate;

1,1,1-trifluoro-2-methylpropan-2-yl ((2R,6S,7S,9R,13aS,14aR,16aS,Z)-7-ethyl-2-((7-fluoro-6-methoxyisoquinolin-1-yl)oxy)-14a-(((1-(fluoromethyl)cyclopropyl)sulfonyl)carbamoyl)-9-methyl-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate;

1,1,1-trifluoro-2-methylpropan-2-yl ((2R,6S,7S,9R,13aS,14aR,16aS,Z)-2-((3,6-dimethoxyisoquinolin-1-yl)oxy)-7-ethyl-14a-(((1-(fluoromethyl)cyclopropyl)sulfonyl)carbamoyl)-9-methyl-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate;

1,1,1-trifluoro-2-methylpropan-2-yl ((2R,6S,7S,9R,13aS,14aR,16aS,Z)-7-ethyl-14a-(((1-(fluoromethyl)cyclopropyl)sulfonyl)carbamoyl)-2-((4-methoxyisoquinolin-1-yl)oxy)-9-methyl-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate;

1,1,1-trifluoro-2-methylpropan-2-yl ((2R,6S,7S,9R,13aS,14aR,16aS,Z)-7-ethyl-2-((7-methoxy-3-(trifluoromethyl)quinoxalin-2-yl)oxy)-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate;

3,3-difluoro-2-methylbutan-2-yl ((2R,6S,7S,9R,13aS,14aR,16aS,Z)-7-ethyl-2-((7-methoxy-3-(trifluoromethyl)quinoxalin-2-yl)oxy)-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate;

1,1,1-trifluoro-2-methylpropan-2-yl ((2R,6S,7S,9R,13aS,14aR,16aS,Z)-7-ethyl-2-((8-fluoro-9-methoxy-2,3-dihydro-1H-pyrano[2,3-c]isoquinolin-6-yl)oxy)-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate;

1,1,1-trifluoro-2-methylpropan-2-yl ((2R,6S,7S,9R,13aS,14aR,16aS,Z)-7-ethyl-2-((6-fluoro-2,7-dimethoxyquinolin-4-yl)oxy)-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate;

1,1,1-trifluoro-2-methylpropan-2-yl ((2R,6S,7S,9R,13aS,14aR,16aS,Z)-2-((2,7-dimethoxyquinolin-4-yl)oxy)-7-ethyl-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate;

3,3-difluoro-2-methylbutan-2-yl ((2R,6S,7S,9R,13aS,14aR,16aS,Z)-2-((2,7-dimethoxyquinolin-4-yl)oxy)-7-ethyl-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate;

tert-butyl ((2R,6S,7S,9R,13aS,14aR,16aS,Z)-2-((6-methoxyisoquinolin-1-yl)oxy)-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate;

1,1,1-trifluoro-2-methylpropan-2-yl ((2R,6S,7S,9R,13aS,14aR,16aS,Z)-2-((6-methoxyisoquinolin-1-yl)oxy)-7, 9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate;

1,1,1-trifluoro-2-methylpropan-2-yl ((2R,6S,7S,9R,13aS,14aR,16aS,Z)-2-((4-methoxyisoquinolin-1-yl)oxy)-7,9-dimethyl-14a-(((1-methylcyclopropyl) sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5, 8]oxadiazacyclopentadecin-6-yl)carbamate;

1,1,1-trifluoro-2-methylpropan-2-yl ((2R,6S,7S,9R,13aS,14aR,16aS,Z)-2-((4-ethoxyisoquinolin-1-yl)oxy)-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5, 8]oxadiazacyclopentadecin-6-yl)carbamate;

1,1,1-trifluoro-2-methylpropan-2-yl ((2R,6S,7S,9R,13aS,14aR,16aS,Z)-2-((7-fluoro-6-methoxyisoquinolin-1-yl)oxy)-7,9-dimethyl-14a-(((1-methylcyclopropyl) sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5, 8]oxadiazacyclopentadecin-6-yl)carbamate;

3,3-difluoro-2-methylbutan-2-yl ((2R,6S,7S,9R,13aS,14aR,16aS,Z)-2-((7-fluoro-6-methoxyisoquinolin-1-yl)oxy)-7,9-dimethyl-14a-(((1-methylcyclopropyl) sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate;

1,1,1-trifluoro-2-methylpropan-2-yl ((2R,6S,7S,9R,13aS,14aR,16aS,Z)-2-((7-fluoro-4-methoxyisoquinolin-1-yl)oxy)-7,9-dimethyl-14a-(((1-methylcyclopropyl) sulfonyl)carbamoyl)-5,16-dioxo-2,3,5,6,7,9,10, 11,13a,14,14a,15,16,16a-tetradecahydro-1H-cyclopropa[i]pyrrolo[1,2-e][1,5, 8]oxadiazacyclopentadecin-6-yl)carbamate;

3,3-difluoro-2-methylbutan-2-yl ((2R,6S,7S,9R,13aS,14aR,16aS,Z)-2-((7-fluoro-4-methoxyisoquinolin-1-yl)oxy)-7,9-dimethyl-14a-(((1-methylcyclopropyl) sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate;

1,1,1-trifluoro-2-methylpropan-2-yl ((2R,6S,7S,9R,13aS,14aR,16aS,Z)-2-((2,3-dihydro-[1,4]dioxino[2,3 f]isoquinolin-7-yl)oxy)-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5, 8]oxadiazacyclopentadecin-6-yl)carbamate;

3,3-difluoro-2-methylbutan-2-yl((2R,6S,7S,9R,13aS,14aR,16aS,Z)-2-((2,3-dihydro-[1,4]dioxino[2,3 soquinolin-7-yl)oxy)-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5, 8]oxadiazacyclopentadecin-6-yl)carbamate;

1,1,1-trifluoro-2-methylpropan-2-yl ((2R,6S,7S,9R,13aS,14aR,16aS,Z)-2-((3-(5-isopropoxypyridin-2-yl)-6-methoxyisoquinolin-1-yl)oxy)-7,9-dimethyl-14a-(((1-methylcyclopropyl)sulfonyl]carbamoyl)-5,16-dioxo-2,3,5,6,7,9,10,11,13a, 14,14a, 15,16,16a-tetradecahydro-1H-cyclopropa[i]pyrrolo[1,2-e][1,5,8]oxadiazacyclopentadecin-6-yl)carbamate;

3,3-difluoro-2-methylbutan-2-yl 42R,6S,7S,9R,13aS,14aR,16aS,Z)-2-((3-(5-isopropoxypyridin-2-yl)-6-methoxyisoquinolin-1-yl)oxy)-7,9-dimethyl-14a-(((1-methylcyclopropyl)sulfonyOcarbamoyl)-5,16-dioxo-2,3,5,6,7,9,10,11,13a,14,14a,15,16,16a-tetradecahydro-1H-cyclopropa[i]pyrrolo[1,2-e][1,5,8] oxadiazacyclopentadecin-6-yl)carbamate;

1,1,1-trifluoro-2-methylpropan-2-yl ((2R,6S,7S,9R,13aS,14aR,16aS,Z)-14a-(((1-(fluoromethyl)cyclopropyl)sulfonyl)carbamoyl)-2-((6-methoxyisoquinolin-1-yl)oxy)-7,9-dimethyl-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate;

3,3-difluoro-2-methylbutan-2-yl ((2R,6S,7S,9R,13aS,14aR,16aS,Z)-14a-(((1-(fluoromethyl)cyclopropyl)sulfonyl)carbamoyl)-2-((6-methoxyisoquinolin-1-yl)oxy)-7,9-dimethyl-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate;

1,1,1-trifluoro-2-methylpropan-2-yl ((2R,6S,7S,9R,13aS,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate;

1,1-difluoro-2-methylpropan-2-yl ((2R,6S,7S,9R,13aS,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate;

1,1,1-trifluoro-2-methylpropan-2-yl ((2R,6S,7S,9R,13aS,14aR,16aS,Z)-2-((7-fluoro-5-methoxyisoquinolin-1-yl)oxy)-7,9-dimethyl-14a-(((1-methylcyclopropyl)sulfonyl)carbamoyl)-5,16-dioxo-2,3,5,6,7,9,10,11,13aS,14,14a,15,16,16a-tetradecahydro-1H-cyclopropa[i]pyrrolo[1,2-e][1,5,8]oxadiazacyclopentadecin-6-yl)carbamate;

3,3-difluoro-2-methylbutan-2-yl ((2R,6S,7S,9R,13aS,14aR,16aS,Z)-2-((7-fluoro-5-methoxyisoquinolin-1-yl)oxy)-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate;

1,1-difluoro-2-methylpropan-2-yl ((2R,6S,7S,9R,13aS,14aR,16aS,Z)-2-((7-fluoro-5-methoxyisoquinolin-1-yl)oxy)-7,9-dimethyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate;

1,1,1-trifluoro-2-methylpropan-2-yl ((2R,6S,7S,9R,13aS,14aR,16aS,Z)-2-((7-fluoro-5-methoxyisoquinolin-1-yl)oxy)-14a-(((1-(fluoromethyl)cyclopropyl)sulfonyl)carbamoyl)-7,9-dimethyl-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate;

3,3-difluoro-2-methylbutan-2-yl ((2R,6S,7S,9R,13aS,14aR,16aS,Z)-2-((7-fluoro-5-methoxyisoquinolin-1-yl)oxy)-14a-(((1-(fluoromethyl)cyclopropyl)sulfonyl)carbamoyl)-7,9-dimethyl-5,16-dioxo-2,3,5,6,7,9,10,11,13a,14,14a,15,16,16a-tetradecahydro-1H- cyclopropa[i]pyrrolo[1,2-e][1,5,8]
oxadiazacyclopentadecin-6-yl)carbamate;
1,1-difluoro-2-methylpropan-2-yl ((2R,6S,7S,9R,13aS,
14aR,16aS,Z)-2-((7-fluoro-5-methoxyisoquinolin-1-
yl)oxy)-14a-(((1-(fluoromethyl)cyclopropyl)sulfonyl)
carbamoyl)-7,9-dimethyl-5,16-dioxo-2,3,5,6,7,9,10,
11,13a,14,14a,15,16,16a-tetradecahydro-1H-
cyclopropa[i]pyrrolo[1,2-e][1,5,8]
oxadiazacyclopentadecin-6-yl)carbamate;
3,3-difluoro-2-methylbutan-2-yl ((2R,6S,7S,9R,13aS,
14aR,16aS,Z)-2-((2,3-dihydro-1H-pyrano[2,3-c]iso-
quinolin-6-yl)oxy)-7-ethyl-9-methyl-14a-(((1-methyl-
cyclopropyl)sulfonyOcarbamoyl)-5,16-dioxo-2,3,5,6,
7,9,10,11,13a,14,14a,15,16,16a-tetradecahydro-1H-
cyclopropa[i]pyrrolo[1,2-e][1,5,
8]oxadiazacyclopentadecin-6-yl)carbamate;
1,1,1-trifluoro-2-methylpropan-2-yl ((2R,6S,7S,9R,13aS,
14aR,16aS,Z)-2-((2,3-dihydro-1H-pyrano[2,3-c]iso-
quinolin-6-yl)oxy)-7-ethyl-9-methyl-14a-(((1-methyl-
cyclopropyl)sulfonyOcarbamoyl)-5,16-dioxo-2,3,5,6,
7,9,10,11,13a,14,14a,15,16,16a-tetradecahydro-1H-
cyclopropa[i]pyrrolo[1,2-e][1,5,8]
oxadiazacyclopentadecin-6-yl)carbamate;
3,3-difluoro-2-methylbutan-2-yl ((2R,6S,7S,9R,13aS,
14aR,16aS,Z)-2-((2,3-dihydro-1H-pyrano[2,3-c]iso-
quinolin-6-yl)oxy)-7,9-dimethyl-14a-(((1-methylcy-
clopropyl)sulfonyOcarbamoyl)-5,16-dioxo-2,3,5,6,7,9,
10,11,13a,14,14a,15,16,16a-tetradecahydro-1H-
cyclopropa[i]pyrrolo[1,2-e][1,5,
8]oxadiazacyclopentadecin-6-yl)carbamate;
1,1-difluoro-2-methylpropan-2-yl ((2R,6S,7S,9R,13aS,
14aR,16aS,Z)-2-((2,3-dihydro-1H-pyrano[2,3-c]iso-
quinolin-6-yl)oxy)-7,9-dimethyl-14a-(((1-methylcy-
clopropyl)sulfonyOcarbamoyl)-5,16-dioxo-2,3,5,6,7,9,
10,11,13a,14,14a,15,16,16a-tetradecahydro-1H-
cyclopropa[i]pyrrolo[1,2-e][1,5,
8]oxadiazacyclopentadecin-6-yl)carbamate;
1,1,1-trifluoro-2-methylpropan-2-yl ((2R,6S,7S,9R,13aS,
14aR,16aS,Z)-2-((2,3-dihydro-1H-pyrano[2,3-c]iso-
quinolin-6-yl)oxy)-7,9-dimethyl-14a-(((1-methylcy-
clopropyl)sulfonyOcarbamoyl)-5,16-dioxo-2,3,5,6,7,9,
10,11,13a,14,14a,15,16,16a-tetradecahydro-1H-
cyclopropa[i]pyrrolo[1,2-e][1,5,8]
oxadiazacyclopentadecin-6-yl)carbamate;
1,1,1-trifluoro-2-methylpropan-2-yl ((2R,6S,7S,9R,13aS,
14aR, 16aS,Z)-2-((9-methoxy-2,3-dihydro-1H-pyrano
[2,3-c]isoquinolin-6-yl)oxy)-7,9-dimethyl-14a-(((1-
methylcyclopropyl)sulfonyOcarbamoyl)-5,16-dioxo-2,
3,5,6,7,9,10,11,13a,14,14a,15,16,16a-tetradecahydro-
1H-cyclopropa[i]pyrrolo[1,2-e][1,5,8]
oxadiazacyclopentadecin-6-yl)carbamate;
1,1,1-trifluoro-2-methylpropan-2-yl ((2R,6S,7S,9R,13aS,
14aR,16aS,Z)-7-ethyl-2-((9-methoxy-2,3-dihydro-1H-
pyrano[2,3-c]isoquinolin-6-yl)oxy)-9-methyl-14a-(((1-
methylcyclopropyl)sulfonyOcarbamoyl)-5,16-dioxo-2,
3,5,6,7,9,10,11,13a,14,14a,15,16,16a-tetradecahydro-
1H-cyclopropa[i]pyrrolo[1,2-e][1,5,8]
oxadiazacyclopentadecin-6-yl)carbamate;
3,3-difluoro-2-methylbutan-2-yl ((2R,6S,7S,9R,13aS,
14aR, 16aS,Z)-7-ethyl-2-((9-methoxy-2,3-dihydro-1H-
pyrano[2,3-c]isoquinolin-6-yl)oxy)-9-methyl-14a-(((1-
methylcyclopropyl)sulfonyOcarbamoyl)-5,16-dioxo-2,
3,5,6,7,9,10,11,13a,14,14a,15,16,16a-tetradecahydro-
1H-cyclopropa[i]pyrrolo[1,2-e][1,5,8]
oxadiazacyclopentadecin-6-yl)carbamate;
3,3-difluoro-2-methylbutan-2-yl ((2R,6S,7S,9R,13aS,
14aR, 16aS,Z)-2-((9-methoxy-2,3-dihydro-1H-pyrano
[2,3-c]isoquinolin-6-yl)oxy)-7,9-dimethyl-14a-(((1-
methylcyclopropyl)sulfonyOcarbamoyl)-5,16-dioxo-2,
3,5,6,7,9,10,11,13a,14,14a,15,16,16a-tetradecahydro-
1H-cyclopropa[i]pyrrolo[1,2-e][1,5,8]
oxadiazacyclopentadecin-6-yl)carbamate;
1,1-difluoro-2-methylpropan-2-yl ((2R,6S,7S,9R,13aS,
14aR,16aS,Z)-2-((9-methoxy-2,3-dihydro-1H-pyrano
[2,3-c]isoquinolin-6-yl)oxy)-7,9-dimethyl-14a-(((1-
methylcyclopropyl)sulfonyOcarbamoyl)-5,16-dioxo-2,
3,5,6,7,9,10,11,13a,14,14a,15,16,16a-tetradecahydro-
1H-cyclopropa[i]pyrrolo[1,2-e][1,5,8]
oxadiazacyclopentadecin-6-yl)carbamate;
1,1-difluoro-2-methylpropan-2-yl ((2R,6S,7S,9R,13aS,
14aR,16aS,Z)-7-ethyl-2-((9-methoxy-2,3-dihydro-1H-
pyrano[2,3-c]isoquinolin-6-yl)oxy)-9-me thyl-14a-
(((1-methylcyclopropyl)sulfonyOcarbamoyl)-5,16-di-
oxo-2,3,5,6,7,9,10,11,13a,14,14a,15,16,16a-
tetradecahydro-1H-cyclopropa[i]pyrrolo[1,2-e][1,5,8]
oxadiazacyclopentadecin-6-yl)carbamate;
tert-butyl ((2R,6S,7R,9S,13aS, 14aR, 16aS,Z)-2-((4-
methoxyisoquinolin-1-yl)oxy)-7,9-dimethyl-14a-(((1-
methylcyclopropyl)sulfonyl)carbamoyl)-5,16-dioxo-2,
3,5,6,7,8,9,11,13a,14,14a,15,16,16a-tetradecahydro-
1H-cyclopropa[e]pyrrolo[2,1-i][1,7,10]
oxadiazacyclopentadecin-6-yl)carbamate;
tert-butyl ((2R,6S,7R,9S, 13aS, 14aR, 16aS,Z)-2-((6-
methoxyisoquinolin-1-yl)oxy)-7,9-dimethyl-14a-(((1-
methylcyclopropyl)sulfonyl)carbamoyl)-5,16-dioxo-2,
3,5,6,7,8,9,11,13a,14,14a,15,16,16a-tetradecahydro-
1H-cyclopropa[e]pyrrolo[2,1-i][1,7,10]
oxadiazacyclopentadecin-6-yl)carbamate;
tert-butyl ((2R,6S,7R,9S, 13aS, 14aR, 16aS,Z)-14a-((cy-
clopropylsulfonyl)carbamoyl)-2-((6-methoxyisoquino-
lin-1-yl)oxy)-7,9-dimethyl-5,16-dioxo-2,3,5,6,7,8,9,
11,13a,14,14a,15,16,16a-tetradecahydro-1H-
cyclopropa[e]pyrrolo[2,1-i][1,7,10]
oxadiazacyclopentadecin-6-yl)carbamate;
1,1,1-trifluoro-2-methylpropan-2-yl ((2R,6S,7R,9S,13aS,
14aR,16aS,Z)-14a-((cyclopropylsulfonyl)carbamoyl)-
2-((6-me thoxyisoquinolin-1-yl)oxy)-7,9-dimethyl-5,
16-dioxo-2,3,5,6,7,8,9,11,13a,14,14a,15,16,16a-
tetradecahydro-1H-cyclopropa[e]pyrrolo[2,1-i][1,7,
10]oxadiazacyclopentadecin-6-yl)carbamate;
3,3-difluoro-2-methylbutan-2-yl ((2R,6S,7S,9R,13aS,
14aR,16aS,Z)-7-ethyl-2-((7-fluoro-4-methoxyisoqui-
nolin-1-yl)oxy)-9-methyl-14a-(((1-methylcyclopropyl)
sulfonyl)carbamoyl)-5,16-dioxo-2,3,5,6,7,9,10,11,13a,
14,14a,15,16,16a-tetradecahydro-1H-cyclopropa[i]
pyrrolo[1,2-e][1,5,8]oxadiazacyclopentadecin-6-yl)
carbamate;
1,1,1-trifluoro-2-methylpropan-2-yl ((2R,6S,7S,9R,13aS,
14aR,16aS,Z)-7-ethyl-2-((7-fluoro-4-methoxyisoqui-
nolin-1-yl)oxy)-9-methyl-14a-(((1-methylcyclopropyl)
sulfonyOcarbamoyl)-5,16-dioxo-2,3,5,6,7,9,10,11,13a,
14,14a,15,16,16a-tetradecahydro-1H-cyclopropa[i]
pyrrolo[1,2-e][1,5, 8]oxadiazacyclopentadecin-6-yl)
carbamate;
3,3-difluoro-2-methylbutan-2-yl ((2R,6S,7S,9R,13aS,
14aR,16aS,Z)-2-((6-ethoxy-7-fluoroisoquinolin-1-yl)
oxy)-7-ethyl-9-methyl-14a-(((1-methylcyclopropyl)
sulfonyl)carbamoyl)-5,16-dioxo-2,3,5,6,7,9,10,11,13a,
14,14a,15,16,16a-tetradecahydro-1H-cyclopropa[i]
pyrrolo[1,2-e][1,5,8]oxadiazacyclopentadecin-6-yl)
carbamate;
1,1,1-trifluoro-2-methylpropan-2-yl ((2R,6S,7S,9R,13aS,
14aR,16aS,Z)-2-((6-ethoxy-7-fluoroisoquinolin-1-yl)
oxy)-7-ethyl-9-methyl-14a-(((1-methylcyclopropyl)

sulfonyl)carbamoyl)-5,16-dioxo-2,3,5,6,7,9,10,11,13a, 14,14a,15,16,16a-tetradecahydro-1H-cyclopropa[i] pyrrolo[1,2-e][1,5,8]oxadiazacyclopentadecin-6-yl) carbamate;

3,3-difluoro-2-methylbutan-2-yl ((2R,6S,7S,9R,13aS, 14aR,16aS,Z)-2-((2,3-dihydro-[1,4]dioxino[2,3-f]isoquinolin-7-yl)oxy)-7-ethyl-9-methyl-14a-(((1-methylcyclopropyl)sulfonyOcarbamoyl)-5,16-dioxo-2,3,5,6, 7,9,10,11,13a,14,14a,15,16,16a-tetradecahydro-1H-cyclopropa[i]pyrrolo[1,2-e][1,5, 8]oxadiazacyclopentadecin-6-yl)carbamate;

1,1,1-trifluoro-2-methylpropan-2-yl ((2R,6S,7S,9R,13aS, 14aR,16aS,Z)-2-((2,3-dihydro-[1,4]dioxino[2,3-f]isoquinolin-7-yl)oxy)-7-ethyl-9-methyl-14a-(((1-methylcyclopropyl)sulfonyOcarbamoyl)-5,16-dioxo-2,3,5,6, 7,9,10,11,13a,14,14a,15,16,16a-tetradecahydro-1H-cyclopropa[i]pyrrolo[1,2-e][1,5, 8]oxadiazacyclopentadecin-6-yl)carbamate;

tert-butyl ((2R,6S,7S,9R,13aS,14aR,16aS,Z)-2-((2,3-dihydro-[1,4]dioxino[2,3-f]isoquinolin-7-yl)oxy)-7-ethyl-9-methyl-14a-(((1-methylcyclopropyl)sulfonyl) carbamoyl)-5,16-dioxo-2,3,5,6,7,9,10,11,13a,14,14a, 15,16,16a-tetradecahydro-1H-cyclopropa[i]pyrrolo[1, 2-e][1,5,8]oxadiazacyclopentadecin-6-yl)carbamate;

1,1,1-trifluoro-2-methylpropan-2-yl ((2R,6S,7S,9R,13aS, 14aR,16aS,Z)-7-ethyl-2-((3-(5-isopropoxypyridin-2-yl)-6-methoxyisoquinolin-1-yl)oxy)-9-methyl-14a-(((1-methylcyclopropyl)sulfonyOcarbamoyl)-5,16-dioxo-2,3,5,6,7,9,10,11,13a,14,14a,15,16,16a-tetradecahydro-1H-cyclopropa[i]pyrrolo[1,2-e][1,5,8] oxadiazacyclopentadecin-6-yl)carbamate;

3,3-difluoro-2-methylbutan-2-yl ((2R,6S,7S,9R,13aS, 14aR,16aS,Z)-7-ethyl-2-((3-(5-isopropoxypyridin-2-yl)-6-methoxyisoquinolin-1-yl)oxy)-9-methyl-14a-(((1-methylcyclopropyl)sulfonyOcarbamoyl)-5,16-dioxo-2,3,5,6,7,9,10,11,13a,14,14a,15,16,16a-tetradecahydro-1H-cyclopropa[i]pyrrolo[1,2-e][1,5,8] oxadiazacyclopentadecin-6-yl)carbamate;

1,1-difluoro-2-methylpropan-2-yl ((2R,6S,7S,9R,13aS, 14aR,16aS,Z)-7-ethyl-2-((3-(5-isopropoxypyridin-2-yl)-6-methoxyisoquinolin-1-yl)oxy)-9-methyl-14a-(((1-methylcyclopropyl)sulfonyOcarbamoyl)-5,16-dioxo-2,3,5,6,7,9,10,11,13a,14,14a,15,16,16a-tetradecahydro-1H-cyclopropa[i]pyrrolo[1,2-e][1,5,8] oxadiazacyclopentadecin-6-yl)carbamate;

1,1-difluoro-2-methylpropan-2-yl ((2R,6S,7S,9R,13aS, 14aR,16aS,Z)-2-((6-ethoxy-7-fluoroisoquinolin-1-yl) oxy)-7-ethyl-9-methyl-14a-(((1-methylcyclopropyl) sulfonyl)carbamoyl)-5,16-dioxo-2,3,5,6,7,9,10,11,13a, 14,14a,15,16,16a-tetradecahydro-1H-cyclopropa[i] pyrrolo[1,2-e][1,5,8]oxadiazacyclopentadecin-6-yl) carbamate;

1,1-difluoro-2-methylpropan-2-yl ((2R,6S,7S,9R,13aS, 14aR,16aS,Z)-7-ethyl-2-((7-fluoro-6-methoxyisoquinolin-1-yl)oxy)-9-methyl-14a-(((1-methylcyclopropyl) sulfonyOcarbamoyl)-5,16-dioxo-2,3,5,6,7,9,10,11,13a, 14,14a,15,16,16a-tetradecahydro-1H-cyclopropa[i] pyrrolo[1,2-e][1,5,8]oxadiazacyclopentadecin-6-yl) carbamate;

1,1-difluoro-2-methylpropan-2-yl ((2R,6S,7S,9R,13aS, 14aR,16aS,Z)-7-ethyl-2-((7-fluoro-4-methoxyisoquinolin-1-yl)oxy)-9-methyl-14a-(((1-methylcyclopropyl) sulfonyOcarbamoyl)-5,16-dioxo-2,3,5,6,7,9,10,11,13a, 14,14a,15,16,16a-tetradecahydro-1H-cyclopropa[i] pyrrolo[1,2-e][1,5,8]oxadiazacyclopentadecin-6-yl) carbamate; and 1,1-difluoro-2-methylpropan-2-yl ((2R,6S,7S,9R,13aS, 14aR,16aS,Z)-7-ethyl-2-((4-methoxyisoquinolin-1-yl) oxy)-9-methyl-14a-(((1-methylcyclopropyl)sulfonyl) carbamoyl)-5,16-dioxo-2,3,5,6,7,9,10,11,13a,14,14a, 15,16,16a-tetradecahydro-1H-cyclopropa[i]pyrrolo[1, 2-e][1,5,8]oxadiazacyclopentadecin-6-yl)carbamate;

or a pharmaceutically acceptable salt thereof.

5. A composition comprising a compound of claim 1, or a pharmaceutically acceptable salt thereof, and a pharmaceutically acceptable carrier.

6. A method of treating an HCV infection in a patient, comprising administering to the patient a therapeutically effective amount of a compound of claim 1, or a pharmaceutically acceptable salt thereof.

* * * * *

UNITED STATES PATENT AND TRADEMARK OFFICE
CERTIFICATE OF CORRECTION

PATENT NO.       : 9,598,433 B2
APPLICATION NO.  : 14/435047
DATED            : March 21, 2017
INVENTOR(S)      : Sun et al.

Page 1 of 5

It is certified that error appears in the above-identified patent and that said Letters Patent is hereby corrected as shown below:

On the Title Page

Column 2, Line 42 Assistant Examiner:
Delete "Stephaine Springer" and insert -- Stephanie Springer --.

In the Claims

Claim 4, Column 129, Line 44:
Delete "6-dime thoxyisoquinolin-1-yl)" and insert -- 6-dimethoxyisoquinolin-1-yl) --.

Claim 4, Column 129, Line 45:
Delete "2,3,5,6,7,9,10, 11," and insert -- 2,3,5,6,7,9,10,11, --.

Claim 4, Column 131, Line 7:
Delete "(((1-methylcyclopropyl) sulfonyl)" and insert -- (((1-methylcyclopropyl)sulfonyl) --.

Claim 4, Column 131, Line 10:
Delete "[1,5, 8]" and insert -- [1,5,8] --.

Claim 4, Column 131, Line 16:
Delete "[1,5, 8]" and insert -- [1,5,8] --.

Claim 4, Column 131, Lines 19-20:
Delete "(((1-methylcyclopropyl) sulfonyl)" and insert -- (((1-methylcyclopropyl)sulfonyl) --.

Claim 4, Column 131, Line 22:
Delete "[1,5, 8]" and insert -- [1,5,8] --.

Signed and Sealed this
Fourth Day of December, 2018

Andrei Iancu
*Director of the United States Patent and Trademark Office*

Claim 4, Column 131, Lines 26-27:
Delete "(((1-methylcyclopropyl) sulfonyl)" and insert -- (((1-methylcyclopropyl)sulfonyl) --.

Claim 4, Column 131, Lines 33-34:
Delete "(((1-methylcyclopropyl) sulfonyl)" and insert -- (((1-methylcyclopropyl)sulfonyl) --.

Claim 4, Column 131, Line 34:
Delete "9,10, 11" and insert -- 9,10,11 --.

Claim 4, Column 131, Line 36:
Delete "[1,5, 8]" and insert -- [1,5,8] --.

Claim 4, Column 131, Lines 40-41:
Delete "(((1-methylcyclopropyl) sulfonyl)" and insert -- (((1-methylcyclopropyl)sulfonyl) --.

Claim 4, Column 131, Line 46:
Delete "[2,3f]" and insert -- [2,3-f] --.

Claim 4, Column 131, Lines 50-51:
Delete "[1,5, 8]" and insert -- [1,5,8] --.

Claim 4, Column 131, Line 52:
Delete "yl((2R," and insert -- yl ((2R, --.

Claim 4, Column 131, Lines 53-54:
Delete "[2,3 soquinolin" and insert -- [2,3-f]isoquinolin --.

Claim 4, Column 131, Lines 57-58:
Delete "[1,5, 8]" and insert -- [1,5,8] --.

Claim 4, Column 131, Line 62:
Delete "sulfonyl]" and insert -- sulfonyl) --.

Claim 4, Column 131, Line 63:
Delete "14,14a, 15," and insert -- 14,14a,15, --.

Claim 4, Column 131, Line 66:
Delete "yl 42R" and insert -- yl ((2R --.

Claim 4, Column 132, Line 2:
Delete "sulfonyOcarbamoyl)" and insert -- sulfonyl)carbamoyl) --.

Claim 4, Column 132, Line 22:
Delete "14a-((1-" and insert -- 14a-(((1- --.

Claim 4, Column 133, Line 13:
Delete "sulfonyOcarbamoyl)" and insert -- sulfonyl)carbamoyl) --.

Claim 4, Column 133, Lines 15-16:
Delete "[1,5, 8]" and insert -- [1,5,8] --.

Claim 4, Column 133, Line 20:
Delete "sulfonyOcarbamoyl)" and insert -- sulfonyl)carbamoyl) --.

Claim 4, Column 133, Line 27:
Delete "sulfonyOcarbamoyl)" and insert -- sulfonyl)carbamoyl) --.

Claim 4, Column 133, Lines 29-30:
Delete "[1,5, 8]" and insert -- [1,5,8] --.

Claim 4, Column 133, Line 34:
Delete "sulfonyOcarbamoyl)" and insert -- sulfonyl)carbamoyl) --.

Claim 4, Column 133, Lines 36-37:
Delete "[1,5, 8]" and insert -- [1,5,8] --.

Claim 4, Column 133, Line 41:
Delete "sulfonyOcarbamoyl)" and insert -- sulfonyl)carbamoyl) --.

Claim 4, Column 133, Line 46:
Delete "14aR, 16aS," and insert -- 14aR,16aS, --.

Claim 4, Column 133, Line 48:
Delete "sulfonyOcarbamoyl)" and insert -- sulfonyl)carbamoyl) --.

Claim 4, Column 133, Line 55:
Delete "sulfonyOcarbamoyl)" and insert -- sulfonyl)carbamoyl) --.

Claim 4, Column 133, Line 60:
Delete "14aR, 16aS," and insert -- 14aR,16aS, --.

Claim 4, Column 133, Line 62:
Delete "sulfonyOcarbamoyl)" and insert -- sulfonyl)carbamoyl) --.

Claim 4, Column 133, Line 67:
Delete "14aR, 16aS," and insert -- 14aR,16aS, --.

Claim 4, Column 134, Line 2:
Delete "sulfonyOcarbamoyl)" and insert -- sulfonyl)carbamoyl) --.

CERTIFICATE OF CORRECTION (continued)
U.S. Pat. No. 9,598,433 B2

Claim 4, Column 134, Line 9:
Delete "sulfonyOcarbamoyl)" and insert -- sulfonyl)carbamoyl) --.

Claim 4, Column 134, Line 15:
Delete "9-me thyl" and insert -- 9-methyl --.

Claim 4, Column 134, Line 16:
Delete "sulfonyOcarbamoyl)" and insert -- sulfonyl)carbamoyl) --.

Claim 4, Column 134, Line 20:
Delete "9S,13aS, 14aR, 16aS," and insert -- 9S,13aS,14aR,16aS, --.

Claim 4, Column 134, Line 26:
Delete "9S, 13aS, 14aR, 16aS," and insert -- 9S,13aS,14aR,16aS, --.

Claim 4, Column 134, Line 32:
Delete "9S, 13aS, 14aR, 16aS," and insert -- 9S,13aS,14aR,16aS, --.

Claim 4, Column 134, Line 40:
Delete "((6-me thoxyisoquinolin" and insert -- ((6-methoxyisoquinolin --.

Claim 4, Column 134, Line 54:
Delete "sulfonyOcarbamoyl)" and insert -- sulfonyl)carbamoyl) --.

Claim 4, Column 134, Line 56:
Delete "[1,5, 8]" and insert -- [1,5,8] --.

Claim 4, Column 135, Line 8:
Delete "sulfonyOcarbamoyl)" and insert -- sulfonyl)carbamoyl) --.

Claim 4, Column 135, Lines 10-11:
Delete "[1,5, 8]" and insert -- [1,5,8] --.

Claim 4, Column 135, Line 15:
Delete "sulfonyOcarbamoyl)" and insert -- sulfonyl)carbamoyl) --.

Claim 4, Column 135, Lines 17-18:
Delete "[1,5, 8]" and insert -- [1,5,8] --.

Claim 4, Column 135, Line 28:
Delete "sulfonyOcarbamoyl)" and insert -- sulfonyl)carbamoyl) --.

Claim 4, Column 135, Line 35:
Delete "sulfonyOcarbamoyl)" and insert -- sulfonyl)carbamoyl) --.

CERTIFICATE OF CORRECTION (continued)
U.S. Pat. No. 9,598,433 B2

Claim 4, Column 136, Line 1:
Delete "sulfonyOcarbamoyl)" and insert -- sulfonyl)carbamoyl) --.

Claim 4, Column 136, Line 15:
Delete "sulfonyOcarbamoyl)" and insert -- sulfonyl)carbamoyl) --.

Claim 4, Column 136, Line 22:
Delete "sulfonyOcarbamoyl)" and insert -- sulfonyl)carbamoyl) --.